(12) United States Patent
Buckner et al.

(10) Patent No.: US 10,913,736 B2
(45) Date of Patent: Feb. 9, 2021

(54) SPECIFIC INHIBITORS OF METHIONYL-TRNA SYNTHETASE

(71) Applicant: UNIVERSITY OF WASHINGTON, Seattle, WA (US)

(72) Inventors: Frederick S. Buckner, Seattle, WA (US); Ximena Barros Alvarez, Seattle, WA (US); Erkang Fan, Seattle, WA (US); John Robert Gillespie, Seattle, WA (US); Wilhelmus G.J. Hol, Seattle, WA (US); Wenlin Huang, Seattle, WA (US); Cho Yeow Koh, Seattle, WA (US); Ranae M. Ranade, Seattle, WA (US); Sayaka Shibata, Seattle, WA (US); Christophe L.M. Verlinde, Seattle, WA (US); Zhongsheng Zhang, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 15/504,969

(22) PCT Filed: Aug. 21, 2015

(86) PCT No.: PCT/US2015/046357
§ 371 (c)(1),
(2) Date: Feb. 17, 2017

(87) PCT Pub. No.: WO2016/029146
PCT Pub. Date: Feb. 25, 2016

(65) Prior Publication Data
US 2017/0275279 A1    Sep. 28, 2017

Related U.S. Application Data

(60) Provisional application No. 62/130,967, filed on Mar. 10, 2015, provisional application No. 62/040,899, filed on Aug. 22, 2014.

(51) Int. Cl.
| | | |
|---|---|---|
| *C07D 471/04* | (2006.01) | |
| *C07D 209/14* | (2006.01) | |
| *C07D 235/14* | (2006.01) | |
| *C07D 401/04* | (2006.01) | |
| *C07D 403/06* | (2006.01) | |
| *C07D 405/12* | (2006.01) | |

(52) U.S. Cl.
CPC ......... *C07D 471/04* (2013.01); *C07D 209/14* (2013.01); *C07D 235/14* (2013.01); *C07D 401/04* (2013.01); *C07D 403/06* (2013.01); *C07D 405/12* (2013.01)

(58) Field of Classification Search
CPC .. C07D 471/04; C07D 209/14; C07D 234/14; C07D 401/04; C07D 403/06; C07D 405/12
See application file for complete search history.

(56) References Cited

U.S. PATENT DOCUMENTS

| | | | | |
|---|---|---|---|---|
| 5,792,768 A | * | 8/1998 | Kulagowski | ......... C07D 409/12 514/254.06 |
| 6,333,344 B1 | * | 12/2001 | Hammond | ........... C07D 403/12 514/263.2 |
| 7,973,050 B2 | | 7/2011 | Guiles | |
| 8,697,720 B2 | | 4/2014 | Guiles | |
| 2004/0019037 A1 | | 1/2004 | Askew et al. | |
| 2004/0224981 A1 | | 11/2004 | Janjic | |
| 2005/0209282 A1 | * | 9/2005 | Wilson | .................. C04B 35/632 514/320 |
| 2007/0129548 A1 | * | 6/2007 | Tan | ........................ C07J 73/005 546/77 |
| 2007/0213362 A1 | | 9/2007 | Berge et al. | |
| 2008/0287468 A1 | | 11/2008 | Ohlmeyer | |
| 2009/0163536 A1 | | 6/2009 | Guiles | |
| 2010/0055071 A1 | * | 3/2010 | Leivers | ................ C07D 207/08 424/85.4 |
| 2012/0264943 A1 | | 10/2012 | Bjork et al. | |
| 2013/0065896 A1 | * | 3/2013 | Masaki | ................ C07D 235/12 514/234.5 |
| 2014/0163008 A1 | * | 6/2014 | Yamamoto | ........... C07D 413/14 514/210.21 |

FOREIGN PATENT DOCUMENTS

| | | | | |
|---|---|---|---|---|
| EP | 0151826 A1 | * | 8/1985 | ........... C07D 409/14 |
| WO | 2000/071522 | | 11/2000 | |
| WO | WO-2013045028 A1 | * | 4/2013 | ......... A61K 31/4545 |

OTHER PUBLICATIONS

CAS Registry Entry for Registry No. 1261788-43-5, which entered STN on Feb. 3, 2011 (Year: 2011).*
Augustine et al. J. Org. Chem. 1973, 38, 3004-3011 (Year: 1973).*
McCauley et al. J. Med. Chem. 2004, 47, 2089-2096 (Year: 2004).*
CAS Registry Entry for Registry No. 1390455-48-7, which entered STN on Aug. 13, 2012 (Year: 2012).*
CAS Registry Entry for Registry No. 89174-71-0, which entered STN on Nov. 16, 1984 (Year: 1984).*
Patani et al. Chem. Rev. 1996, 96, 3147-3176 (Year: 1996).*
Sheridan, R.P. J. Chem. Inf. Comput. Sci. 2002, 42, 103-108 (Year: 2002).*
CAS Registry No. 1170496-02-2, which entered STN on Jul. 30, 2009 (Year: 2009).*
The International Search Report (ISR) with Written Opinion for PCT/US2015/046357 dated Oct. 15, 2015, pp. 1-18.
Pubchem CID 73012917, pp. 1-10, Create Date: Mar. 7, 2014; Modify Date: Oct. 10, 2015; p. 3; [retrieved on Oct. 14, 2015). Retrieved from the Internet: <URL: http://pubchem.ncbi .nlm.nih. gov/compound/73012917>.

(Continued)

*Primary Examiner* — Matthew P Coughlin
(74) *Attorney, Agent, or Firm* — McDonnell Boehnen Hulbert & Berghoff LLP

(57) ABSTRACT

The present disclosure is generally directed to compositions useful in the inhibition of MetRS and methods for treating diseases that are ameliorated by the inhibition of MetRS.

2 Claims, No Drawings

(56) References Cited

OTHER PUBLICATIONS

Kim, Su Yeon et al., "3-D-QSAR Study and Molecular Docking of Methionyl-tRNA Synthetase Inhibitors" Bioorganic & Medicinal Chemistry (2003) vol. 11, pp. 5325-5331.

Perkins et al., "Synthesis of 2-(Alkylamino)benzimidazoles," Tetrahedron Letters 40: 1103-1106 (1999).

Shibata et al., "Urea-Based Inhibitors of Trypanosome brucei Methionyl-tRNA Synthetase: Selectivity and in Vivo Characterization," J. Med. Chem. 55: 6342-6351 (2012).

Pletsas et al., "Synthesis and Quantitative Structure-Activity Relationship of Imidazotetrazine Prodrugs with Activity Independent of O6-Methylguanine-DNA-methyltransferase, DNA Mismatch Repair and p53," J Med Chem. 56(17): 7120-7132 (2013).

Tikhe et al., "Design, Synthesis, and Evaluation of 3,4-Dihydro-2H-[1,4]diazepino[6,7,1-hi]indol-1-ones as Inhibitors of Poly(ADP-Ribose) Polymerase," J. Med. Chem. 47: 5467-5481 (2004).

Tanuwidjaja et al., "One-Pot Asymmetric Synthesis of Either Diastereomer of tert-Butanesulfinyl-protected Amines from Ketones," J. Org. Chem 72: 626-629 (2007).

Colyer et al., "Reversal of Diastereofacial Selectivity in Hydride Reductions of N-tert-Butanesulfinyl Imines," J. Org. Chem. 71(18): 6859-6862 (2006).

Shibata et al., "Selective Inhibitors of Methionyl-tRNA Synthetase Have Potent Activity against Trypanosoma brucei Infection in Mice," Antimicrob Agents Chemother 55: 1982-1989 (2011).

Koh et al., "Distinct States of Methionyl-tRNA Synthetase Indicate Inhibitor Binding by Conformational Selection," Structure 20: 1681-1691 (2012).

Yamashita et al., "New Procedure for the Synthesis of 2-Alkylbenzimidazoles," Synthetic Communications, 39(16): 2982-2988 (2009).

Khatik et al., "Reversal of Selectivity in Acetate Aldol Reactions of N-Acetyl-(S)-4-isopropyl-1-[(R)-1-phenylethyl] imidazolidin-2-one," Organic Letters 14(10): 2442-2445 (2012).

Kumar et al., "SiO2 Catalysed expedient synthesis of [E]-3-alkenoic acids in dry media," Tetrahedron Letters 40(12): 2401-2404 (1999).

Verma et al., "Design and Synthesis of Benzimidazole-Linked meta-Substituted Benzylidenes/Benzyls as Biologically Significant New Chemical Entities," Synthetic Communications 43(14): 1882-1895 (2013).

Ranade et al, "Induced Resistance to Methionyl-tRNA Synthetase Inhibitors in Trypanosoma brucei Is Due to Overexpression of the Target," Antimicrobial Agents and Chemotherapy 57(7): 3021-3028 (2013).

Jarvest et al., "Definition of the heterocyclic pharmacophore of bacterial methionyl tRNA synthetase inhibitors: potent antibacterially active non-quinolone analogues," Bioorg. Med. Chem. Lett. 14: 3937-3941 (2004).

* cited by examiner

SPECIFIC INHIBITORS OF METHIONYL-TRNA SYNTHETASE

This application is a U.S. National Phase of International Application No. PCT/US2015/046357, filed on Aug. 21, 2015, which claims priority to U.S. Provisional Application No. 62/040,899, filed Aug. 22, 2014 and U.S. Provisional Application No. 62/130,967, filed Mar. 10, 2015, all of which are incorporated by reference herein in their entirety.

STATEMENT OF GOVERNMENT SUPPORT

This invention was made with government support under R01 AI084004 and AI097177 awarded by the National Institutes of Health (NIH). The government has certain rights in the invention.

BACKGROUND OF THE INVENTION

Field of the Invention

The present disclosure is generally directed to compositions and methods for treating diseases that are ameliorated by the inhibition of methionyl-tRNA synthetase (MetRS).

Description of Related Art

Anti-bacterial compounds kill or inhibit the growth of bacteria by interfering with major processes of cellular function that are essential for survival. The β-lactams (penicillins and cephalosporins) and the glycopeptides (vancomycin and teicoplanin) inhibit synthesis of the cell wall. Macrolides (erythromycin, clarithromycin, and azithromycin), clindamycin, chloramphenicol, aminoglycosides (streptomycin, gentamicin, and amikacin) and the tetracyclines inhibit protein synthesis. Also inhibiting protein synthesis are synthetic oxazolidinones. Rifampin inhibits RNA synthesis, the fluoroquinolones (such as ciprofloxacin) inhibit DNA synthesis indirectly by inhibiting the enzymes that maintain the topological state of DNA. Trimethoprim and the sulfonamides inhibit folate biosynthesis directly and DNA synthesis indirectly by depleting the pools of one of the required nucleotides (Chambers, H. F. and Sande, M. A. (1996) antimicrobial agents. Goodman & Gilman's the pharmacological basis of therapeutics, McGraw-Hill, New York). The disclosure of this reference, and of all other patents, patent applications, and publications referred to herein, are incorporated by reference herein in their entirety.

Antibiotic resistance is increasingly common. These circumstances have prompted efforts to develop new antibiotics that overcome the emerging antibiotic-resistant bacteria. MetRS has emerged as an attractive target for the development of new antibiotics, since compounds that inhibit this enzyme have the ability to circumvent existing resistance mechanisms.

DETAILED DESCRIPTION OF THE INVENTION

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

In view of the present disclosure, the compounds described herein can be configured by the person of ordinary skill in the art to meet the desired need. In general, the disclosed compounds provide improvements in treatment of diseases that are ameliorated by the inhibition of MetRS. For example, in certain aspects, the compounds of the disclosure are effective against bacterial infection. In certain embodiments the bacterial infection is in the form an infection from Gram positive cocci, including but not limited to *Staphylococcus aureus* and *Enterococcus faecalis*. In certain embodiments, the compounds of the present disclosure are effective in treating or ameliorating infections from *Staphylococcus* (including MRSA), *Enterococcus* (including VRE), *Streptococcus*, *Clostridium*, and others. In certain embodiments, the compositions are effective in treating Mycobacterial infections, including infections from *Mycobacterium tuberculosis, Mycobacterium avium* complex, *Mycobacterium fortuitum*, and others. In certain embodiments, the compositions are effective in treating protozoan infections, including infections caused by *Trypanosoma, Leishmania, Giardia, Trichomonas*, and others.

In certain embodiments, the present disclosure provides pyridine-imidazole (PI) containing compounds capable of blocking protein synthesis by inhibiting MetRS. An important advance of these compounds over related compounds in the literature is their favorable pharmacokinetic profile (as shown in rodents) that potentially makes them suitable for oral administration. The addition of fluorine to the pyridine ring improves the permeability properties.

In a first aspect, the present disclosure provides compounds of formula (I)

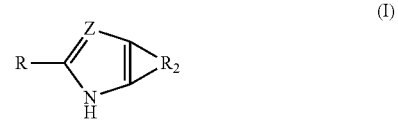

or a pharmaceutically acceptable salt thereof, wherein $R_2$ is a aryl or heteroaryl ring which is optionally substituted with from 1 to 3 substituents independently selected from halogen, cyano, hydroxy, (C1-6)alkyl (optionally substituted by halogen, hydroxy, amino, mono to perfluoro(C1-3)alkyl, carboxy or (C1-6)alkoxycarbonyl), (C3-7)cycloalkyl, C(1-6)alkoxy, amino, mono- or di-(C1-6)alkylamino, acylamino, carboxy, (C1-6)alkoxycarbonyl, carboxy(C1-6)alkyloxy, (C1-6)alkylthio, (C1-6)alkylsulphinyl, (C1-6)alkylsulphonyl, sulphamoyl, mono- and di-(C1-6)alkylsulphamoyl, carbamoyl, mono- and di-(C1-6)alkylcarbamoyl, and heterocyclyl;

Z is N or $CR_6$, wherein $R_6$ selected from H, $C_{1-12}$ alkyl, $C_{1-12}$ halogen-alkyl, $C_{1-12}$ alkenyl, $C_{1-12}$ alkynyl, optionally substituted aryl, optionally substituted heteroaryl, optionally substituted cyclic, optionally substituted heterocyclic, $C_{1-12}$ alcohol, halogen, cyano, ether, thio ether, ester, amine, amide, carbamate, and urea groups; and R is

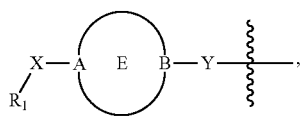

wherein
R₁ is an aryl or heteroaryl ring, each optionally substituted with from 1 to 3 substituents independently selected from halogen, cyano, hydroxy, (C1-6)alkyl (optionally substituted by halogen, hydroxy, amino, mono to perfluoro(C1-3)alkyl, carboxy or (C1-6)alkoxycarbonyl), (C1-6)alkenyl (C3-7)cycloalkyl, C(1-6)alkoxy, amino;

X is absent or a linker selected from one of the optionally substituted groups consisting of $C_{1-6}$ alkanes, $C_{1-6}$ alkenes, $C_{1-6}$ alkynes, $C_{1-6}$ alcohols, ethers, thio ethers, amines, amides, carbamates, ureas and combinations thereof;

E is absent or a 3- to 8-membered cycloalkyl, heterocycloalkyl, cycloalkenyl, heterocycloalkenyl, aryl, or heteroaryl group wherein A and B disposed in the 1,2-, 1,3-, or 1,4-positions are independently selected from the group consisting of —C—, —CH—, —CH₂—, —N— or —N(R⁷), where R⁷ is H or $C_{1-12}$ alkyl, wherein E is optionally substituted with (C1-6)alkyl, —O—(C1-6)alkyl, aryl —O-aryl, heteroaryl, —O-heteroaryl, heterocycloalkyl, —OH, —NH₂, —NH(C1-6)alkyl, —N((C1-6)alkyl)₂, —NH-aryl, —NH-heteroaryl, —N(H)C(O)(C1-6)alkyl, —C(O)N(H)(C1-6)alkyl, —C(O)N((C1-6)alkyl)₂, —N(H)C(O)O(C1-6)alkyl, —OC(O)N(H)(C1-6)alkyl, —OC(O)N((C1-6)alkyl)₂, —N(H)C(O)N(H)(C1-6)alkyl, —N(H)C(O)N((C1-6)alkyl)₂, halogen, nitrile or —NH—CH₂-heteroaryl, where the aryl, heterocycloalkyl and heteroaryl are optionally substituted with —OH, —NH₂, —NH(C1-6)alkyl, —N((C1-6)alkyl)₂, —N(H)C(O)(C1-6)alkyl, —C(O)N(H)(C1-6)alkyl, —C(O)N((C1-6)alkyl)₂, —N(H)C(O)O(C1-6)alkyl, —OC(O)N(H)(C1-6)alkyl, —OC(O)N((C1-6)alkyl)₂, —N(H)C(O)N(H)(C1-6)alkyl, —N(H)C(O)N((C1-6)alkyl)₂, nitrile, heteroaryl, halogen, or (C1-6)alkyloxy; and Y is absent or a linker selected from the group consisting of $C_{1-3}$ alkyl, secondary and tertiary amine, thiol, thiol ether, alcohol, ether, ester, amine, amide, carbamate, and urea groups and combinations thereof, provided that 1) when E is absent, Z is NH and R₂ is unsubstituted heteroaryl, unsubstituted phenyl, or pyridinyl substituted with 1-2 fluoro groups, X and Y, alone or in combination, do not form —CH₂—NH—CH₂—CH₂—NH—, —CH₂—NH—CH₂—CH₂—CH₂—NH— or —CH₂—NH—CH₂—CH₂—CH₂—CH₂—NH—;

2) when E is pyrimidine and Z is NH, R₂ is not phenyl;

or R is $C_{1-6}$ alkyl, $C_{2-6}$ alkenyl, $C_{1-6}$ haloalkyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR⁷, —SR⁷, —N(R⁷)₂, —C(O)R⁷, —C(O)OR⁷, —C(O)N(R⁷)₂, —S(O)₂R⁷, —OC(O)R⁷, —OC(O)OR⁷, —OC(O)N(R⁷)₂, —N(R⁷)C(O)R⁷, —N(R⁷)C(O)OR⁷, or —N(R⁷)C(O)N(R⁷)₂, wherein each R⁷ is independently hydrogen or $C_{1-6}$ alkyl, or R is

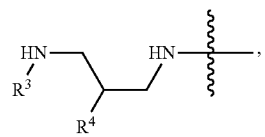

wherein
R³ is $C_{1-6}$ alkyl, $C_{2-6}$ alkenyl, $C_{1-6}$ haloalkyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR⁷, —SR⁷, —N(R⁷)₂, —C(O)R⁷, —C(O)OR⁷, —C(O)N(R⁷)₂, —S(O)₂R⁷, —OC(O)R⁷, —OC(O)OR⁷, —OC(O)N(R⁷)₂, —N(R⁷)C(O)R⁷, —N(R⁷)C(O)OR⁷, or —N(R⁷)C(O)N(R⁷)₂, wherein each R⁷ is independently hydrogen or C1-6 alkyl; and R⁴ is hydrogen, halogen, $C_{1-6}$ alkyl, or —OR⁸, where R⁸ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR⁷, —SR⁷, —N(R⁷)₂, —C(O)R⁷, —C(O)OR⁷, —C(O)N(R⁷)₂, —S(O)₂R⁷, —OC(O)R⁷, —OC(O)OR⁷, —OC(O)N(R⁷)₂, —N(R⁷)C(O)R⁷, —N(R⁷)C(O)OR⁷, or —N(R⁷)C(O)N(R⁷)₂, wherein each R⁷ is independently hydrogen or C1-6 alkyl.

In some embodiments, the present disclosure provides compounds of formula (I), provided that:
when Z is NH and R₂ is unsubstituted phenyl, or pyridinyl substituted with 1-2 fluoro groups, X and Y, alone or in combination, do not form —CH₂—NH—CH₂—CH₂—CH₂—NH—;

In some embodiments of the first aspect, the compound of formula (I) is one of the following compounds (or a pharmaceutically acceptable salt, prodrug, solvate or hydrate thereof):

| No. | Chemical Structure | Chemical Name |
|---|---|---|
| 1575 | 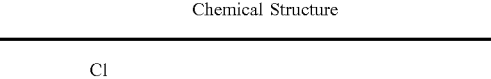 | N1-(3,5-dichlorobenzyl)-N3-(1H-imidazo[4,5-b]pyridin-2-yl)propane-1,3-diamine |

-continued

| No. | Chemical Structure | Chemical Name |
|---|---|---|
| 1576 | 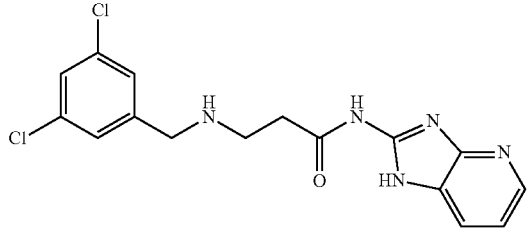 [SMILES: O=C(CCNCc1cc(Cl)cc(Cl)c1)Nc1nc2ncccc2[nH]1] | 3-{[(3,5-dichlorophenyl)methyl]amino}-N-{1H-imidazo[4,5-b]pyridin-2-yl}propanamide |
| 1599 | 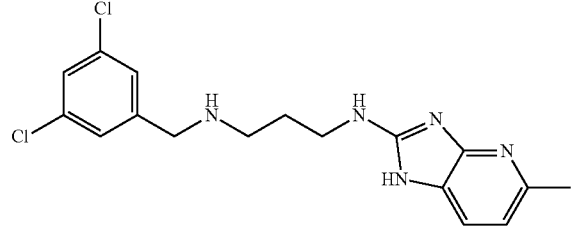 [SMILES: Cc1ccc2[nH]c(NCCCNCc3cc(Cl)cc(Cl)c3)nc2n1] | N1-(3,5-dichlorobenzyl)-N3-(5-methyl-1H-imidazo[4,5-b]pyridin-2-yl)propane-1,3-diamine |
| 1614 | 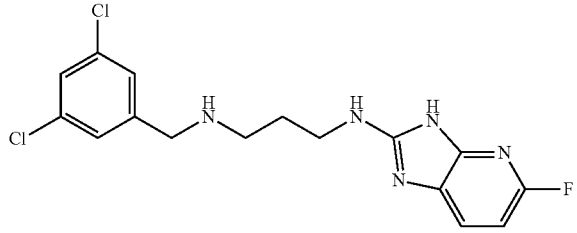 [SMILES: Fc1ccc2nc(NCCCNCc3cc(Cl)cc(Cl)c3)[nH]c2n1] | [(3,5-dichlorophenyl)methyl][3-({5-fluoro-3H-imidazo[4,5-b]pyridin-2-yl}amino)propyl]amine |
| 1634 | 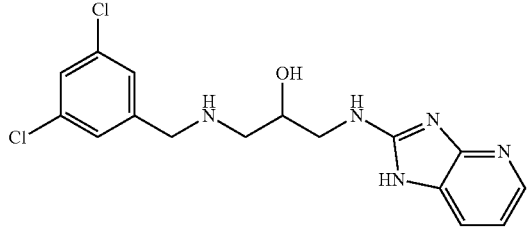 | 1-((1H-imidazo[4,5-b]pyridin-2-yl)amino)-3-((3,5-dichlorobenzyl)amino)propan-2-ol |
| 1641 | 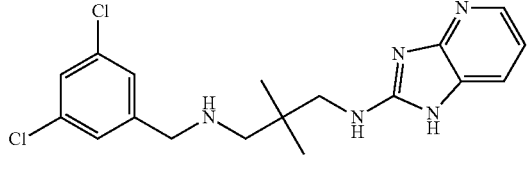 [SMILES: CC(C)(CNCc1cc(Cl)cc(Cl)c1)CNc1nc2ncccc2[nH]1] | N1-(3,5-dichlorobenzyl)-N3-(1H-imidazo[4,5-b]pyridin-2-yl)-2,2-dimethylpropane-1,3-diamine |
| 1655 | 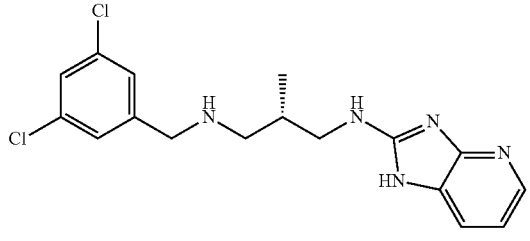 [SMILES: C[C@@H](CNCc1cc(Cl)cc(Cl)c1)CNc1nc2ncccc2[nH]1] | (S)-N1-(3,5-dichlorobenzyl)-N3-(1H-imidazo[4,5-b]pyridin-2-yl)-2-methylpropane-1,3-diamine |

-continued

| No. | Chemical Structure | Chemical Name |
|---|---|---|
| 1673 | 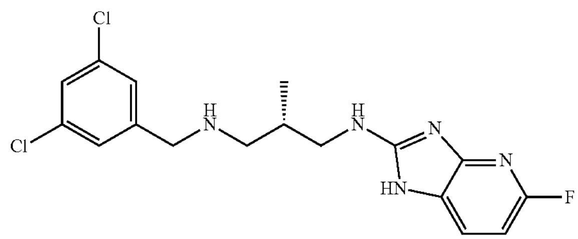 [SMILES: C[C@@H](CNCc1cc(Cl)cc(Cl)c1)CNc1nc2nc(F)ccc2[nH]1] | [(3,5-dichlorophenyl)methyl][(2S)-3-({5-fluoro-3H-imidazo[4,5-b]pyridin-2-yl}amino)-2-methylpropyl]amine |
| 1683 | 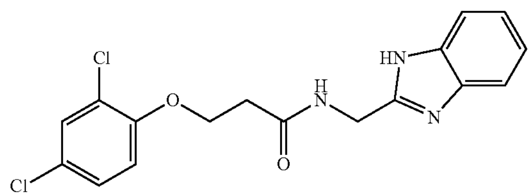 | N-(1H-1,3-benzodiazol-2-ylmethyl)-3-(2,4-dichlorophenoxy)propanamide |
| 1704 | 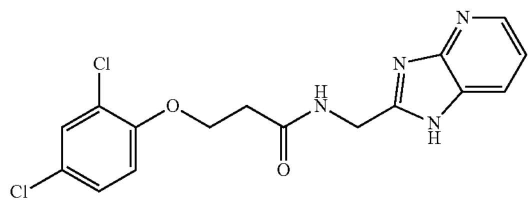 [SMILES: O=C(CCOc1ccc(Cl)cc1Cl)NCc1nc2ncccc2[nH]1] | 3-(2,4-dichlorophenoxy)-N-{3H-imidazo[4,5-b]pyridin-2-ylmethyl}propanamide |
| 1705 | 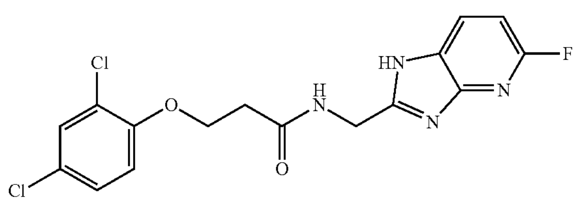 [SMILES: O=C(CCOc1ccc(Cl)cc1Cl)NCc1nc2nc(F)ccc2[nH]1] | 3-(2,4-dichlorophenoxy)-N-({5-fluoro-3H-imidazo[4,5-b]pyridin-2-yl}methyl)propanamide |
| 1709 | 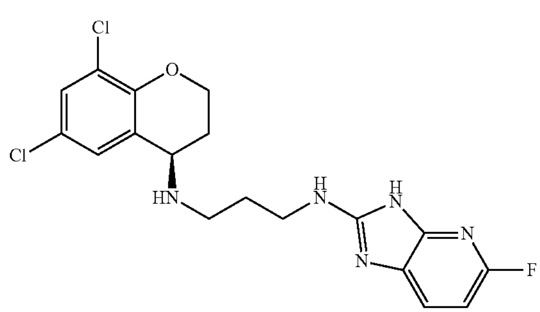 [SMILES: Fc1ccc2nc(NCCCN[C@@H]3CCOc4c(Cl)cc(Cl)cc43)[nH]c2n1] | (4R)-6,8-dichloro-N-[3-({5-fluoro-3H-imidazo[4,5-b]pyridin-2-yl}amino)propyl]-3,4-dihydro-2H-1-benzopyran-4-amine |
| 1710 | 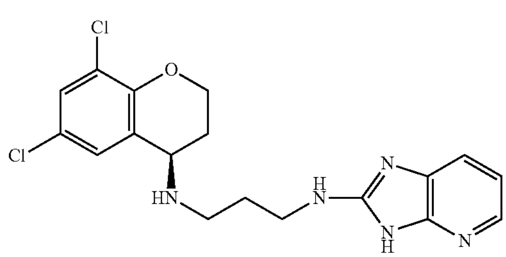 [SMILES: Clc1cc(Cl)c2c(c1)[C@H](NCCCNc1nc3cccnc3[nH]1)CCO2] | (R)-N1-(6,8-dichlorochroman-4-yl)-N3-(3H-imidazo[4,5-b]pyridin-2-yl)propane-1,3-diamine |

| No. | Chemical Structure | Chemical Name |
|---|---|---|
| 1711 | 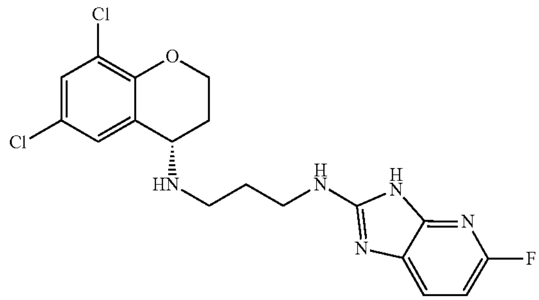 [SMILES: Fc1ccc2nc(NCCCN[C@H]3CCOc4c(Cl)cc(Cl)cc43)[nH]c2n1] | (4S)-6,8-dichloro-N-[3-({5-fluoro-3H-imidazo[4,5-b]pyridin-2-yl}amino)propyl]-3,4-dihydro-2H-1-benzopyran-4-amine |
| 1717 | 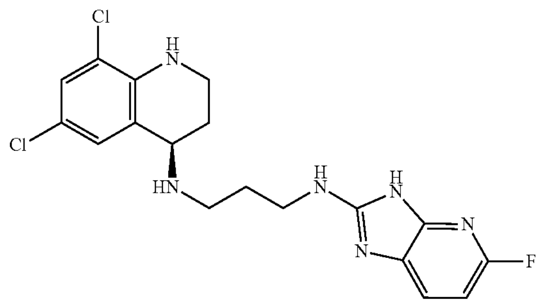 [SMILES: Fc1ccc2nc(NCCCN[C@@H]3CCNc4c(Cl)cc(Cl)cc43)[nH]c2n1] | (4R)-6,8-dichloro-N-[3-({5-fluoro-3H-imidazo[4,5-b]pyridin-2-yl}amino)propyl]-1,2,3,4-tetrahydroquinolin-4-amine |
| 1727 | 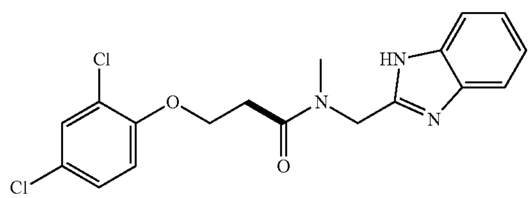 | N-(1H-1,3-benzodiazol-2-ylmethyl)-3-(2,4-dichlorophenoxy)-N-methylpropanamide |
| 1729 | 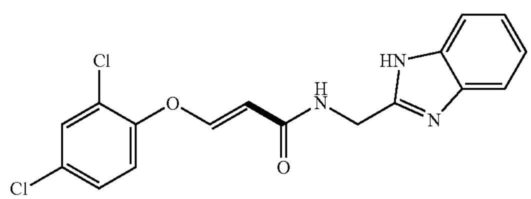 | (2E)-N-(1H-1,3-benzodiazol-2-ylmethyl)-3-(2,4-dichlorophenoxy)prop-2-enamide |
| 1730 | 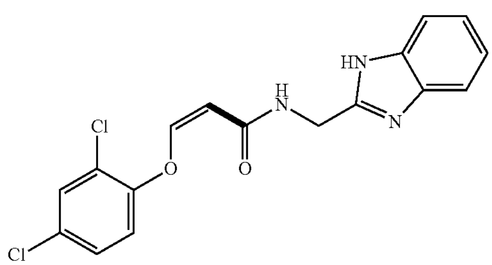 | (2Z)-N-(1H-1,3-benzodiazol-2-ylmethyl)-3-(2,4-dichlorophenoxy)prop-2-enamide |
| 1627 | 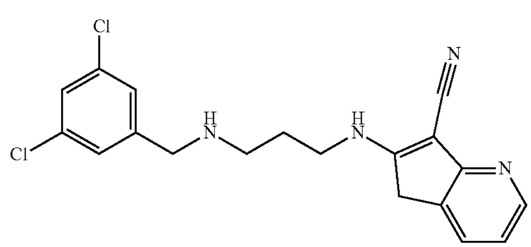 [SMILES: N#CC1=C(NCCCNCc2cc(Cl)cc(Cl)c2)Cc2cccnc21] | 2-[(3-{[(3,5-dichlorophenyl)methyl]amino}propyl)amino]-1H-pyrrolo[3,2-b]pyridine-3-carbonitrile |

| No. | Chemical Structure | Chemical Name |
|---|---|---|
| 1671 | 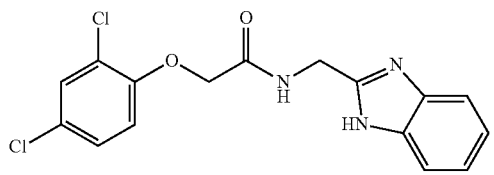 [SMILES: O=C(COc1ccc(Cl)cc1Cl)NCc1nc2ccccc2[nH]1] | N-(1H-1,3-benzodiazol-2-ylmethyl)-2-(2,4-dichlorophenoxy)acetamide |
| 1674 | 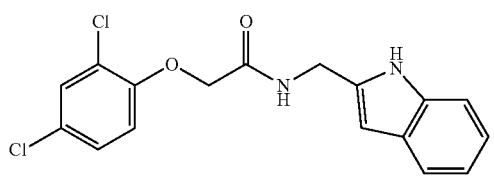 [SMILES: O=C(COc1ccc(Cl)cc1Cl)NCc1cc2ccccc2[nH]1] | 2-(2,4-dichlorophenoxy)-N-(1H-indol-2-ylmethyl)acetamide |
| 1675 | 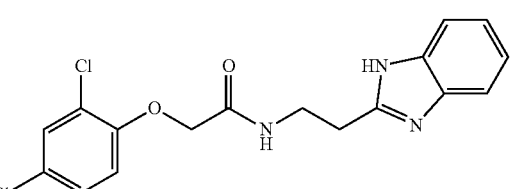 | N-[2-(1H-1,3-benzodiazol-2-yl)ethyl]-2-(2,4-dichlorophenoxy)acetamide |
| 1699 | 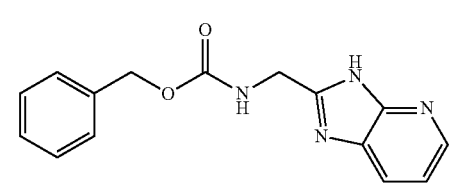 [SMILES: O=C(NCc1nc2cccnc2[nH]1)OCc1ccccc1] | benzyl N-{3H-imidazo[4,5-b]pyridin-2-ylmethyl}carbamate |
| 1701 | 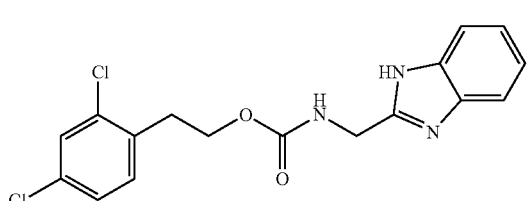 | 2-(2,4-dichlorophenyl)ethyl N-(1H-1,3-benzodiazol-2-ylmethyl)carbamate |
| 1702 | 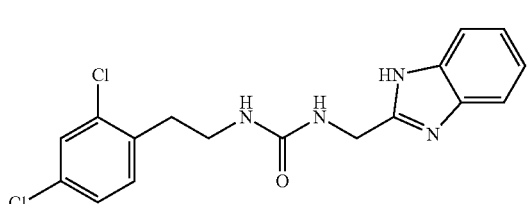 | 3-(1H-1,3-benzodiazol-2-ylmethyl)-1-[2-(2,4-dichlorophenyl)ethyl]urea |
| 1703 | 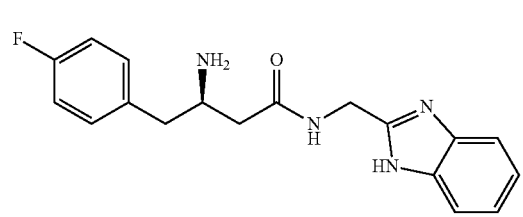 [SMILES: N[C@@H](CC(=O)NCc1nc2ccccc2[nH]1)Cc1ccc(F)cc1] | (3R)-3-amino-N-(1H-1,3-benzodiazol-2-ylmethyl)-4-(4-fluorophenyl)butanamide |
| 1706 | 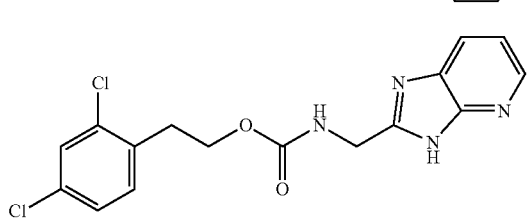 | 2-(2,4-dichlorophenyl)ethyl N-{3H-imidazo[4,5-b]pyridin-2-ylmethyl}carbamate |

| No. | Chemical Structure | Chemical Name |
|---|---|---|
| 1707 | 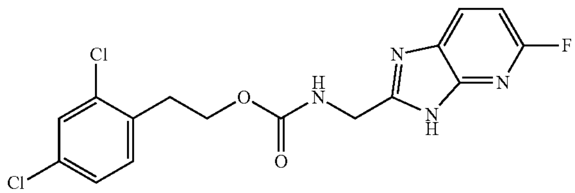 [SMILES: O=C(NCc1nc2ccc(F)nc2[nH]1)OCCc1ccc(Cl)cc1Cl] | 2-(2,4-dichlorophenyl)ethyl N-({5-fluoro-3H-imidazo[4,5-b]pyridin-2-yl}methyl)carbamate |
| 1708 | 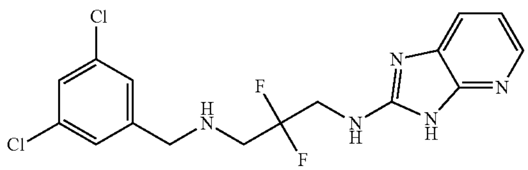 [SMILES: FC(F)(CNCc1cc(Cl)cc(Cl)c1)CNc1nc2cccnc2[nH]1] | [(3,5-dichlorophenyl)methyl][2,2-difluoro-3-({3H-imidazo[4,5-b]pyridin-2-yl}amino)propyl]amine |
| 1716 | 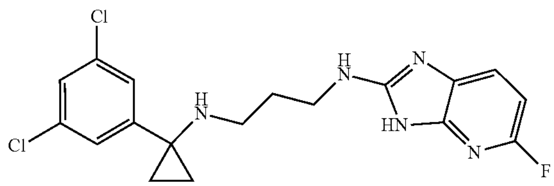 [SMILES: Fc1ccc2nc(NCCCNC3(c4cc(Cl)cc(Cl)c4)CC3)[nH]c2n1] | N-(3-{[1-(3,5-dichlorophenyl)cyclopropyl]amino}propyl)-5-fluoro-3H-imidazo[4,5-b]pyridin-2-amine |
| 1720 | 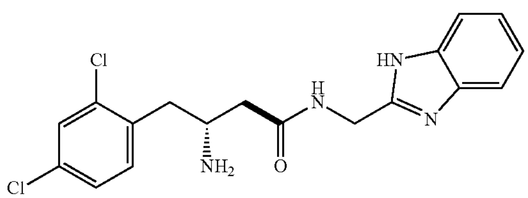 | (3R)-3-amino-N-(1H-1,3-benzodiazol-2-ylmethyl)-4-(2,4-dichlorophenyl)butanamide |
| 1726 | 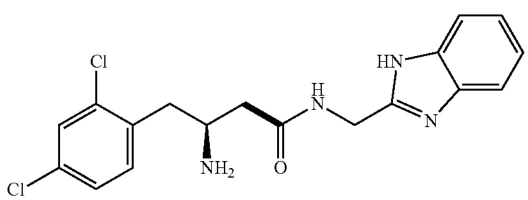 | (3S)-3-amino-N-(1H-1,3-benzodiazol-2-ylmethyl)-4-(2,4-dichlorophenyl)butanamide |
| 1728 | 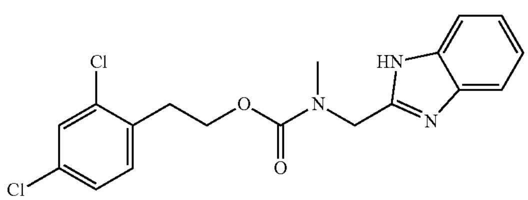 [SMILES: CN(Cc1nc2ccccc2[nH]1)C(=O)OCCc1ccc(Cl)cc1Cl] | 2-(2,4-dichlorophenyl)ethyl N-(1H-1,3-benzodiazol-2-ylmethyl)-N-methylcarbamate |
| 1731 | 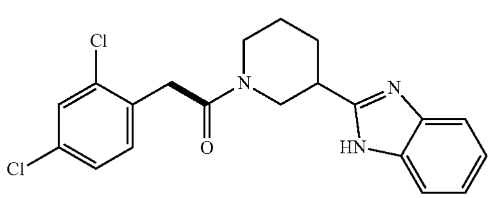 | 1-[3-(1H-1,3-benzodiazol-2-yl)piperidin-1-yl]-2-(2,4-dichlorophenyl)ethan-1-one |
| 1732 | 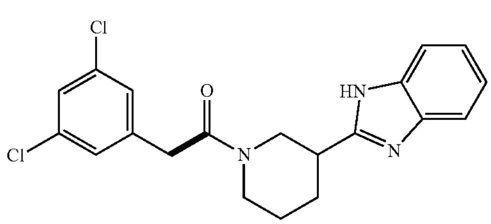 | 1-[3-(1H-1,3-benzodiazol-2-yl)piperidin-1-yl]-2-(3,5-dichlorophenyl)ethan-1-one |

| No. | Chemical Structure | Chemical Name |
|---|---|---|
| 1733 | 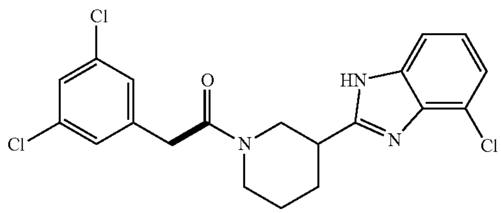 | 1-[3-(4-chloro-1H-1,3-benzodiazol-2-yl)piperidin-1-yl]-2-(3,5-dichlorophenyl)ethan-1-one |
| 1734 | 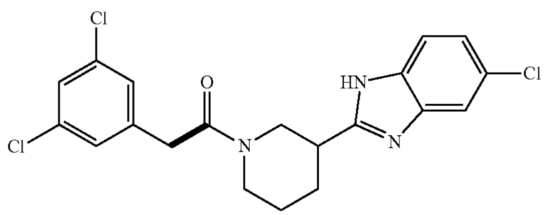 | 1-[3-(5-chloro-1H-1,3-benzodiazol-2-yl)piperidin-1-yl]-2-(3,5-dichlorophenyl)ethan-1-one |
| 1735 | 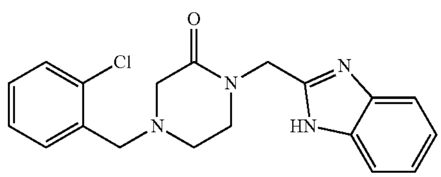 [SMILES: O=C1CN(Cc2ccccc2Cl)CCN1Cc1nc2ccccc2[nH]1] | 1-(1H-1,3-benzodiazol-2-ylmethyl)-4-[(2-chlorophenyl)methyl]piperazin-2-one |
| 1736 | 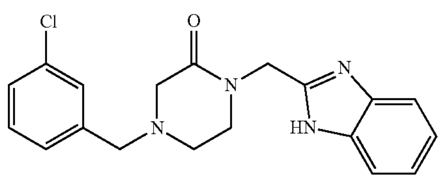 [SMILES: O=C1CN(Cc2cccc(Cl)c2)CCN1Cc1nc2ccccc2[nH]1] | 1-(1H-1,3-benzodiazol-2-ylmethyl)-4-[(3-chlorophenyl)methyl]piperazin-2-one |
| 1737 | 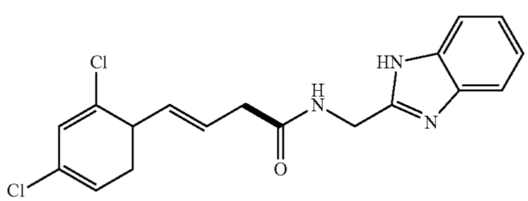 | (3E)-N-(3H-1,3-benzodiazol-2-ylmethyl)-4-(2,4-dichlorophenyl)but-3-enamide |
| 1738 | 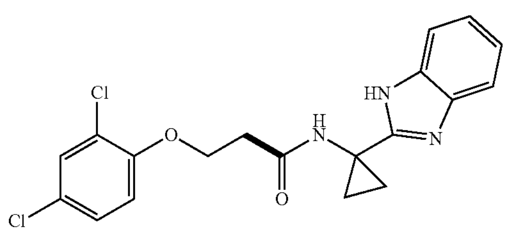 | N-[1-(1H-1,3-benzodiazol-2-yl)cyclopropyl]-3-(2,4-dichlorophenoxy)propanamide |
| 1739 | 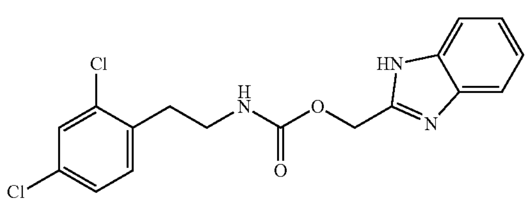 [SMILES: O=C(NCCc1ccc(Cl)cc1Cl)OCc1nc2ccccc2[nH]1] | 1H-1,3-benzodiazol-2-ylmethyl N-[2-(2,4-dichlorophenyl)ethyl]carbamate |

-continued

| No. | Chemical Structure | Chemical Name |
|---|---|---|
| 1740 | 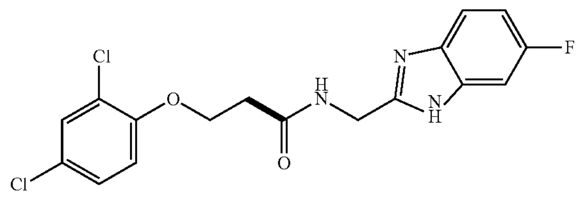 | 3-(2,4-dichlorophenoxy)-N-[(6-fluoro-1H-1,3-benzodiazol-2-yl)methyl]propanamide |
| 1741 | 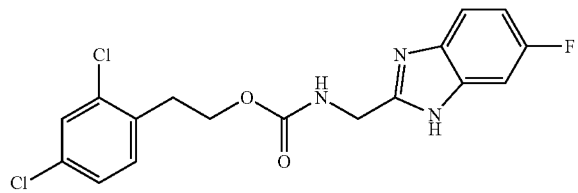 [SMILES: O=C(NCc1nc2ccc(F)cc2[nH]1)OCCc1ccc(Cl)cc1Cl] | 2-(2,4-dichlorophenyl)ethyl N-[(6-fluoro-1H-1,3-benzodiazol-2-yl)methyl]carbamate |
| 1744 | 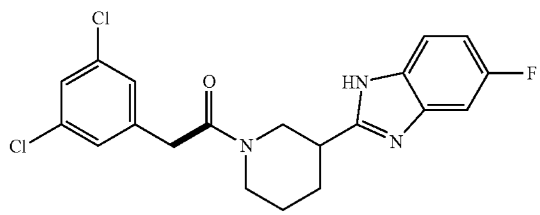 | 2-(3,5-dichlorophenyl)-1-[3-(5-fluoro-1H-1,3-benzodiazol-2-yl)piperidin-1-yl]ethan-1-one |
| 1745 | 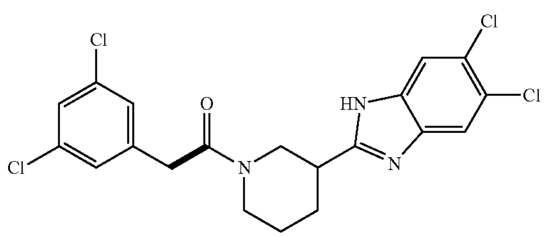 | 1-[3-(5,6-dichloro-1H-1,3-benzodiazol-2-yl)piperidin-1-yl]-2-(3,5-dichlorophenyl)ethan-1-one |
| 1746 | 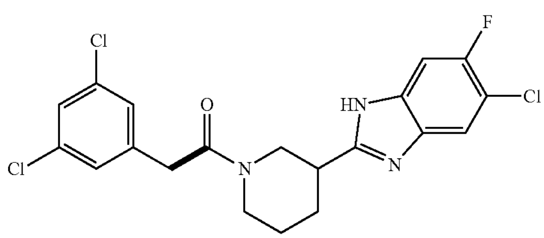 | 1-[3-(5-chloro-6-fluoro-1H-1,3-benzodiazol-2-yl)piperidin-1-yl]-2-(3,5-dichlorophenyl)ethan-1-one |
| 1747 | 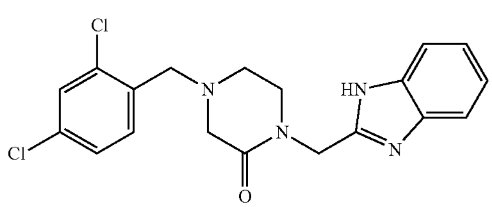 [SMILES: O=C1CN(Cc2ccc(Cl)cc2Cl)CCN1Cc1nc2ccccc2[nH]1] | 1-(1H-1,3-benzodiazol-2-ylmethyl)-4-[(2,4-dichlorophenyl)methyl]piperazin-2-one |
| 1748 | 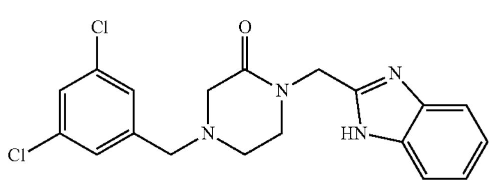 [SMILES: O=C1CN(Cc2cc(Cl)cc(Cl)c2)CCN1Cc1nc2ccccc2[nH]1] | 1-(1H-1,3-benzodiazol-2-ylmethyl)-4-[(3,5-dichlorophenyl)methyl]piperazin-2-one |

-continued

| No. | Chemical Structure | Chemical Name |
|---|---|---|
| 1752 | 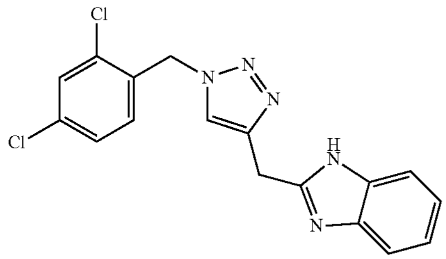 [SMILES: Clc1ccc(Cn2cc(Cc3nc4ccccc4[nH]3)nn2)c(Cl)c1] | 2-({1-[(2,4-dichlorophenyl)methyl]-1H-1,2,3-triazol-4-yl}methyl)-1H-1,3-benzodiazole |
| 1753 | 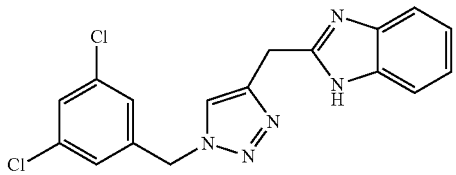 [SMILES: Clc1cc(Cl)cc(Cn2cc(Cc3nc4ccccc4[nH]3)nn2)c1] | 2-({1-[(3,5-dichlorophenyl)methyl]-1H-1,2,3-triazol-4-yl}methyl)-1H-1,3-benzodiazole |
| 1754 | 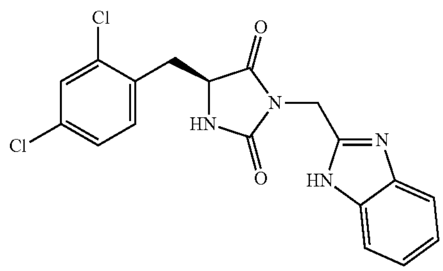 [SMILES: O=C1N[C@@H](Cc2ccc(Cl)cc2Cl)C(=O)N1Cc1nc2ccccc2[nH]1] | (5S)-3-(1H-1,3-benzodiazol-2-ylmethyl)-5-[(2,4-dichlorophenyl)methyl]imidazolidine-2,4-dione |
| 1755 | 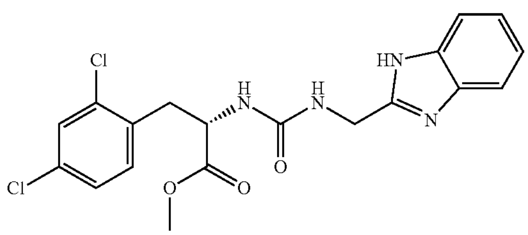 [SMILES: COC(=O)[C@H](Cc1ccc(Cl)cc1Cl)NC(=O)NCc1nc2ccccc2[nH]1] | methyl (2S)-2-{[(1H-1,3-benzodiazol-2-ylmethyl)carbamoyl]amino}-3-(2,4-dichlorophenyl)propanoate |
| 1756 | 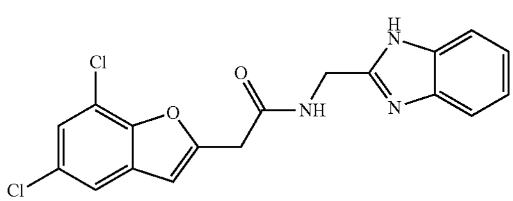 [SMILES: O=C(Cc1cc2cc(Cl)cc(Cl)c2o1)NCc1nc2ccccc2[nH]1] | N-(1H-1,3-benzodiazol-2-ylmethyl)-2-(5,7-dichloro-1-benzofuran-2-yl)acetamide |
| 1757 | 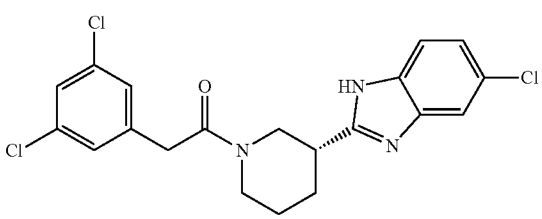 [SMILES: O=C(Cc1cc(Cl)cc(Cl)c1)N1CCC[C@@H](c2nc3cc(Cl)ccc3[nH]2)C1] | 1-[(3R)-3-(5-chloro-1H-1,3-benzodiazol-2-yl)piperidin-1-yl]-2-(3,5-dichlorophenyl)ethan-1-one |
| 1758 | 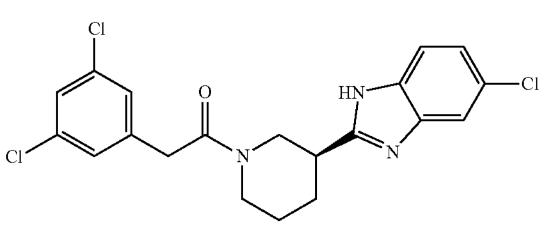 [SMILES: O=C(Cc1cc(Cl)cc(Cl)c1)N1CCC[C@H](c2nc3cc(Cl)ccc3[nH]2)C1] | 1-[(3S)-3-(5-chloro-1H-1,3-benzodiazol-2-yl)piperidin-1-yl]-2-(3,5-dichlorophenyl)ethan-1-one |

-continued

| No. | Chemical Structure | Chemical Name |
|---|---|---|
| 1759 | 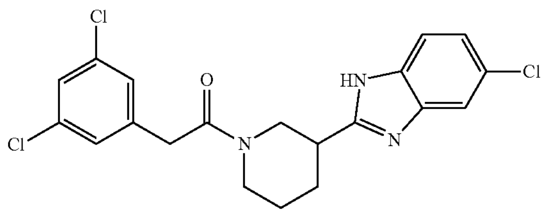 [SMILES: O=C(Cc1cc(Cl)cc(Cl)c1)N1CCCC(c2nc3cc(Cl)ccc3[nH]2)C1] | 3-(5-chloro-1H-1,3-benzodiazol-2-yl)-N-(3,5-dichlorophenyl)piperidine-1-carboxamide |
| 1760 | 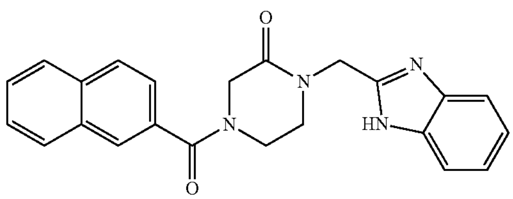 [SMILES: O=C1CN(C(=O)c2ccc3ccccc3c2)CCN1Cc1nc2ccccc2[nH]1] | 1-(1H-1,3-benzodiazol-2-ylmethyl)-4-(naphthalene-2-carbonyl)piperazin-2-one |
| 1761 | 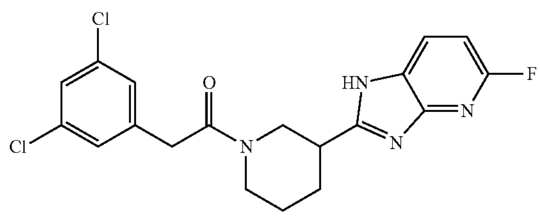 [SMILES: O=C(Cc1cc(Cl)cc(Cl)c1)N1CCCC(c2nc3nc(F)ccc3[nH]2)C1] | 2-(3,5-dichlorophenyl)-1-(3-{5-fluoro-1H-imidazo[4,5-b]pyridin-2-yl}piperidin-1-yl)ethan-1-one |
| 1762 | 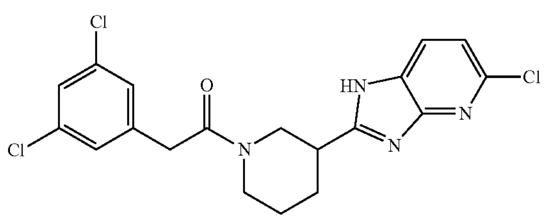 [SMILES: O=C(Cc1cc(Cl)cc(Cl)c1)N1CCCC(c2nc3nc(Cl)ccc3[nH]2)C1] | 1-(3-{5-chloro-1H-imidazo[4,5-b]pyridin-2-yl}piperidin-1-yl)-2-(3,5-dichlorophenyl)ethan-1-one |
| 1763 | 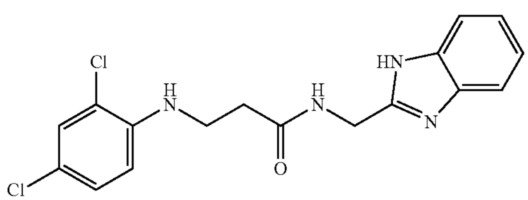 [SMILES: O=C(CCNc1ccc(Cl)cc1Cl)NCc1nc2ccccc2[nH]1] | N-(1H-1,3-benzodiazol-2-ylmethyl)-3-[(2,4-dichlorophenyl)amino]propanamide |
| 1764 | 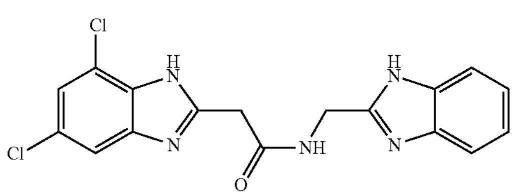 [SMILES: O=C(Cc1nc2cc(Cl)cc(Cl)c2[nH]1)NCc1nc2ccccc2[nH]1] | N-(1H-1,3-benzodiazol-2-ylmethyl)-2-(5,7-dichloro-1H-1,3-benzodiazol-2-yl)acetamide |
| 1765 | 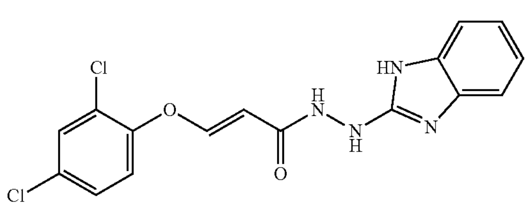 [SMILES: O=C(/C=C/Oc1ccc(Cl)cc1Cl)NNc1nc2ccccc2[nH]1] | (2E)-N'-(1H-1,3-benzodiazol-2-yl)-3-(2,4-dichlorophenoxy)prop-2-enehydrazide |

-continued

| No. | Chemical Structure | Chemical Name |
|---|---|---|
| 1766 | 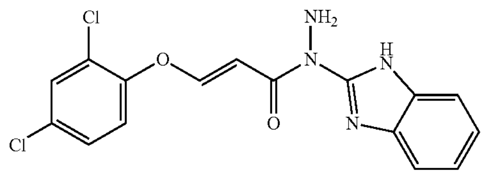 [SMILES: NN(C(=O)/C=C/Oc1ccc(Cl)cc1Cl)c1nc2ccccc2[nH]1] | (2E)-N-(1H-1,3-benzodiazol-2-yl)-3-(2,4-dichlorophenoxy)prop-2-enehydrazide |
| 1767 | 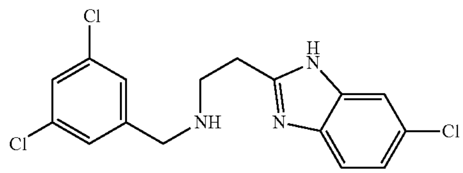 [SMILES: Clc1cc(Cl)cc(CNCCc2nc3ccc(Cl)cc3[nH]2)c1] | [2-(6-chloro-1H-1,3-benzodiazol-2-yl)ethyl][(3,5-dichlorophenyl)methyl]amine |
| 1768 | 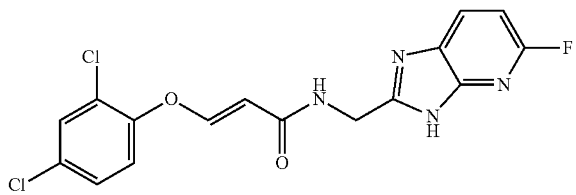 [SMILES: O=C(/C=C/Oc1ccc(Cl)cc1Cl)NCc1nc2ccc(F)nc2[nH]1] | (2E)-3-(2,4-dichlorophenoxy)-N-({5-fluoro-3H-imidazo[4,5-b]pyridin-2-yl}methyl)prop-2-enamide |
| 1769 | 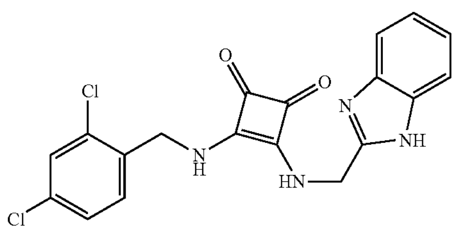 [SMILES: O=c1c(NCc2nc3ccccc3[nH]2)c(NCc2ccc(Cl)cc2Cl)c1=O] | 3-[(1H-1,3-benzodiazol-2-ylmethyl)amino]-4-{[(2,4-dichlorophenyl)methyl]amino}cyclobut-3-ene-1,2-dione |
| 1779 | 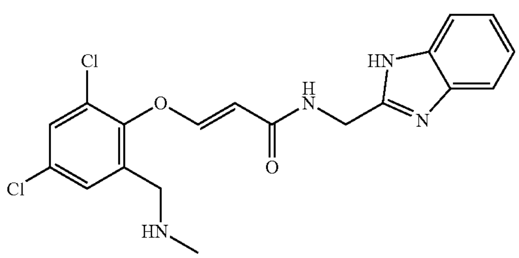 [SMILES: CNCc1cc(Cl)cc(Cl)c1O/C=C/C(=O)NCc1nc2ccccc2[nH]1] | (2E)-N-(1H-1,3-benzodiazol-2-ylmethyl)-3-{2,4-dichloro-6-[(methylamino)methyl]phenoxy}prop-2-enamide |
| 1780 | 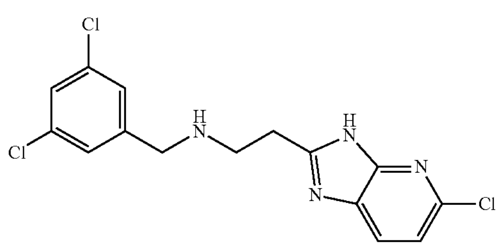 [SMILES: Clc1cc(Cl)cc(CNCCc2nc3ccc(Cl)nc3[nH]2)c1] | (2-{5-chloro-3H-imidazo[4,5-b]pyridin-2-yl}ethyl)[(3,5-dichlorophenyl)methyl]amine |
| 1785 | 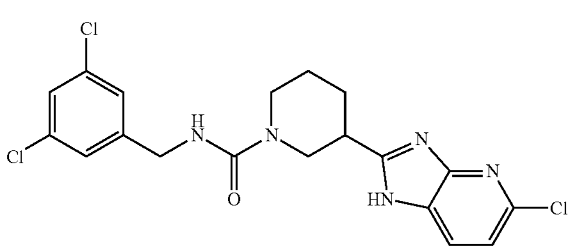 [SMILES: O=C(NCc1cc(Cl)cc(Cl)c1)N1CCCC(c2nc3nc(Cl)ccc3[nH]2)C1] | 3{5-chloro-1H-imidazo[4,5-b]pyridin-2-yl}-N-[(3,5-dichlorophenyl)methyl]piperidine-1-carboxamide |

| No. | Chemical Structure | Chemical Name |
|-----|---|---|
| 1786 | 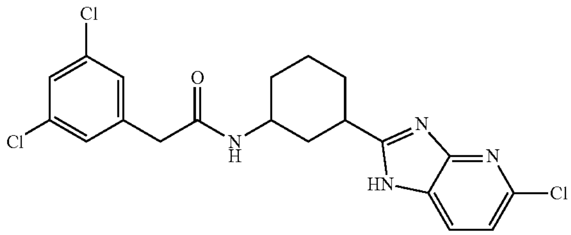 [SMILES: O=C(Cc1cc(Cl)cc(Cl)c1)NC1CCCC(c2nc3nc(Cl)ccc3[nH]2)C1] | N-(3-{5-chloro-1H-imidazo[4,5-b]pyridin-2-yl}cyclohexyl)-2-(3,5-dichlorophenyl)acetamide |
| 1787 | 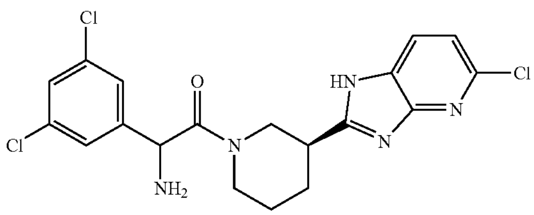 [SMILES: NC(C(=O)N1CCC[C@H](c2nc3nc(Cl)ccc3[nH]2)C1)c1cc(Cl)cc(Cl)c1] | 2-amino-1-[(3S)-3-{5-chloro-1H-imidazo[4,5-b]pyridin-2-yl}piperidin-1-yl]-2-(3,5-dichlorophenyl)ethan-1-one |
| 1788 | 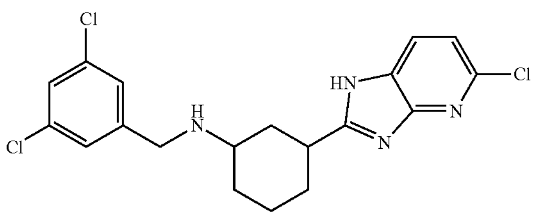 | 3-{5-chloro-1H-imidazo[4,5-b]pyridin-2-yl}-N-[(3,5-dichlorophenyl)methyl]cyclohexan-1-amine |
| 1789 | 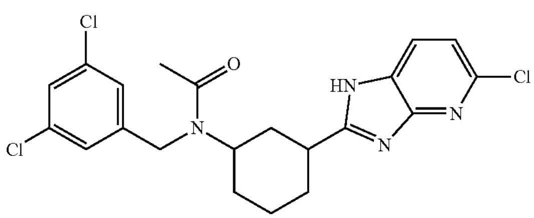 [SMILES: CC(=O)N(Cc1cc(Cl)cc(Cl)c1)C1CCCC(c2nc3nc(Cl)ccc3[nH]2)C1] | N-(3-{5-chloro-1H-imidazo[4,5-b]pyridin-2-yl}cyclohexyl)-N-[(3,5-dichlorophenyl)methyl]acetamide |
| 1790 | 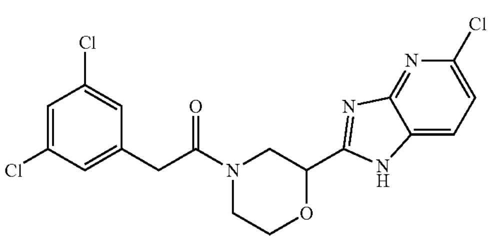 [SMILES: O=C(Cc1cc(Cl)cc(Cl)c1)N1CCOC(c2nc3nc(Cl)ccc3[nH]2)C1] | 1-(2-{5-chloro-1H-imidazo[4,5-b]pyridin-2-yl}morpholin-4-yl)-2-(3,5-dichlorophenyl)ethan-1-one |
| 1791 | 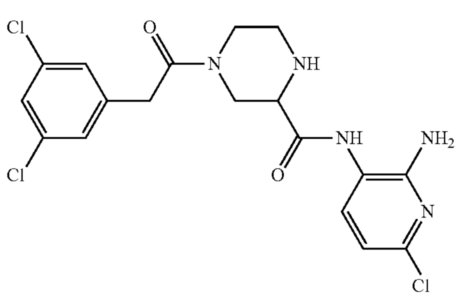 [SMILES: Nc1nc(Cl)ccc1NC(=O)C1CN(C(=O)Cc2cc(Cl)cc(Cl)c2)CCN1] | N-(2-amino-6-chloropyridin-3-yl)-4-[2-(3,5-dichlorophenyl)acetyl]piperazine-2-carboxamide |

| No. | Chemical Structure | Chemical Name |
|---|---|---|
| 1792 | 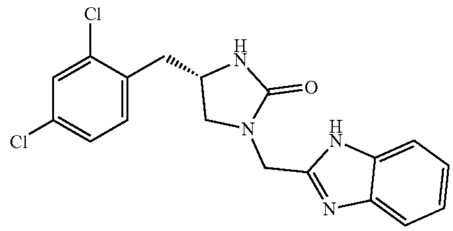 [SMILES: O=C1N[C@@H](Cc2ccc(Cl)cc2Cl)CN1Cc1nc2ccccc2[nH]1] | (4S)-1-(1H-1,3-benzodiazol-2-ylmethyl)-4-[(2,4-dichlorophenyl)methyl]imidazolidin-2-one |
| 1793 | 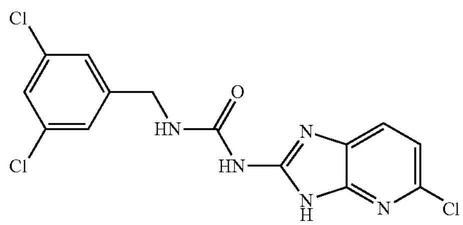 [SMILES: O=C(NCc1cc(Cl)cc(Cl)c1)Nc1nc2ccc(Cl)nc2[nH]1] | 3-{5-chloro-3H-imidazo[4,5-b]pyridin-2-yl}-1-[(3,5-dichlorophenyl)methyl]urea |
| 1794 | 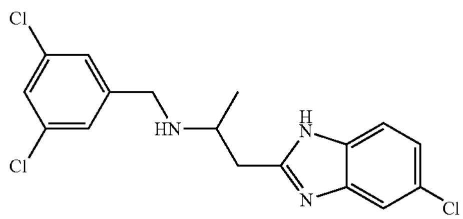 [SMILES: CC(Cc1nc2cc(Cl)ccc2[nH]1)NCc1cc(Cl)cc(Cl)c1] | [1-(5-chloro-1H-1,3-benzodiazol-2-yl)propan-2-yl][(3,5-dichlorophenyl)methyl]amine |
| 1795 | 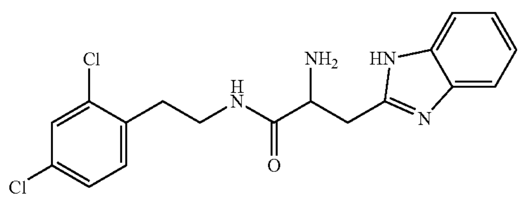 [SMILES: NC(Cc1nc2ccccc2[nH]1)C(=O)NCCc1ccc(Cl)cc1Cl] | 2-amino-3-(1H-1,3-benzodiazol-2-yl)-N-[2-(2,4-dichlorophenyl)ethyl]propanamide |
| 1796 | 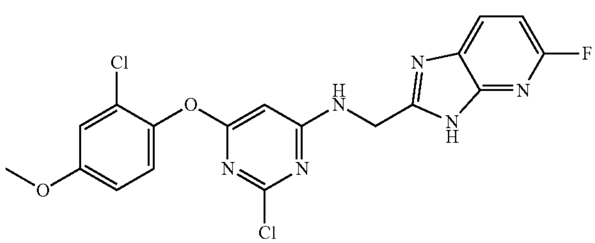 [SMILES: COc1ccc(Oc2cc(NCc3nc4ccc(F)nc4[nH]3)nc(Cl)n2)c(Cl)c1] | 2-chloro-6-(2-chloro-4-methoxyphenoxy)-N-({5-fluoro-3H-imidazo[4,5-b]pyridin-2-yl}methyl)pyrimidin-4-amine |
| 1797 | 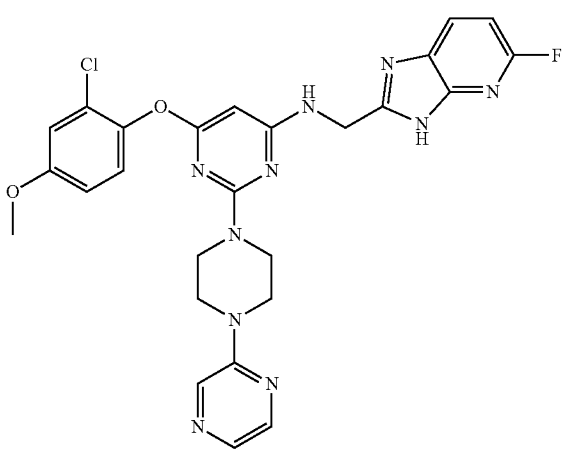 [SMILES: COc1ccc(Oc2cc(NCc3nc4ccc(F)nc4[nH]3)nc(N3CCN(c4cnccn4)CC3)n2)c(Cl)c1] | 6-(2-chloro-4-methoxyphenoxy)-N-({5-fluoro-3H-imidazo[4,5-b]pyridin-2-yl}methyl)-2-[4-(pyrazin-2-yl)piperazin-1-yl]pyrimidin-4-amine |

-continued

| No. | Chemical Structure | Chemical Name |
|---|---|---|
| 1798 | 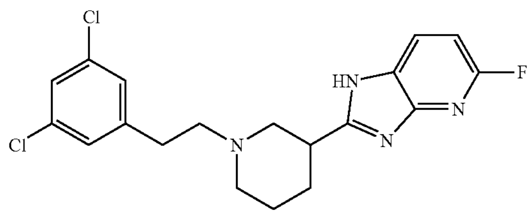 [SMILES: Fc1ccc2[nH]c(C3CCCN(CCc4cc(Cl)cc(Cl)c4)C3)nc2n1] | 1-[2-(3,5-dichlorophenyl)ethyl]-3-{5-fluoro-1H-imidazo[4,5-b]pyridin-2-yl}piperidine |
| 1799 | 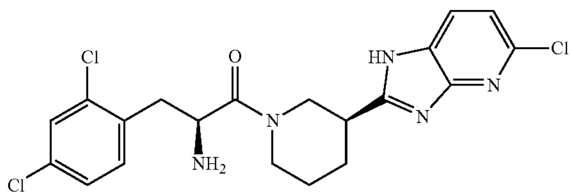 [SMILES: N[C@@H](Cc1ccc(Cl)cc1Cl)C(=O)N1CCC[C@H](c2nc3nc(Cl)ccc3[nH]2)C1] | (2S)-2-amino-1-[(3S)-3-{5-chloro-1H-imidazo[4,5-b]pyridin-2-yl}piperidin-1-yl]-3-(2,4-dichlorophenyl)propan-1-one |
| 1800 | 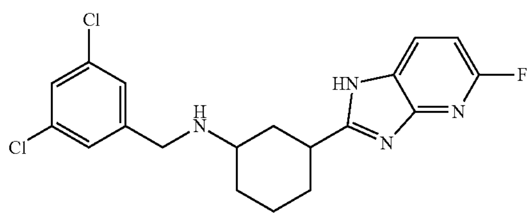 [SMILES: Fc1ccc2[nH]c(C3CCCC(NCc4cc(Cl)cc(Cl)c4)C3)nc2n1] | N-[(3,5-dichlorophenyl)methyl]-3-{5-fluoro-1H-imidazo[4,5-b]pyridin-2-yl}cyclohexan-1-amine |
| 1801 | 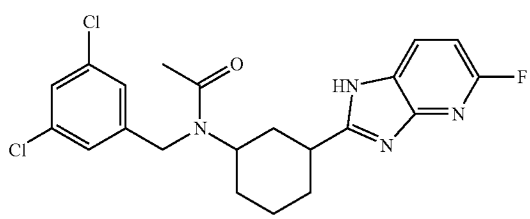 [SMILES: CC(=O)N(Cc1cc(Cl)cc(Cl)c1)C1CCCC(c2nc3nc(F)ccc3[nH]2)C1] | N-[(3,5-dichlorophenyl)methyl]-N-(3-{5-fluoro-1H-imidazo[4,5-b]pyridin-2-yl}cyclohexyl)acetamide |
| 1802 | 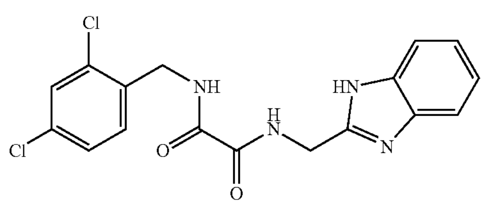 [SMILES: O=C(NCc1nc2ccccc2[nH]1)C(=O)NCc1ccc(Cl)cc1Cl] | N-(1H-1,3-benzodiazol-2-ylmethyl)-N'-[(2,4-dichlorophenyl)methyl]ethanediamide |
| 1803 | 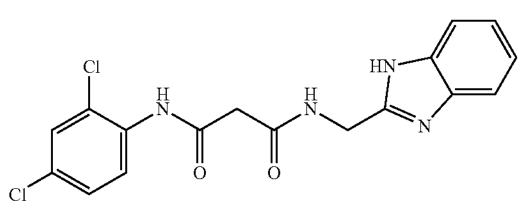 [SMILES: O=C(CC(=O)Nc1ccc(Cl)cc1Cl)NCc1nc2ccccc2[nH]1] | N-(1H-1,3-benzodiazol-2-ylmethyl)-N'-(2,4-dichlorophenyl)propanediamide |
| 1804 | 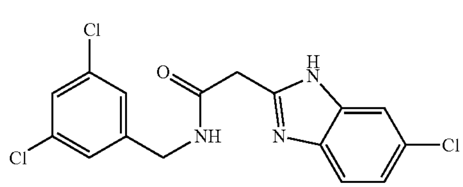 [SMILES: O=C(Cc1nc2ccc(Cl)cc2[nH]1)NCc1cc(Cl)cc(Cl)c1] | 2-(6-chloro-3H-1,3-benzodiazol-2-yl)-N-[(3,5-dichlorophenyl)methyl]acetamide |

-continued

| No. | Chemical Structure | Chemical Name |
|---|---|---|
| 1805 | 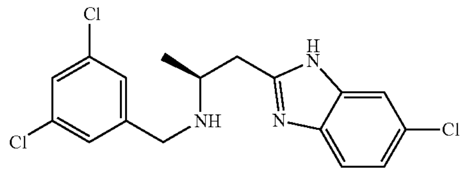 [SMILES: C[C@@H](Cc1nc2ccc(Cl)cc2[nH]1)NCc1cc(Cl)cc(Cl)c1] | [(2S)-1-(6-chloro-1H-1,3-benzodiazol-2-yl)propan-2-yl][(3,5-dichlorophenyl)methyl]amine |
| 1806 | 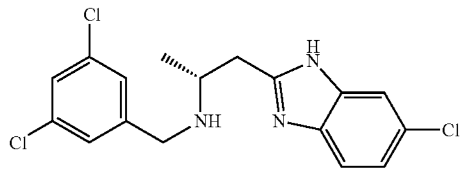 | [(2R)-1-(6-chloro-1H-1,3-benzodiazol-2-yl)propan-2-yl][(3,5-dichlorophenyl)methyl]amine |
| 1807 | 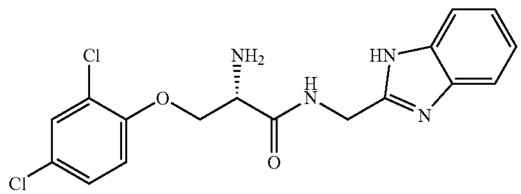 [SMILES: N[C@@H](COc1ccc(Cl)cc1Cl)C(=O)NCc1nc2ccccc2[nH]1] | (2S)-2-animo-N-(1H-1,3-benzodiazol-2-ylmethyl)-3-(2,4-dichlorophenoxy)propanamide |
| 1808 | 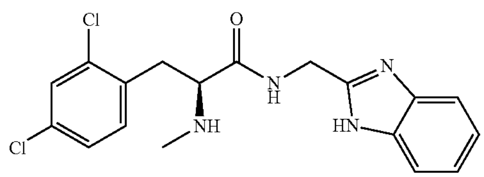 [SMILES: CN[C@@H](Cc1ccc(Cl)cc1Cl)C(=O)NCc1nc2ccccc2[nH]1] | (2S)-N-(1H-1,3-benzodiazol-2-ylmethyl)-3-(2,4-dichlorophenyl)-2-(methylamino)propanamide |
| 1809 | 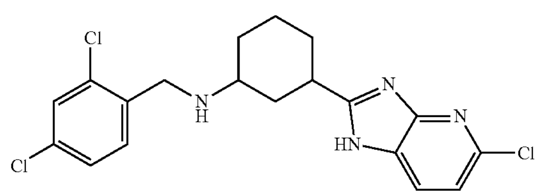 [SMILES: Clc1ccc(CNC2CCCC(c3nc4nc(Cl)ccc4[nH]3)C2)c(Cl)c1] | 3-{5-chloro-1H-imidazo[4,5-b]pyridin-2-yl}-N-[(2,4-dichlorophenyl)methyl]cyclohexan-1-amine |
| 1810 | 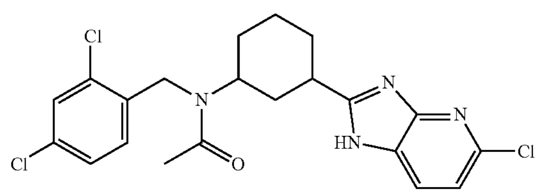 [SMILES: CC(=O)N(Cc1ccc(Cl)cc1Cl)C1CCCC(c2nc3nc(Cl)ccc3[nH]2)C1] | N-(3-{5-chloro-1H-imidazo[4,5-b]pyridin-2-yl}cyclohexyl)-N-[(2,4-dichlorophenyl)methyl]acetamide |
| 1811 | 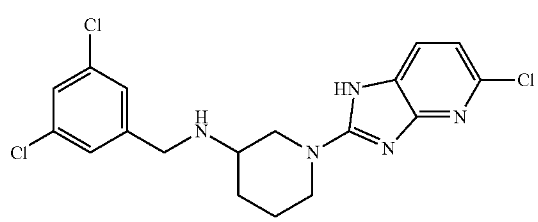 [SMILES: Clc1cc(Cl)cc(CNC2CCCN(c3nc4nc(Cl)ccc4[nH]3)C2)c1] | 1-{5-chloro-1H-imidazo[4,5-b]pyridin-2-yl}-N-[(3,5-dichlorophenyl)methyl]piperidin-3-amine |
| 1812 | 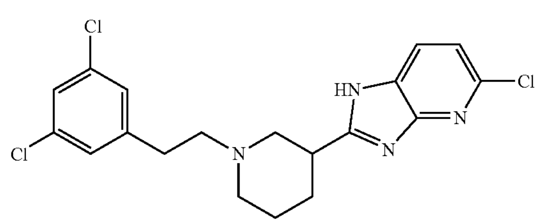 [SMILES: Clc1cc(Cl)cc(CCN2CCCC(c3nc4nc(Cl)ccc4[nH]3)C2)c1] | 3-{5-chloro-1H-imidazo[4,5-b]pyridin-2-yl}-1-[2-(3,5-dichlorophenyl)ethyl]piperidine |

-continued

| No. | Chemical Structure | Chemical Name |
|---|---|---|
| 1813 | 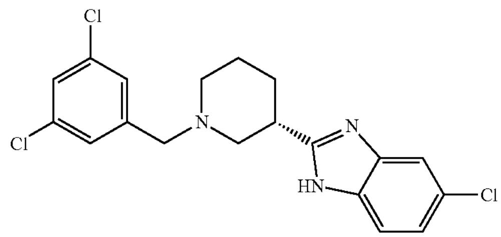 [SMILES: Clc1cc(Cl)cc(CN2CCC[C@H](c3nc4cc(Cl)ccc4[nH]3)C2)c1] | 5-chloro-2-[(3S)-1-[(3,5-dichlorophenyl)methyl]piperidin-3-yl]-1H-1,3-benzodiazole |
| 1814 | 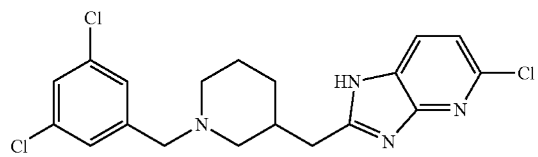 [SMILES: Clc1cc(Cl)cc(CN2CCCC(Cc3nc4nc(Cl)ccc4[nH]3)C2)c1] | 3-({5-chloro-1H-imidazo[4,5-b]pyridin-2-yl}methyl)-1-[(3,5-dichlorophenyl)methyl]piperidine |
| 1815 | 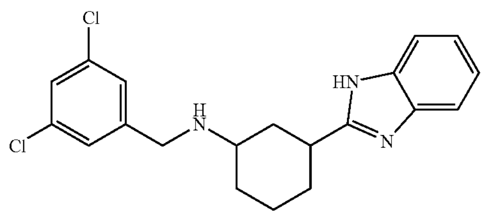 [SMILES: Clc1cc(Cl)cc(CNC2CCCC(c3nc4ccccc4[nH]3)C2)c1] | 3-(1H-1,3-benzodiazol-2-yl)-N-[(3,5-dichlorophenyl)methyl]cyclohexan-1-amine |
| 1816 | 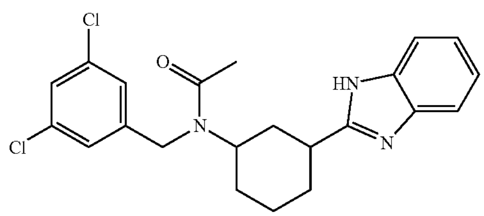 [SMILES: CC(=O)N(Cc1cc(Cl)cc(Cl)c1)C1CCCC(c2nc3ccccc3[nH]2)C1] | N-[3-(1H-1,3-benzodiazol-2-yl)cyclohexyl]-N-[(3,5-dichlorophenyl)methyl]acetamide |
| 1817 | 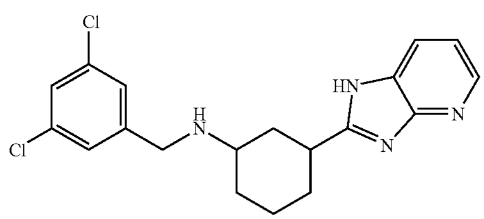 [SMILES: Clc1cc(Cl)cc(CNC2CCCC(c3nc4ncccc4[nH]3)C2)c1] | N-[(3,5-dichlorophenyl)methyl]-3-{1H-imidazo[4,5-b]pyridin-2-yl}cyclohexan-1-amine |
| 1818 | 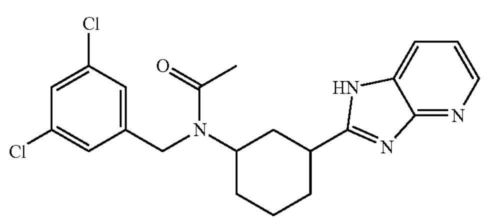 [SMILES: CC(=O)N(Cc1cc(Cl)cc(Cl)c1)C1CCCC(c2nc3ncccc3[nH]2)C1] | N-[(3,5-dichlorophenyl)methyl]-N-(3-{1H-imidazo[4,5-b]pyridin-2-yl}cyclohexyl)acetamide |
| 1819 | 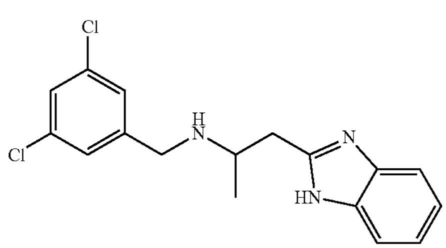 [SMILES: CC(Cc1nc2ccccc2[nH]1)NCc1cc(Cl)cc(Cl)c1] | [1-(1H-1,3-benzodiazol-2-yl)propan-2-yl][(3,5-dichlorophenyl)methyl]amine |

| No. | Chemical Structure | Chemical Name |
|---|---|---|
| 1820 | 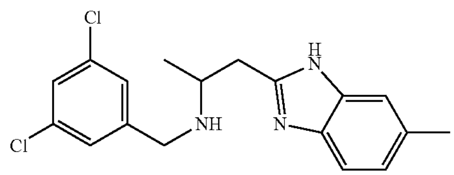 [SMILES: Cc1ccc2nc(CC(C)NCc3cc(Cl)cc(Cl)c3)[nH]c2c1] | [(3,5-dichlorophenyl)methyl][1-(6-methyl-1H-1,3-benzodiazol-2-yl)propan-2-yl]amine |
| 1821 | 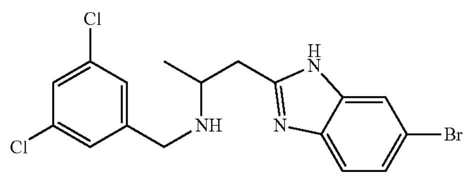 [SMILES: CC(Cc1nc2ccc(Br)cc2[nH]1)NCc1cc(Cl)cc(Cl)c1] | [1-(6-bromo-1H-1,3-benzodiazol-2-yl)propan-2-yl][(3,5-dichlorophenyl)methyl]amine |
| 1822 | 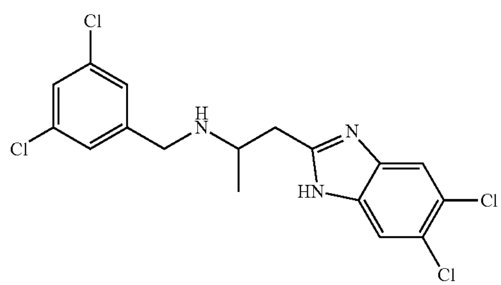 [SMILES: CC(Cc1nc2cc(Cl)c(Cl)cc2[nH]1)NCc1cc(Cl)cc(Cl)c1] | [1-(5,6-dichloro-1H-1,3-benzodiazol-2-yl)propan-2-yl][(3,5-dichlorophenyl)methyl]amine |
| 1823 | 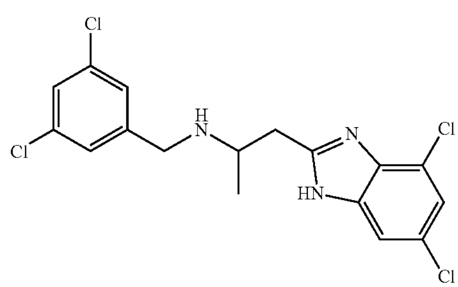 [SMILES: CC(Cc1nc2c(Cl)cc(Cl)cc2[nH]1)NCc1cc(Cl)cc(Cl)c1] | [1-(4,6-dichloro-1H-1,3-benzodiazol-2-yl)propan-2-yl][(3,5-dichlorophenyl)methyl]amine |
| 1824 | 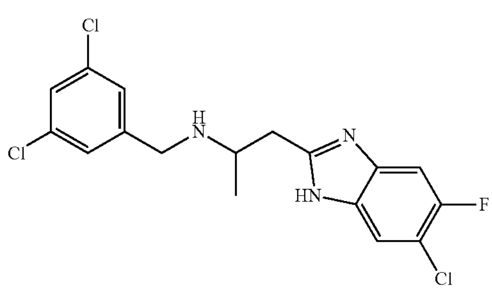 [SMILES: CC(Cc1nc2cc(F)c(Cl)cc2[nH]1)NCc1cc(Cl)cc(Cl)c1] | [1-(6-chloro-5-fluoro-1H-1,3-benzodiazol-2-yl)propan-2-yl][(3,5-dichlorophenyl)methyl]amine |
| 1825 | 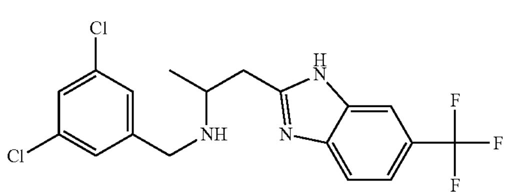 [SMILES: CC(Cc1nc2ccc(C(F)(F)F)cc2[nH]1)NCc1cc(Cl)cc(Cl)c1] | [(3,5-dichlorophenyl)methyl]({1-[6-(trifluoromethyl)-1H-1,3-benzodiazol-2-yl]propan-2-yl})amine |

| No. | Chemical Structure | Chemical Name |
|---|---|---|
| 1826 | 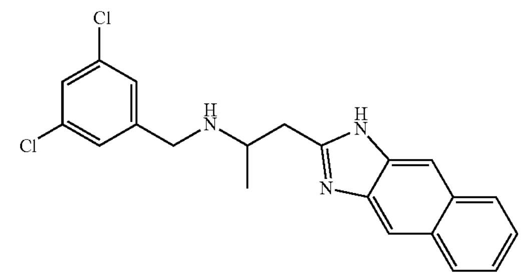 [SMILES: CC(Cc1nc2cc3ccccc3cc2[nH]1)NCc1cc(Cl)cc(Cl)c1] | [(3,5-dichlorophenyl)methyl](1-{1H-naphtho[2,3-d]imidazol-2-yl}propan-2-yl)amine |
| 1827 | 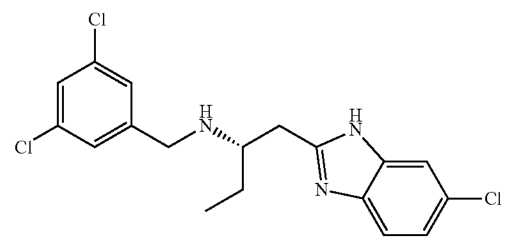 [SMILES: CC[C@@H](Cc1nc2ccc(Cl)cc2[nH]1)NCc1cc(Cl)cc(Cl)c1] | [(2S)-1-(6-chloro-1H-1,3-benzodiazol-2-yl)butan-2-yl][(3,5-dichlorophenyl)methyl]amine |
| 1828 | 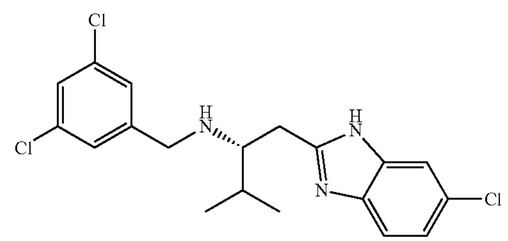 [SMILES: CC(C)[C@@H](Cc1nc2ccc(Cl)cc2[nH]1)NCc1cc(Cl)cc(Cl)c1] | [(2R)-1-(6-chloro-1H-1,3-benzodiazol-2-yl)-3-methylbutan-2-yl][(3,5-dichlorophenyl)methyl]amine |
| 1829 | 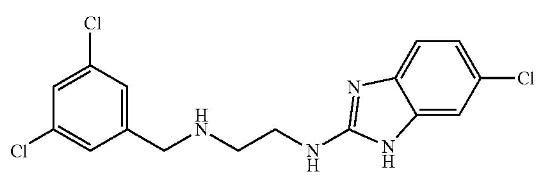 [SMILES: Clc1cc(Cl)cc(CNCCNc2nc3ccc(Cl)cc3[nH]2)c1] | {2-[(6-chloro-1H-1,3-benzodiazol-2-yl)amino]ethyl}[(3,5-dichlorophenyl)methyl]amine |
| 1830 | 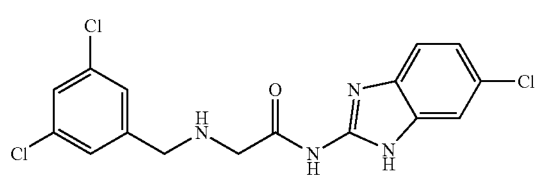 [SMILES: O=C(CNCc1cc(Cl)cc(Cl)c1)Nc1nc2ccc(Cl)cc2[nH]1] | N-(6-chloro-1H-1,3-benzodiazol-2-yl)-2-{[(3,5-dichlorophenyl)methyl]amino}acetamide |
| 1831 | 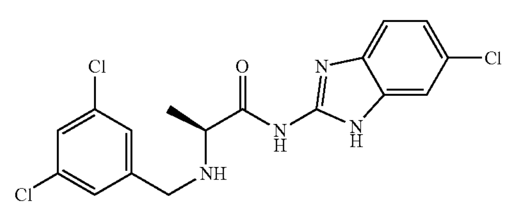 [SMILES: C[C@H](NCc1cc(Cl)cc(Cl)c1)C(=O)Nc1nc2ccc(Cl)cc2[nH]1] | (2S)-N-(6-chloro-1H-1,3-benzodiazol-2-yl)-2-{[(3,5-dichlorophenyl)methyl]amino}propanamide |
| 1832 | 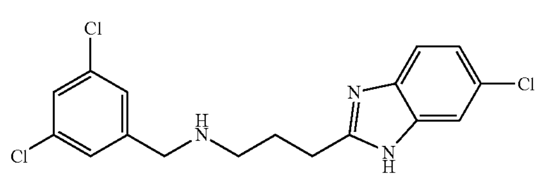 [SMILES: Clc1cc(Cl)cc(CNCCCc2nc3ccc(Cl)cc3[nH]2)c1] | [3-(6-chloro-1H-1,3-benzodiazol-2-yl)propyl][(3,5-dichlorophenyl)methyl]amine |

-continued

| No. | Chemical Structure | Chemical Name |
|---|---|---|
| 1833 | 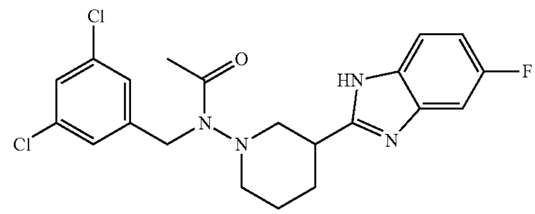 | N-[(3,5-dichlorophenyl)methyl]-N-[3-(5-fluoro-1H-1,3-benzodiazol-2-yl)piperidin-1-yl]acetamide |
| 1835 | 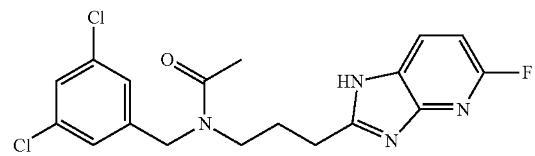 [SMILES: CC(=O)N(CCCc1nc2nc(F)ccc2[nH]1)Cc1cc(Cl)cc(Cl)c1] | N-[(3,5-dichlorophenyl)methyl]-N-(3-{5-fluoro-1H-imidazo[4,5-b]pyridin-2-yl}propyl)acetamide |
| 1836 | 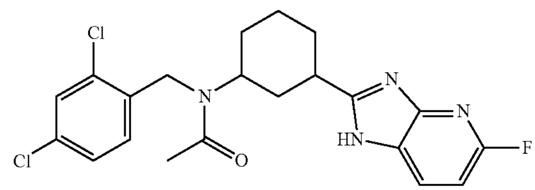 [SMILES: CC(=O)N(Cc1ccc(Cl)cc1Cl)C1CCCC(c2nc3nc(F)ccc3[nH]2)C1] | N-[(2,4-dichlorophenyl)methyl]-N-(3-{5-fluoro-1H-imidazo[4,5-b]pyridin-2-yl}cyclohexyl)acetamide |
| 1837 | 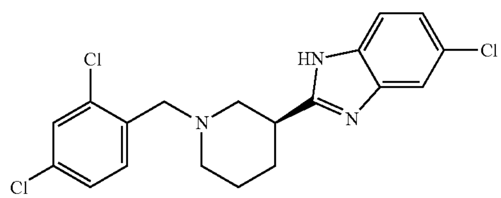 [SMILES: Clc1ccc(CN2CCC[C@H](c3nc4cc(Cl)ccc4[nH]3)C2)c(Cl)c1] | 5-chloro-2-[(3S)-1-[(2,4-dichlorophenyl)methyl]piperidin-3-yl]-1H-1,3-benzodiazole |
| 1838 | 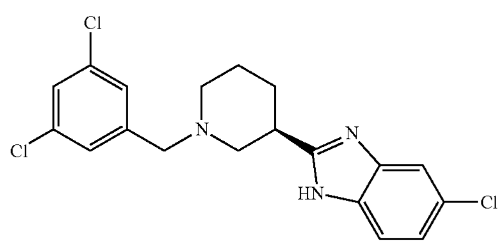 [SMILES: Clc1cc(Cl)cc(CN2CCC[C@@H](c3nc4cc(Cl)ccc4[nH]3)C2)c1] | 5-chloro-2-[(3R)-1-[(3,5-dichlorophenyl)methyl]piperidin-3-yl]-1H-1,3-benzodiazole |
| 1839 | 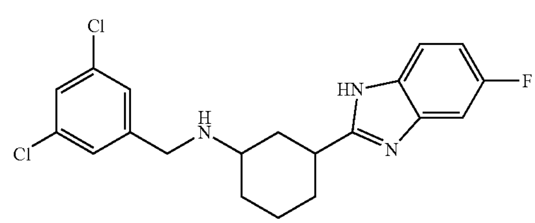 [SMILES: Fc1ccc2[nH]c(C3CCCC(NCc4cc(Cl)cc(Cl)c4)C3)nc2c1] | N-[(3,5-dichlorophenyl)methyl]-3-(5-fluoro-1H-1,3-benzodiazol-2-yl)cyclohexan-1-amine |
| 1840 | 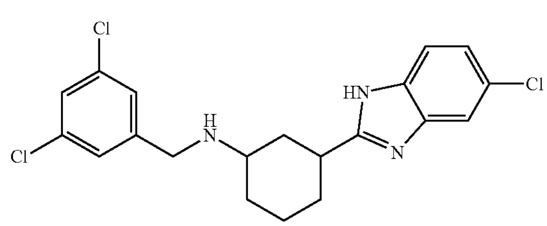 [SMILES: Clc1cc(Cl)cc(CNC2CCCC(c3nc4cc(Cl)ccc4[nH]3)C2)c1] | 3-(5-chloro-1H-1,3-benzodiazol-2-yl)-N-[(3,5-dichlorophenyl)methyl]cyclohexan-1-amine |

| No. | Chemical Name |
|---|---|
| 1841 | 3-{6-chloro-3H-imidazo[4,5-b]pyridin-2-yl}-N-[(3,5-dichlorophenyl)methyl]cyclohexan-1-amine |
| 1842 | N-(3-{6-chloro-3H-imidazo[4,5-b]pyridin-2-yl}cyclohexyl)-N-[(3,5-dichlorophenyl)methyl]acetamide |
| 1844 | (2-{6-chloro-3H-imidazo[4,5-b]pyridin-2-yl}ethyl)[(3,5-dichlorophenyl)methyl]amine |
| 1845 | (3S)-1-{5-chloro-3H-imidazo[4,5-b]pyridin-2-yl}-N-[(3,5-dichlorophenyl)methyl]pyrrolidin-3-amine |
| 1846 | (3S)-1-{5-chloro-3H-imidazo[4,5-b]pyridin-2-yl}-N-[(2,4-dichlorophenyl)methyl]pyrrolidin-3-amine |
| 1847 | (3R)-1-{5-chloro-3H-imidazo[4,5-b]pyridin-2-yl}-N-[(3,5-dichlorophenyl)methyl]pyrrolidin-3-amine |
| 1848 | (3R)-1-{5-chloro-3H-imidazo[4,5-b]pyridin-2-yl}-N-[(2,4-dichlorophenyl}methyl]pyrrolidin-3-amine |
| 1849 | [2-({5-chloro-3H-imidazo[4,5-b]pyridin-2-yl}amino)ethyl][(3,5-dichlorophenyl)methyl]amine |

| No. | Chemical Structure | Chemical Name |
|---|---|---|
| 1850 | 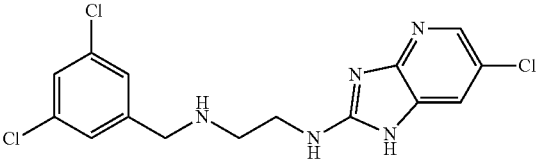 [SMILES: Clc1cc(Cl)cc(CNCCNc2nc3ncc(Cl)cc3[nH]2)c1] | [2-({6-chloro-1H-imidazo[4,5-b]pyridin-2-yl}amino)ethyl][(3,5-dichlorophenyl)methyl]amine |
| 1851 | 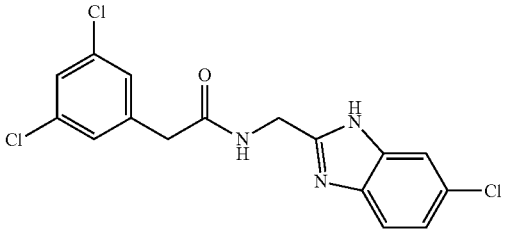 [SMILES: O=C(Cc1cc(Cl)cc(Cl)c1)NCc1nc2ccc(Cl)cc2[nH]1] | N-[(6-chloro-1H-1,3-benzodiazol-2-yl)methyl]-2-(3,5-dichlorophenyl)acetamide |
| 1852 | 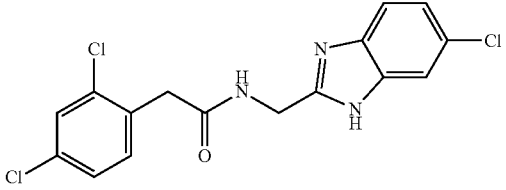 [SMILES: O=C(Cc1ccc(Cl)cc1Cl)NCc1nc2ccc(Cl)cc2[nH]1] | N-[(6-chloro-1H-1,3-benzodiazol-2-yl)methyl]-2-(2,4-dichlorophenyl)acetamide |
| 1853 | 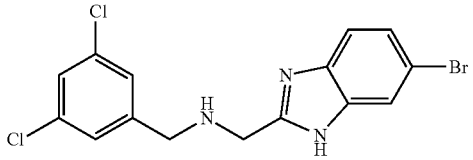 [SMILES: Clc1cc(Cl)cc(CNCc2nc3ccc(Br)cc3[nH]2)c1] | [(6-bromo-3H-1,3-benzodiazol-2-yl)methyl][(3,5-dichlorophenyl)methyl]amine |
| 1854 | 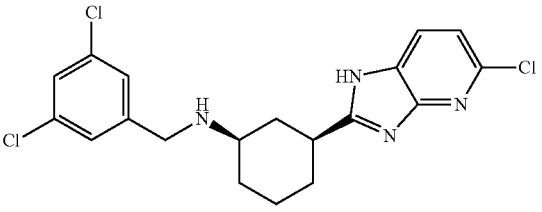 [SMILES: Clc1cc(Cl)cc(CN[C@@H]2CCC[C@H](c3nc4nc(Cl)ccc4[nH]3)C2)c1] | (1R,3S)-3-{5-chloro-3H-imidazo[4,5-b]pyridin-2-yl}-N-[(3,5-dichlorophenyl)methyl]cyclohexan-1-amine |
| 1855 | 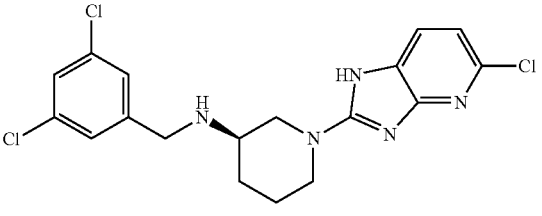 [SMILES: Clc1cc(Cl)cc(CN[C@@H]2CCCN(c3nc4nc(Cl)ccc4[nH]3)C2)c1] | (3R)-1-{5-chloro-1H-imidazo[4,5-b]pyridin-2-yl}-N-[(3,5-dichlorophenyl)methyl]piperidin-3-amine |
| 1856 | 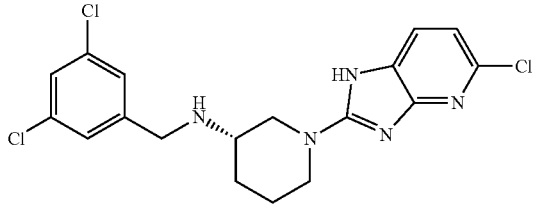 | (3S)-1-{5-chloro-3H-imidazo[4,5-b]pyridin-2-yl}-N-[(3,5-dichlorophenyl)methyl]piperidin-3-amine |

| No. | Chemical Structure | Chemical Name |
|---|---|---|
| 1857 | 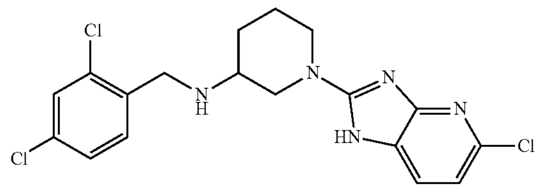 [SMILES: Clc1ccc(CNC2CCCN(c3nc4nc(Cl)ccc4[nH]3)C2)c(Cl)c1] | 1-{5-chloro-1H-imidazo[4,5-b]pyridin-2-yl}-N-[(2,4-dichlorophenyl)methyl]piperidin-3-amine |
| 1858 | 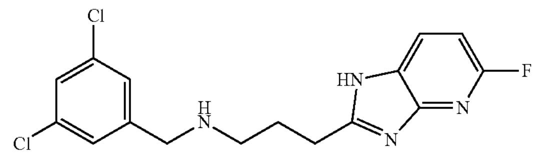 [SMILES: Fc1ccc2[nH]c(CCCNCc3cc(Cl)cc(Cl)c3)nc2n1] | [(3,5-dichlorophenyl)methyl](3-{5-fluoro-1H-imidazo[4,5-b]pyridin-2-yl}propyl)amine |
| 1859 | 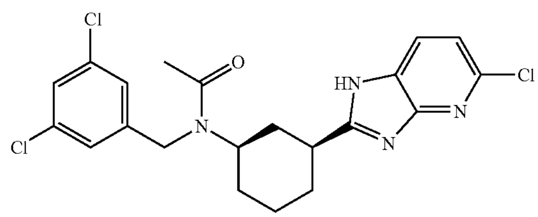 [SMILES: CC(=O)N(Cc1cc(Cl)cc(Cl)c1)[C@@H]1CCC[C@H](c2nc3nc(Cl)ccc3[nH]2)C1] | N-[(1R,3S)-3-{5-chloro-1H-imidazo[4,5-b]pyridin-2-yl}cyclohexyl]-N-[(3,5-dichlorophenyl)methyl]acetamide |
| 1860 | 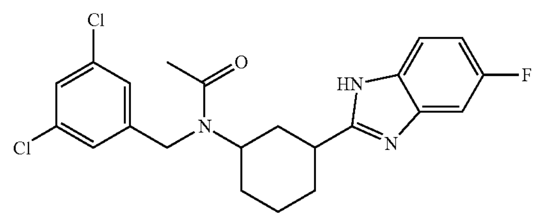 [SMILES: CC(=O)N(Cc1cc(Cl)cc(Cl)c1)C1CCCC(c2nc3cc(F)ccc3[nH]2)C1] | N-[(3,5-dichlorophenyl)methyl]-N-[3-(5-fluoro-1H-1,3-benzodiazol-2-yl)cyclohexyl]acetamide |
| 1861 | 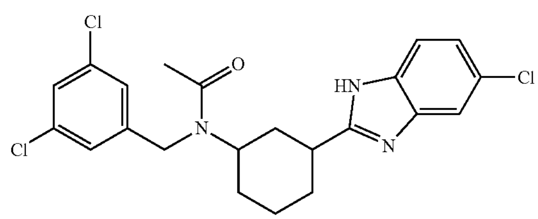 [SMILES: CC(=O)N(Cc1cc(Cl)cc(Cl)c1)C1CCCC(c2nc3cc(Cl)ccc3[nH]2)C1] | N-[3-(5-chloro-1H-1,3-benzodiazol-2-yl)cyclohexyl]-N-[(3,5-dichlorophenyl)methyl]acetamide |
| 1862 | 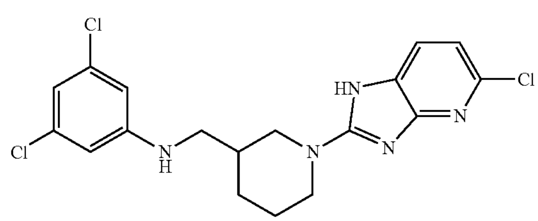 [SMILES: Clc1cc(Cl)cc(NCC2CCCN(c3nc4nc(Cl)ccc4[nH]3)C2)c1] | 3,5-dichloro-N-[(1-{5-chloro-1H-imidazo[4,5-b]pyridin-2-yl}piperidin-3-yl)methyl]aniline |
| 1863 | 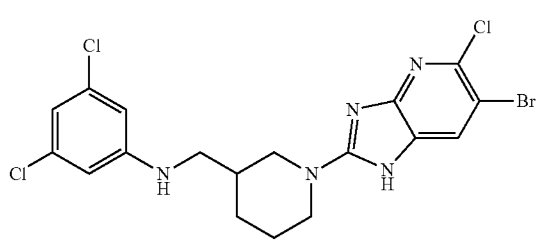 [SMILES: Clc1cc(Cl)cc(NCC2CCCN(c3nc4nc(Cl)c(Br)cc4[nH]3)C2)c1] | N-[(1-{6-bromo-5-chloro-1H-imidazo[4,5-b]pyridin-2-yl}piperidin-3-yl)methyl]-3,5-dichloroaniline |

| No. | Chemical Structure | Chemical Name |
|---|---|---|
| 1864 | 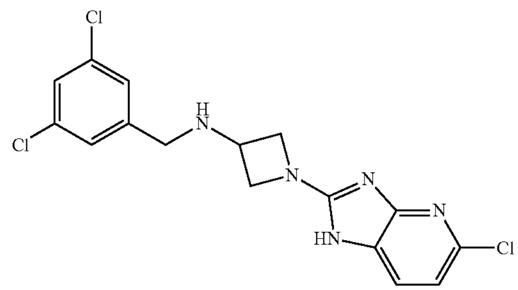 [SMILES: Clc1cc(Cl)cc(CNC2CN(c3nc4nc(Cl)ccc4[nH]3)C2)c1] | 1-{5-chloro-1H-imidazo[4,5-b]pyridin-2-yl}-N-[(3,5-dichlorophenyl)methyl]azetidin-3-amine |
| 1865 | 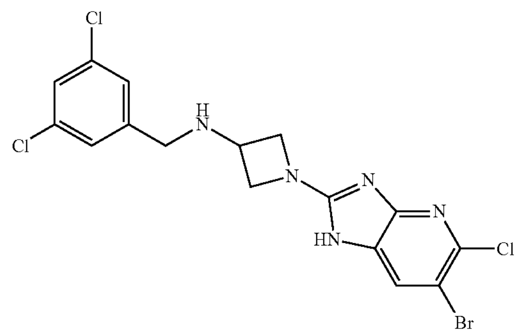 [SMILES: Clc1cc(Cl)cc(CNC2CN(c3nc4nc(Cl)c(Br)cc4[nH]3)C2)c1] | 1-{6-bromo-5-chloro-1H-imidazo[4,5-b]pyridin-2-yl}-N-[(3,5-dichlorophenyl)methyl]azetidin-3-amine |
| 1866 | 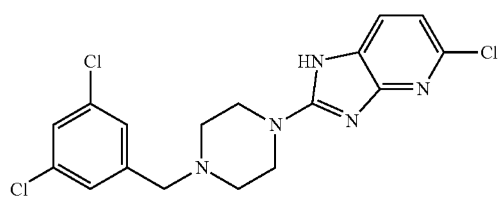 [SMILES: Clc1cc(Cl)cc(CN2CCN(c3nc4nc(Cl)ccc4[nH]3)CC2)c1] | 1-{5-chloro-1H-imidazo[4,5-b]pyridin-2-yl}-4-[(3,5-dichlorophenyl)methyl]piperazine |
| 1867 | 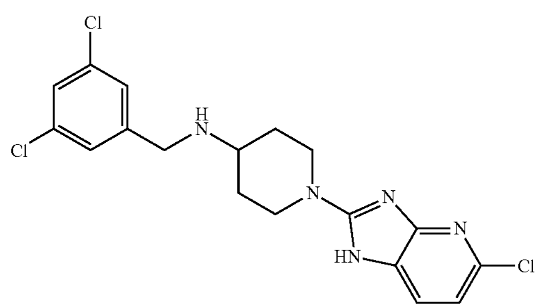 [SMILES: Clc1cc(Cl)cc(CNC2CCN(c3nc4nc(Cl)ccc4[nH]3)CC2)c1] | 1-{5-chloro-1H-imidazo[4,5-b]pyridin-2-yl}-N-[(3,5-dichlorophenyl)methyl]piperidin-4-amine |
| 1868 | 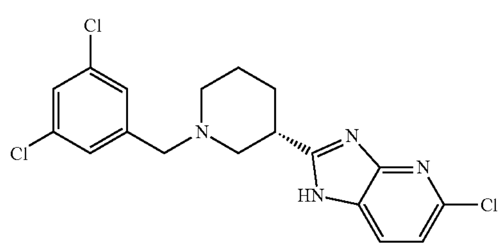 [SMILES: Clc1cc(Cl)cc(CN2CCC[C@H](c3nc4nc(Cl)ccc4[nH]3)C2)c1] | (3S)-3-{5-chloro-1H-imidazo[4,5-b]pyridin-2-yl}-1-[(3,5-dichlorophenyl)methyl]piperidine |
| 1869 | 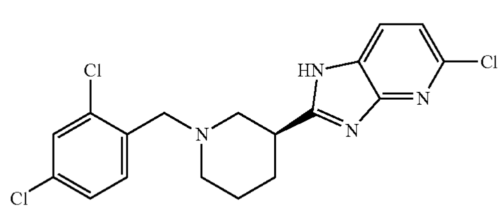 [SMILES: Clc1ccc(CN2CCC[C@H](c3nc4nc(Cl)ccc4[nH]3)C2)c(Cl)c1] | (3S)-3-{5-chloro-1H-imidazo[4,5-b]pyridin-2-yl}-1-[(2,4-dichlorophenyl)methyl]piperidine |

-continued

| No. | Chemical Structure | Chemical Name |
|---|---|---|
| 1870 | 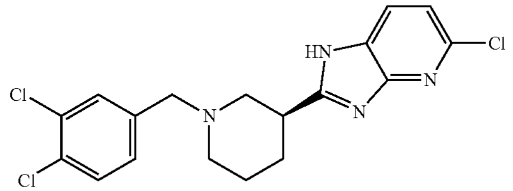 [SMILES: Clc1ccc2[nH]c([C@H]3CCCN(Cc4ccc(Cl)c(Cl)c4)C3)nc2n1] | (3S)-3-{5-chloro-1H-imidazo[4,5-b]pyridin-2-yl}-1-[(3,4-dichlorophenyl)methyl]piperidine |
| 1871 | 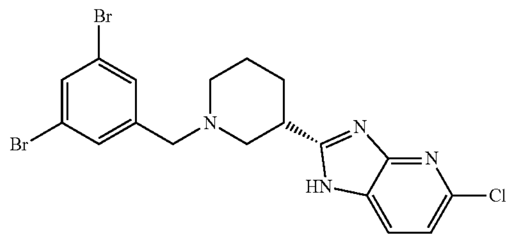 | (3S)-3-{5-chloro-1H-imidazo[4,5-b]pyridin-2-yl}-1-[(3,5-dibromophenyl)methyl]piperidine |
| 1872 | 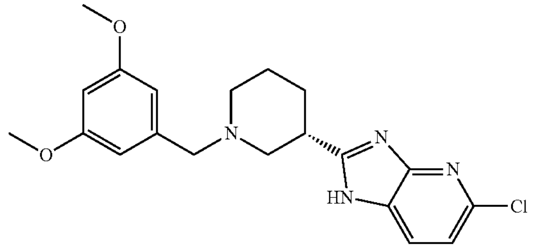 [SMILES: COc1cc(CN2CCC[C@H](c3nc4nc(Cl)ccc4[nH]3)C2)cc(OC)c1] | (3S)-3-{5-chloro-1H-imidazo[4,5-b]pyridin-2-yl}-1-[(3,5-dimethoxyphenyl)methyl]piperidine |
| 1873 | 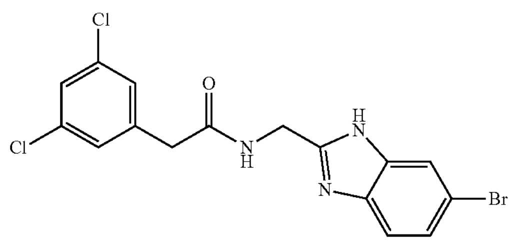 [SMILES: O=C(Cc1cc(Cl)cc(Cl)c1)NCc1nc2ccc(Br)cc2[nH]1] | N-[(6-bromo-1H-1,3-benzodiazol-2-yl)methyl]-2-(3,5-dichlorophenyl)acetamide |
| 1874 | 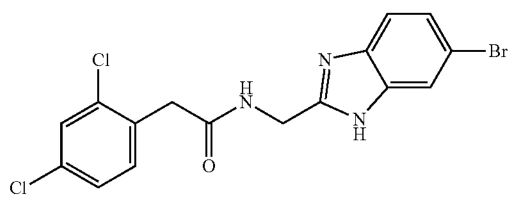 [SMILES: O=C(Cc1ccc(Cl)cc1Cl)NCc1nc2ccc(Br)cc2[nH]1] | N-[(6-bromo-1H-1,3-benzodiazol-2-yl)methyl]-2-(2,4-dichlorophenyl)acetamide |
| 1875 | 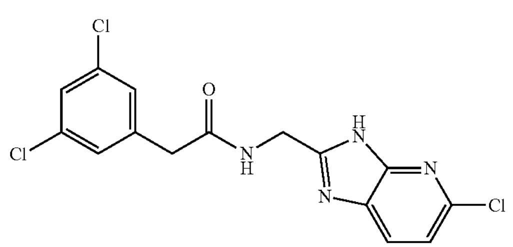 [SMILES: O=C(Cc1cc(Cl)cc(Cl)c1)NCc1nc2ccc(Cl)nc2[nH]1] | N-({5-chloro-3H-imidazo[4,5-b]pyridin-2-yl}methyl)-2-(3,5-dichlorophenyl)acetamide |
| 1876 | 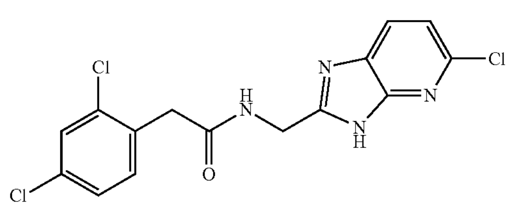 [SMILES: O=C(Cc1ccc(Cl)cc1Cl)NCc1nc2ccc(Cl)nc2[nH]1] | N-({5-chloro-3H-imidazo[4,5-b]pyridin-2-yl}methyl)-2-(2,4-dichlorophenyl)acetamide |

-continued

| No. | Chemical Structure | Chemical Name |
|---|---|---|
| 1877 | 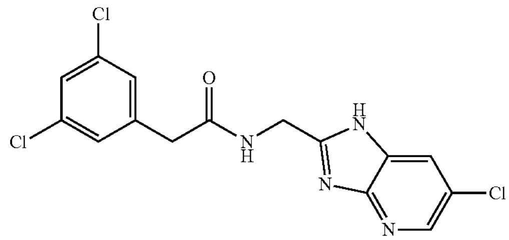 [SMILES: O=C(Cc1cc(Cl)cc(Cl)c1)NCc1nc2ncc(Cl)cc2[nH]1] | N-({6-chloro-1H-imidazo[4,5-b]pyridin-2-yl}methyl)-2-(3,5-dichlorophenyl)acetamide |
| 1878 | 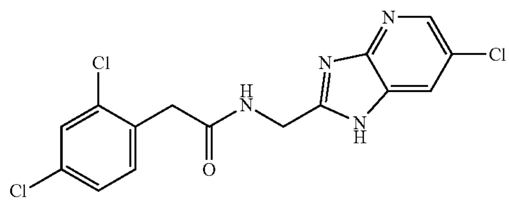 [SMILES: O=C(Cc1ccc(Cl)cc1Cl)NCc1nc2ncc(Cl)cc2[nH]1] | N-({6-chloro-1H-imidazo[4,5-b]pyridin-2-yl}methyl)-2-(2,4-dichlorophenyl)acetamide |
| 1879 | 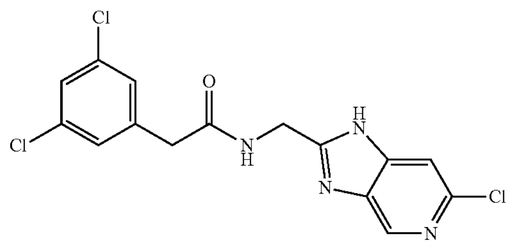 [SMILES: O=C(Cc1cc(Cl)cc(Cl)c1)NCc1nc2cnc(Cl)cc2[nH]1] | N-({6-chloro-1H-imidazo[4,5-c]pyridin-2-yl}methyl)-2-(3,5-dichlorophenyl)acetamide |
| 1880 | 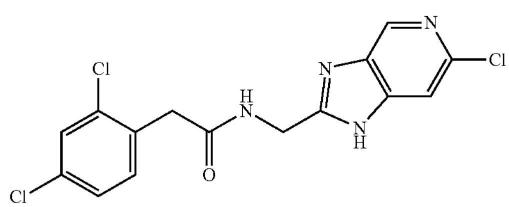 [SMILES: O=C(Cc1ccc(Cl)cc1Cl)NCc1nc2cnc(Cl)cc2[nH]1] | N-({6-chloro-1H-imidazo[4,5-c]pyridin-2-yl}methyl)-2-(2,4-dichlorophenyl)acetamide |
| 1881 | 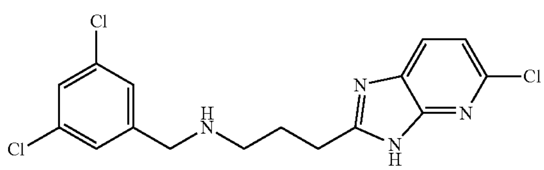 [SMILES: Clc1cc(Cl)cc(CNCCCc2nc3ccc(Cl)nc3[nH]2)c1] | (3-{5-chloro-3H-imidazo[4,5-b]pyridin-2-yl}propyl)[(3,5-dichlorophenyl)methyl]amine |
| 1882 | 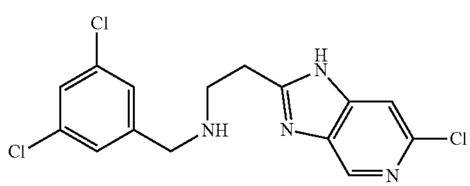 [SMILES: Clc1cc(Cl)cc(CNCCc2nc3cnc(Cl)cc3[nH]2)c1] | (2-{6-chloro-1H-imidazo[4,5-c]pyridin-2-yl}ethyl)[(3,5-dichlorophenyl)methyl]amine |
| 1883 | 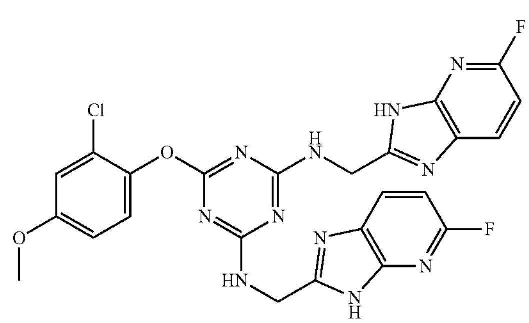 [SMILES: COc1ccc(Oc2nc(NCc3nc4ccc(F)nc4[nH]3)nc(NCc3nc4ccc(F)nc4[nH]3)n2)c(Cl)c1] | 6-(2-chloro-4-methoxyphenoxy)-2-N,4-N-bis({5-fluoro-3H-imidazo[4,5-b]pyridin-2-yl}methyl)-1,3,5-triazine-2,4-diamine |

-continued

| No. | Chemical Structure | Chemical Name |
| --- | --- | --- |
| 1884 | 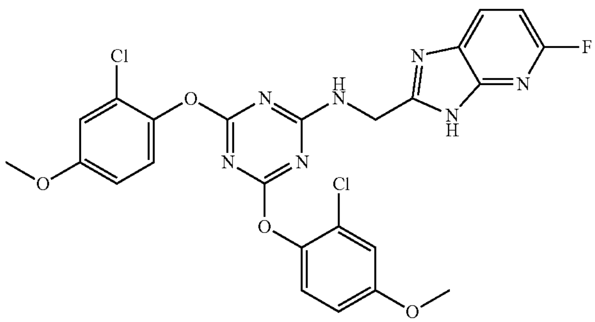 [SMILES: COc1ccc(Oc2nc(NCc3nc4ccc(F)nc4[nH]3)nc(Oc3ccc(OC)cc3Cl)n2)c(Cl)c1] | 4,6-bis(2-chloro-4-methoxyphenoxy)-N-({5-fluoro-3H-imidazo[4,5-b]pyridin-2-yl}methyl)-1,3,5-triazin-2-amine |
| 1885 | 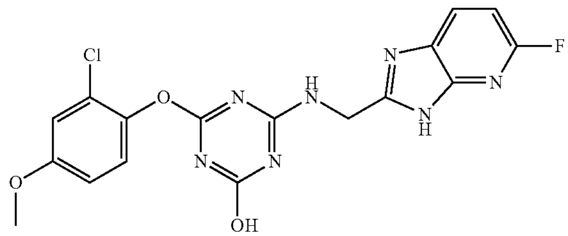 [SMILES: COc1ccc(Oc2nc(O)nc(NCc3nc4ccc(F)nc4[nH]3)n2)c(Cl)c1] | 4-(2-chloro-4-methoxyphenoxy)-6-[({5-fluoro-3H-imidazo[4,5-b]pyridin-2-yl}methyl)amino]-1,3,5-triazin-2-ol |
| 1886 | 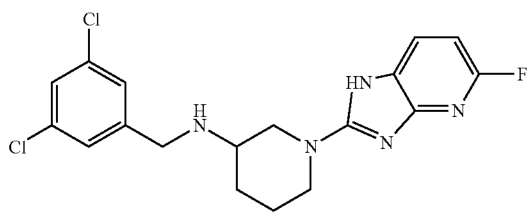 [SMILES: Fc1ccc2[nH]c(N3CCCC(NCc4cc(Cl)cc(Cl)c4)C3)nc2n1] | N-[(3,5-dichlorophenyl)methyl]-1-{5-fluoro-1H-imidazo[4,5-b]pyridin-2-yl}piperidn-3-amine |
| 1887 | 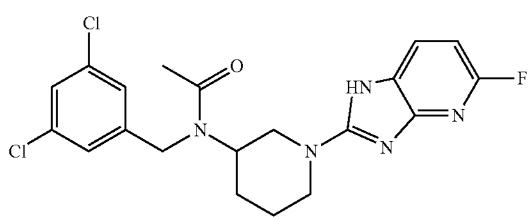 [SMILES: CC(=O)N(Cc1cc(Cl)cc(Cl)c1)C1CCCN(c2nc3nc(F)ccc3[nH]2)C1] | N-[(3,5-dichlorophenyl)methyl]-N-(1-{5-fluoro-1H-imidazo[4,5-b]pyridin-2-yl}piperidin-3-yl)acetamide |
| 1888 | 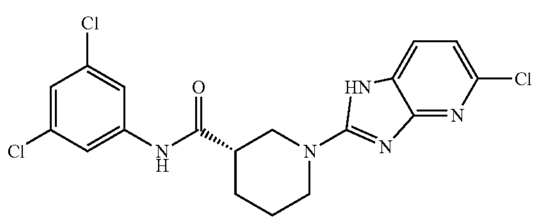 [SMILES: O=C(Nc1cc(Cl)cc(Cl)c1)[C@H]1CCCN(c2nc3nc(Cl)ccc3[nH]2)C1] | (3S)-3-{5-chloro-1H-imidazo[4,5-b]pyridin-2-yl}-N-(3,5-dichlorophenyl)piperidine-3-carboxamide |
| 1889 | 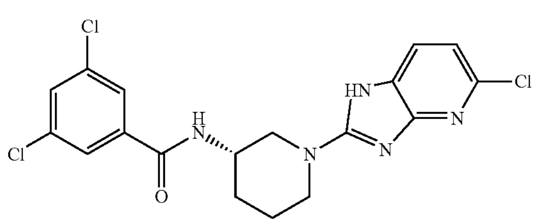 [SMILES: O=C(N[C@H]1CCCN(c2nc3nc(Cl)ccc3[nH]2)C1)c1cc(Cl)cc(Cl)c1] | 3,5-dichloro-N-[(3S)-1-{5-chloro-1H-imidazo[4,5-b]pyridin-2-yl}piperidin-3-yl]benzamide |

| No. | Chemical Structure | Chemical Name |
|---|---|---|
| 1890 | 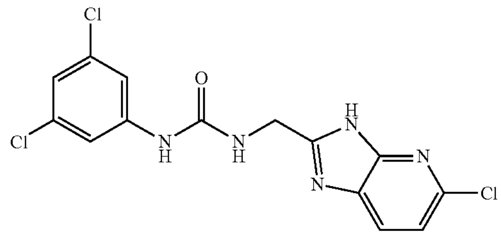 [SMILES: O=C(NCc1nc2ccc(Cl)nc2[nH]1)Nc1cc(Cl)cc(Cl)c1] | 3-({5-chloro-3H-imidazo[4,5-b]pyridin-2-yl}methyl)-1-(3,5-dichlorophenyl)urea |
| 1891 | 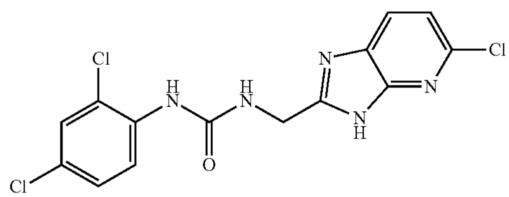 [SMILES: O=C(NCc1nc2ccc(Cl)nc2[nH]1)Nc1ccc(Cl)cc1Cl] | 3-({5-chloro-3H-imidazo[4,5-b]pyridin-2-yl}methyl)-1-(2,4-dichlorophenyl)urea |
| 1892 | 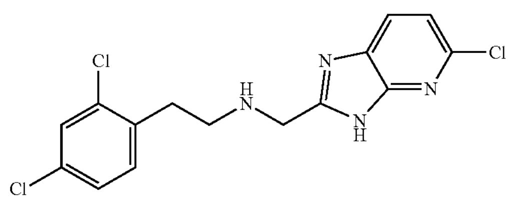 [SMILES: Clc1ccc(CCNCc2nc3ccc(Cl)nc3[nH]2)c(Cl)c1] | ({5-chloro-3H-imidazo[4,5-b]pyridin-2-yl}methyl)[2-(2,4-dichlorophenyl)ethyl]amine |
| 1893 | 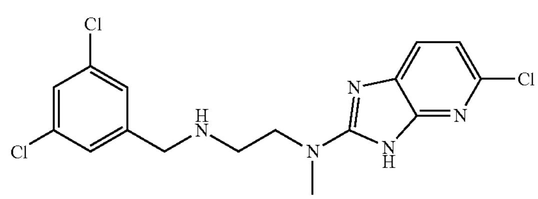 [SMILES: CN(CCNCc1cc(Cl)cc(Cl)c1)c1nc2ccc(Cl)nc2[nH]1] | 5-chloro-N-(2-{[(3,5-dichlorophenyl)methyl]amino}ethyl)-N-methyl-3H-imidazo[4,5-b]pyridin-2-amine |
| 1894 | 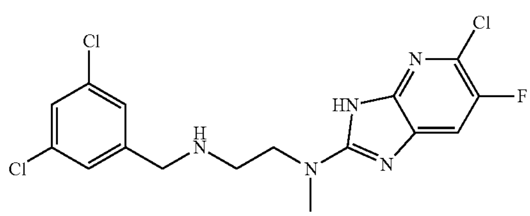 [SMILES: CN(CCNCc1cc(Cl)cc(Cl)c1)c1nc2cc(F)c(Cl)nc2[nH]1] | 6-bromo-5-chloro-N-(2-{[(3,5-dichlorophenyl)methyl]amino}ethyl)-N-methyl-3H-imidazo[4,5-b]pyridin-2-amine |
| 1895 | 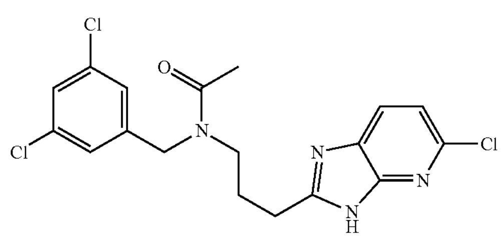 [SMILES: CC(=O)N(CCCc1nc2ccc(Cl)nc2[nH]1)Cc1cc(Cl)cc(Cl)c1] | N-(3-{5-chloro-3H-imidazo[4,5-b]pyridin-2-yl}propyl)-N-[(3,5-dichlorophenyl)methyl]acetamide |
| 1896 | 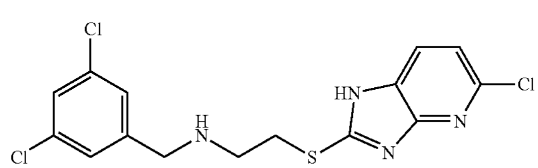 [SMILES: Clc1cc(Cl)cc(CNCCSc2nc3nc(Cl)ccc3[nH]2)c1] | [2-({5-chloro-1H-imidazo[4,5-b]pyridin-2-yl}sulfanyl)ethyl][(3,5-dichlorophenyl)methyl]amine |

-continued

| No. | Chemical Structure | Chemical Name |
|---|---|---|
| 1897 | 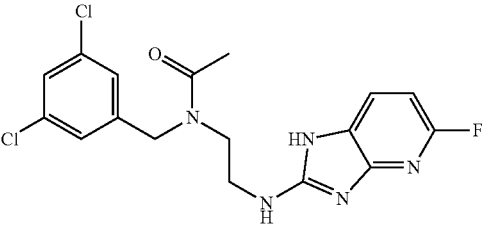 [SMILES: CC(=O)N(CCNc1nc2nc(F)ccc2[nH]1)Cc1cc(Cl)cc(Cl)c1] | N-[(3,5-dichlorophenyl)methyl]-N-[2-({5-fluoro-1H-imidazo[4,5-b]pyridin-2-yl}amino)ethyl]acetaimde |
| 1898 | 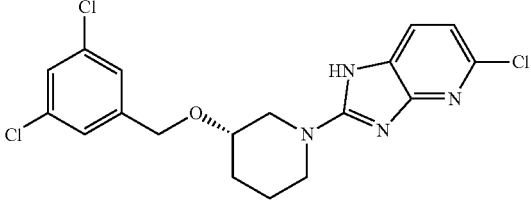 [SMILES: Clc1cc(Cl)cc(CO[C@H]2CCCN(c3nc4nc(Cl)ccc4[nH]3)C2)c1] | (3S)-3-{5-chloro-1H-imidazo[4,5-b]pyridin-2-yl}-3-[(3,5-dichlorophenyl)methoxy]piperidine |
| 1899 | 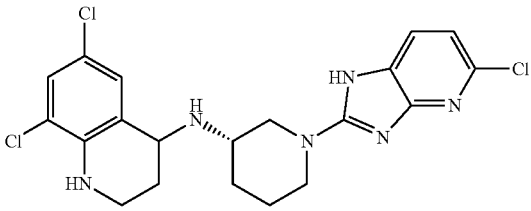 [SMILES: Clc1cc(Cl)c2c(c1)C(N[C@H]1CCCN(c3nc4nc(Cl)ccc4[nH]3)C1)CCN2] | 6,8-dichloro-N-[(3S)-1-{5-chloro-3H-imidazo[4,5-b]pyridin-2-yl}piperidin-3-yl]-1,2,3,4-tetrahydroquinolin-4-amine |
| 1900 | 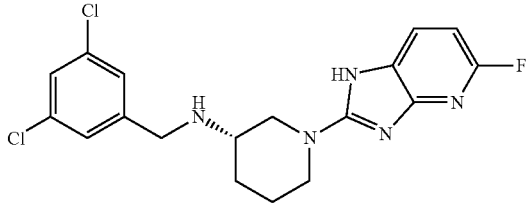 [SMILES: Fc1ccc2[nH]c(N3CCC[C@H](NCc4cc(Cl)cc(Cl)c4)C3)nc2n1] | (3S)-N-[(3,5-dichlorophenyl)methyl]-1-{5-fluoro-1H-imidazo[4,5-b]pyridin-2-yl}piperidin-3-amine |
| 1901 | 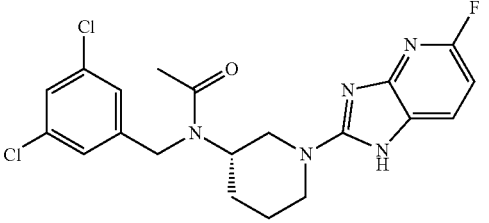 [SMILES: CC(=O)N(Cc1cc(Cl)cc(Cl)c1)[C@H]1CCCN(c2nc3nc(F)ccc3[nH]2)C1] | N-[(3,5-dichlorophenyl)methyl]-N-[(3S)-1-{5-fluoro-3H-imidazo[4,5-b]pyridin-2-yl}piperidin-3-yl]acetamide |
| 1902 | 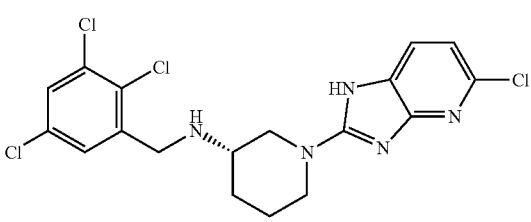 [SMILES: Clc1cc(Cl)c(Cl)c(CN[C@H]2CCCN(c3nc4nc(Cl)ccc4[nH]3)C2)c1] | (3S)-1-{5-chloro-1H-imidazo[4,5-b]pyridin-2-yl}-N-[(2,3,5-trichlorophenyl)methyl]piperidin-3-amine |
| 1903 | 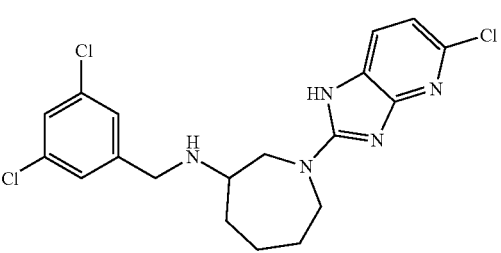 [SMILES: Clc1cc(Cl)cc(CNC2CCCCN(c3nc4nc(Cl)ccc4[nH]3)C2)c1] | 1-{5-chloro-1H-imidazo[4,5-b]pyridin-2-yl}-N-[(3,5-dichlorophenyl)methyl]azepan-3-amine |

-continued

| No. | Chemical Structure | Chemical Name |
|---|---|---|
| 1904 | 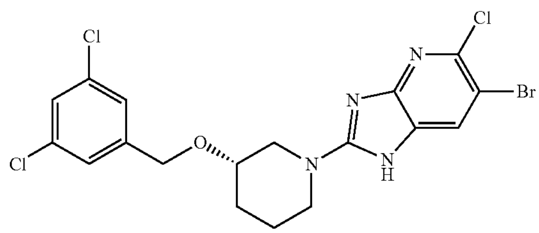 [SMILES: Clc1cc(Cl)cc(CO[C@H]2CCCN(c3nc4nc(Cl)c(Br)cc4[nH]3)C2)c1] | (3S)-1-{6-bromo-5-chloro-1H-imidazo[4,5-b]pyridin-2-yl}-3-[(3,5-dichlorophenyl)methoxy]piperidine |
| 1905 | 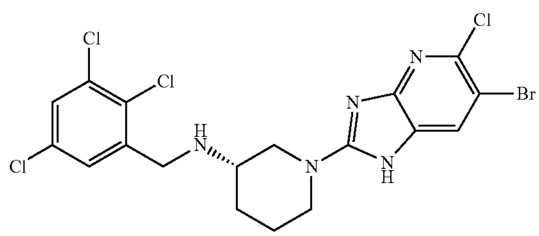 [SMILES: Clc1cc(Cl)c(Cl)c(CN[C@H]2CCCN(c3nc4nc(Cl)c(Br)cc4[nH]3)C2)c1] | (3S)-1-{6-bromo-5-chloro-1H-imidazo[4,5-b]pyridin-2-yl}-N-[(2,3,5-trichlorophenyl)methyl]piperidin-3-amine |
| 1906 | 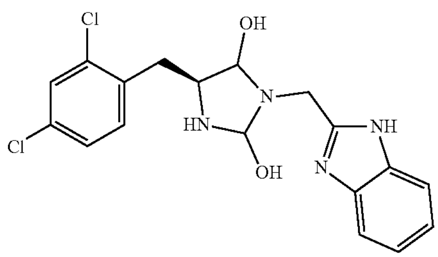 [SMILES: OC1N[C@@H](Cc2ccc(Cl)cc2Cl)C(O)N1Cc1nc2ccccc2[nH]1] | (5S)-3-(1H-1,3-benzodiazol-2-ylmethyl)-5-[(2,4-dichlorophenyl)methyl]imidazolidine-2,4-diol |
| 1907 | 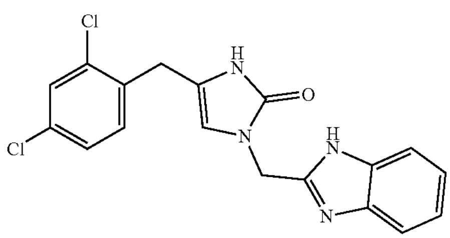 [SMILES: O=c1[nH]c(Cc2ccc(Cl)cc2Cl)cn1Cc1nc2ccccc2[nH]1] | 1-(1H-1,3-benzodiazol-2-ylmethyl)-4-[(2,4-dichlorophenyl)methyl]-2,3-dihydro-1H-imidazol-2-one |
| 1908 | 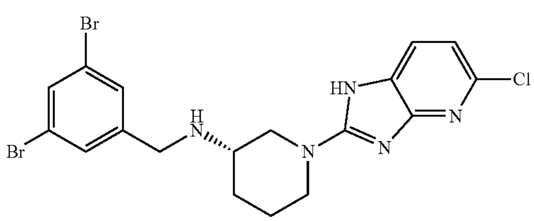 [SMILES: Clc1ccc2[nH]c(N3CCC[C@H](NCc4cc(Br)cc(Br)c4)C3)nc2n1] | (3S)-1-{5-chloro-1H-imidazo[4,5-b]pyridin-2-yl}-N-[(3,5-dibromophenyl)methyl]piperidin-3-amine |
| 1909 | 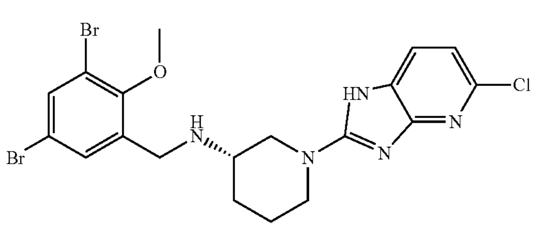 [SMILES: COc1c(Br)cc(Br)cc1CN[C@H]1CCCN(c2nc3nc(Cl)ccc3[nH]2)C1] | (3S)-1-{5-chloro-1H-imidazo[4,5-b]pyridin-2-yl}-N-[(3,5-dibromo-2-methoxyphenyl)methyl]piperidin-3-amine |

| No. | Chemical Structure | Chemical Name |
|---|---|---|
| 1910 | 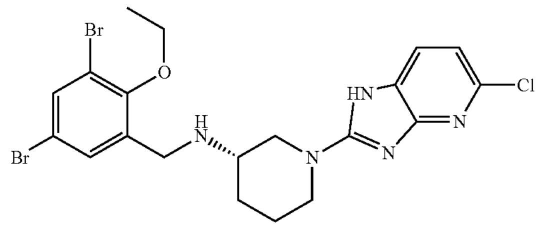 [SMILES: CCOc1c(Br)cc(Br)cc1CN[C@H]1CCCN(c2nc3nc(Cl)ccc3[nH]2)C1] | (3S)-1-{5-chloro-1H-imidazo[4,5-b]pyridin-2-yl}-N-[(3,5-dibromo-2-ethoxyphenyl)methyl]piperidin-3-amine |
| 1911 | 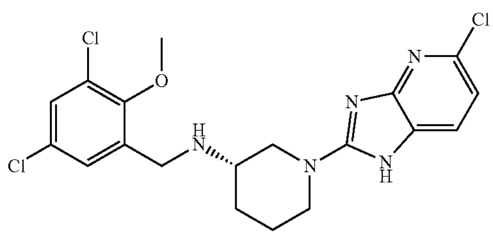 [SMILES: COc1c(Cl)cc(Cl)cc1CN[C@H]1CCCN(c2nc3nc(Cl)ccc3[nH]2)C1] | (3S)-1-{5-chloro-1H-imidazo[4,5-b]pyridin-2-yl}-N-[(3,5-dichloro-2-methoxyphenyl)methyl]piperidin-3-amine |
| 1912 | 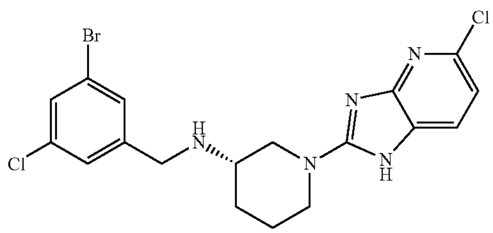 [SMILES: Clc1cc(Br)cc(CN[C@H]2CCCN(c3nc4nc(Cl)ccc4[nH]3)C2)c1] | (3S)-N-[(3-bromo-5-chlorophenyl)methyl]-1-{5-chloro-1H-imidazo[4,5-b]pyridin-2-yl}piperidin-3-amine |
| 1913 | 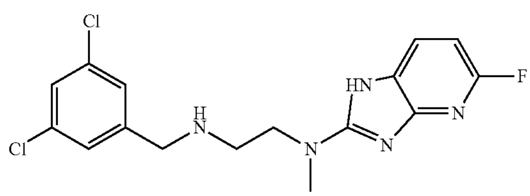 [SMILES: CN(CCNCc1cc(Cl)cc(Cl)c1)c1nc2nc(F)ccc2[nH]1] | N-(2-{[(3,5-dichlorophenyl)methyl]amino}ethyl)-5-fluoro-N-methyl-1H-imidazo[4,5-b]pyridin-2-amine |
| 1914 | 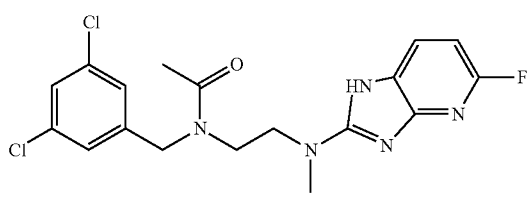 [SMILES: CC(=O)N(CCN(C)c1nc2nc(F)ccc2[nH]1)Cc1cc(Cl)cc(Cl)c1] | N-[(3,5-dichlorophenyl)methyl]-N-[2-({5-fluoro-1H-imidazo[4,5-b]pyridin-2-yl}(methyl)amino)ethyl]acetamide |
| 1915 | 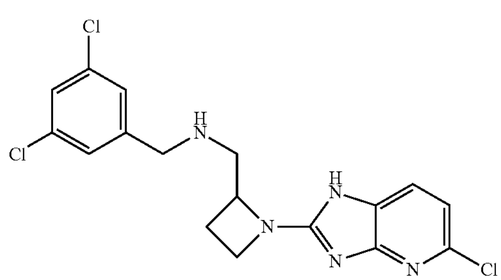 [SMILES: Clc1cc(Cl)cc(CNCC2CCN2c2nc3nc(Cl)ccc3[nH]2)c1] | [(1-{5-chloro-1H-imidazo[4,5-b]pyridin-2-yl}azetidin-2-yl)methyl][(3,5-dichlorophenyl)methyl]amine |

| No. | Chemical Structure | Chemical Name |
|---|---|---|
| 1916 | 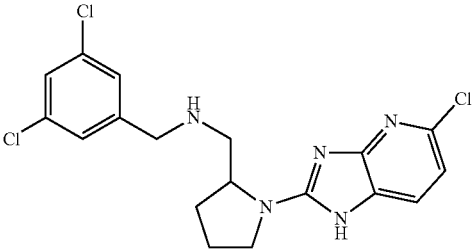 [SMILES: Clc1cc(Cl)cc(CNCC2CCCN2c2nc3nc(Cl)ccc3[nH]2)c1] | [(1-{5-chloro-1H-imidazo[4,5-b]pyridin-2-yl}pyrrolidin-2-yl)methyl][(3,5-dichlorophenyl)methyl]amine |
| 1917 | 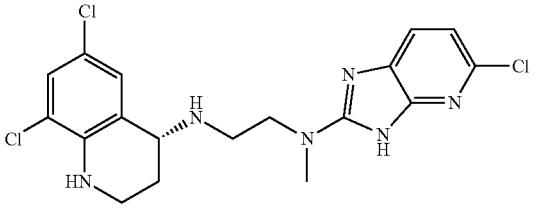 [SMILES: CN(CCN[C@@H]1CCNc2c(Cl)cc(Cl)cc21)c1nc2ccc(Cl)nc2[nH]1] | 5-chloro-N-(2-{[(4R)-6,8-dichloro-1,2,3,4-tetrahydroquinolin-4-yl]amino}ethyl)-N-methyl-3H-imidazo[4,5-b]pyridin-2-amine |
| 1918 | 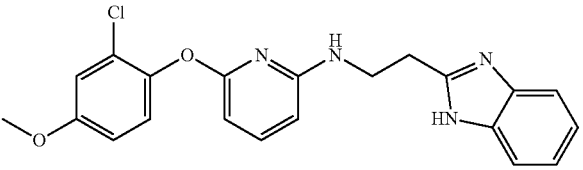 [SMILES: COc1ccc(Oc2cccc(NCCc3nc4ccccc4[nH]3)n2)c(Cl)c1] | N-[2-(1H-1,3-benzodiazol-2-yl)ethyl]-6-(2-chloro-4-methoxyphenoxy)pyridin-2-amine |
| 1919 | 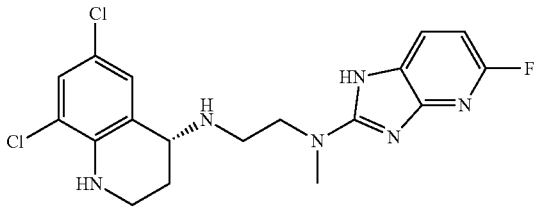 [SMILES: CN(CCN[C@@H]1CCNc2c(Cl)cc(Cl)cc21)c1nc2nc(F)ccc2[nH]1] | N-(2-{[(4R)-6,8-dichloro-1,2,3,4-tetrahydroquinolin-4-yl]amino}ethyl)-5-fluoro-N-methyl-1H-imidazo[4,5-b]pyridin-2-amine |
| 1920 | 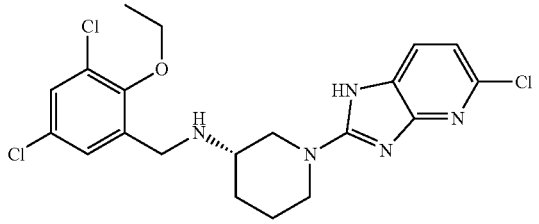 [SMILES: CCOc1c(Cl)cc(Cl)cc1CN[C@H]1CCCN(c2nc3nc(Cl)ccc3[nH]2)C1] | (3S)-1-{5-chloro-1H-imidazo[4,5-b]pyridin-2-yl}-N-[(3,5-dichloro-2-ethoxyphenyl)methyl]piperidin-3-amine |
| 1921 | 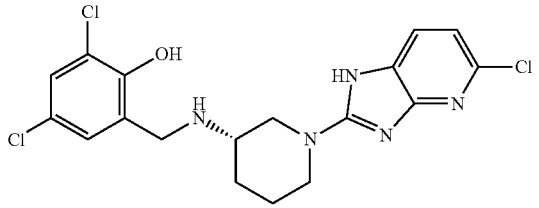 [SMILES: Oc1c(Cl)cc(Cl)cc1CN[C@H]1CCCN(c2nc3nc(Cl)ccc3[nH]2)C1] | 2,4-dichloro-6-({[(3S)-1-{5-chloro-1H-imidazo[4,5-b]pyridin-2-yl}piperidin-3-yl]amino}methyl)phenol |
| 1922 | 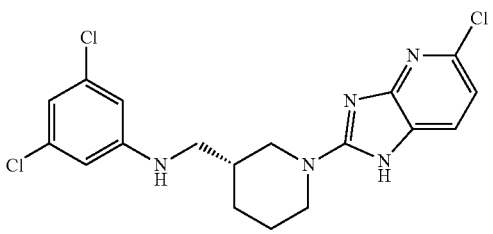 [SMILES: Clc1cc(Cl)cc(NC[C@H]2CCCN(c3nc4nc(Cl)ccc4[nH]3)C2)c1] | 3,5-dichloro-N-{[(3R)-1-{5-chloro-1H-imidazo[4,5-b]pyridin-2-yl}piperidin-3-yl]methyl}aniline |

| No. | Chemical Structure | Chemical Name |
|---|---|---|
| 1923 | 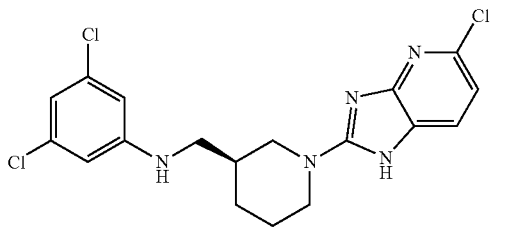 [SMILES: Clc1cc(Cl)cc(NC[C@@H]2CCCN(c3nc4nc(Cl)ccc4[nH]3)C2)c1] | 3,5-dichloro-N-{[(3S)-1-{5-chloro-1H-imidazo[4,5-b]pyridin-2-yl}piperidin-3-yl]methyl}aniline |
| 1924 | 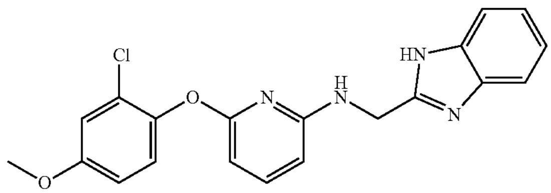 [SMILES: COc1ccc(Oc2cccc(NCc3nc4ccccc4[nH]3)n2)c(Cl)c1] | N-(1H-1,3-benzodiazol-2-ylmethyl)-6-(2-chloro-4-methoxyphenoxy)pyridin-2-amine |
| 1925 | 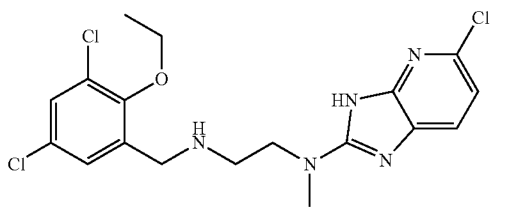 [SMILES: CCOc1c(Cl)cc(Cl)cc1CNCCN(C)c1nc2ccc(Cl)nc2[nH]1] | 5-chloro-N-(2-{[(3,5-dichloro-2-ethoxyphenyl)methyl]amino}ethyl)-N-methyl-3H-imidazo[4,5-b]pyridin-2-amine |
| 1926 | 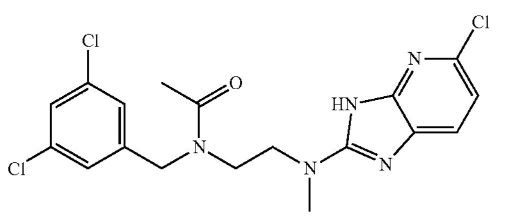 [SMILES: CC(=O)N(CCN(C)c1nc2ccc(Cl)nc2[nH]1)Cc1cc(Cl)cc(Cl)c1] | N-[2-({5-chloro-3H-imidazo[4,5-b]pyridin-2-yl}(methyl)amino)ethyl]-N-[(3,5-dichlorophenyl)methyl]acetamide |
| 1927 | 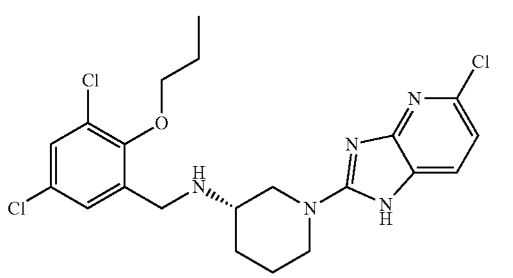 | (3S)-1-{5-chloro-1H-imidazo[4,5-b]pyridin-2-yl}-N-[(3,5-dichloro-2-propoxyphenyl)methyl]piperidin-3-amine |
| 1928 | 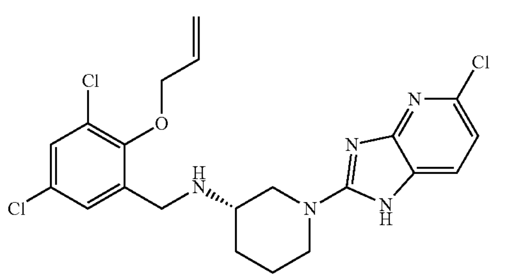 [SMILES: C=CCOc1c(Cl)cc(Cl)cc1CN[C@H]1CCCN(c2nc3nc(Cl)ccc3[nH]2)C1] | (3S)-1-{5-chloro-1H-imidazo[4,5-b]pyridin-2-yl}-N-{[3,5-dichloro-2-(prop-2-en-1-yloxy)phenyl]methyl}piperidin-3-amine |

| No. | Chemical Structure | Chemical Name |
|---|---|---|
| 1929 | 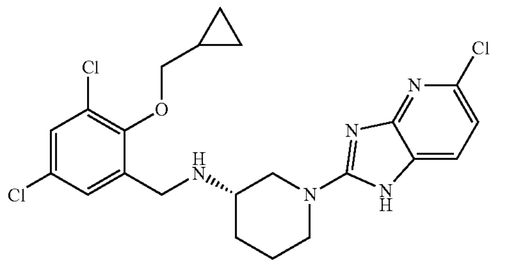 [SMILES: Clc1cc(Cl)c(OCC2CC2)c(CN[C@H]2CCCN(c3nc4nc(Cl)ccc4[nH]3)C2)c1] | (3S)-1-{5-chloro-1H-imidazo[4,5-b]pyridin-2-yl}-N-{[3,5-dichloro-2-(cyclopropylmethoxy)phenyl]methyl}piperidin-3-amine |
| 1930 | 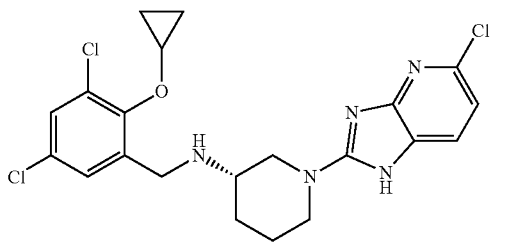 [SMILES: Clc1cc(Cl)c(OC2CC2)c(CN[C@H]2CCCN(c3nc4nc(Cl)ccc4[nH]3)C2)c1] | (3S)-1-{5-chloro-1H-imidazo[4,5-b]pyridin-2-yl}-N-[(3,5-dichloro-2-cyclopropoxyphenyl)methyl]piperidin-3-amine |
| 1931 | 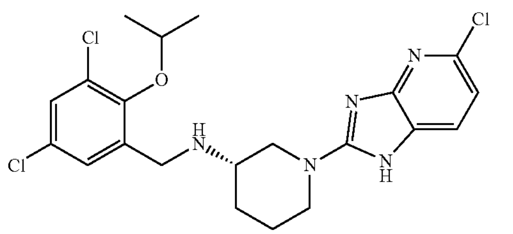 [SMILES: CC(C)Oc1c(Cl)cc(Cl)cc1CN[C@H]1CCCN(c2nc3nc(Cl)ccc3[nH]2)C1] | (3S)-1-{5-chloro-1H-imidazo[4,5-b]pyridin-2-yl}-N-{[3,5-dichloro-2-(propan-2-yloxy)phenyl]methyl}piperidin-3-amine |
| 1932 | 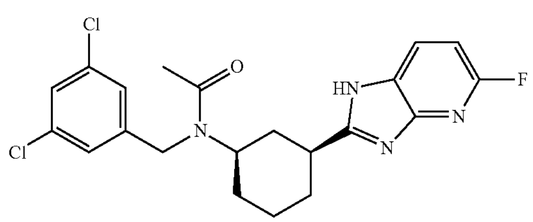 [SMILES: CC(=O)N(Cc1cc(Cl)cc(Cl)c1)[C@@H]1CCC[C@H](c2nc3nc(F)ccc3[nH]2)C1] | N-[(3,5-dichlorophenyl)methyl]-N-[(1R,3S)-3-{5-fluoro-1H-imidazo[4,5-b]pyridin-2-yl}cyclohexyl]acetamide |
| 1933 | 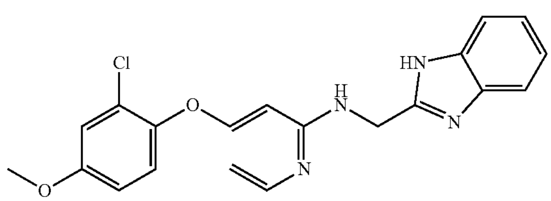 [SMILES: C=C/N=C(\C=C\Oc1ccc(OC)cc1Cl)NCc1nc2ccccc2[nH]1] | N-(1H-1,3-benzodiazol-2-ylmethyl)-4-(2-chloro-4-methoxyphenoxy)pyridin-2-amine |
| 1934 | 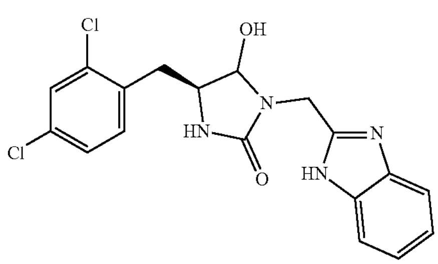 [SMILES: O=C1N[C@@H](Cc2ccc(Cl)cc2Cl)C(O)N1Cc1nc2ccccc2[nH]1] | (4S)-1-(1H-3,3-benzodiazol-2-ylmethyl)-4-[(2,4-dichlorophenyl)methyl]-5-hydroxyimidazolidin-2-one |

| No. | Chemical Structure | Chemical Name |
|---|---|---|
| 1935 | 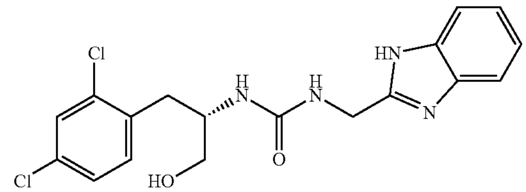 [SMILES: O=C(NCc1nc2ccccc2[nH]1)N[C@H](CO)Cc1ccc(Cl)cc1Cl] | 3-(1H-1,3-benzodiazol-2-ylmethyl)-1-[(2S)-1-(2,4-dichlorophenyl)-3-hydroxypropan-2-yl]urea |
| 1936 | 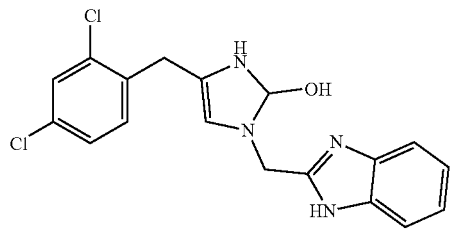 [SMILES: OC1NC(Cc2ccc(Cl)cc2Cl)=CN1Cc1nc2ccccc2[nH]1] | 1-(1H-1,3-benzodiazol-2-ylmethyl)-4-[(2,4-dichlorophenyl)methyl]-2,3-dihydro-3H-imidazol-2-ol |
| 1937 | 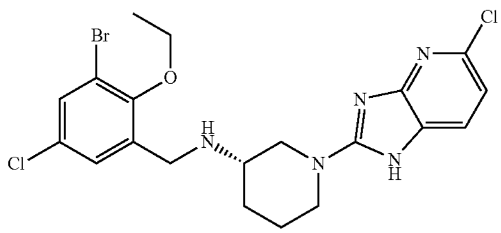 [SMILES: CCOc1c(Br)cc(Cl)cc1CN[C@H]1CCCN(c2nc3nc(Cl)ccc3[nH]2)C1] | (3S)-N-[(3-bromo-5-chloro-2-ethoxyphenyl)methyl]-1-{5-chloro-1H-imidazo[4,5-b]pyridin-2-yl}piperidin-3-amine |
| 1938 | 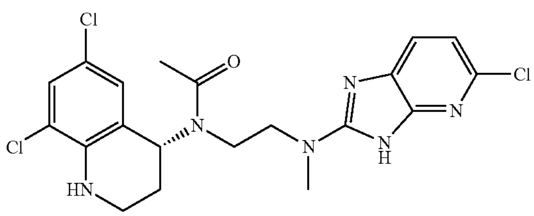 [SMILES: CC(=O)N(CCN(C)c1nc2ccc(Cl)nc2[nH]1)[C@@H]1CCNc2c(Cl)cc(Cl)cc21] | N-[2-({5-chloro-3H-imidazo[4,5-b]pyridin-2-yl}(methyl)amino)ethyl]-N-[(4R)-6,8-dichloro-1,2,3,4-tetrahydroquinolin-4-yl]acetamide |
| 1939 | 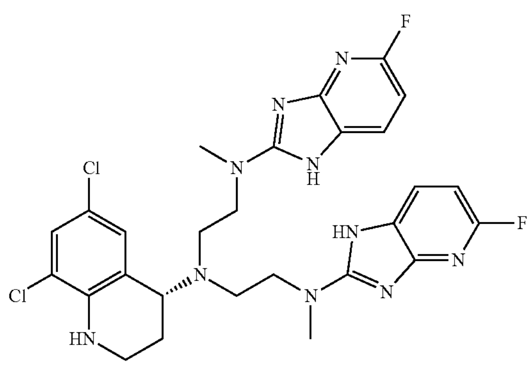 [SMILES: CN(CCN(CCN(C)c1nc2nc(F)ccc2[nH]1)[C@@H]1CCNc2c(Cl)cc(Cl)cc21)c1nc2nc(F)ccc2[nH]1] | N-(2-{[(4R)-6,8-dichloro-1,2,3,4-tetrahydroquinolin-4-yl][2-({5-fluoro-1H-imidazo[4,5-b]pyridin-2-yl}(methyl)amino)ethyl]amino}ethyl)-5-fluoro-N-methyl-1H-imidazo[4,5-b]pyridin-2-amine |
| 1940 | 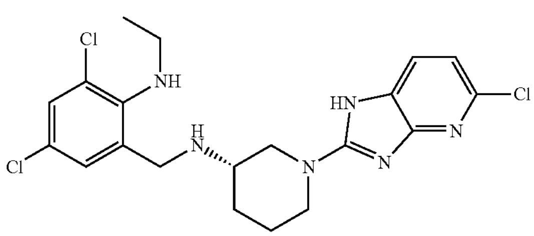 [SMILES: CCNc1c(Cl)cc(Cl)cc1CN[C@H]1CCCN(c2nc3nc(Cl)ccc3[nH]2)C1] | (3S)-1-{5-chloro-1H-imidazo[4,5-b]pyridin-2-yl}-N-{[3,5-dichloro-2-(ethylamino)phenyl]methyl}piperidin-3-amine |

-continued

| No. | Chemical Structure | Chemical Name |
|---|---|---|
| 1941 | 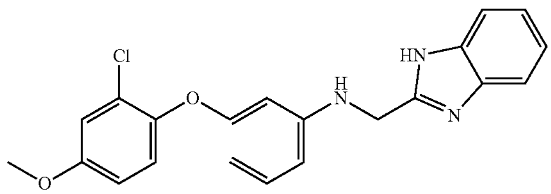 [SMILES: C=C/C=C(\C=C\Oc1ccc(OC)cc1Cl)NCc1nc2ccccc2[nH]1] | N-(1H-1,3-benzodiazol-2-ylmethyl)-3-(2-chloro-4-methoxyphenoxy)aniline |
| 1942 | 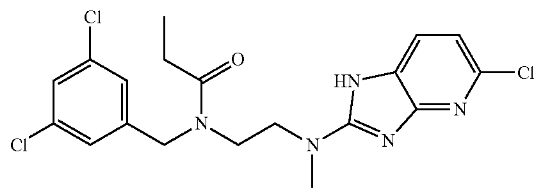 [SMILES: CCC(=O)N(CCN(C)c1nc2nc(Cl)ccc2[nH]1)Cc1cc(Cl)cc(Cl)c1] | N-[2-({5-chloro-1H-imidazo[4,5-b]pyridin-2-yl}(methyl)amino)ethyl]-N-[(3,5-dichlorophenyl)methyl]propanamide |
| 1943 | 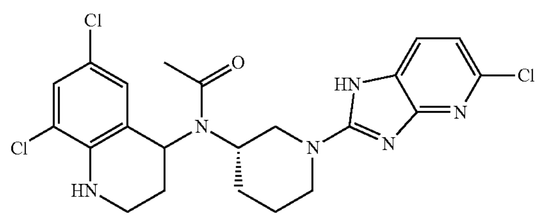 [SMILES: CC(=O)N(C1CCNc2c(Cl)cc(Cl)cc21)[C@H]1CCCN(c2nc3nc(Cl)ccc3[nH]2)C1] | N-[(3S)-2-{5-chloro-1H-imidazo[4,5-b]pyridin-2-yl}piperidin-3-yl]-N-(6,8-dichloro-1,2,3,4-tetrahydroquinolin-4-yl)acetamide |
| 1944 | 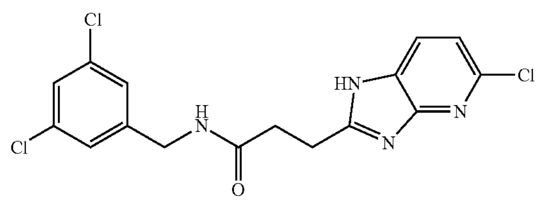 [SMILES: O=C(CCc1nc2nc(Cl)ccc2[nH]1)NCc1cc(Cl)cc(Cl)c1] | 3-{5-chloro-1H-imidazo[4,5-b]pyridin-2-yl}-N-[(3,5-dichlorophenyl)methyl]propanamide |
| 1945 | 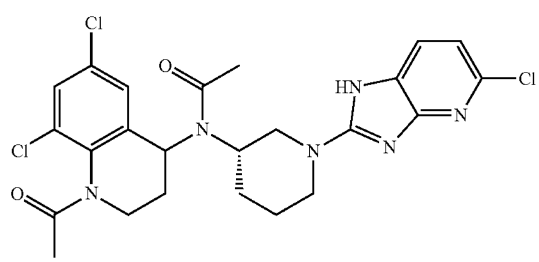 [SMILES: CC(=O)N1CCC(N(C(C)=O)[C@H]2CCCN(c3nc4nc(Cl)ccc4[nH]3)C2)c2cc(Cl)cc(Cl)c21] | N-(1-acetyl-6,8-dichloro-1,2,3,4-tetrahydroquinolin-4-yl)-N-[(3S)-3-{5-chloro-1H-imidazo[4,5-b]pyridin-2-yl}piperidin-3-yl]acetamide |
| 1949 | 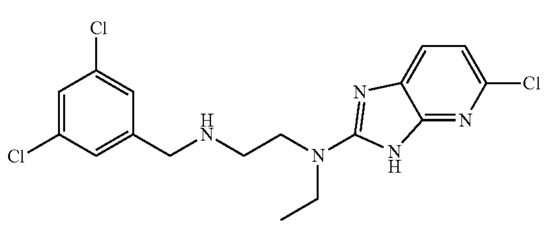 [SMILES: CCN(CCNCc1cc(Cl)cc(Cl)c1)c1nc2ccc(Cl)nc2[nH]1] | 5-chloro-N-(2-{[(3,5-dichlorophenyl)methyl]amino}ethyl)-N-ethyl-3H-imidazo[4,5-b]pyridin-2-amine |
| 1950 | 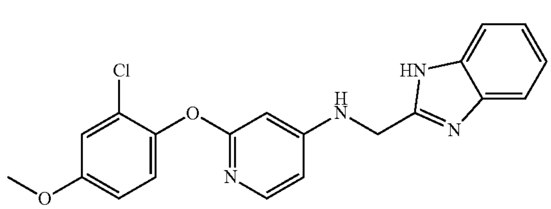 [SMILES: COc1ccc(Oc2cc(NCc3nc4ccccc4[nH]3)ccn2)c(Cl)c1] | N-(1H-1,3-benzodiazol-2-ylmethyl)-2-(2-chloro-4-methoxyphenoxy)pyridin-4-amine |

| No. | Chemical Structure | Chemical Name |
|---|---|---|
| 1951 | 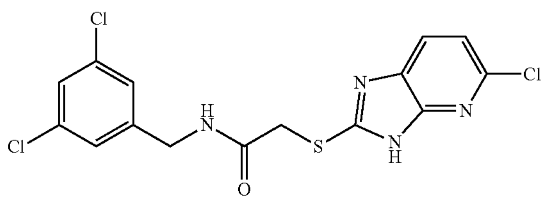 [SMILES: O=C(CSc1nc2ccc(Cl)nc2[nH]1)NCc1cc(Cl)cc(Cl)c1] | 2-({5-chloro-3H-imidazo[4,5-b]pyridin-2-yl}sulfanyl)-N-[(3,5-dichlorophenyl)methyl]acetamide |
| 1952 | 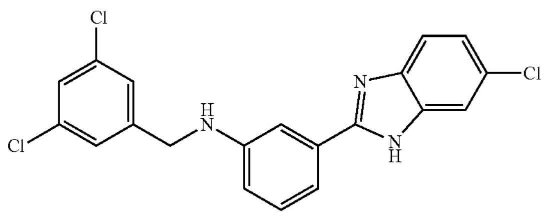 [SMILES: Clc1cc(Cl)cc(CNc2cccc(-c3nc4ccc(Cl)cc4[nH]3)c2)c1] | 3-(6-chloro-1H-1,3-benzodiazol-2-yl)-N-[(3,5-dichlorophenyl)methyl]aniline |
| 1953 | 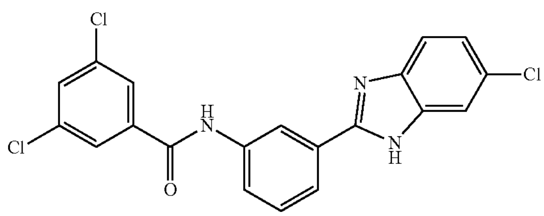 [SMILES: O=C(Nc1cccc(-c2nc3ccc(Cl)cc3[nH]2)c1)c1cc(Cl)cc(Cl)c1] | 3,5-dichloro-N-[3-(6-chloro-1H-1,3-benzodiazol-2-yl)phenyl]benzamide |
| 1954 | 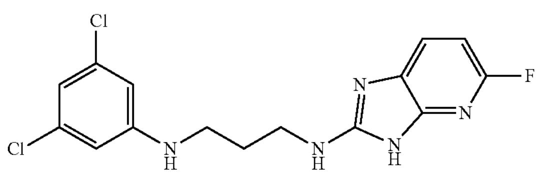 [SMILES: Fc1ccc2nc(NCCCNc3cc(Cl)cc(Cl)c3)[nH]c2n1] | 3,5-dichloro-N-[3-({5-fluoro-3H-imidazo[4,5-b]pyridin-2-yl}amino)propyl]aniline |
| 1955 | 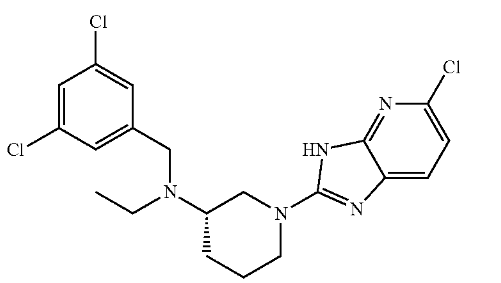 [SMILES: CCN(Cc1cc(Cl)cc(Cl)c1)[C@H]1CCCN(c2nc3ccc(Cl)nc3[nH]2)C1] | (3S)-1-{5-chloro-3H-imidazo[4,5-b]pyridin-2-yl}-N-[(3,5-dichlorophenyl)methyl]-N-ethylpiperidin-3-amine |
| 1956 | 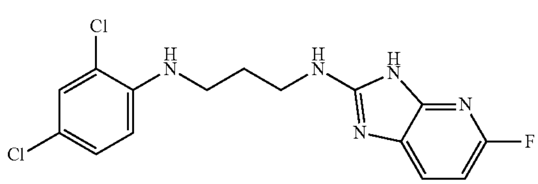 [SMILES: Fc1ccc2nc(NCCCNc3ccc(Cl)cc3Cl)[nH]c2n1] | 2,4-dichloro-N-[3-({5-fluoro-3H-imidazo[4,5-b]pyridin-2-yl}amino)propyl]aniline |
| 1957 | 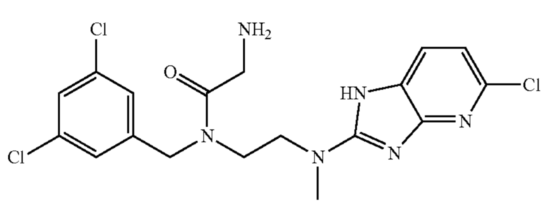 [SMILES: CN(CCN(Cc1cc(Cl)cc(Cl)c1)C(=O)CN)c1nc2nc(Cl)ccc2[nH]1] | 2-amino-N-[2-({5-chloro-1H-imidazo[4,5-b]pyridin-2-yl}(methyl)amino)ethyl]-N-[(3,5-dichlorophenyl)methyl]acetamide |

| No. | Chemical Name |
|---|---|
| 1958 | 3-amino-N-[2-({5-chloro-1H-imidazo[4,5-b]pyridin-2-yl}(methyl)amino)ethyl]-N-[(3,5-dichlorophenyl)methyl] propanamide |
| 1959 | N-[(3,5-dichlorophenyl)methyl]-N-[3-({5-fluoro-3H-imidazo[4,5-b]pyridin-2-yl}amino)propyl]acetamide |
| 1960 | 4-(2-chloro-4-methoxyphenoxy)-N-({5-fluoro-3H-imidazo[4,5-b]pyridin-2-yl}methyl)pyridin-2-amine |
| 1962 | 4-[(2,4-dichlorophenyl)methyl]-1-({5-fluoro-3H-imidazo[4,5-b]pyridin-2-yl}methyl)-2,3-dihydro-1H-imidazol-2-one |
| 1963 | methyl N-[2-({5-chloro-3H-imidazo[4,5-b]pyridin-2-yl}(methyl)amino)ethyl]-N-[(3,5-dichlorophenyl)methyl]carbamate |
| 1964 | methyl N-[(3,5-dichlorophenyl)methyl]-N-[3-({5-fluoro-3H-imidazo[4,5-b]pyridin-2-yl}amino)propyl]carbamate |
| 1965 | methyl 2-[(3-{[(3,5-dichlorophenyl)methyl](methoxycarbonyl)amino}propyl)amino]-5-fluoro-3H-imidazo[4,5-b]pyridine-3-carboxylate |

-continued

| No. | Chemical Structure | Chemical Name |
|---|---|---|
| 1966 | 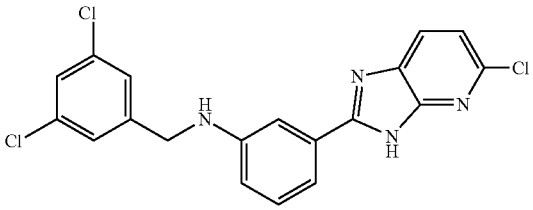 [SMILES: Clc1cc(Cl)cc(CNc2cccc(-c3nc4ccc(Cl)nc4[nH]3)c2)c1] | 3-{5-chloro-3H-imidazo[4,5-b]pyridin-2-yl}-N-[(3,5-dichlorophenyl)methyl]amine |
| 1967 | 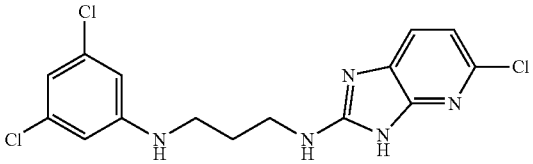 [SMILES: Clc1cc(Cl)cc(NCCCNc2nc3ccc(Cl)nc3[nH]2)c1] | 3,5-dichloro-N-[3-({5-chloro-3H-imidazo[4,5-b]pyridin-2-yl}amino)propyl]aniline |
| 1968 | 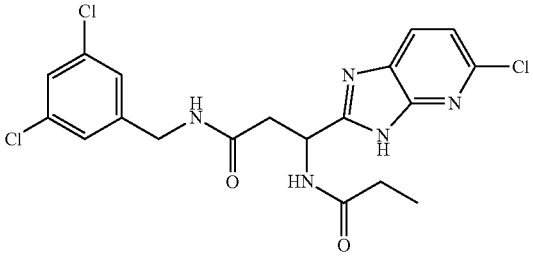 [SMILES: CCC(=O)NC(CC(=O)NCc1cc(Cl)cc(Cl)c1)c1nc2ccc(Cl)nc2[nH]1] | 3-{5-chloro-3H-imidazo[4,5-b]pyridin-2-yl}-N-[(3,5-dichlorophenyl)methyl]-3-propanamidopropanamide |
| 1969 | 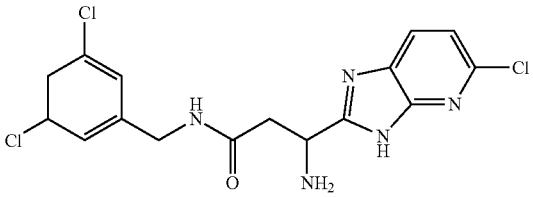 [SMILES: NC(CC(=O)NCC1=CC(Cl)CC(Cl)=C1)c1nc2ccc(Cl)nc2[nH]1] | 3-amino-3-{5-chloro-3H-imidazo[4,5-b]pyridin-2-yl}-N-[(3,5-dichlorophenyl)methyl]propanamide |
| 1970 | 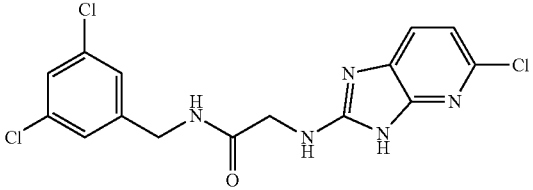 [SMILES: O=C(CNc1nc2ccc(Cl)nc2[nH]1)NCc1cc(Cl)cc(Cl)c1] | 2-({5-chloro-3H-imidazo[4,5-b]pyridin-2-yl}amino)-N-[(3,5-dichlorophenyl)methyl]acetamide |
| 1971 | 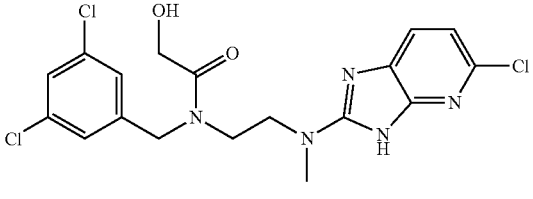 [SMILES: CN(CCN(Cc1cc(Cl)cc(Cl)c1)C(=O)CO)c1nc2ccc(Cl)nc2[nH]1] | N-[2-({5-chloro-3H-imidazo[4,5-b]pyridin-2-yl}(methyl)amino)ethyl]-N-[(3,5-dichlorophenyl)methyl]-2-hydroxyacetamide |
| 1972 | 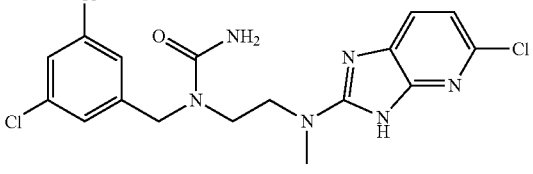 | 1-[2-({5-chloro-3H-imidazo[4,5-b]pyridin-2-yl}(methyl)amino)ethyl]-1-[(3,5-dichlorophenyl)methyl]urea |

-continued

| No. | Chemical Structure | Chemical Name |
|---|---|---|
| 1973 | 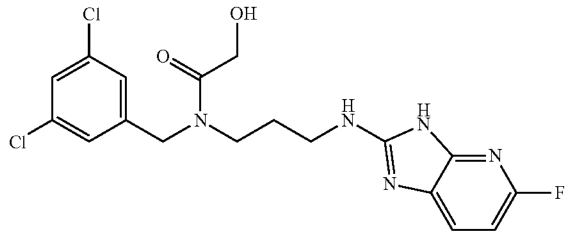 [SMILES: O=C(CO)N(CCCNc1nc2ccc(F)nc2[nH]1)Cc1cc(Cl)cc(Cl)c1] | N-[(3,5-dichlorophenyl)methyl]-N-[3-({5-fluoro-3H-imidazo[4,5-b]pyridin-2-yl}amino)propyl]-2-hydroxyacetamide |
| 1974 | 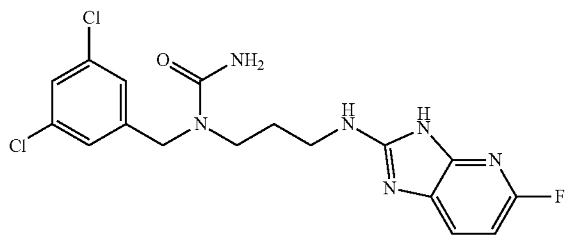 [SMILES: NC(=O)N(CCCNc1nc2ccc(F)nc2[nH]1)Cc1cc(Cl)cc(Cl)c1] | 1-[(3,5-dichlorophenyl)methyl]-1-[3-({5-fluoro-3H-imidazo[4,5-b]pyridin-2-yl}amino)propyl]urea |
| 1990 | 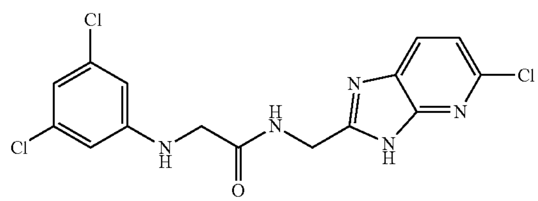 [SMILES: O=C(CNc1cc(Cl)cc(Cl)c1)NCc1nc2ccc(Cl)nc2[nH]1] | N-({5-chloro-3H-imidazo[4,5-b]pyridin-2-yl}methyl)-2-[(3,5-dichlorophenyl)amino]acetamide |
| 1991 | 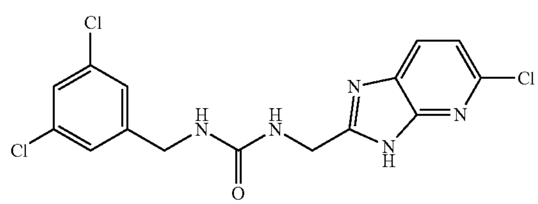 [SMILES: O=C(NCc1cc(Cl)cc(Cl)c1)NCc1nc2ccc(Cl)nc2[nH]1] | 3-({5-chloro-3H-imidazo[4,5-b]pyridin-2-yl}methyl)-1-[(3,5-dichlorophenyl)methyl]urea |
| 1992 | 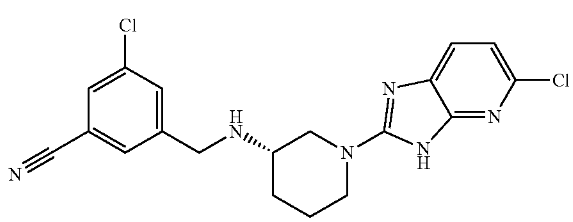 [SMILES: N#Cc1cc(Cl)cc(CN[C@H]2CCCN(c3nc4ccc(Cl)nc4[nH]3)C2)c1] | 3-chloro-5-({[(3S)-1-{5-chloro-3H-imidazo[4,5-b]pyridin-2-yl}piperidin-3-yl]amino}methyl)benzonitrile |
| 1994 | 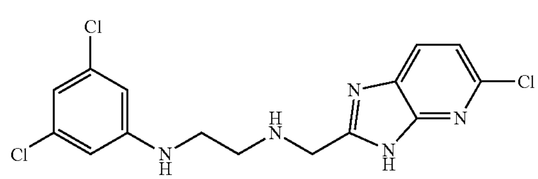 [SMILES: Clc1cc(Cl)cc(NCCNCc2nc3ccc(Cl)nc3[nH]2)c1] | ({5-chloro-3H-imidazo[4,5-b]pyridin-2-yl}methyl)({2-[(3,5-dichlorophenyl)amino]ethyl})amine |
| 1996 | 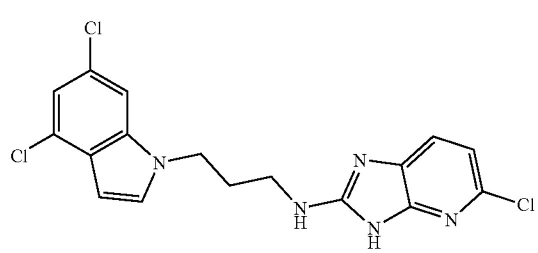 [SMILES: Clc1cc(Cl)c2ccn(CCCNc3nc4ccc(Cl)nc4[nH]3)c2c1] | 5-chloro-N-[3-(4,6-dichloro-1H-indol-1-yl)propyl]-3H-imidazo[4,5-b]pyridin-2-amine |

In one embodiment, the compound has the structure of formula (II):

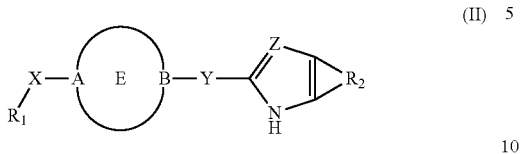

or a pharmaceutically acceptable salt thereof,
wherein
- $R_1$ is an aryl or heteroaryl ring, each optionally substituted with from 1 to 3 substituents independently selected from halogen, cyano, hydroxy, (C1-6)alkyl (optionally substituted by halogen, hydroxy, amino, mono to perfluoro(C1-3)alkyl, carboxy or (C1-6)alkoxycarbonyl), (C1-6)alkenyl (C3-7)cycloalkyl, C(1-6)alkoxy, amino;
- $R_2$ is a aryl or heteroaryl ring which is optionally substituted with from 1 to 3 substituents independently selected from halogen, cyano, hydroxy, (C1-6)alkyl (optionally substituted by halogen, hydroxy, amino, mono to perfluoro(C1-3)alkyl, carboxy or (C1-6)alkoxycarbonyl), (C3-7)cycloalkyl, C(1-6)alkoxy, amino, mono- or di-(C1-6)alkylamino, acylamino, carboxy, (C1-6)alkoxycarbonyl, carboxy(C1-6)alkyloxy, (C1-6)alkylthio, (C1-6)alkylsulphinyl, (C1-6)alkylsulphonyl, sulphamoyl, mono- and di-(C1-6)alkylsulphamoyl, carbamoyl, mono- and di-(C1-6)alkylcarbamoyl, and heterocyclyl;
- X is absent or a linker selected from the optionally substituted groups consisting of $C_{1-6}$ alkanes, $C_{1-6}$alkenes, $C_{1-6}$alkynes, $C_{1-6}$ alcohols, ethers, thio ethers, amines, amides, carbamates, ureas and combinations thereof,
- E is absent or a 3- to 8-membered cycloalkyl, heterocycloalkyl, cycloalkenyl, heterocycloalkenyl, aryl, or heteroaryl group wherein A and B disposed in the 1,2-, 1,3-, or 1,4-positions are independently selected from the group consisting of —C—, —CH—, —CH$_2$—, —N— or —N($R^7$), where $R^7$ is H or $C_{1-12}$ alkyl,
  wherein E is optionally substituted with (C1-6)alkyl, —O—(C1-6)alkyl, aryl —O-aryl, heteroaryl, —O-heteroaryl, heterocycloalkyl, —OH, —NH$_2$, —NH(C1-6)alkyl, —N((C1-6)alkyl)$_2$, —NH-aryl, —NH-heteroaryl, —N(H)C(O)(C1-6)alkyl, —C(O)N(H)(C1-6)alkyl, —C(O)N((C1-6)alkyl)$_2$, —N(H)C(O)O(C1-6)alkyl, —OC(O)N(H)(C1-6)alkyl, —OC(O)N((C1-6)alkyl)$_2$, —N(H)C(O)N(H)(C1-6)alkyl, —N(H)C(O)N((C1-6)alkyl)$_2$, halogen, nitrile or —NH—CH$_2$-heteroaryl, where the aryl, heterocycloalkyl and heteroaryl are optionally substituted with —OH, —NH$_2$, —NH(C1-6)alkyl, —N((C1-6)alkyl)$_2$, —N(H)C(O)(C1-6)alkyl, —C(O)N(H)(C1-6)alkyl, —C(O)N((C1-6)alkyl)$_2$, —N(H)C(O)O(C1-6)alkyl, —OC(O)N(H)(C1-6)alkyl, —OC(O)N((C1-6)alkyl)$_2$, —N(H)C(O)N(H)(C1-6)alkyl, —N(H)C(O)N((C1-6)alkyl)$_2$, nitrile, heteroaryl, halogen, or (C1-6)alkyloxy
- Y is absent or a linker selected from the optionally substituted group consisting of C1-3 alkyl, secondary and tertiary amine, thiol, thiol ether, alcohol, ether, ester, amine, amide, carbamate, and urea groups and combinations thereof; and
- Z is N or CR$_6$, wherein R$_6$ selected from H, $C_{1-12}$ alkyl, $C_{1-12}$ halogen-alkyl, $C_{1-12}$ alkenyl, $C_{1-12}$ alkynyl, optionally substituted aryl, optionally substituted heteroaryl, optionally substituted cyclic, optionally substituted heterocyclic, $C_{1-12}$ alcohol, halogen, cyano, ether, thio ether, ester, amine, amide, carbamate, and urea groups; provided that 1) when E is absent, Z is NH and $R_2$ is unsubstituted heteroaryl, X and Y, alone or in combination, do not form —CH$_2$—NH—CH$_2$—CH$_2$—NH—, —CH$_2$—NH—CH$_2$—CH$_2$—CH$_2$—NH— or —CH$_2$—NH—CH$_2$—CH$_2$—CH$_2$—CH$_2$—NH—;

2) when E is pyrimidine and Z is NH, $R_2$ is not phenyl;

3) when E is absent, Z is NH and $R_2$ is unsubstituted phenyl, or pyridinyl substituted with 1-2 fluoro groups, X and Y, alone or in combination, do not form —CH$_2$—NH—CH$_2$—CH$_2$—CH$_2$—NH—;

4) (a) when E is absent, Z is NH and $R_2$ is pyridinyl substituted with methyl, X and Y, alone or in combination, do not form —CH$_2$—NH—CH$_2$—CH$_2$—CH$_2$—NH—;

(b) when E is absent and $R_2$ is pyridinyl or unsubstituted phenyl, X and Y, alone or in combination, do not form —O—CH$_2$—CH$_2$—C(O)—NH—CH$_2$— or —O—CH$_2$—CH$_2$—C(O)—N(Me)-CH$_2$—;

(c) when E is absent, $R_1$ is dichlorophenyl and $R_2$ is unsubstituted phenyl, X and Y, alone or in combination, do not form —O—CH═CH—C(O)—NH—CH$_2$—; and (d) when E is absent and $R_2$ is pyridinyl, X and Y, alone or in combination, do not form —CH$_2$—NH—CH$_2$—CH(Me)-CH$_2$—NH—, —CH$_2$—NH—CH$_2$—CH(OH)—CH$_2$—NH—, —CH$_2$—NH—CH$_2$—C(Me)$_2$-CH$_2$—NH— or —CH$_2$—NH—CH$_2$—CH$_2$—C(O)—NH—.

In some embodiments, E is optionally substituted with —O-aryl, heterocycloalkyl, —OH, halogen or —NH—CH$_2$-heteroaryl, where the aryl, heterocycloalkyl and heteroaryl are optionally substituted with heteroaryl, halogen, or (C1-6)alkyloxy.

In some embodiments, the compound of formula (II) has the structure of formula (IIa):

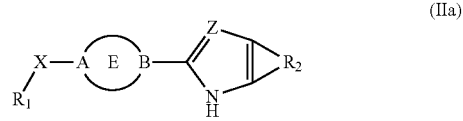

or a pharmaceutically acceptable salt thereof.

In some embodiments, the compound of formula (II) has the structure of formula (IIb):

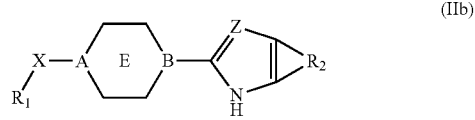

or a pharmaceutically acceptable salt thereof,
wherein A and B are in the 1,4-positions.

In some embodiments, the compound of formula (II) has the structure of formula (IIc):

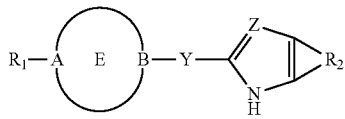

(IIc)

or a pharmaceutically acceptable salt thereof.

In some embodiments, the compound of formula (II) has the structure of formula (IId):

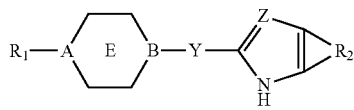

(IId)

or a pharmaceutically acceptable salt thereof, wherein A and B are in the 1,4-positions.

In some embodiments, the compound of formula (II) has the structure of formula (IIe):

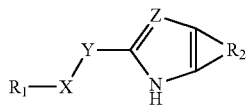

(IIe)

or a pharmaceutically acceptable salt thereof.

In some embodiments, A and B are independently —N— or —CH—.

In some embodiments, $R_1$ is aryl optionally substituted with from 1 to 3 substituents independently selected from halogen, cyano, hydroxy, (C1-6)alkyl (optionally substituted by halogen, hydroxy and amino), (C3-7)cycloalkyl and C(1-6)alkoxy.

In some embodiments, $R_1$ is phenyl substituted with from 1 to 3 substituents independently selected from halogen and C(1-6)alkoxy. For example, $R_1$ may be phenyl substituted with 2 substituents independently selected from halogen and C(1-6)alkoxy.

In some embodiments, $R_1$ is phenyl substituted with two chloro groups.

In some embodiments, $R_2$ is a 5 or 6-membered aryl or heteroaryl ring which is optionally substituted with from 1 to 3 substituents independently selected from halogen, cyano, hydroxy, (C1-6)alkyl, perfluoro(C1-3)alkyl, (C3-7) cycloalkyl, C(1-6)alkoxy, amino, mono- or di-(C1-6)alkylamino, acylamino or carboxy.

In other embodiments, $R_2$ is aryl optionally substituted with from 1 to 3 substituents independently selected from halogen, cyano, hydroxy, (C1-6)alkyl, perfluoro(C1-3)alkyl, (C3-7)cycloalkyl, C(1-6)alkoxy, amino, mono- or di-(C1-6) alkylamino, acylamino or carboxy. For example, $R_2$ may be phenyl optionally substituted with from 1 to 3 substituents independently selected from halogen, (C1-6)alkyl, perfluoro (C1-3)alkyl or amino.

In some embodiments, $R_2$ is unsubstituted phenyl. In other embodiments, $R_2$ is phenyl substituted with two substituents independently selected from halogen, (C1-6)alkyl and perfluoro(C1-3)alkyl. For example, $R_2$ may be phenyl substituted with one halogen. In some examples, the halogen is fluoro.

In some embodiments, $R_2$ is heteroaryl optionally substituted with from 1 to 3 substituents independently selected from halogen, cyano, hydroxy, (C1-6)alkyl, perfluoro(C1-3)alkyl, (C3-7)cycloalkyl, C(1-6)alkoxy, amino, mono- or di-(C1-6)alkylamino, acylamino or carboxy. For example, $R_2$ may be pyridyl optionally substituted with from 1 to 3 substituents independently selected from halogen, (C1-6) alkyl, perfluoro(C1-3)alkyl or amino.

In some embodiments, $R_2$ is unsubstituted pyridyl. In other embodiments, $R_2$ is pyridyl substituted with two substituents independently selected from halogen, (C1-6)alkyl and perfluoro(C1-3)alkyl. For example, $R_2$ may be pyridyl substituted with one halogen. In some embodiments, the halogen is fluoro.

In some embodiments, X is (C1-6)alkyl, —N($R_8$)—, —(C1-6)alkyl-N($R_8$)—, (C1-6)alkyl-N($R_8$)—(C1-6)alkyl, —O—, —(C1-6)alkyl-O—, (C1-6)alkyl-O—(C1-6)alkyl, —(C1-6)alkenyl-O—, (C1-6)alkenyl-O—(C1-6)alkenyl, —S—, —(C1-6)alkyl-S—, (C1-6)alkyl-S—(C1-6)alkyl, —C(O)N($R_8$)—, —C(O)N($R_8$)—(C1-6)alkyl-, —(C1-6)alkyl-C(O)N($R_8$)—, —(C1-6)alkyl-C(O)N($R_8$)—(C1-6)alkyl-, —C(O)—, —(C1-6)alkyl-C(O)—, —(C1-6)alkyl-C(O)—(C1-6)alkyl-, —C(O)O—, —(C1-6)alkyl-C(O)O—, —C(O)O—(C1-6)alkyl-, —(C1-6)alkyl-C(O)O—(C1-6)alkyl-, —OC(O)N($R_8$)—, —OC(O)N($R_8$)—(C1-6)alkyl-, —(C1-6)alkyl-OC(O)N($R_8$)—, —(C1-6)alkyl-OC(O)N ($R_8$)—(C1-6)alkyl-, —N($R_8$)C(O)N($R_8$)—, —N($R_8$)C(O)N ($R_8$)—(C1-6)alkyl-, —(C1-6)alkyl-N($R_8$)C(O)N($R_8$)—(C1-6)alkyl-, wherein $R_8$ is hydrogen, (C1-6)alkyl, —C(O)—(C1-6) alkyl, —C(O)O—(C1-6)alkyl, and wherein each (C1-6)alkyl is optionally substituted with (C1-6)alkyl, —N($R_8$)$_2$, —OH or —O—(C1-6)alkyl.

In other embodiments, X is —CH$_2$—, —CH$_2$CH$_2$—, —CH$_2$CH$_2$CH$_2$—, —CH(CH$_3$)CH2-, —CH$_2$—N($R_8$)—, —CH$_2$—N($R_8$)—CH$_2$—, —CH$_2$CH$_2$—N($R_8$)—, —CH$_2$CH$_2$—N($R_8$)—CH$_2$CH$_2$—, —CH(CH$_3$)CH$_2$—N ($R_8$)—, —CH(OH)CH$_2$—N($R_8$)—, —CH$_2$—O—, —CH$_2$—O—CH$_2$—, —CH$_2$CH$_2$—O—, —CH$_2$CH$_2$—O—CH$_2$CH$_2$—, —CH$_2$—C(O)—, —CH$_2$—C(O)—CH$_2$—, —CH$_2$CH$_2$—C(O)—, —CH$_2$CH$_2$—C(O)—CH$_2$CH$_2$—, —CH$_2$—C(O)N($R_8$)—, —CH$_2$—C(O)N($R_8$)—CH$_2$—, —CH$_2$CH$_2$—C(O)N($R_8$)—, —CH$_2$CH$_2$—C(O)N($R_8$)—CH$_2$CH$_2$—, —CH$_2$—C(O)O—, —CH$_2$—C(O)O—CH$_2$—, —CH$_2$CH$_2$—C(O)O—, —CH$_2$CH$_2$—C(O)O—CH$_2$CH$_2$—, wherein $R_8$ is hydrogen or —C(O)CH$_3$.

In some embodiments, Y is (C1-6)alkyl, —N($R_8$)—, —(C1-6)alkyl-N($R_8$)—, (C1-6)alkyl-N($R_8$)—(C1-6)alkyl, —O—, —(C1-6)alkyl-O—, (C1-6)alkyl-O—(C1-6)alkyl, —(C1-6)alkenyl-O—, (C1-6)alkenyl-O—(C1-6)alkenyl, —S—, —(C1-6)alkyl-S—, (C1-6)alkyl-S—(C1-6)alkyl, —C(O)N($R_8$)—, —C(O)N($R_8$)—(C1-6)alkyl-, —(C1-6)alkyl-C(O)N($R_8$)—, —(C1-6)alkyl-C(O)N($R_8$)—(C1-6)alkyl-, —C(O)—, —(C1-6)alkyl-C(O)—, —(C1-6)alkyl-C(O)—(C1-6)alkyl-, —C(O)O—, —(C1-6)alkyl-C(O)O—, —C(O)O—(C1-6)alkyl-, —(C1-6)alkyl-C(O)O—(C1-6)alkyl-, —OC(O)N($R_8$)—, —OC(O)N($R_8$)—(C1-6)alkyl-, —(C1-6)alkyl-OC(O)N($R_8$)—, —(C1-6)alkyl-OC(O)N ($R_8$)—(C1-6)alkyl-, —N($R_8$)C(O)N($R_8$)—, —N($R_8$)C(O)N ($R_8$)—(C1-6)alkyl-, —(C1-6)alkyl-N($R_8$)C(O)N($R_8$)—(C1-6)alkyl-, wherein $R_8$ is hydrogen, (C1-6)alkyl, —C(O)—(C1-6) alkyl, —C(O)O—(C1-6)alkyl, and wherein each (C1-6)alkyl is optionally substituted with (C1-6)alkyl, —N(R$_8$)$_2$, —OH or —O—(C1-6)alkyl.

In other embodiments, Y is —CH$_2$—, —CH$_2$CH$_2$—, —CH$_2$CH$_2$CH$_2$—, —CH (CH$_3$)CH2-, —CH$_2$—N(R$_8$)—, —CH$_2$—N(R$_8$)—CH$_2$—, —CH$_2$CH$_2$—N(R$_8$)—, —CH$_2$CH$_2$—N(R$_8$)—CH$_2$CH$_2$—, —CH(CH$_3$)CH$_2$—N(R$_8$)—, —CH(OH)CH$_2$—N(R$_8$)—, —CH$_2$—O—, —CH$_2$—O—CH$_2$—, —CH$_2$CH$_2$—O—, —CH$_2$CH$_2$—O—CH$_2$CH$_2$—, —CH$_2$—C(O)—, —CH$_2$—C(O)—CH$_2$—, —CH$_2$CH$_2$—C(O)—, —CH$_2$CH$_2$—C(O)—CH$_2$CH$_2$—, —CH$_2$—C(O)N(R$_8$)—, —CH$_2$—C(O)N(R$_8$)—CH$_2$—, —CH$_2$CH$_2$—C(O)N(R$_8$)—, —CH$_2$CH$_2$—C(O)N(R$_8$)—CH$_2$CH$_2$—, —CH$_2$—C(O)O—, —CH$_2$—C(O)O—CH$_2$—, —CH$_2$CH$_2$—C(O)O—, —CH$_2$CH$_2$—C(O)O—CH$_2$CH$_2$—, wherein R$_8$ is hydrogen or —C(O)CH$_3$.

In some embodiments, the compound of formula (II) is one of the following compounds (or a pharmaceutically acceptable salt, prodrug, solvate or hydrate thereof):

| No. | Chemical Name |
|---|---|
| 1627 | 2-[(3-{[(3,5-dichlorophenyl)methyl]amino}propyl)amino]-1H-pyrrolo[3,2-b]pyridine-3-carbonitrile |
| 1671 | N-(1H-1,3-benzodiazol-2-ylmethyl)-2-(2,4-dichlorophenoxy)acetamide |
| 1674 | 2-(2,4-dichlorophenoxy)-N-(1H-indol-2-ylmethyl)acetamide |
| 1675 | N-[2-(1H-1,3-benzodiazol-2-yl)ethyl]-2-(2,4-dichlorophenoxy)acetamide |
| 1699 | benzyl N-{3H-imidazo[4,5-b]pyridin-2-ylmethyl}carbamate |
| 1701 | 2-(2,4-dichlorophenyl)ethyl N-(1H-1,3-benzodiazol-2-ylmethyl)carbamate |
| 1702 | 3-(1H-1,3-benzodiazol-2-ylmethyl)-1-[2-(2,4-dichlorophenyl)ethyl]urea |
| 1703 | (3R)-3-amino-N-(1H-1,3-benzodiazol-2-ylmethyl)-4-(4-fluorophenyl)butanamide |
| 1706 | 2-(2,4-dichlorophenyl)ethyl N-{3H-imidazo[4,5-b]pyridin-2-ylmethyl}carbamate |
| 1707 | 2-(2,4-dichlorophenyl)ethy N-({5-fluoro-3H-imidazo[4,5-b]pyridin-2-yl}methyl)carbamate |
| 1708 | [(3,5-dichlorophenyl)methyl][2,2-difluoro-3-({3H-imidazo[4,5-b]pyridin-2-yl}amino)propyl]amine |
| 1716 | N-(3-{[1-(3,5-dichlorophenyl)cyclopropyl]amino}propyl)-5-fluoro-3H-imidazo[4,5-b]pyridin-2-amine |
| 1720 | (3R)-3-amino-N-(1H-1,3-benzodiazol-2-ylmethyl)-4-(2,4-dichlorophenyl)butanamide |
| 1726 | (3S)-3-amino-N-(1H-1,3-benzodiazol-2-ylmethyl)-4-(2,4-dichlorophenyl)butanamide |
| 1728 | 2-(2,4-dichlorophenyl)ethyl N-(1H-1,3-benzodiazol-2-ylmethyl)-N-methylcarbamate |
| 1731 | 1-[3-(1H-1,3-benzodiazol-2-yl)piperidin-1-yl]-2-(2,4-dichlorophenyl)ethan-1-one |
| 1732 | 1-[3-(1H-1,3-benzodiazol-2-yl)piperidin-1-yl]-2-(3,5-dichlorophenyl)ethan-1-one |
| 1733 | 1-[3-(4-chloro-1H-1,3-benzodiazol-2-yl)piperidin-1-yl]-2-(3,5-dichlorophenyl)ethan-1-one |
| 1734 | 1-[3-(5-chloro-1H-1,3-benzodiazol-2-yl)piperidin-1-yl]-2-(3,5-dichlorophenyl)ethan-1-one |
| 1735 | 1-(1H-1,3-benzodiazol-2-ylmethyl)-4-[(2-chlorophenyl)methyl]piperazin-2-one |
| 1736 | 1-(1H-1,3-benzodiazol-2-ylmethyl)-4-[(3-chlorophenyl)methyl]piperazin-2-one |
| 1737 | (3E)-N-(1H-1,3-benzodiazol-2-ylmethyl)-4-(2,4-dichlorophenyl)but-3-enamide |
| 1738 | N-[1-(1H-1,3-benzodiazol-2-yl)cyclopropyl]-3-(2,4-dichlorophenoxy)propanamide |
| 1739 | 1H-1,3-benzodiazol-2-ylmethyl N-[2-(2,4-dichlorophenyl)ethyl]carbamate |
| 1740 | 3-(2,4-dichlorophenoxy)-N-[(6-fluoro-1H-1,3-benzodiazol-2-yl)methyl]propanamide |
| 1741 | 2-(2,4-dichlorophenyl)ethyl N-[(6-ffuoro-1H-1,3-benzodiazol-2-yl)methyl]carbamate |
| 1744 | 2-(3,5-dichlorophenyl)-1-[3-(5-fluoro-1H-1,3-benzodiazol-2-yl)piperidin-1-yl]ethan-1-one |
| 1745 | 1-[3-(5,6-dichloro-1H-1,3-benzodiazol-2-yl)piperidin-1-yl]-2-(3,5-dichlorophenyl)ethan-1-one |
| 1746 | 1-[3-(5-chloro-6-fluoro-1H-1,3-benzodiazol-2-yl)piperidin-1-yl]-2-(3,5-dichlorophenyl)ethan-1-one |
| 1747 | 1-(1H-1,3-benzodiazol-2-ylmethyl)-4-[(2,4-dichlorophenyl)methyl]piperazin-2-one |
| 1748 | 1-(1H-1,3-benzodiazol-2-ylmethyl)-4-[(3,5-dichlorophenyl)methyl]piperazin-2-one |
| 1752 | 2-({1-[(2,4-dichlorophenyl)methyl]-1H-1,2,3-triazol-4-yl}methyl)-1H-1,3-benzodiazole |
| 1753 | 2-({1-[(3,5-dichlorophenyl)methyl]-1H-1,2,3-triazol-4-yl}methyl)-1H-1,3-benzodiazole |
| 1754 | (5S)-3-(1H-1,3-benzodiazol-2-ylmethyl)-5-[(2,4-dichlorophenyl)methyl]imidazolidine-2,4-dione |
| 1755 | methyl (2S)-2-{[(1H-1,3-benzodiazol-2-ylmethyl)carbamoyl]amino}-3-(2,4-dichlorophenyl)propanoate |
| 1756 | N-(1H-1,3-benzodiazol-2-ylmethyl)-2-(5,7-dichloro-1-benzofuran-2-yl)acetamide |
| 1757 | 1-[(3R)-3-(5-chloro-1H-1,3-benzodiazol-2-yl)piperidin-1-yl]-2-(3,5-dichlorophenyl)ethan-1-one |
| 1758 | 1-[(3S)-3-(5-chloro-1H-1,3-benzodiazol-2-yl)piperidin-1-yl]-2-(3,5-dichlorophenyl)ethan-1-one |

-continued

| No. | Chemical Name |
|---|---|
| 1759 | 3-(5-chloro-1H-1,3-benzodiazol-2-yl)-N-(3,5-dichlorophenyl)piperidine-1-carboxamide |
| 1760 | 1-(1H-1,3-benzodiazol-2-ylmethyl)-4-(naphthalene-2-carbonyl)piperazin-2-one |
| 1761 | 2-(3,5-dichlorophenyl)-1-(3-{5-fluoro-1H-imidazo[4,5-b]pyridin-2-yl}piperidin-1-yl)ethan-1-one |
| 1762 | 1-(3-{5-chloro-1H-imidazo[4,5-b]pyridin-2-yl}piperidin-1-yl)-2-(3,5-dichlorophenyl)ethan-1-one |
| 1763 | N-(1H-1,3-benzodiazol-2-ylmethyl)-3-[(2,4-dichlorophenyl)amino]propanamide |
| 1764 | N-(1H-1,3-benzodiazol-2-ylmethyl)-2-(5,7-dichloro-1H-1,3-benzodiazol-2-yl)acetamide |
| 1765 | (2E)-N'-(1H-1,3-benzodiazol-2-yl)-3-(2,4-dichlorophenoxy)prop-2-enehydrazide |
| 1766 | (2E)-N-(1H-1,3-benzodiazol-2-yl)-3-(2,4-dichlorophenoxy)prop-2-enehydrazide |
| 1767 | [2-(6-chloro-1H-1,3-benzodiazol-2-yl)ethyl][(3,5-dichlorophenyl)methyl]amine |
| 1768 | (2E)-3-(2,4-dichlorophenoxy)-N-({5-fluoro-3H-imidazo[4,5-b]pyridin-2-yl}methyl)prop-2-enamide |
| 1769 | 3-[(1H-1,3-benzodiazol-2-ylmethyl)amino]-4-{[(2,4-dichlorophenyl)methyl]amino}cyclobut-3-ene-1,2-dione |
| 1779 | (2E)-N-(1H-1,3-benzodiazol-2-ylmethyl)-3-{2,4-dichloro-6-[(methylamino)methyl]phenoxy}prop-2-enamide |
| 1780 | (2-{5-chloro-3H-imidazo[4,5-b]pyridin-2-yl}ethyl)[(3,5-dichlorophenyl)methyl]amine |
| 1785 | 3-{5-chloro-1H-imidazo[4,5-b]pyridin-2-yl}-N-[(3,5-dichlorophenyl)methyl]piperidine-1-carboxamide |
| 1786 | N-(3-{5-chloro-1H-imidazo[4,5-b]pyridin-2-yl}cyclohexyl)-2-(3,5-dichlorophenyl)acetamide |
| 1787 | 2-amino-1-[(3S)-3-{5-chloro-1H-imidazo[4,5-b]pyridin-2-yl}piperidin-1-yl]-2-(3,5-dichlorophenyl)ethan-1-one |
| 1788 | 3-{5-chloro-1H-imidazo[4,5-b]pyridin-2-yl}-N-[(3,5-dichlorophenyl)methyl]cyclohexan-1-amine |
| 1789 | N-(3-{5-chloro-1H-imidazo[4,5-b]pyridin-2-yl}cyclohexyl)-N-[(3,5-dichlorophenyl)methyl]acetamide |
| 1790 | 1-(2-{5-chloro-1H-imidazo[4,5-b]pyridin-2-yl}morpholin-4-yl)-2-(3,5-dichlorophenyl)ethan-1-one |
| 1791 | N-(2-amnio-6-chloropyridin-3-yl)-4-[2-(3,5-dichlorophenyl)acetyl]piperazine-2-carboxamide |
| 1792 | (4S)-1-(1H-1,3-benzodiazol-2-ylmethyl)-4-[(2,4-dichlorophenyl)methyl]imidazolidin-2-one |
| 1793 | 3-{5-chloro-3H-imidazo[4,5-b]pyridin-2-yl}-1-[(3,5-dichlorophenyl)methyl]urea |
| 1794 | [1-(5-chloro-1H-1,3-benzodiazol-2-yl)propan-2-yl][(3,5-dichlorophenyl)methyl]amine |
| 1795 | 2-amino-3-(1H-1,3-benzodiazol-2-yl)-N-[2-(2,4-dichlorophenyl)ethyl]propanamide |
| 1796 | 2-chloro-6-(2-chloro-4-methoxyphenoxy)-N-({5-fluoro-3H-imidazo[4,5-b]pyridin-2-yl}methyl)pyrimidin-4-amine |
| 1797 | 6-(2-chloro-4-methoxyphenoxy)-N-({5-fluoro-3H-imidazo[4,5-b]pyridin-2-yl}methyl)-2-[4-(pyrazin-2-yl)piperazin-1-yl]pyrimidin-4-amine |
| 1798 | 1-[2-(3,5-dichlorophenyl)ethyl]-3-{5-fluoro-1H-imidazo[4,5-b]pyridin-2-yl}piperidine |
| 1799 | (2S)-2-amino-1-[(3S)-3-{5-chloro-1H-imidazo[4,5-b]pyridin-2-yl}piperidin-1-yl]-3-(2,4-dichlorophenyl)propan-1-one |
| 1800 | N-[(3,5-dichlorophenyl)methyl]-3-{5-fluoro-1H-imidazo[4,5-b]pyridin-2-yl}cyclohexan-1-amine |
| 1801 | N-[(3,5-dichlorophenyl)methyl]-N-(3-{5-fluoro-1H-imidazo[4,5-b]pyridin-2-yl}cyclohexyl)acetamide |
| 1802 | N-(1H-1,3-benzodiazol-2-ylmethyl)-N'-[(2,4-dichlorophenyl)methyl]ethanediamide |
| 1803 | N-(1H-1,3-benzodiazol-2-ylmethyl)-N'-(2,4-dichlorophenyl)propanediamide |
| 1804 | 2-(6-chloro-1H-1,3-benzodiazol-2-yl)-N-[(3,5-dichlorophenyl)methyl]acetamide |
| 1805 | [(2S)-1-(6-chloro-1H-1,3-benzodiazol-2-yl)propan-2-yl][(3,5-dichlorophenyl)methyl]amine |
| 1806 | [(2R)-1-(6-chloro-1H-1,3-benzodiazol-2-yl)propan-2-yl][(3,5-dichlorophenyl)methyl]amine |
| 1807 | (2S)-2-amino-N-(1H-1,3-benzodiazol-2-ylmethyl)-3-(2,4-dichlorophenoxy)propanamide |
| 1808 | (2S)-N-(1H-1,3-benzodiazol-2-ylmethyl)-3-(2,4-dichlorophenyl)-2-(methylamino)propanamide |
| 1809 | 3-{5-chloro-1H-imidazo[4,5-b]pyridin-2-yl}-N-[(2,4-dichlorophenyl)methyl]cyclohexan-1-amine |
| 1810 | N-(3-{5-chloro-1H-imidazo[4,5-b]pyridin-2-yl}cyclohexyl)-N-[(2,4-dichlorophenyl)methyl]acetamide |
| 1811 | 1-{5-chloro-1H-imidazo[4,5-b]pyridin-2-yl}-N-[(3,5-dichlorophenyl)methyl]piperidin-3-amine |

-continued

| No. | Chemical Name |
|---|---|
| 1812 | 3-{5-chloro-1H-imidazo[4,5-b]pyridin-2-yl}-1-[2-(3,5-dichlorophenyl)ethyl]piperidine |
| 1813 | 5-chloro-2-[(3S)-1-[(3,5-dichlorophenyl)methyl]piperidin-3-yl]-1H-1,3-benzodiazole |
| 1814 | 3-({5-chloro-1H-imidazo[4,5-b]pyridin-2-yl}methyl)-1-[(3,5-dichlorophenyl)methyl]piperidine |
| 1815 | 3-(1H-1,3-benzodiazol-2-yl)-N-[(3,5-dichlorophenyl)methyl]cyclohexan-1-amine |
| 1816 | N-[3-(1H-1,3-benzodiazol-2-yl)cyclohexyl]-N-[(3,5-dichlorophenyl)methyl]acetamide |
| 1817 | N-[(3,5-dichlorophenyl)methyl]-3-{1H-imidazo[4,5-b]pyridin-2-yl}cyclohexan-1-amine |
| 1818 | N-[(3,5-dichlorophenyl)methyl]-N-(3-{1H-imidazo[4,5-b]pyridin-2-yl}cyclohexyl)acetamide |
| 1819 | [1-(1H-1,3-benzodiazol-2-yl)propan-2-yl][(3,5-dichlorophenyl)methyl]amine |
| 1820 | [(3,5-dichlorophenyl)methyl][1-(6-methyl-1H-1,3-benzodiazol-2-yl)propan-2-yl]amine |
| 1821 | [1-(6-bromo-1H-1,3-benzodiazol-2-yl)propan-2-yl][(3,5-dichlorophenyl)methyl]amine |
| 1822 | [1-(5,6-dichloro-1H-1,3-benzodiazol-2-yl)propan-2-yl][(3,5-dichlorophenyl)methyl]amine |
| 1823 | [1-(4,6-dichloro-1H-1,3-benzodiazol-2-yl)propan-2-yl][(3,5-dichlorophenyl)methyl]amine |
| 1824 | [1-(6-chloro-5-fluoro-1H-1,3-benzodiazol-2-yl)propan-2-yl][(3,5-dichlorophenyl)methyl]amine |
| 1825 | [(3,5-dichlorophenyl)methyl]({1-[6-(trifluoromethyl)-1H-1,3-benzodiazol-2-yl]propan-2-yl})amine |
| 1826 | [(3,5-dichlorophenyl)methyl](1-{1H-naphtho[2,3-d]imidazol-2-yl}propan-2-yl)amine |
| 1827 | [(2S)-1-(6-chloro-1H-1,3-benzodiazol-2-yl)butan-2-yl][(3,5-dichlorophenyl)methyl]amine |
| 1828 | [(2R)-1-(6-chloro-1H-1,3-benzodiazol-2-yl)-3-methylbutan-2-yl][(3,5-dichlorophenyl)methyl]amine |
| 1829 | {2-[(6-chloro-1H-1,3-benzodiazol-2-yl)amino]ethyl}[(3,5-dichlorophenyl)methyl]amine |
| 1830 | N-(6-chloro-1H-1,3-benzodiazol-2-yl)-2-{[(3,5-dichlorophenyl)methyl]amino}acetamide |
| 1831 | (2S)-N-(6-chloro-1H-1,3-benzodiazol-2-yl)-2-{[(3,5-dichlorophenyl)methyl]amino}propanamide |
| 1832 | [3-(6-chloro-1H-1,3-benzodiazol-2-yl)propyl][(3,5-dichlorophenyl)methyl]amine |
| 1833 | N-[(3,5-dichlorophenyl)methyl]-N-[3-(5-fluoro-1H-1,3-benzodiazol-2-yl)piperidin-1-yl]acetamide |
| 1835 | N-[(3,5-dichlorophenyl)methyl]-N-(3-{5-fluoro-1H-imidazo[4,5-b]pyridin-2-yl}propyl)acetamide |
| 1836 | N-[(2,4-dichlorophenyl)methyl]-N-(3-{5-fluoro-1H-imidazo[4,5-b]pyridin-2-yl}cyclohexyl)acetamide |
| 1837 | 5-chloro-2-[(3S)-1-[(2,4-dichlorophenyl)methyl]piperidin-3-yl]-1H-1,3-benzodiazole |
| 1838 | 5-chloro-2-[(3R)-1-[(3,5-dichlorophenyl)methyl]piperidin-3-yl]-1H-1,3-benzodiazole |
| 1839 | N-[(3,5-dichlorophenyl)methyl]-3-(5-fluoro-1H-1,3-benzodiazol-2-yl)cyclohexan-1-amine |
| 1840 | 3-(5-chloro-1H-1,3-benzodiazol-2-yl)-N-[(3,5-dichlorophenyl)methyl]cyclohexan-1-amine |
| 1841 | 3-{6-chloro-3H-imidazo[4,5-b]pyridin-2-yl}-N-[(3,5-dichlorophenyl)methyl]cyclohexan-1-amine |
| 1842 | N-(3-{6-chloro-3H-imidazo[4,5-b]pyridin-2-yl}cyclohexyl)-N-[(3,5-dichlorophenyl)methyl]acetamide |
| 1844 | (2-{6-chloro-3H-imidazo[4,5-b]pyridin-2-yl}ethyl)[(3,5-dichlorophenyl)methyl]amine |
| 1845 | (3S)-1-{5-chloro-3H-imidazo[4,5-b]pyridin-2-yl}-N-[(3,5-dichlorophenyl)methyl]pyrrolidin-3-amine |
| 1846 | (3S)-1-{5-chloro-3H-imidazo[4,5-b]pyridin-2-yl}-N-[(2,4-dichlorophenyl)methyl]pyrrolidin-3-amine |
| 1847 | (3R)-1-{5-chloro-3H-imidazo[4,5-b]pyridin-2-yl}-N-[(3,5-dichlorophenyl)methyl]pyrrolidin-3-amine |
| 1848 | (3R)-1-{5-chloro-3H-imidazo[4,5-b]pyridin-2-yl}-N-[(2,4-dichlorophenyl)methyl]pyrrolidin-3-amine |
| 1849 | [2-({5-chloro-3H-imidazo[4,5-b]pyridin-2-yl}amino)ethyl][(3,5-dichlorophenyl)methyl]amine |
| 1850 | [2-({6-chloro-1H-imidazo[4,5-b]pyridin-2-yl}amino)ethyl][(3,5-dichlorophenyl)methyl]amine |
| 1851 | N-[(6-chloro-1H-1,3-benzodiazol-2-yl)methyl]-2-(3,5-dichlorophenyl)acetamide |
| 1852 | N-[(6-chloro-1H-1,3-benzodiazol-2-yl)methyl]-2-(2,4-dichlorophenyl)acetamide |

| No. | Chemical Name |
|---|---|
| 1853 | [(6-bromo-1H-1,3-benzodiazol-2-yl)methyl][(3,5-dichlorophenyl)methyl]amine |
| 1854 | (1R,3S)-3-{5-chloro-1H-imidazo[4,5-b]pyridin-2-yl}-N-[(3,5-dichlorophenyl)methyl]cyclohexan-1-amine |
| 1855 | (3R)-1-{5-chloro-1H-imidazo[4,5-b]pyridin-2-yl}-N-[(3,5-dichlorophenyl)methyl]piperidin-3-amine |
| 1856 | (3S)-1-{5-chloro-1H-imidazo[4,5-b]pyridin-2-yl}-N-[(3,5-dichlorophenyl)methyl]piperidin-3-amine |
| 1857 | 1-{5-chloro-3H-imidazo[4,5-b]pyridin-2-yl}-N-[(2,4-dichlorophenyl)methyl]piperidin-3-amine |
| 1858 | [(3,5-dichlorophenyl)methyl](3-{5-fluoro-1H-imidazo[4,5-b]pyridin-2-yl}propyl)amine |
| 1859 | N-[(1R,3S)-3-{5-chloro-1H-imidazo[4,5-b]pyridin-2-yl}cyclohexyl]-N-[(3,5-dichlorophenyl)methyl]acetamide |
| 1860 | N-[(3,5-dichlorophenyl)methyl]-N-[3-(5-fluoro-1H-1,3-benzodiazol-2-yl)cyclohexyl]acetamide |
| 1861 | N-[3-(5-chloro-1H-1,3-benzodiazol-2-yl)cyclohexyl]-N-[(3,5-dichlorophenyl)methyl]acetamide |
| 1862 | 3,5-dichloro-N-[(1-{5-chloro-1H-imidazo[4,5-b]pyridin-2-yl}piperidin-3-yl)methyl]aniline |
| 1863 | N-[(1-{6-bromo-5-chloro-1H-imidazo[4,5-b]pyridin-2-yl}piperidin-3-yl)methyl]-3,5-dichloroaniline |
| 1864 | 1-{5-chloro-1H-imidazo[4,5-b]pyridin-2-yl}-N-[(3,5-dichlorophenyl)methyl]azetidin-3-amine |
| 1865 | 1-{6-bromo-5-chloro-1H-imidazo[4,5-b]pyridin-2-yl}-N-[(3,5-dichlorophenyl)methyl]azetidin-3-amine |
| 1866 | 1-{5-chloro-1H-imidazo[4,5-b]pyridin-2-yl}-4-[(3,5-dichlorophenyl)methyl]piperazine |
| 1867 | 1-{5-chloro-1H-imidazo[4,5-b]pyridin-2-yl}-N-[(3,5-dichlorophenyl)methyl]piperidin-4-amine |
| 1868 | (3S)-3-{5-chloro-1H-imidazo[4,5-b]pyridin-2-yl}-1-[(3,5-dichlorophenyl)methyl]piperidine |
| 1869 | (3S)-3-{5-chloro-1H-imidazo[4,5-b]pyridin-2-yl}-1-[(2,4-dichlorophenyl)methyl]piperidine |
| 1870 | (3S)-3-{5-chloro-1H-imidazo[4,5-b]pyridin-2-yl}-1-[(3,4-dichlorophenyl)methyl]piperidine |
| 1871 | (3S)-3-{5-chloro-1H-imidazo[4,5-b]pyridin-2-yl}-1-[(3,5-dibromophenyl)methyl]piperidine |
| 1872 | (3S)-3-{5-chloro-1H-imidazo[4,5-b]pyridin-2-yl}-1-[(3,5-dimethoxyphenyl)methyl]piperidine |
| 1873 | N-[(6-bromo-1H-1,3-benzodiazol-2-yl)methyl]-2-(3,5-dichlorophenyl)acetamide |
| 1874 | N-[(6-bromo-1H-1,3-benzodiazol-2-yl)methyl]-2-(2,4-dichlorophenyl)acetamide |
| 1875 | N-({5-chloro-3H-imidazo[4,5-b]pyridin-2-yl}methyl)-2-(3,5-dichlorophenyl)acetamide |
| 1876 | N-({5-chloro-3H-imidazo[4,5-b]pyridin-2-yl}methyl)-2-(2,4-dichlorophenyl)acetamide |
| 1877 | N-({6-chloro-1H-imidazo[4,5-b]pyridin-2-yl}methyl)-2-(3,5-dichlorophenyl)acetamide |
| 1878 | N-({6-chloro-1H-imidazo[4,5-b]pyridin-2-yl}methyl)-2-(2,4-dichlorophenyl)acetamide |
| 1879 | N-({6-chloro-1H-imidazo[4,5-c]pyridin-2-yl}methyl)-2-(3,5-dichlorophenyl)acetamide |
| 1880 | N-({6-chloro-1H-imidazo[4,5-c]pyridin-2-yl}methyl)-2-(2,4-dichlorophenyl)acetamide |
| 1881 | (3-{5-chloro-3H-imidazo[4,5-b]pyridin-2-yl}propyl)[(3,5-dichlorophenyl)methyl]amine |
| 1882 | (2-{6-chloro-1H-imidazo[4,5-c]pyridin-2-yl}ethyl)[(3,5-dichlorophenyl)methyl]amine |
| 1883 | 6-(2-chloro-4-methoxyphenoxy)-2-N,4-N-bis({5-fluoro-3H-imidazo[4,5-b]pyridin-2-yl}methyl)-1,3,5-triazine-2,4-diamine |
| 1884 | 4,6-bis(2-chloro-4-methoxyphenoxy)-N-({5-fluoro-3H-imidazo[4,5-b]pyridin-2-yl}methyl)-1,3,5-triazin-2-amine |
| 1885 | 4-(2-chloro-4-methoxyphenoxy)-6-[({5-fluoro-3H-imidazo[4,5-b]pyridin-2-yl}methyl)amino]-1,3,5-triazin-2-ol |
| 1886 | N-[(3,5-dichlorophenyl)methyl]-1-{5-fluoro-1H-imidazo[4,5-b]pyridin-2-yl}piperidin-3-amine |
| 1887 | N-[(3,5-dichlorophenyl)methyl]-N-(1-{5-fluoro-3H-imidazo[4,5-b]pyridin-2-yl}piperidin-3-yl)acetamide |
| 1888 | (3S)-1-{5-chloro-1H-imidazo[4,5-b]pyridin-2-yl}-N-(3,5-dichlorophenyl)piperidine-3-carboxamide |
| 1889 | 3,5-dichloro-N-[(3S)-1-{5-chloro-1H-imidazo[4,5-b]pyridin-2-yl}piperidin-3-yl]benzamide |
| 1890 | 3-({5-chloro-3H-imidazo[4,5-b]pyridin-2-yl}methyl)-1-(3,5-dichlorophenyl)urea |
| 1891 | 3-({5-chloro-3H-imidazo[4,5-b]pyridin-2-yl}methyl)-1-(2,4-dichlorophenyl)urea |

-continued

| No. | Chemical Name |
|---|---|
| 1892 | ({5-chloro-3H-imidazo[4,5-b]pyridin-2-yl}methyl)[2-(2,4-dichlorophenyl)ethyl]amine |
| 1893 | 5-chloro-N-(2-{[(3,5-dichlorophenyl)methyl]amino}ethyl)-N-methyl-3H-imidazo[4,5-b]pyridin-2-amine |
| 1894 | 6-bromo-5-chloro-N-(2-{[(3,5-dichlorophenyl)methyl]amino}ethyl)-N-methyl-3H-imidazo[4,5-b]pyridin-2-amine |
| 1895 | N-(3-{5-chloro-3H-imidazo[4,5-b]pyridin-2-yl}propyl)-N-[(3,5-dichlorophenyl)methyl]acetamide |
| 1896 | [2-({5-chloro-1H-imidazo[4,5-b]pyridin-2-yl}sulfanyl)ethyl][(3,5-dichlorophenyl)methyl]amine |
| 1897 | N-[(3,5-dichlorophenyl)methyl]-N-[2-({5-fluoro-1H-imidazo[4,5-b]pyridin-2-yl}amino)ethyl]acetamide |
| 1898 | (3S)-1-{5-chloro-1H-imidazo[4,5-b]pyridin-2-yl}-3-[(3,5-dichlorophenyl)methoxy]piperidine |
| 1899 | 6,8-dichloro-N-[(3S)-1-{5-chloro-1H-imidazo[4,5-b]pyridin-2-yl}piperidin-3-yl]-1,2,3,4-tetrahydroquinolin-4-amine |
| 1900 | (3S)-N-[(3,5-dichlorophenyl)methyl]-1-{5-fluoro-1H-imidazo[4,5-b]pyridin-2-yl}piperidin-3-amine |
| 1901 | N-[(3,5-dichlorophenyl)methyl]-N-[(3S)-1-{5-fluoro-1H-imidazo[4,5-b]pyridin-2-yl}piperidin-3-yl]acetamide |
| 1902 | (3S)-1-{5-chloro-1H-imidazo[4,5-b]pyridin-2-yl}-N-[(2,3,5-trichlorophenyl)methyl]piperidin-3-amine |
| 1903 | 1-{5-chloro-1H-imidazo[4,5-b]pyridin-2-yl}-N-[(3,5-dichlorophenyl)methyl]azepan-3-amine |
| 1904 | (3S)-1-{6-bromo-5-chloro-1H-imidazo[4,5-b]pyridin-2-yl}-3-[(3,5-dichlorophenyl)methoxy]piperidine |
| 1905 | (3S)-1-{6-bromo-5-chloro-1H-imidazo[4,5-b]pyridin-2-yl}-N-[(2,3,5-trichlorophenyl)methyl]piperidin-3-amine |
| 1906 | (5S)-3-(1H-1,3-benzodiazol-2-ylmethyl)-5-[(2,4-dichlorophenyl)methyl]imidazolidine-2,4-diol |
| 1907 | 1-(1H-1,3-benzodiazol-2-ylmethyl)-4-[(2,4-dichlorophenyl)methyl]-2,3-dihydro-1H-imidazol-2-one |
| 1908 | (3S)-1-{5-chloro-1H-imidazo[4,5-b]pyridin-2-yl}-N-[(3,5-dibromophenyl)methyl]piperidin-3-amine |
| 1909 | (3S)-1-{5-chloro-1H-imidazo[4,5-b]pyridin-2-yl}-N-[(3,5-dibromo-2-methoxyphenyl)methyl]piperidin-3-amine |
| 1910 | (3S)-1-{5-chloro-1H-imidazo[4,5-b]pyridin-2-yl}-N-[(3,5-dibromo-2-ethoxyphenyl)methyl]piperidin-3-amine |
| 1911 | (3S)-1-{5-chloro-1H-imidazo[4,5-b]pyridin-2-yl}-N-[(3,5-dichloro-2-methoxyphenyl)methyl]piperidin-3-amine |
| 1912 | (3S)-N-[(3-bromo-5-chlorophenyl)methyl]-1-{5-chloro-1H-imidazo[4,5-b]pyridin-2-yl}piperidin-3-amine |
| 1913 | N-(2-{[(3,5-dichlorophenyl)methyl]amino}ethyl)-5-fluoro-N-methyl-1H-imidazo[4,5-b]pyridin-2-amine |
| 1914 | N-[(3,5-dichlorophenyl)methyl]-N-[2-({5-fluoro-1H-imidazo[4,5-b]pyridin-2-yl}(methyl)amino)ethyl]acetamide |
| 1915 | [(1-{5-chloro-1H-imidazo[4,5-b]pyridin-2-yl}azetidin-2-yl)methyl][(3,5-dichlorophenyl)methyl]amine |
| 1916 | [(1-{5-chloro-1H-imidazo[4,5-b]pyridin-2-yl}pyrrolidin-2-yl)methyl][(3,5-dichlorophenyl)methyl]amine |
| 1917 | 5-chloro-N-(2-{[(4R)-6,8-dichloro-1,2,3,4-tetrahydroquinolin-4-yl]amino}ethyl)-N-methyl-3H-imidazo[4,5-b]pyridin-2-amine |
| 1918 | N-[2-(1H-1,3-beiizodiazol-2-yl)ethyl]-6-(2-chloro-4-methoxyphenoxy)pyridin-2-amine |
| 1919 | N-(2-{[(4R)-6,8-dichloro-1,2,3,4-tetrahydroquinolin-4-yl]amino}ethyl)-5-fluoro-N-methyl-1H-imidazo[4,5-b]pyridin-2-amine |
| 1920 | (3S)-1-{5-chloro-1H-imidazo[4,5-b]pyridin-2-yl}-N-[(3,5-dichloro-2-ethoxyphenyl)methyl]piperidin-3-amine |
| 1921 | 2,4-dichloro-6-({[(3S)-1-{5-chloro-1H-imidazo[4,5-b]pyridin-2-yl}piperidin-3-yl]amino}methyl)phenol |
| 1922 | 3,5-dichloro-N-{[(3R)-1-{5-chloro-1H-imidazo[4,5-b]pyridin-2-yl}piperidin-3-yl]methyl}aniline |
| 1923 | 3,5-dichloro-N-{[(3S)-1-{5-chloro-1H-imidazo[4,5-b]pyridin-2-yl}piperidin-3-yl]methyl}aniline |
| 1924 | N-(1H-1,3-benzodiazol-2-ylmethyl)-6-(2-chloro-4-methoxyphenoxy)pyridin-2-amine |
| 1925 | 5-chloro-N-(2-{[(3,5-dichloro-2-ethoxyphenyl)methyl]amino}ethyl)-N-methyl-3H-imidazo[4,5-b]pyridin-2-amine |
| 1926 | N-[2-({5-chloro-3H-imidazo[4,5-b]pyridin-2-yl}(methyl)amino)ethyl]-N-[(3,5-dichlorophenyl)methyl]acetamide |
| 1927 | (3S)-1-{5-chloro-1H-imidazo[4,5-b]pyridin-2-yl}-N-[(3,5-dichloro-2-propoxyphenyl)methyl]piperidin-3-amine |
| 1928 | (3S)-1-{5-chloro-1H-imidazo[4,5-b]pyridin-2-yl}-N-{[3,5-dichloro-2-(prop-2-en-1-yloxy)phenyl]methyl}piperidin-3-amine |
| 1929 | (3S)-1-{5-chloro-1H-imidazo[4,5-b]pyridin-2-yl}-N-{[3,5-dichloro-2-(cyclopropylmethoxy)phenyl]methyl}piperidin-3-amine |

| No. | Chemical Name |
|---|---|
| 1930 | (3S)-1-{5-chloro-1H-imidazo[4,5-b]pyridin-2-yl}-N-[(3,5-dichloro-2-cyclopropoxyphenyl)methyl]piperidin-3-amine |
| 1931 | (3S)-1-{5-chloro-1H-imidazo[4,5-b]pyridin-2-yl}-N-{[3,5-dichloro-2-(propan-2-yloxy)phenyl]methyl}piperidin-3-amine |
| 1932 | N-[(3,5-dichlorophenyl)methyl]-N-[(1R,3S)-3-{5-fluoro-1H-imidazo[4,5-b]pyridin-2-yl}cyclohexyl]acetamide |
| 1933 | N-(1H-1,3-benzodiazol-2-ylmethyl)-4-(2-chloro-4-methoxyphenoxy)pyridin-2-amine |
| 1934 | (4S)-1-(1H-1,3-benzodiazol-2-ylmethyl)-4-[(2,4-dichlorophenyl)methyl]-5-hydroxyimidazolidin-2-one |
| 1935 | 3-(1H-1,3-benzodiazol-2-ylmethyl)-1-[(2S)-1-(2,4-dichlorophenyl)-3-hydroxypropan-2-yl]urea |
| 1936 | 1-(1H-1,3-benzodiazol-2-ylmethyl)-4-[(2,4-dichlorophenyl)methyl]-2,3-dihydro-1H-imidazol-2-ol |
| 1937 | (3S)-N-[(3-bromo-5-chloro-2-ethoxyphenyl)methyl]-1-{5-chloro-1H-imidazo[4,5-b]pyridin-2-yl}piperidin-3-amine |
| 1938 | N-[2-({5-chloro-3H-imidazo[4,5-b]pyridin-2-yl}(methyl)amino)ethyl]-N-[(4R)-6,8-dichloro-1,2,3,4-tetrahydroquinolin-4-yl]acetamide |
| 1939 | N-(2-{[(4R)-6,8-dichloro-1,2,3,4-tetrahydroquinolin-4-yl][2-({5-fluoro-1H-imidazo[4,5-b]pyridin-2-yl}(methyl)ammo)ethyl]amino}ethyl)-5-fluoro-N-methyl-1H-imidazo[4,5-b]pyridin-2-amine |
| 1940 | (3S)-1-{5-chloro-1H-imidazo[4,5-b]pyridin-2-yl}-N-{[3,5-dichloro-2-(ethylamino)phenyl]methyl}piperidin-3-amine |
| 1941 | N-(1H-1,3-benzodiazol-2-ylmethyl)-3-(2-chloro-4-methoxyphenoxy)aniline |
| 1942 | N-[2-({5-chloro-1H-imidazo[4,5-b]pyridin-2-yl}(methyl)amino)ethyl]-N-[(3,5-dichlorophenyl)methyl]propanamide |
| 1943 | N-[(3S)-1-{5-chloro-1H-imidazo[4,5-b]pyridin-2-yl}piperidin-3-yl]-N-(6,8-dichloro-1,2,3,4-tetrahydroquinolin-4-yl)acetamide |
| 1944 | 3-{5-chloro-1H-imidazo[4,5-b]pyridin-2-yl}-N-[(3,5-dichlorophenyl)methyl]propanamide |
| 1945 | N-(1-acetyl-6,8-dichloro-1,2,3,4-tetrahydroquinolin-4-yl)-N-[(3S)-1-{5-chloro-1H-imidazo[4,5-b]pyridin-2-yl}piperidin-3-yl]acetamide |
| 1949 | 5-chloro-N-(2-{[(3,5-dichlorophenyl)methyl]amino}ethyl)-N-ethyl-3H-imidazo[4,5-b]pyridin-2-amine |
| 1950 | N-(1H-1,3-benzodiazol-2-ylmethyl)-2-(2-chloro-4-methoxyphenoxy)pyridin-4-amine |
| 1951 | 2-({5-chloro-3H-imidazo[4,5-b]pyridin-2-yl}sulfanyl)-N-[(3,5-dichlorophenyl)methyl]acetamide |
| 1952 | 3-(6-chloro-1H-1,3-benzodiazol-2-yl)-N-[(3,5-dichlorophenyl)methyl]aniline |
| 1953 | 3,5-dichloro-N-[3-(6-chloro-1H-1,3-benzodiazol-2-yl)phenyl]benzamide |
| 1954 | 3,5-dichloro-N-[3-({5-fluoro-3H-imidazo[4,5-b]pyridin-2-yl}amino)propyl]aniline |
| 1955 | (3S)-1-{5-chloro-3H-imidazo[4,5-b]pyridin-2-yl}-N-[(3,5-dichlorophenyl)methyl]-N-ethylpiperidin-3-amine |
| 1956 | 2,4-dichloro-N-[3-({5-fluoro-3H-imidazo[4,5-b]pyridin-2-yl}amino)propyl]aniline |
| 1957 | 2-amino-N-[2-({5-chloro-1H-imidazo[4,5-b]pyridin-2-yl}(methyl)amino)ethyl]-N-[(3,5-dichlorophenyl)methyl]acetamide |
| 1958 | 3-amino-N-[2-({5-chloro-1H-imidazo[4,5-b]pyridin-2-yl}(methyl)amino)ethyl]-N-[(3,5-dichlorophenyl)methyl]propanamide |
| 1959 | N-[(3,5-dichlorophenyl)methyl]-N-[3-({5-fluoro-3H-imidazo[4,5-b]pyridin-2-yl}amino)propyl]acetamide |
| 1960 | 4-(2-chloro-4-methoxyphenoxy)-N-({5-fluoro-3H-imidazo[4,5-b]pyridin-2-yl}methyl)pyridin-2-amine |
| 1962 | 4-[(2,4-dichlorophenyl)methyl]-1-({5-fluoro-3H-imidazo[4,5-b]pyridin-2-yl}methyl)-2,3-dihydro-1H-imidazol-2-one |
| 1963 | methyl N-[2-({5-chloro-1H-imidazo[4,5-b]pyridin-2-yl}(methyl)amino)ethyl]-N-[(3,5-dichlorophenyl)methyl]carbamate |
| 1964 | methyl N-[(3,5-dichlorophenyl)methyl]-N-[3-({5-fluoro-3H-imidazo[4,5-b]pyridin-2-yl}amino)propyl]carbamate |
| 1965 | methyl 2-[(3-{[(3,5-dichlorophenyl)methyl](methoxycarbonyl)amino}propyl)amino]-5-fluoro-3H-imidazo[4,5-b]pyridine-3-carboxylate |
| 1966 | 3-{5-chloro-3H-imidazo[4,5-b]pyridin-2-yl}-N-[(3,5-dichlorophenyl)methyl]aniline |
| 1967 | 3,5-dichloro-N-[3-({5-chloro-3H-imidazo[4,5-b]pyridin-2-yl}amino)propyl]aniline |
| 1968 | 3-{5-chloro-3H-imidazo[4,5-b]pyridin-2-yl}-N-[(3,5-dichlorophenyl)methyl]-3-propanamidopropanamide |
| 1969 | 3-amino-3-{5-chloro-3H-imidazo[4,5-b]pyridin-2-yl}-N-[(3,5-dichlorophenyl)methyl]propanamide |
| 1970 | 2-({5-chloro-3H-imidazo[4,5-b]pyridin-2-yl}amino)-N-[(3,5-dichlorophenyl)methyl]acetamide |
| 1971 | N-[2-({5-chloro-3H-imidazo[4,5-b]pyridin-2-yl}(methyl)amino)ethyl]-N-[(3,5-dichlorophenyl)methyl]-2-hydroxyacetamide |
| 1972 | 1-[2-({5-chloro-3H-imidazo[4,5-b]pyridin-2-yl}(methyl)amino)ethyl]-1-[(3,5-dichlorophenyl)methyl]urea |

| No. | Chemical Name |
|---|---|
| 1973 | N-[(3,5-dichlorophenyl)methyl]-N-[3-({5-fluoro-3H-imidazo[4,5-b]pyridin-2-yl}amino)propyl]-2-hydroxyacetamide |
| 1974 | 1-[(3,5-dichlorophenyl)methyl]-1-[3-({5-fluoro-3H-imidazo[4,5-b]pyridin-2-yl}amino)propyl]urea |
| 1990 | N-({5-chloro-3H-imidazo[4,5-b]pyridin-2-yl}methyl)-2-[(3,5-dichlorophenyl)amino]acetamide |
| 1991 | 3-({5-chloro-3H-imidazo[4,5-b]pyridin-2-yl}methyl)-1-[(3,5-dichlorophenyl)methyl]urea |
| 1992 | 3-chloro-5-({[(3S)-1-{5-chloro-3H-imidazo[4,5-b]pyridin-2-yl}piperidin-3-yl]amino}methyl)benzonitrile |
| 1994 | ({5-chloro-3H-imidazo[4,5-b]pyridin-2-yl}methyl)({2-[(3,5-dichlorophenyl)amino]ethyl})amine |
| 1996 | 5-chloro-N-[3-(4,6-dichloro-1H-indol-1-yl)propyl]-3H-imidazo[4,5-b]pyridin-2-amine |

In another embodiment, the compound has the structure of formula (III):

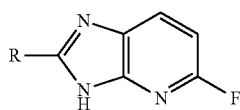

(III)

or a pharmaceutically acceptable salt thereof, wherein

R is $C_{1-6}$ alkyl, $C_{2-6}$ alkenyl, $C_{1-6}$ haloalkyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR$^8$, —SR$^8$, —N(R$^8$)$_2$, —C(O)R$^8$, —C(O)OR$^8$, —C(O)N(R$^8$)$_2$, —S(O)$_2$R$^8$, —OC(O)R$^8$, —OC(O)OR$^8$, —OC(O)N(R$^8$)$_2$, —N(R$^8$)C(O)R$^8$, —N(R$^8$)C(O)OR$^8$, or —N(R$^8$)C(O)N(R$^8$)$_2$, wherein each R$^8$ is independently hydrogen or C1-6 alkyl.

In another embodiment, the compound has the structure of formula (IV):

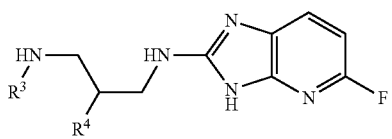

(IV)

or a pharmaceutically acceptable salt thereof, wherein

R$_3$ is $C_{1-6}$ alkyl, $C_{2-6}$ alkenyl, $C_{1-6}$ haloalkyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR$^9$, —SR$^9$, —N(R$^9$)$_2$, —C(O)R$^9$, —C(O)OR$^9$, —C(O)N(R$^9$)$_2$, —S(O)$_2$R$^9$, —OC(O)R$^9$, —OC(O)OR$^9$, —OC(O)N(R$^9$)$_2$, —N(R$^9$)C(O)R$^9$, —N(R$^9$)C(O)OR$^9$, or —N(R$^9$)C(O)N(R$^9$)$_2$, wherein each R$^9$ is independently hydrogen or C1-6 alkyl; and R$^4$ is hydrogen, halogen, $C_{1-6}$ alkyl, or —OR$^{10}$, where R$^{10}$ is selected from the group consisting of hydrogen, $C_{1-6}$ alkyl, $C_{2-6}$ alkenyl, $C_{2-6}$ alkynyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR$^9$, —SR$^9$, —N(R$^9$)$_2$, —C(O)R$^9$, —C(O)OR$^9$, —C(O)N(R$^9$)$_2$, —S(O)$_2$R$^9$, —OC(O)R$^9$, —OC(O)OR$^9$, —OC(O)N(R$^9$)$_2$, —N(R$^9$)C(O)R$^9$, —N(R$^9$)C(O)OR$^9$, or —N(R$^9$)C(O)N(R$^9$)$_2$, wherein each R$^9$ is independently hydrogen or C1-6 alkyl.

In another embodiment, the compound has the structure of formula (V):

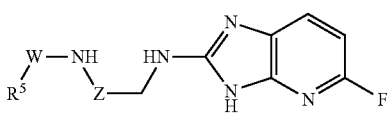

(V)

or a pharmaceutically acceptable salt thereof, wherein

R$^5$ is $C_{1-6}$ alkyl, $C_{2-6}$ alkenyl, $C_{1-6}$ haloalkyl, $C_{3-12}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR$^9$, —SR$^9$, —N(R$^9$)$_2$, —C(O)R$^9$, —C(O)OR$^9$, —C(O)N(R$^9$)$_2$, —S(O)$_2$R$^9$, —OC(O)R$^9$, —OC(O)OR$^9$, —OC(O)N(R$^9$)$_2$, —N(R$^9$)C(O)R$^9$, —N(R$^9$)C(O)OR$^9$, or —N(R$^9$)C(O)N(R$^9$)$_2$, wherein each R$^9$ is independently hydrogen or $C_{1-6}$ alkyl.

In some embodiments, the compound of formulae (III) or (IV) is one of the following compounds (or a pharmaceutically acceptable salt, prodrug, solvate or hydrate thereof):

| No. | Chemical Name |
|---|---|
| 1575 | N1-(3,5-dichlorobenzyl)-N3-(1H-imidazo[4,5-b]pyridin-2-yl)propane-1,3-diamine |
| 1576 | 3-{[(3,5-dichlorophenyl)methyl]amino}-N-{1H-imidazo[4,5-b]pyridin-2-yl}propanamide |

| No. | Chemical Name |
|---|---|
| 1599 | N1-(3,5-dichlorobenzyl)-N3-(5-methyl-1H-imidazo[4,5-b]pyridin-2-yl)propane-1,3-diamine |
| 1614 | [(3,5-dichlorophenyl)methyl][3-({5-fluoro-3H-imidazo[4,5-b]pyridin-2-yl}amino)propyl]amine |
| 1634 | 1-((1H-imidazo[4,5-b]pyridin-2-yl)amino)-3-((3,5-dichlorobenzyl)amino)propan-2-ol |
| 1641 | N1-(3,5-dichlorobenzyl)-N3-(1H-imidazo[4,5-b]pyridin-2-yl)-2,2-dimethylpropane-1,3-diamine |
| 1655 | (S)-N1-(3,5-dichlorobenzyl)-N3-(1H-imidazo[4,5-b]pyridin-2-yl)-2-methylpropane-1,3-diamine |
| 1673 | [(3,5-dichlorophenyl)methyl][(2S)-3-({5-fluoro-3H-imidazo[4,5-b]pyridin-2-yl}amino)-2-methylpropyl]amine |
| 1683 | N-(1H-1,3-benzodiazol-2-ylmethyl)-3-(2,4-dichlorophenoxy)propanamide |
| 1704 | 3-(2,4-dichlorophenoxy)-N-{3H-imidazo[4,5-b]pyridin-2-ylmethyl}propanamide |
| 1705 | 3-(2,4-dichlorophenoxy)-N-({5-fluoro-3H-imidazo[4,5-b]pyridin-2-yl}methyl)propanamide |
| 1709 | (4R)-6,8-dichloro-N-[3-({5-fluoro-3H-imidazo[4,5-b]pyridin-2-yl}amino)propyl]-3,4-dihydro-2H-1-benzopyran-4-amine |
| 1710 | (R)-N1-(6,8-dichlorochroman-4-yl)-N3-(3H-imidazo[4,5-b]pyridin-2-yl)propane-1,3-diamine |
| 1711 | (4S)-6,8-dichloro-N-[3-({5-fluoro-3H-imidazo[4,5-b]pyridin-2-yl}amino)propyl]-3,4-dihydro-2H-1-benzopyran-4-amine |
| 1717 | (4R)-6,8-dichloro-N-[3-({5-fluoro-3H-imidazo[4,5-b]pyridin-2-yl}amino)propyl]-1,2,3,4-tetrahydroquinolin-4-amine |
| 1727 | N-(1H-1,3-benzodiazol-2-ylmethyl)-3-(2,4-dichlorophenoxy)-N-methylpropanamide |
| 1729 | (2E)-N-(1H-1,3-benzodiazol-2-ylmethyl)-3-(2,4-dichlorophenoxy)prop-2-enamide |
| 1730 | (2Z)-N-(1H-1,3-benzodiazol-2-ylmethyl)-3-(2,4-dichlorophenoxy)prop-2-enamide |

In some embodiments, the compound of formulae (III) or (IV) is one of the following compounds (or a pharmaceutically acceptable salt, prodrug, solvate or hydrate thereof):

| No. | Chemical Name |
|---|---|
| 1614 | [(3,5-dichlorophenyl)methyl][3-({5-fluoro-3H-imidazo[4,5-b]pyridin-2-yl}amino)propyl]amine |
| 1634 | 1-((1H-imidazo[4,5-b]pyridin-2-yl)amino)-3-((3,5-dichlorobenzyl)amino)propan-2-ol |
| 1641 | N1-(3,5-dichlorobenzyl)-N3-(1H-imidazo[4,5-b]pyridin-2-yl)-2,2-dimethylpropane-1,3-diamine |
| 1673 | [(3,5-dichlorophenyl)methyl][(2S)-3-({5-fluoro-3H-imidazo[4,5-b]pyridin-2-yl}amino)-2-methylpropyl]amine |
| 1705 | 3-(2,4-dichlorophenoxy)-N-({5-fluoro-3H-imidazo[4,5-b]pyridin-2-yl}methyl)propanamide |
| 1709 | (4R)-6,8-dichloro-N-[3-({5-fluoro-3H-imidazo[4,5-b]pyridin-2-yl}amino)propyl]-3,4-dihydro-2H-1-benzopyran-4-amine |
| 1711 | (4S)-6,8-dichloro-N-[3-({5-fluoro-3H-imidazo[4,5-b]pyridin-2-yl}amino)propyl]-3,4-dihydro-2H-1-benzopyran-4-amine |
| 1717 | (4R)-6,8-dichloro-N-[3-({5-fluoro-3H-imidazo[4,5-b]pyridin-2-yl}amino)propyl]-1,2,3,4-tetrahydroquinolin-4-amine |

In some embodiments, the compound of formulae (III) or (IV) is one of the following compounds (or a pharmaceutically acceptable salt, prodrug, solvate or hydrate thereof).

| No. | Chemical Name |
|---|---|
| 1576 | 3-{[(3,5-dichlorophenyl)methyl]amino}-N-{1H-imidazo[4,5-b]pyridin-2-yl}propanamide |
| 1634 | 1-((1H-imidazo[4,5-b]pyridin-2-yl)amino)-3-((3,5-dichlorobenzyl)amino)propan-2-ol |
| 1641 | N1-(3,5-dichlorobenzyl)-N3-(1H-imidazo[4,5-b]pyridin-2-yl)-2,2-dimethylpropane-1,3-diamine |
| 1655 | (S)-N1-(3,5-dichlorobenzyl)-N3-(1H-imidazo[4,5-b]pyridin-2-yl)-2-methylpropane-1,3-diamine |

-continued

| No. | Chemical Name |
|---|---|
| 1673 | [(3,5-dichlorophenyl)methyl][(2S)-3-({5-fluoro-3H-imidazo[4,5-b]pyridin-2-yl}amino)-2-methylpropyl]amine |
| 1683 | N-(1H-1,3-benzodiazol-2-ylmethyl)-3-(2,4-dichlorophenoxy)propanamide |
| 1704 | 3-(2,4-dichlorophenoxy)-N-{3H-imidazo[4,5-b]pyridin-2-ylmethyl}propanamide |
| 1705 | 3-(2,4-dichlorophenoxy)-N-({5-fluoro-3H-imidazo[4,5-b]pyridin-2-yl}methyl)propanamide |
| 1727 | N-(1H-1,3-benzodiazol-2-ylmethyl)-3-(2,4-dichlorophenoxy)-N-methylpropanamide |
| 1729 | (2E)-N-(1H-1,3-benzodiazol-2-ylmethyl)-3-(2,4-dichlorophenoxy)prop-2-enamide |
| 1730 | (2Z)-N-(1H-1,3-benzodiazol-2-ylmethyl)-3-(2,4-dichlorophenoxy)prop-2-enamide |

In some embodiments, the compound of formulae (III) or (IV) is one of the following compounds (or a pharmaceutically acceptable salt, prodrug, solvate or hydrate thereof):

| No. | Chemical Name |
|---|---|
| 1673 | [(3,5-dichlorophenyl)methyl][(2S)-3-({5-fluoro-3H-imidazo[4,5-b]pyridin-2-yl}amino)-2-methylpropyl]amine |
| 1683 | N-(1H-1,3-benzodiazol-2-ylmethyl)-3-(2,4-dichlorophenoxy)propanamide |
| 1705 | 3-(2,4-dichlorophenoxy)-N-({5-fluoro-3H-imidazo[4,5-b]pyridin-2-yl}methyl)propanamide |

In a third aspect, also disclosed are compounds used in the synthesis a compound of formulae (I)-(V). For example, the compound may have the structure of compound A or compound B:

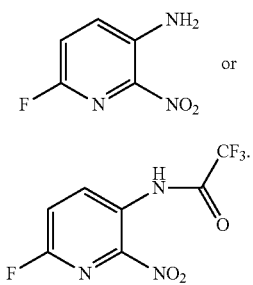

In an embodiment of the third aspect, a method for the synthesis of a compound of formulae (I)-(V), wherein compound A or B is an intermediate. For example, Scheme 71 shows the use of compounds A and B in the synthesis of 6-fluoropyridine-2,3-diamine, which is used in the synthesis of compound 1614 in Scheme 72.

In a fourth aspect, the compounds of the disclosure are capable of inhibiting the activity of MetRS. Inhibition of MetRS may be either in vivo and/or in vitro. Accordingly, in a third aspect the disclosure provides methods for treating diseases that are ameliorated by the inhibition of MetRS providing to a patient in need of such treatment a therapeutically effective amount of either a compound of the disclosure (e.g., compounds formulae (I-(V) or any preceding embodiment), or a pharmaceutical composition comprising one or more of compounds of the disclosure.

Examples of diseases that are ameliorated by the inhibition of MetRS by the compounds of the present disclosure include *Staphylococcus* infections (including MRSA infections), *Enterococcus* infections (including VRE infections), *Streptococcus* infections, and *Clostridium* infections. Further examples of diseases that are ameliorated by the inhibition of MetRS by the compounds of the present disclosure include Mycobacterial infections, including infections from *Mycobacterium tuberculosis, Mycobacterium avium* complex, *Mycobacterium* fortuitum, and others. Further examples of diseases that are ameliorated by the inhibition of MetRS by the compounds of the present disclosure include protozoan infections, including infections caused by *Trypanosoma, Leishmania, Giardia, Trichomonas*, and others.

For example, the present disclosure provides methods for treating diseases that are ameliorated by the inhibition of MetRS, the method comprising administering to a patient in need thereof a therapeutically effective amount of a compound according to any of formulae (I)-(V) or a pharmaceutical composition thereof. In such methods, the disease may be selected from the group consisting of Protozoan, Mycobacterial, *Staphylococcus, Enterococcus, Streptococcus*, and *Clostridium* infections.

In other embodiments, the disease is a bacterial infection, such as, for example, a Gram positive bacterial infection. In some embodiments, the Gram positive bacterial infection is selected from one of *Staphylococcus, Enterococcus, Streptococcus, Clostridium, Bacillus, Helicobacter pylori*, and *Listeria*. In other embodiments, the bacteria is a Gram negative bacteria, such as, for example, *Brucella*.

In other embodiments, the disease is a *Mycobacterium tuberculosis* infection.

In other embodiments, the disease is a Trypanosomatid protozoa infection. For example, the Trypanosomatid protozoa may be one of *Trypanosoma brucei, Trypanosoma cruzi*, and *Leishmania* species.

In a fifth aspect, the present disclosure also provides a pharmaceutical composition comprising one or more of compounds according to any of formulae (I)-(V) and a pharmaceutically acceptable carrier, diluent, or excipient.

The development of the compositions of the present application is highly significant as it solves the problem of poor oral bioavailability of MetRS inhibitors. Their development makes possible their use as orally administered antibiotics for treating systemic infections. Importantly, the compounds are active against Gram positive bacteria such as *Staphylococcus aureus* and *Enterococcus faecalis* that are becoming increasingly resistant to existing antibiotics. There is a very large market, particularly in modern hospitals, for antibiotics to treat drug-resistant bacteria. The compounds under study also have potential for development as oral drugs against pathogenic protozoa, such as trypanosomes, that affect millions of people worldwide.

As used herein, the term "subject", "individual," or "patient," used interchangeably, refers to any animal, including mammals, such as mice, rats, other rodents, rabbits, dogs, cats, birds, swine, horses, livestock (e.g., pigs, sheep, goats, cattle), primates or humans. In one embodiment, the patient is a human.

As used here, a subject "in need thereof" refers to a subject that has the disorder or disease to be treated or is predisposed to or otherwise at risk of developing the disease or disorder.

As used here, the terms "treatment" and "treating" means:
inhibiting the progression the disease;
prophylactic use, for example, preventing or limiting development of a disease, condition or disorder in an individual who may be predisposed or otherwise at risk to the disease, condition or disorder but does not yet experience or display the pathology or symptomatology of the disease;
inhibiting the disease; for example, inhibiting a disease, condition or disorder in an individual who is experiencing or displaying the pathology or symptomatology of the disease, condition or disorder;
ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or
eliciting the referenced biological effect.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following: (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

The pharmaceutical compositions described herein generally comprise a combination of one or more of compounds described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In one embodiment, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

Definitions

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkyl" as used herein, means a straight or branched chain hydrocarbon containing from 1 to 12 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "alkynyl" as used herein, means a straight or branched chain hydrocarbon group containing from 2 to 12 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), a bicyclic ring system containing at least one phenyl ring or an aromatic bicyclic ring containing only carbon atoms in the aromatic bicyclic ring system or a multicyclic aryl ring system, provided that the bicyclic or multicyclic aryl ring system does not contain a heteroaryl ring when fully aromatic. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia. Multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic cycloalkyl, a monocyclic or bicyclic cycloalkenyl, and a monocyclic or bicyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. The multicyclic aryl is attached to the parent molecular moiety through any carbon atom contained within the base ring. In certain embodiments, multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a monocyclic cycloalkyl, a monocyclic cycloalkenyl, and a monocyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. Examples of multicyclic aryl groups include but are not limited to anthracen-9-yl and phenanthren-9-yl.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic, bicyclic, or a multicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. Multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkyl is attached to the parent molecular moiety through any carbon atom contained within the base ring. In certain embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

"Cycloalkenyl" as used herein refers to a monocyclic, bicyclic, or a multicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia. Multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkenyl is attached to the parent molecular moiety through any carbon atom contained within the base ring. IN certain embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a monocyclic heteroaryl, a monocyclic cycloalkyl, a monocyclic cycloalkenyl, and a monocyclic heterocyclyl.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic, bicyclic, or a multicyclic heteroaryl ring system. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia. The multicyclic heteroaryl group is a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a bicyclic aryl, a monocyclic or bicyclic heteroaryl, a monocyclic or bicyclic heterocyclyl, a monocyclic or bicyclic cycloalkenyl, and a monocyclic or bicyclic cycloalkyl. The multicyclic heteroaryl group is connected to the parent molecular moiety through any carbon atom or nitrogen atom contained within the base ring. In certain embodiments, multicyclic heteroaryl groups are a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a monocyclic heteroaryl, a monocyclic heterocyclyl, a monocyclic cycloalkenyl, and a monocyclic cycloalkyl. Examples of multicyclic heteroaryls include, but are not limited to 5H-[1,2,4]triazino[5,6-b]indol-5-yl, 2,3,4,9-tetrahydro-1H-carbazol-9-yl, 9H-pyrido[3,4-b]indol-9-yl, 9H-carbazol-9-yl, and acridin-9-yl.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic, bicyclic, or multicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic heterocyclyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In certain embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl. As used herein, heterocyclyl groups may be optionally substituted with one or more oxo group.

The term "nitro" as used herein means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)$_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

EXAMPLES

Unless otherwise stated, all chemicals were purchased from commercial suppliers and used without further purification. Inhibitors were synthesized through several different routes. The microwave irradiation was performed in CEM Discover System. The final purity of all compounds was determined by analytical LCMS with Phenomenex Onyx Monolithic C18 column (4.6 mm×100 mm). The products were detected by UV at the detection frequency of 220 nm. All compounds were determined to be >95% pure by this method. The purification by preparative HPLC was performed on Waters Xterra Prep RP18 OBD 5 μM (19 mm×50 mm) with $CH_3CN/H_2O$ and 0.1% TFA as eluent. The mass spectra were recorded with the Agilent Liquid Chromatograph—Ion Trap Mass Spectrometer. NMR spectra were recorded with either a Bruker 500 MHz spectrometer or Bruker 300 MHz spectrometer at ambient temperature. Inhibitors were synthesized through several different routes, as represented in Schemes 1-85. All other syntheses and compound characterization data are presented below.

A general procedure of synthesis of compound 1614, 1673, 1709 and 1717

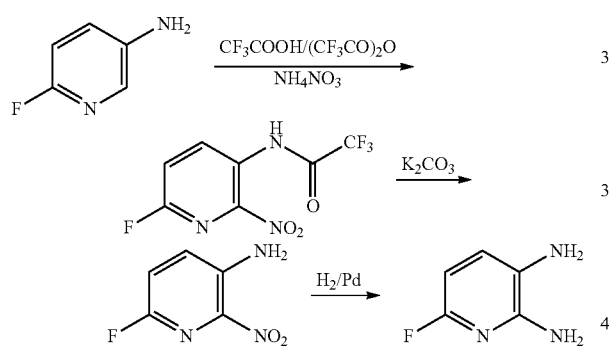

Synthesis of 6-fluoropyridine-2,3-diamine. Trifluoroacetic anhydride (8.8 ml) was slowly added to a solution of 5-amino-2-fluoropyridine (1.0 g) dissolved in trifluoroacetic acid (15.2 ml) at 0° C. After stirring for 5 min, to the clear solution was added ammonium nitrate (1.43 g) in several portions. The mixture was stirred at 0° C. for 3 h, then room temperature for 1 h. After the solvent was removed, the residue was dissolved in EtOAc, washed with brine, dried over $Na_2SO_4$. The orange residue was purified via silica gel column with EtOAc/hexane elution to obtain 1.4 g of 2,2,2-trifluoro-N-(6-fluoro-2-nitropyridin-3-yl)acetamide as a yellow oil. $^1$H NMR (500 MHz, MeOD) δ 8.60 (t, J=10.5 Hz, 1H), 7.61 (d, J=3.4 Hz, 1H).

2,2,2-trifluoro-N-(6-fluoro-2-nitropyridin-3-yl)acetamide (1.4 g) was added into a solution of $K_2CO_3$ (1.0 g) in 10 ml of MeOH and 5 ml of water. After stirring at room temperature for 3 h, the mixture was cooled down at 4° C. overnight. The yellow solid was collected and washed with cooled MeOH to obtain 6-fluoro-2-nitropyridin-3-amine (0.92 g). m/z: 159.2 ([M+H]$^+$ 6-fluoro-2-nitropyridin-3-amine (250 mg) was dissolved in 40 ml of MeOH and reduced with $H_2$ (in a balloon) in the presence of 86 mg of 10% Pd/carbon for 2 h at room temperature. The solution was filtered through a celite pad. After the solvent was removed, the residue was purified via silica gel column with MeOH/DCM elution to obtain 128 mg of 6-fluoropyridine-2,3-diamine as a light pink solid. $^1$H NMR (500 MHz, MeOD) δ 7.00 (dd, J=7.9, 7.2 Hz, 1H), 6.07 (dd, J=8.0, 2.2 Hz, 1H). m/z: 128.8 ([M+H]$^+$

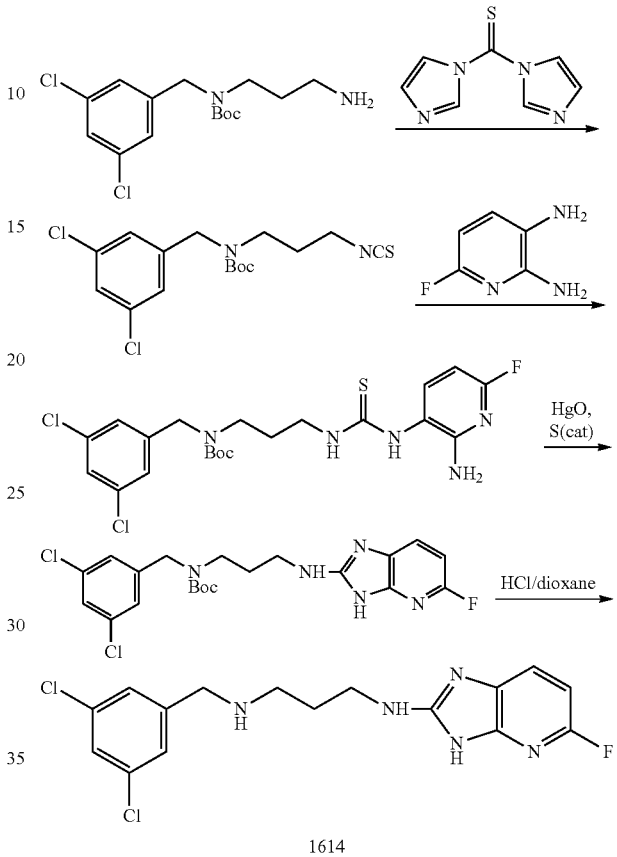

Synthesis of 1614. The synthetic procedure was based on the reference$^1$. (3-amino-propyl)-(3,5-dichloro-benzyl)-carbamic acid tert-butyl ester (1.0 mmol)$^2$ in 10 ml of acetonitrile was dropwise added into the solution of 1,1'-thiocarbonyldiimidazole (1.5 mmol), imidazole (0.3 mmol) in 50 ml of acetonitrile at 0° C. with stirring. After 10 min of stirring at 0° C., the mixture was allowed to warm to room temperature and stirred for 3 h. 6-fluoropyridine-2,3-diamine (1.2 mmol) in 10 ml of acetonitrile was added and the mixture was refluxed overnight. After the solvent was removed, the residue was purified via silica gel chromatography, eluted with MeOH/DCM, to give tert-butyl 3,5-dichlorobenzyl3-(3-(2-amino-6-fluoropyridin-3-yl)thioureido)propylcarbamate as a yellow oil. m/z: 502.8 ([M+H]$^+$ A mixture of tert-butyl 3,5-dichlorobenzyl3-(3-(2-amino-6-fluoropyridin-3-yl)thioureido)propylcarbamate (0.2 mmol), HgO (0.4 mmol), sulfur (0.04 mmol) and EtOH (10 ml) was combined and refluxed for 2 hours. The reaction mixture was cooled and filtered through a celite pad. After the solvent was removed, the residue was purified via silica gel chromatography, eluted with MeOH/DCM to give tert-butyl 3,5-dichlorobenzyl3-(5-fluoro-3H-imidazo[4,5-b]pyridin-2-ylamino)propylcarbamate as an off-white solid. m/z: 468.9 ([M+H]$^+$ tert-butyl 3,5-dichlorobenzyl3-(5-fluoro-3H-imidazo[4,5-b]pyridin-2-ylamino)propylcarbamate (0.15 mmol) was dissolved in a mixture of dioxane (20 ml) and 4 M HCl in dioxane (60 µl). The precipitate was formed in 5 min. The mixture was stirred in 30 min. The solid was collected and washed with cooled dioxane to obtain a white solid of 1614 as HCl salt. m/z: 368.8 ([M+H]$^+$

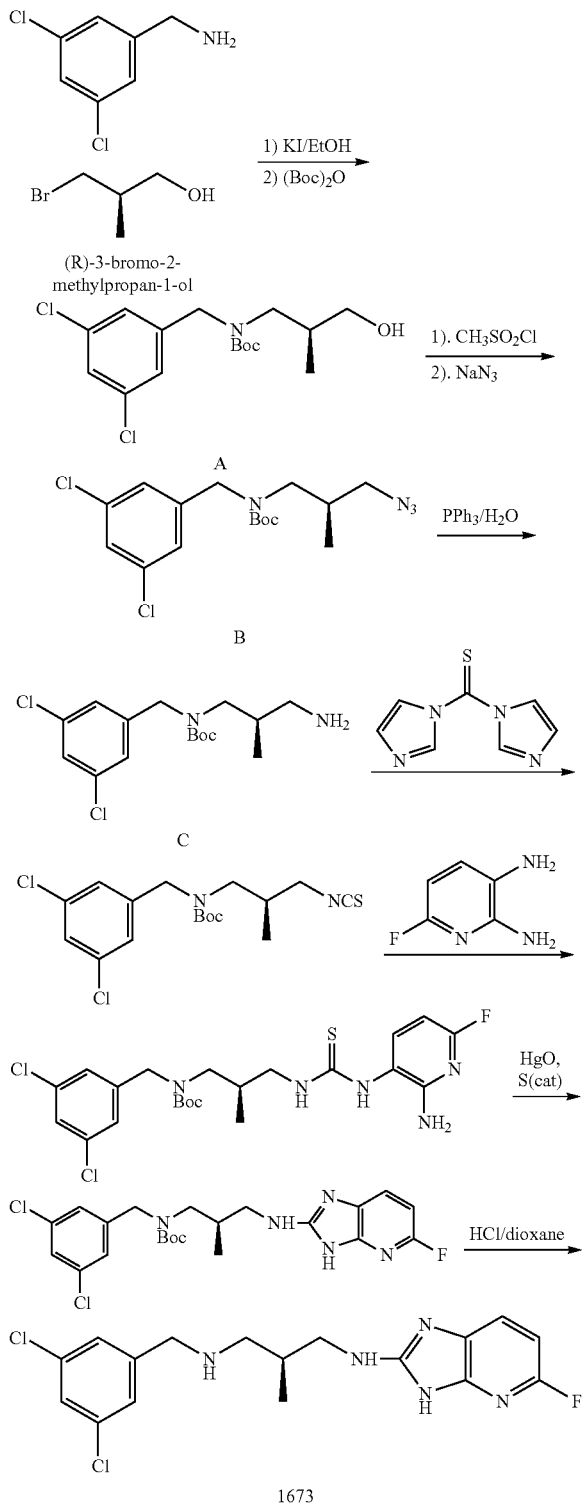

ethanol (1.0 ml) was microwave irradiated at 90° C. for 30 min. To the solution were added (Boc)$_2$O (1.25 mmol) and DIPEA (1.5 mmol) in 2 ml of acetonitrile. The mixture was stirred at room temperature overnight. After the solvents were removed, the residue were dissolved in ethyl acetate, washed with water, brine and dried over Na$_2$SO$_4$. The organic extract was purified via silica gel chromatography to obtain compound A in 50% yield. m/z: 371.0 ([M+Na]$^+$ To a solution of compound A (0.25 mmol) in 20 ml of dry DCM at −10° C. was added DIPEA (0.45 mmol) and methanesulfonyl chloride (0.38 mmol). The mixture was stirred at −10° C. for 30 min. After the solvent was removed, the residue was dissolved in 5 ml of DMF and NaN$_3$ (0.50 mmol) was added. The mixture was stirred at 40-45° C. overnight. The solvent was removed and the residue was dissolved with ethyl acetate. The organic solution was washed with water, brine and dried over Na$_2$SO$_4$. The residue was purified via silica gel chromatography to obtain compound B. $^1$H NMR (500 MHz, CDCl$_3$) δ 7.28 (m, 1H), 7.10 (s, 2H), 4.37 (s, 2H), 3.24 (m, 4H), 2.04 (br, 1H), 1.48 (m, 9H), 0.97 (d, J=6.7 Hz, 3H). m/z: 395.8 ([M+Na]$^+$ A mixture of compound B (0.083 mmol), PPh$_3$ (0.25 mmol) in 1 ml of THF and 15 µl of water was stirred at room temperature overnight. Purification was performed via silica gel chromatography to obtain compound C. m/z: 347.8 ([M+H]$^+$ Following the synthetic procedure of 1614, compound 1673 was synthesized using compound C. $^1$H NMR (500 MHz, MeOD) δ 7.93-7.83 (m, 1H), 7.64 (s, 2H), 7.56 (s, 1H), 6.97 (d, J=8.4 Hz, 1H), 4.30 (q, J=13.3 Hz, 2H), 3.58-3.38 (m, 2H), 3.28 (m, 1H), 3.10-2.96 (m, 1H), 2.42 (s, 1H), 1.20 (d, J=6.7 Hz, 3H). m/z: 383.0 ([M+H]$^+$

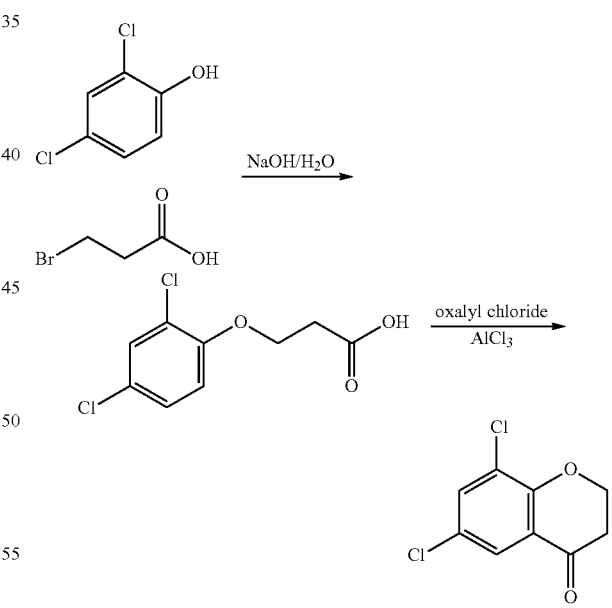

A solution of 2,4-dichlorophenol (10 mmol) and NaOH (10 mmol) in 20 mL of water was heated at 100° C. for 20 min. A solution of 3-bromopropionic acid (20 mmol) and NaOH (20 mmol) in 10 ml of water was added slowly to the above hot solution. The mixture was heated at 100° C. overnight and then cooled to room temperature. The reaction Synthesis of 1673. A mixture of 3,5-dichlorobenzylamine (1.5 mmol) and (R)-(−)-3-bromo-2-methyl-1-propanol (0.5 mmol), DIPEA (0.5 mmol) and trace amount of KI in mixture was made acidic with concentrated HCl. The mixture was extracted into ether (3 times), and the combined organic layer was extracted with saturated NaHCO$_3$. The water layer was made acidic and extracted with ether (3 times). The combined organic layer was washed with brine and dried over Na$_2$SO$_4$. After solvent was removed, the residue was purified via silica gel chromatography, eluted with MeOH/DCM to give 3-(2,4-dichlorophenoxy)propanoic acid as a white solid.

Oxalyl chloride (5.2 mmol)) was added to the solution of 3-(2,4-dichlorophenoxy)propanoic acid (2.6 mmol) in 20 mL of anhydrous DCM followed by a drop of DMF[3]. After 1.5 hours, the solution was cooled in an ice-water bath. AlCl$_3$ (2.86 mmol) was added and the dark red solution was allowed to slowly reach room temperature and stirred overnight. The mixture was poured into ice and the organic layer was separated. The aqueous layer was extracted with ethyl acetate twice. The combined organic layers were washed with 1 N NaOH, brine, dried over Na$_2$SO$_4$ and concentrated. Purification via silica gel chromatography of this residue eluted with hexane and EtOAc provided 6,8-dichloro-2,3-dihydrochromen-4-one as a white solid. m/z: 218.2 ([M+H]$^+$ Methyl 3-(2,4-dichlorophenylamino)propanoate (0.8 mmol) was hydrolyzed in 1 ml of MeOH and 1 ml of 1M NaOH with microwave irradiation at 80° C. for 10 min. The mixture was made acidic and extracted with ethyl acetate. The organic layer was washed with brine and dried over Na$_2$SO$_4$. After the solvent was removed, the residue was purified via silica gel chromatography, eluted with MeOH/DCM to give 3-(2,4-dichlorophenylamino)propanoic acid. m/z: 235.2 ([M+H]$^+$ A mixture of 3-(2,4-dichlorophenylamino)propanoic acid (0.6 mmol) in 2 ml of phosphorus pentoxide-methanesulfonic acid (Eaton's reagent) was microwave irradiated at 70° C. for 20 min[5]. Ice-cold water was added to the reaction mixture. The mixture was made basic (pH 12) with 50 wt % NaOH, and extracted with EtOAc several times. The combined organic extracts were dried over Na$_2$SO$_4$. After the solvent was removed, the residue was purified via silica gel chromatography, eluted with EtOAc/hexane to give 6,8-dichloro-2,3-dihydroquinolin-4(1H)-one as a yellow solid. m/z: 217.4 ([M+H]$^+$

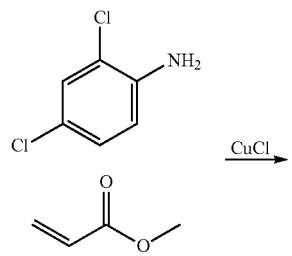

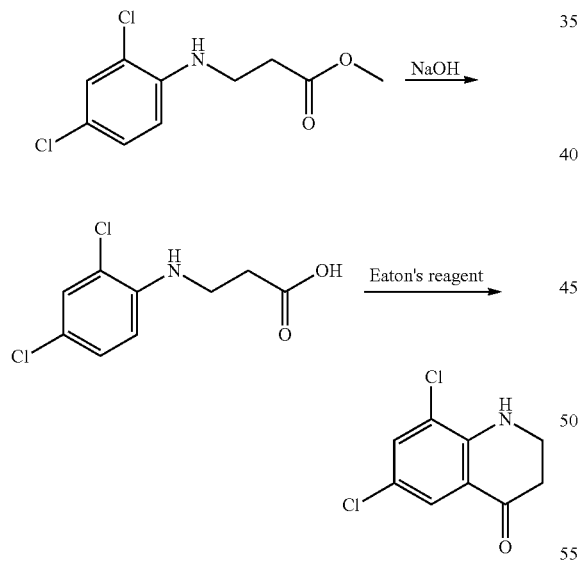

A mixture of 2,4-dichloroaniline (1.2 mmol), methyl acrylate (4.8 mmol), cuprous chloride (0.12 mmol) in 2 ml of AcOH was microwave irradiated at 135° C. for 1 h[4].

Solvents were removed by evaporation and the residue partitioned between EtOAc (30 ml) and water (30 ml). The organic layer was washed with brine and dried over Na$_2$SO$_4$. After solvent was removed, the residue was purified via silica gel chromatography, eluted with EtOAc/hexane to give methyl 3-(2,4-dichlorophenylamino)propanoate. m/z: 249.5 ([M+H]$^+$

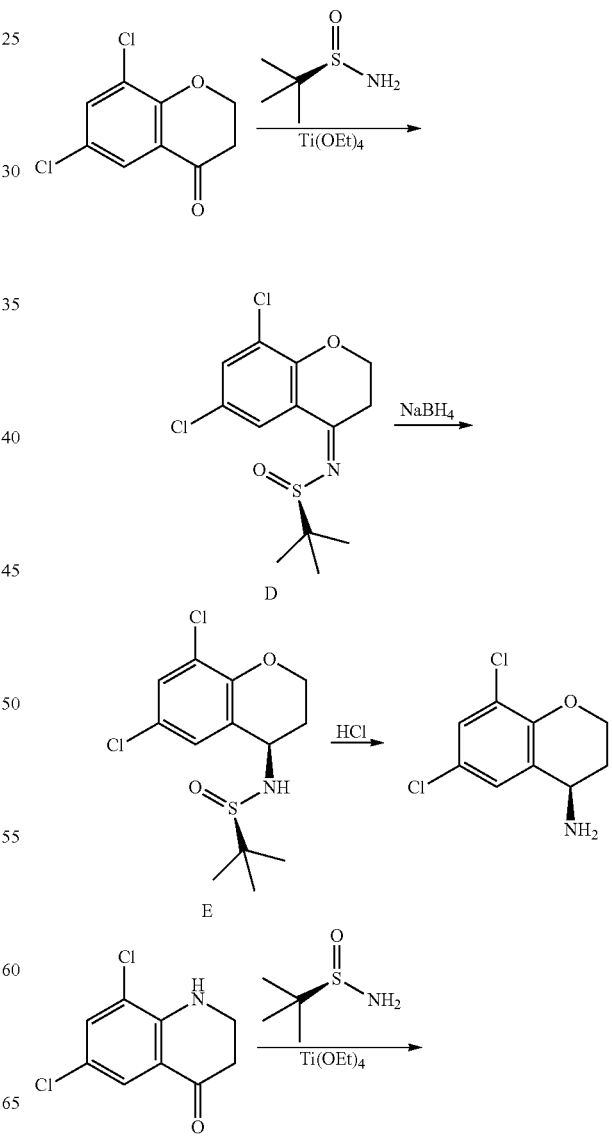

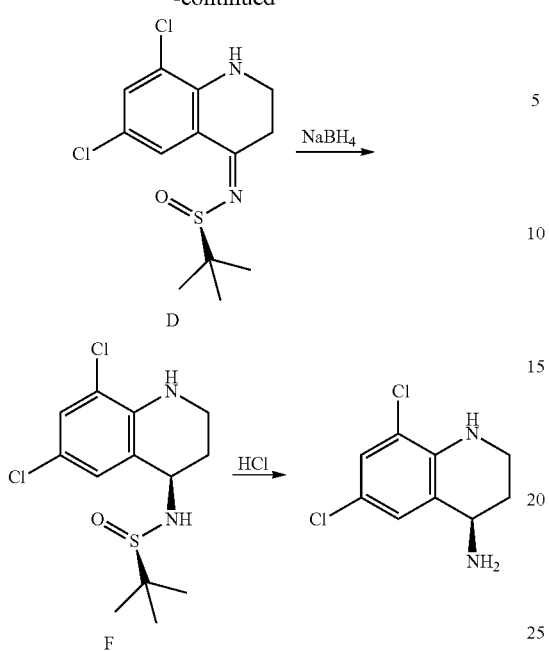

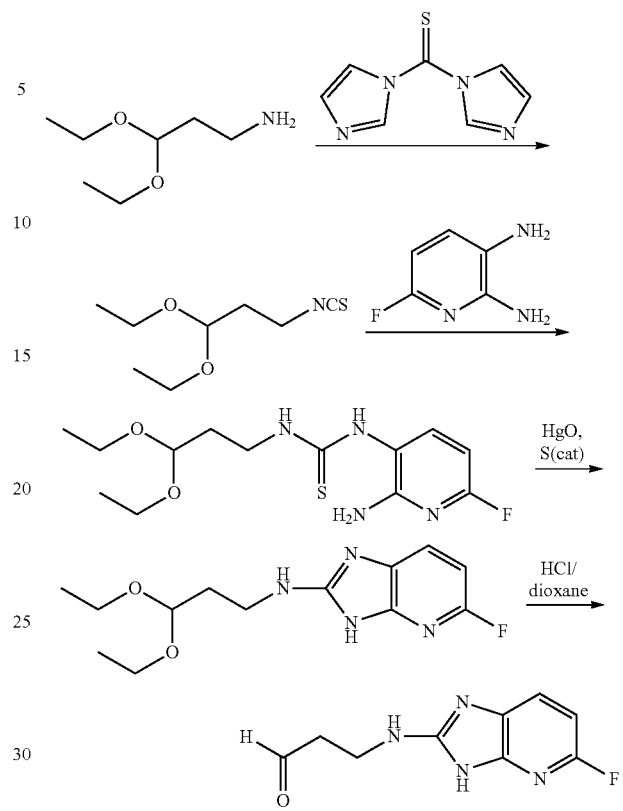

To a solution of (R)-(+)-tert-butylsulfinamide (0.60 mmol) in tetrahydrofuran (4 ml) was added subsequently 6,8-dichloro-2,3-dihydrochromen-4-one (0.30 mmol) and tetraethyl orthotitanate (0.75 mmol) and the solution was microwave irradiated at 80° C. for 1 h[6]. The mixture was cooled to room temperature, treated with brine (400 ml), the suspension was filtered through the celite pad. The layers were separated; the aqueous layer was extracted with ethyl acetate. The combined organic layers were washed with water, dried and concentrated in vacuo. The residue was purified via silica gel chromatography using ethyl acetate/hexane as the eluent to give compound D.

Compound D (0.2 mmol) was dissolved in 98:2 THF/H$_2$O (2 ml) and cooled to −50° C. To the mixture was then added NaBH$_4$ (0.6 mmol), and the resulting solution was warmed to room temperature over a 3 h period[7]. The solvent was then removed in vacuo, and the resulting residue was extracted with ethyl acetate. The organic layer was washed with water, brine, dried and concentrated in vacuo. The residue was purified via silica gel chromatography using ethyl acetate/hexane as the eluent to give compound E. $^1$H NMR (500 MHz, CDCl$_3$) δ 7.32 (m, 1H), 4.57 (br, 1H), 4.42-4.46 (m, 1H), 4.30-4.35 (m, 1H), 3.34 (s, 1H), 2.13-2.17 (m, 2H), 1.26 (s, 9H). m/z: 323.0 ([M+H]$^+$ Hydrogen chloride (3.0 equiv, 4M solution in 1,4-dioxane) was added to a solution of compound E (0.15 mmol) in MeOH (1.5 ml) at room temperature and the reaction was proceeded for 1.5 h. Most of the solvent was removed in vacuum and diethyl ether was added, resulting in the appearance of a solid. The supernatant was removed and the solid was washed several times with diethyl ether and dried in vacuum to give (R)-6,8-dichloro-3,4-dihydro-2H-chromen-4-amine.

(R)-6,8-dichloro-1,2,3,4-tetrahydroquinolin-4-amine was synthesized via the same procedure as (R)-6,8-dichloro-3,4-dihydro-2H-chromen-4-amine by using 6,8-dichloro-2,3-dihydroquinolin-4(1H)-one. m/z: 219.5 ([M+H]$^+$ N-(3,3-diethoxypropyl)-5-fluoro-3H-imidazo[4,5-b]pyridin-2-amine was synthesized using 3-Aminopropionaldehyde diethyl acetal by following the synthetic procedure described for the synthesis of 1614. $^1$H NMR (500 MHz, MeOD) δ 7.55-7.47 (m, 1H), 6.55 (d, J=8.2 Hz, 1H), 4.67 (t, J=5.5 Hz, 1H), 3.73-3.64 (m, 2H), 3.54 (m, 2H), 3.48 (m, 2H), 1.96 (dd, J=12.4, 6.8 Hz, 2H), 1.19 (t, J=7.1 Hz, 6H). m/z: 283.3 ([M+H]$^+$ 2N of HCl (3.0 equiv) was added to a solution of N-(3,3-diethoxypropyl)-5-fluoro-3H-imidazo[4,5-b]pyridin-2-amine (0.15 mmol) in dioxane (1.5 ml) at room temperature and the mixture was stirred for 1.5 h. After the solvent was removed, the residue was purified via silica gel chromatography, eluted with EtOAc/hexane to give 3-(5-fluoro-3H-imidazo[4,5-b]pyridin-2-ylamino)propanal. m/z: 209.5 ([M+H]$^+$

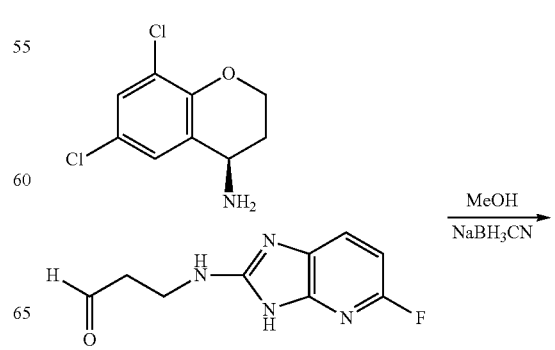

-continued

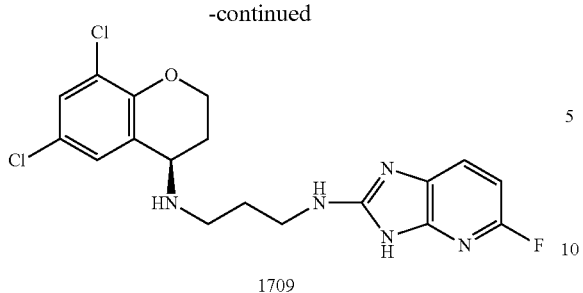

1709

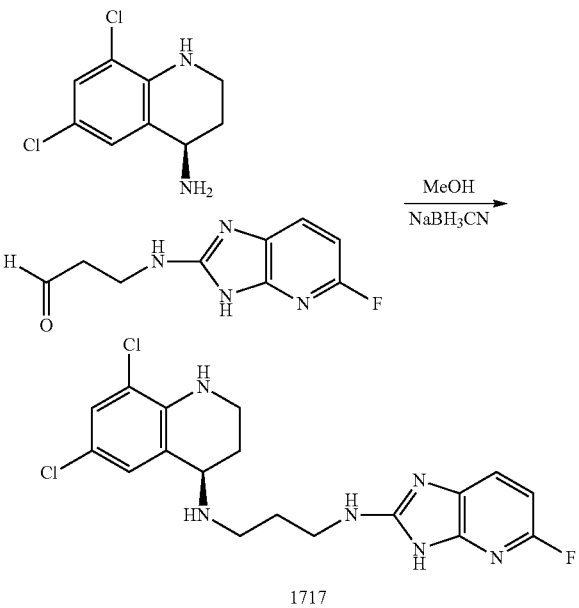

1717

Synthesis of 1709 and 1717. To a solution of (R)-6,8-dichloro-3,4-dihydro-2H-chromen-4-amine HCl salt (0.1 mmol) in 5 ml of methanol was added DIPEA (0.1 mmol), 0.15 ml of HOAc and 3-(5-fluoro-3H-imidazo[4,5-b]pyridin-2-ylamino)propanal (0.12 mmol). The mixture was stirred at room temperature for 30 min, and then NaBH$_3$CN (0.2 mmol) was added. The reaction mixture was stirred at 50° C. for 2 days. After the solvent was removed, the residue was purified via silica gel chromatography, eluted with MeOH/DCM and further purified by using preparative HPLC to give compound 1709 as TFA salt. Conversion of TFA salt to HCl was performed via adding HCl in methanol and removing solvent to give a white solid. m/z: 411.1 ([M+H]$^+$ Following the synthetic procedure of compound 1709, compound 1717 was synthesized using (R)-6,8-dichloro-1,2,3,4-tetrahydroquinolin-4-amine. m/z: 410.2 ([M+H]$^+$ Scheme 1

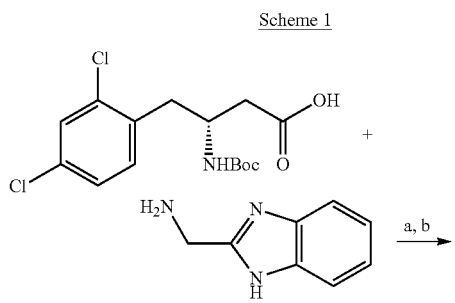

-continued

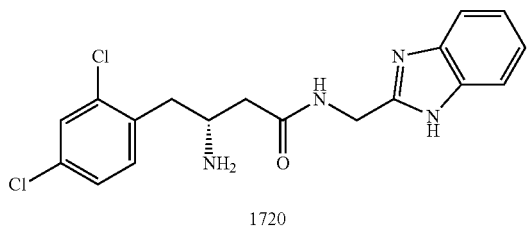

1720

Reagents and conditions (a) EDC, DIPEA, DMAP; (b) TFA, DCM

General Procedure 1 (1720, 1726):

The solution of Boc-(R)-3-amino-4-(2,4-dichlorphenyl)butyric acid (30 mg, 0.086 mmol, 1.0 equiv), DIPEA (3 equiv), EDC HCl (1.5 equiv) and DMAP (1.0 equiv) in DCM (20 mL) was stirred for 10 min. To this reaction mixture (1H-benzo[d]imidazol-2-yl)methanamine (1.0 equiv) was added. The reaction mixture was stirred at room temperature overnight. The organic layer was washed with aq NaHCO$_3$ and brine. It was then dried over anhydrous sodium sulfate and evaporated under vacuum. The residue was purified by flash column chromatography. The above purified compound was dissolved in 3 ml of DCM. To the solution, 1 ml of TFA was added dropwise. The solution was stirred for 40 min at room temperature. The reaction mixture was evaporated under vacuum, neutralized with aq NaHCO$_3$ and extracted with ethyl acetate. The ethyl acetate layer was dried over anhydrous sodium sulfate and concentrated to give 1720. LC/MS: (ESI) (M+H)+=378.3.

1726

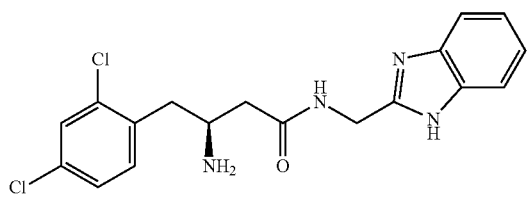

1726 was synthesized using of Boc-(S)-3-amino-4-(2,4-dichlorphenyl)butyric acid following General Procedure 1. LC/MS: (ESI) (M+H)$^+$=378.3

Scheme 2

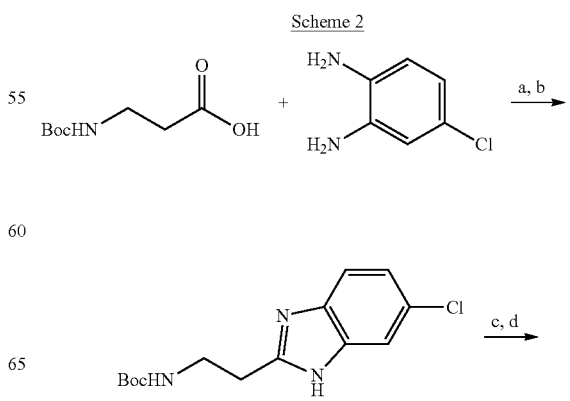

123
-continued

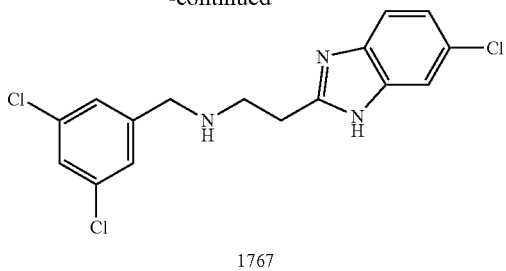

1767

Reagents and conditions (a) EDC, DIPEA, HOBt, CH₂Cl₂; (b) AcOH, 60° C., 4 h; (c) TFA, CH₂Cl₂; (d) 3,5-dichlorobenzaldehyde, MeOH, NaBH₃CN Reagents and conditions (a) EDC, DIPEA, HOBt, CH₂Cl₂; (b) AcOH, 60° C., 4 h; (c) TFA, CH₂Cl₂; (d) 3,5-dichlorobenzaldehyde, MeOH, NaBH₃CN General Procedure 2 (1767, 1794, 1805-1806, 1819-1828):

To a 10 mL DCM solution of Boc-β-alanine (50 mg, 0.265 mmol) were added N,N-diisopropylethylamine (0.80 mmol), EDC HCl (0.40 mmol), HOBt (0.265 mmol), and 4-chlorobenzene-1,2-diamine (0.265 mmol). The reaction mixture was stirred at room temperature for 6 hr. The solution was diluted with 50 ml DCM, washed with water, sat. ammonium chloride, sat. sodium bicarbonate and brine, dried over anhydrous Na₂SO₄, filtered and concentrated. To the residue, 3 ml of acetic acid was added and this mixture was heated for 4 hrs at 60° C. After evaporation, the obtained mixture was purified by flash column chromatography (DCM/MeOH) to give tert-butyl 2-(5-chloro-1H-benzo[d]imidazol-2-yl)ethylcarbamate. TFA (1 ml) was added to tert-butyl 2-(5-chloro-1H-benzo[d]imidazol-2-yl)ethylcarbamate (20 mg. 0.068 mmol) in methylene chloride (3 ml) and the reaction mixture was stirred at room temperature for 1 h. The solvent was evaporated off completely, under vacuum, and the residue was co-distilled 2× with methylene chloride. The residue was dissolved in 3 ml MeOH, neutralized with DIPEA, 0.15 ml AcOH and 3,5-Dichlorobenzaldehyde (1.1 equiv) were added. After the mixture was stirred for 30 min, NaBH₃CN (2 equiv) was added. The mixture was stirred overnight and the solvent was removed under vacuum. The residue was dissolved in EtOAc (50 ml) and washed with sat. sodium bicarbonate and brine. The organic layer was dried over Na₂SO₄ and concentrated under vacuum. The residue was purified by flash column chromatography (DCM/MeOH), yielding [2-(6-Chloro-1H-benzoimidazol-2-yl)-ethyl]-(3,5-dichloro-benzyl)-amine (1716) in colorless oil. The oily product was dissolved in 1 ml of 4 N HCl in MeOH. The solvent was evaporated under vacuum to give solid 1716 in HCl salt form. LC/MS: (ESI) (M+H)⁺= 355.6

1794

124

1794 was synthesized using 3-tert-butoxycarbonylamino-butyric acid in General Procedure 2. LC/MS: (ESI) (M+H)⁺= 369.7.

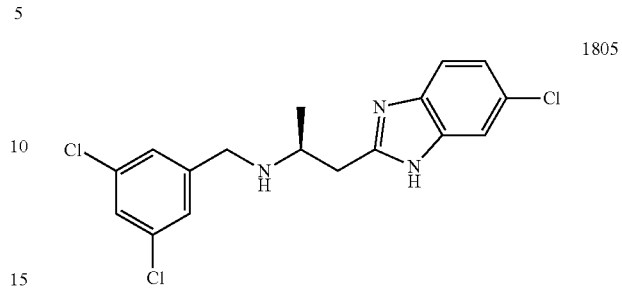

1805

1805 was synthesized using (S)-3-tert-butoxycarbonylamino-butyric acid in General Procedure 2. LC/MS: (ESI) (M+H)⁺=369.7.

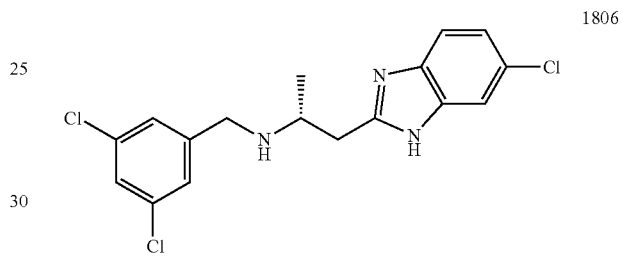

1806

1806 was synthesized using (R)-3-tert-butoxycarbonylamino-butyric acid in General Procedure 2. LC/MS: (ESI) (M+H)⁺=369.7.

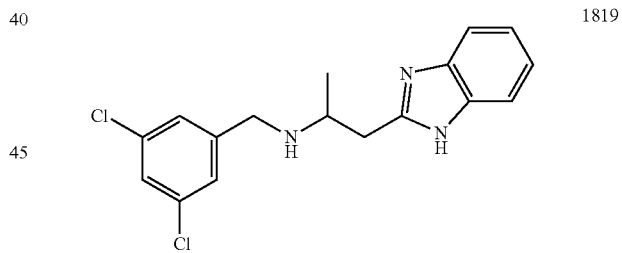

1819

1819 was synthesized using benzene-1,2-diamine in General Procedure 2. LC/MS: (ESI) (M+H)⁺=335.3

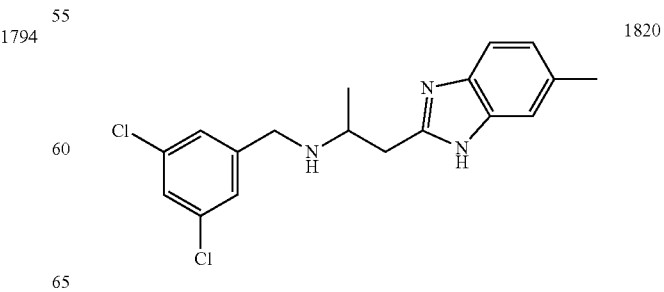

1820

1820 was synthesized using 4-methyl-benzene-1,2-diamine in General Procedure 2. LC/MS: (ESI) (M+H)+= 339.5

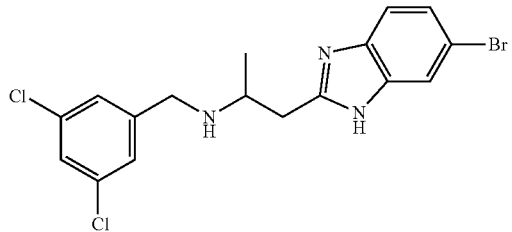

1821 was synthesized using 4-bromobenzene-1,2-diamine in General Procedure 2. LC/MS: (ESI) (M+H)+= 414.1.

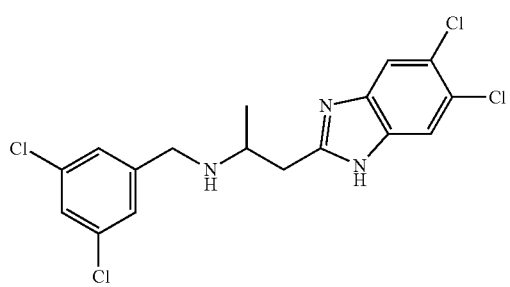

1822 was synthesized using 4,5-dichloro-benzene-1,2-diamine in General Procedure 2. LC/MS: (ESI) (M+H)+= 404.3.

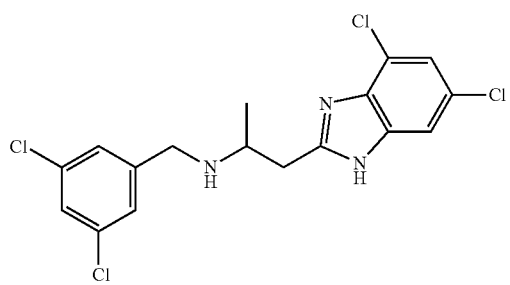

1823 was synthesized using 3,5-dichloro-benzene-1,2-diamine in General Procedure 2. LC/MS: (ESI) (M+H)+= 404.3.

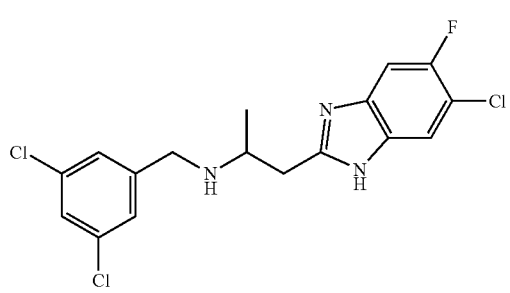

1824 was synthesized using 4-chloro-5-fluoro-benzene-1,2-diamine in General Procedure 2. LC/MS: (ESI) (M+H)+= 387.7.

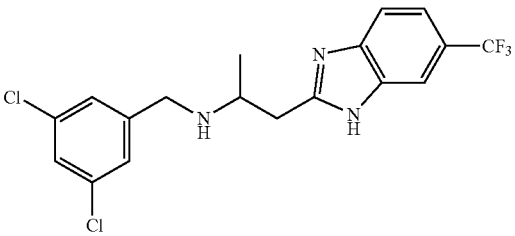

1825 was synthesized using 4-trifluoromethyl-benzene-1,2-diamine in General Procedure 2. LC/MS: (ESI) (M+H)+= 403.4.

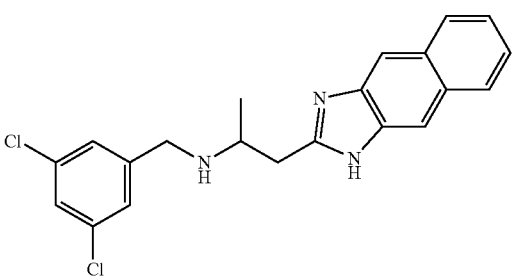

1826 was synthesized using Naphthalene-2,3-diamine in General Procedure 2.
LC/MS: (ESI) (M+H)+=385.2.

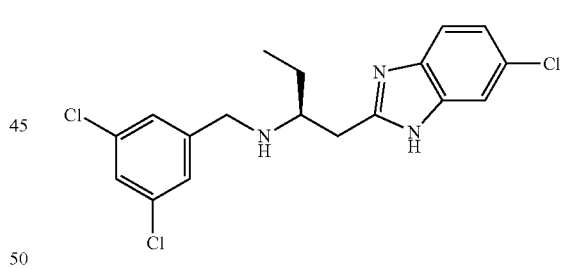

1827 was synthesized using (S)-3-tert-Butoxycarbonylamino-pentanoic acid in General Procedure 2. LC/MS: (ESI) (M+H)+=383.2.

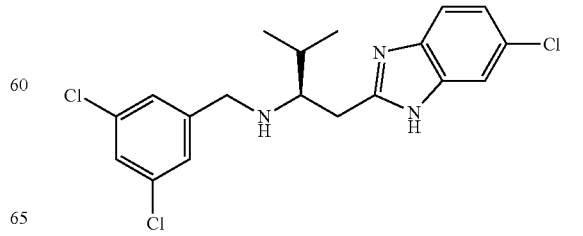

1828 was synthesized using (R)-3-tert-Butoxycarbonylamino-4-methyl-pentanoic acid in General Procedure 2. LC/MS: (ESI) (M+H)+=397.8.

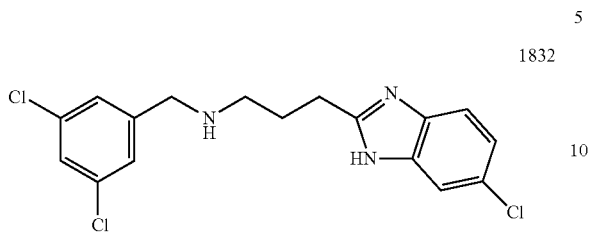

1832

1832 was synthesized using 4-tert-Butoxycarbonylaminobutyric acid and 4-chlorobenzene-1,2-diamine in General Procedure 2. LC/MS: (ESI) (M+H)+=369.6.

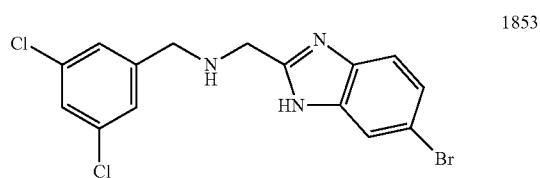 [SMILES: Clc1cc(Cl)cc(CNCc2nc3ccc(Br)cc3[nH]2)c1]

1853

1853 was synthesized using Boc-glycine and 4-bromobenzene-1,2-diamine in General Procedure 2. LC/MS: (ESI) (M+H)+=385.7.

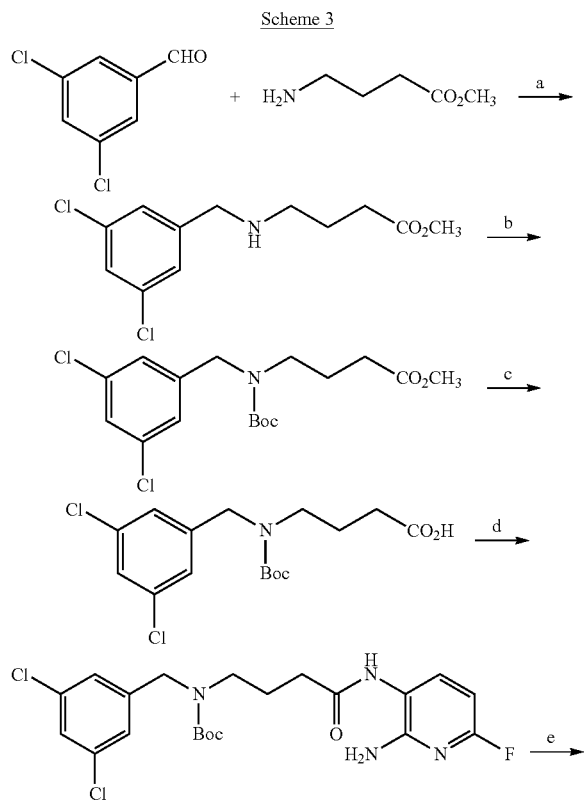

Scheme 3

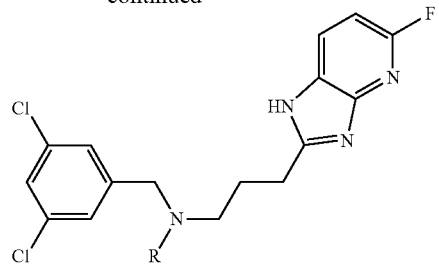

1858: R = H
1835: R = Ac

Reagents and conditions: (a) NaBH₃CN, AcOH, CH₃OH, r.t. overnight; (b) (Boc)₂O, DIPEA, DCM, r.t., 3 h; (c) LiOH, CH₃OH/H₂O, r.t. overnight; (d) EDC, pyridine, r.t. overnight; (e) AcOH, POCl₃, Microwave 150° C., 1 h.

Reagents and conditions: (a) NaBH$_3$CN, AcOH, CH$_3$OH, r.t. overnight; (b) (Boc)$_2$O, DIPEA, DCM, r.t., 3 h; (c) LiOH, CH$_3$OH/H$_2$O, r.t. overnight; (d) EDC, pyridine, r.t. overnight; (e) AcOH, POCl$_3$, Microwave 150° C., 1 h.

(a) 3,5-dichlorobenzaldehyde (88 mg, 0.5 mM) and methyl 4-aminobutanoate (77 mg, 0.5 mM) were dissolved in CH$_3$OH, AcOH (60 mg, 1 mM) and NaBH$_3$CN (63 mg, 1 mM) were added to the solution. The mixture was stirred at r.t. overnight. The solvent was removed under reduced pressure and the residue was extracted by EA. The organic phase was dried over sodium sulfate and the solvent was removed under reduced pressure. The residue was used for the next step without purification.

(b) Intermediate methyl 4-((3,5-dichlorobenzyl)amino)butanoate obtained from above step was dissolved in DCM, DIPEA (1.5 eq) was added to the solution. (Boc)$_2$O was then added in portions at 0° C., the mixture was stirred at r.t. for 3 hours. The solvent was removed under reduced pressure and the residue was extracted by EA. The organic phase was dried over sodium sulfate. Remove solvent in vacuum and purify through flash chromatography on silica gel eluted with EA-hexane to give intermediate methyl 4-((tert-butoxycarbonyl)(3,5-dichlorobenzyl)amino)butanoate.

(c) LiOH.H$_2$O (3 eq) was added to the solution of methyl 4-((tert-butoxycarbonyl)(3,5-dichlorobenzyl)amino)butanoate in CH$_3$OH/H$_2$O (CH$_3$OH:H$_2$O=3:1). The reaction mixture was stirred at r.t. overnight. The solvent was evaporated under reduced pressure, the residue was extracted with EA/1N HCl solution. The organic layer was dried over sodium sulfate, concentrated in vacuum to give the intermediate 4-((tert-butoxycarbonyl)(3,5-dichlorobenzyl)amino)butanoic acid which was used for the next step without further purification.

(d) 4-((tert-butoxycarbonyl)(3,5-dichlorobenzyl)amino)butanoic acid obtained from above step was dissolved in pyridine (2 mL), EDC (1.5 eq) was added and the mixture was stirred at r.t. overnight. Pyridine was removed under reduced pressure, saturated aqueous sodium bicarbonate was added to the residue, and extracted with DCM. The organic layer was dried over anhydrous sodium sulfate, and concentrated in vacuum. Purification through flash chromatography on silica gel eluted with MeOH-DCM (0.5% ammonia hydroxide) gave tert-butyl(4-((2-amino-6-fluoropyridin-3-yl)amino)-4-oxobutyl)(3,5-dichlorobenzyl)carbamate.

(d) Intermediate tert-butyl (4-((2-amino-6-fluoropyridin-3-yl)amino)-4-oxobutyl)(3,5-dichlorobenzyl)carbamate obtained from above step was dissolved in 3 mL glacial acetic acid, POCl$_3$ (3 eq) was added, the mixture was microwave irradiated at 150° C. for 1 hour. The reaction mixture was concentrated in vacuum and the residue partitioned between saturated sodium bicarbonate and DCM. The organic extract was dried over anhydrous sodium sulfate, and concentrated in vacuum. The residue was purified through flash chromatography on silica gel eluted with MeOH-DCM (0.5% ammonia hydroxide) to give compounds 1858 N-(3,5-dichlorobenzyl)-3-(5-fluoro-1H-imidazo[4,5-b]pyridin-2-yl)propan-1-amine. MS (ESI) (M+H)$^+$= 354.3; and 1835 N-(3,5-dichlorobenzyl)-N-(3-(5-fluoro-1H-imidazo[4,5-b]pyridin-2-yl)propyl)acetamide. MS (ESI) (M+H)$^+$=396.8.

1895: N-(3-(5-chloro-1H-imidazo[4,5-b]pyridin-2-yl)propyl)-N-(3,5-dichlorobenzyl)acetamide. MS (ESI) (M+H)$^+$=412.6.

Scheme 4

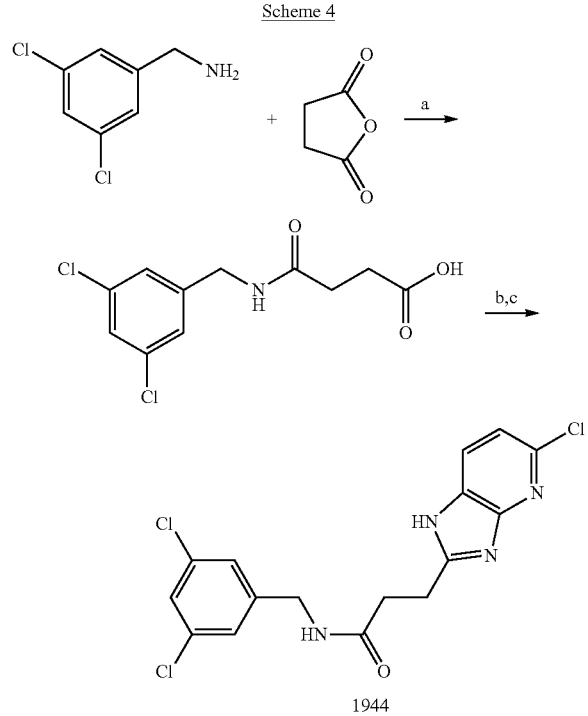

Reagents and conditions: (a) Dioxane, 80° C., 30 min; (b) EDC, pyridine, r.t. overnight; (c) AcOH, POCl$_3$, Microwave 150° C., 1 h.

(a) Succinic anhydride (1 eq) and (3,5-dichlorophenyl)methanamine (1 eq) in dioxane was heated to 80° C. for 30 min. The solvent was evaporated off and residue was purified via flash column chromatography directly eluting with 20% MeOH in DCM to yield 4-((3,5-dichlorobenzyl)amino)-4-oxobutanoic acid.

(b,c) Steps b and c were conducted following steps d and e in Scheme 3 to produce compound 1944. LC/MS: (ESI) (M+H)$^+$=384.8.

Scheme 5

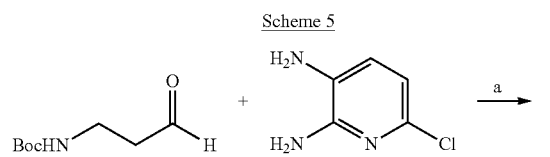

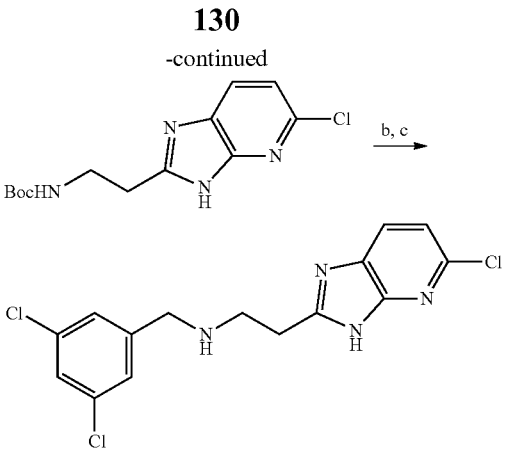

Reagents and conditions (a) NaHSO$_3$, DMF, 100° C.; (b) TFA, CH$_2$Cl$_2$; (c) 3,5-dichlorobenzaldehyde, MeOH, NaBH$_3$CN General Procedure 3 (1780, 1844, 1881, 1882):

DMF (1.0 mL) solution of aldehyde (1.0 mmol) was added dropwise to a mixture of 6-chloropyridine-2,3-diamine (1.0 mmol), and sodium bisulfite (1.0 mmol) in DMF (1.0 mL) over a 10-min period at 100° C. After 2 h, the reaction mixture was concentrated, and the residue was purified by flash column chromatography (DCM/MeOH) to give tert-butyl 2-(5-chloro-3H-imidazo[4,5-b]pyridin-2-yl)ethylcarbamate[1]. Following the general procedure A to remove Boc with TFA/DCM and perform the reductive amination with 3,5-dichlorobenzaldehyde yields [2-(5-chloro-3H-imidazo[4,5-b]pyridin-2-yl)-ethyl]-(3,5-dichloro-benzyl)-amine (1780). LC/MS: (ESI) (M+H)$^+$= 356.6.

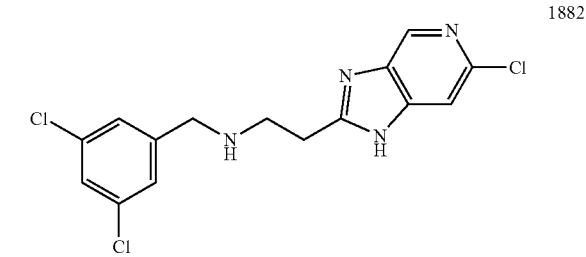 [SMILES: Clc1cc(Cl)cc(CNCCc2nc3cnc(Cl)cc3[nH]2)c1]

1844 was synthesized using 5-chloro-pyridine-2,3-diamine in General Procedure 3.

LC/MS: (ESI) (M+H)$^+$=356.6.

1882 was synthesized using 2,3-diamine-5-chloropyridine in General Procedure 3.

LC/MS: (ESI) (M+H)+=356.6.

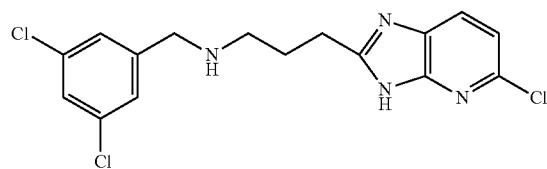

1881

1881 was synthesized using (4-oxo-butyl)-carbamic acid tert-butyl ester in General Procedure 3.

LC/MS: (ESI) (M+H)+=370.7.

Scheme 6

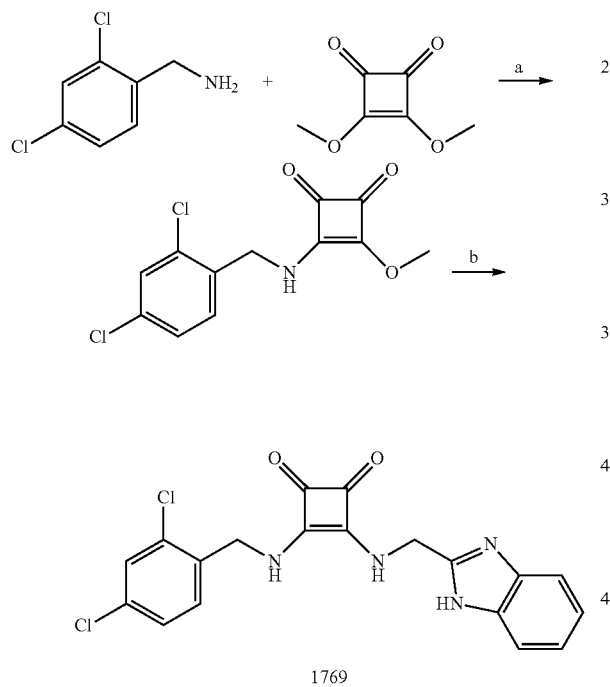

1769

Reagents and conditions (a) MeOH/H₂O, 2 h; (b) C-(1H-Benzoimidazol-2-yl)-methylamine, saturated NaHCO₃

Reagents and conditions (a) MeOH/H₂O, 2 h; (b)C-(1H-Benzoimidazol-2-yl)-methylamine, saturated NaHCO₃

2,4-Dichloro-benzylamine (47.3 mg 0.269 mmol) and 3,4-dimethoxy-3-cylclobutene-1,2-dione (38.2 mg, 0.269 mmol) were combined in MeOH (2 ml) and water (2 ml) and stirred for 2 h. C-(1H-benzoimidazol-2-yl)-methylamine HCl (59.4 mg, 0.269 mmol) and sat. NaHCO₃(1 ml) was added in situ. The mixture was stirred at room temperature overnight. After the mixture was extracted with ethyl acetate, washed with brine, concentrated under vacuum and purified via flash column chromatography to yield 3-[(H-Benzoimidazol-2-ylmethyl)-amino]-4-(2,4-dichloro-benzylamino)-cyclobut-3-ene-1,2-dione (1769). LC/MS: (ESI) (M+H)+=402.5.

Scheme 7

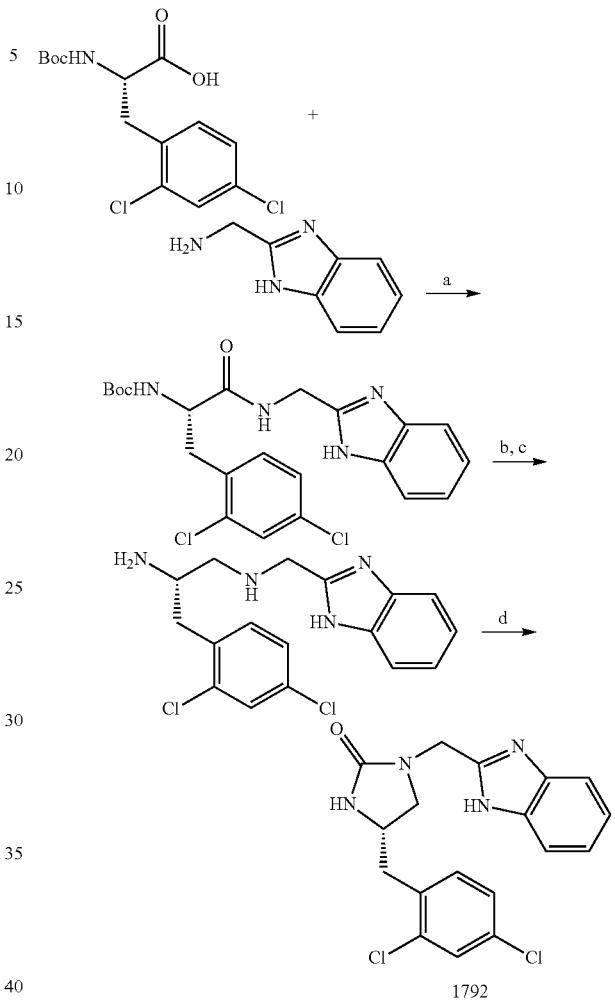

1792

Reagents and conditions (a) EDC, DIPEA, DMAP, DCM; (b) TFA, CH₂Cl₂; (c) LAH,THF, μW 80° C., 30 min; (d) triphosgene, DCM.

Reagents and conditions (a) EDC, DIPEA, DMAP, DCM; (b) TFA, CH₂Cl₂; (c) LAH, THF, μW 80° C., 30 min; (d) triphosgene, DCM.

The solution of (S)-Boc-2-amino-3-(2,4-dichlorophenyl)propionic acid (203 mg, 0.608 mmol, 1.0 equiv), DIPEA (3 equiv), EDC HCl (1.5 equiv) and DMAP (1.0 equiv) in DCM (20 mL) was stirred for 10 min. To this reaction mixture (1H-benzo[d]imidazol-2-yl)methanamine (1.0 equiv) was added. The reaction mixture was stirred at room temperature overnight. The organic layer was washed with aq NaHCO₃ and brine. It was then dried over anhydrous sodium sulphate and evaporated under vacuum to afford tert-butyl (S)-1-((1H-benzo[d]imidazol-2-yl)methylcarbamoyl)-2-(2,4-dichlorophenyl)ethylcarbamate. The above compound was dissolved in 10 ml of DCM. To the solution, 3 ml of TFA was added dropwise. The solution was stirred for 40 min at room temperature. The reaction mixture was evaporated under vacuum, neutralized with aq NaHCO₃ and extracted with ethyl acetate. The ethyl acetate layer was dried over anhydrous sodium sulphate and concentrated give (S)—N-((1H-benzo[d]imidazol-2-yl)methyl)-2-amino-3-(2, 4-dichlorophenyl)propanamide. To the solution of (S)—N-((1H-benzo[d]imidazol-2-yl)methyl)-2-amino-3-(2,4-dichlorophenyl)propanamide (95 mg, 0.262 mmol) in 3 ml of anhydrous THF, lithium aluminium hydride (40 mg, 4.0 equiv) was added in portion-wise at 0° C. The reaction mixture was then microwave irradiated at 80° C. for 30 min. Thereafter it was cooled and slowly quenched with water, aq NaOH and extracted with ethyl acetate. The organic layer was washed with water, brine, and dried over anhydrous sodium sulphate. It was evaporated under vacuum to afford (S)—N1-((1H-benzo[d]imidazol-2-yl)methyl)-3-(2,4-dichlorophenyl)propane-1,2-diamine[3]. To a stirred solution of (S)—N1-((1H-benzo[d]imidazol-2-yl)methyl)-3-(2,4-dichlorophenyl)propane-1,2-diamine (74 mg, 0.213 mmol) in DCM (10 mL) was added DIPEA (5 equiv) and cooled to 0° C. A solution of triphosgene (0.33 equiv) in DCM (2 mL) was added dropwise to the reaction mixture and stirred at room temperature for 4 h. The reaction mixture was washed with brine, dried over anhydrous sodium sulphate and evaporated under vacuum. The residue was purified by flash column chromatography (DCM/MeOH) to give 1-(1H-Benzoimidazol-2-ylmethyl)-4-(2,4-dichloro-benzyl)-imidazolidin-2-one (1792). LC/MS: (ESI) (M+H)$^+$=376.7.

To a solution of (S)-Boc-2-amino-3-(2,4-dichlorophenyl) propionic acid (150 mg, 0.4488 mmol, 1.0 equiv) in 10 ml of DMF was added NaHCO$_3$(4 equiv) and CH$_3$I (10 equiv). The mixture was stirred at room temperature for 2 days. The solvent was removed and the residue was dissolved in ethyl acetate. The solution was washed with water, brine, dried over anhydrous sodium sulfate and evaporated under vacuum. The solid was dissolved in 10 ml of DCM. To the solution, 3 ml of TFA was added dropwise. The solution was stirred for 40 min at room temperature. The reaction mixture was evaporated under vacuum, neutralized with aq NaHCO$_3$ and extracted with ethyl acetate. The ethyl acetate layer was dried over anhydrous sodium sulfate and concentrated give (S)-methyl 2-amino-3-(2,4-dichlorophenyl)propanoate. To a stirred solution of (S)-methyl 2-amino-3-(2,4-dichlorophenyl)propanoate (103 mg, 0.415 mmol) in DCM (10 mL) was added DIPEA (1.5 equiv) and cooled to 0° C. A solution of triphosgene (0.33 equiv) in DCM (2 mL) was added dropwise to the reaction mixture and stirred at room temperature for 2 h. The solution was back to 0° C. and (1H-benzo[d]imidazol-2-yl)methanamine (1.5 equiv) in DCM (2 ml) was added. The reaction mixture was stirred at 0° C. for 30 min. The solution washed with brine, dried over anhydrous sodium sulfate and evaporated under vacuum. The residue was purified by flash column chromatography to give (S)-methyl 2-(3-((1H-benzo[d]imidazol-2-yl)methyl)ureido)-3-(2,4-dichlorophenyl) propanoate. The solution of S)-methyl 2-(3-((1H-benzo[d]imidazol-2-yl)methyl)ureido)-3-(2,4-dichlorophenyl)propanoate (40 mg) in pyridine (2 ml) was microwave irradiated at 120° C. for 15 min. After the solvent was removed under vacuum, residue was dissolved in ethyl acetate. The solution was washed with water, brine, dried over anhydrous sodium sulfate and evaporated under vacuum. The residue was purified by flash column chromatography to give (S)-3-((1H-benzo[d]imidazol-2-yl)methyl)-5-(2,4-dichlorobenzyl)imidazolidine-2,4-dione (1754). LC/MS: (ESI) (M+H)=390.8.

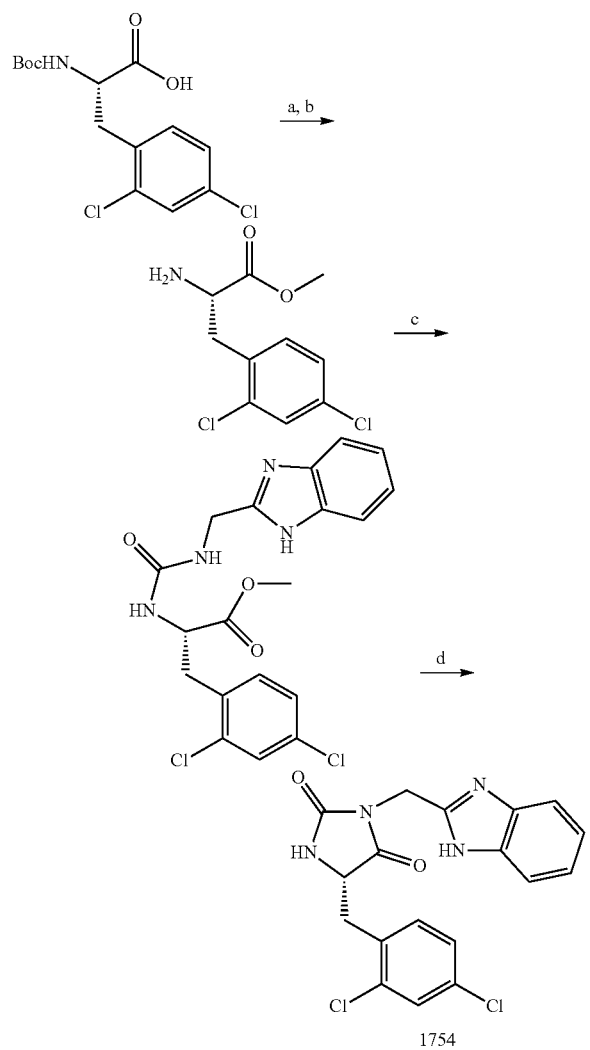

Scheme 8

Reagents and conditions (a) CH$_3$I, NaHCO$_3$, DMF; (b) TFA, CH$_2$Cl$_2$; (c) triphosgene, DCM; (d) pyridine, μW 120° C., 15 min.

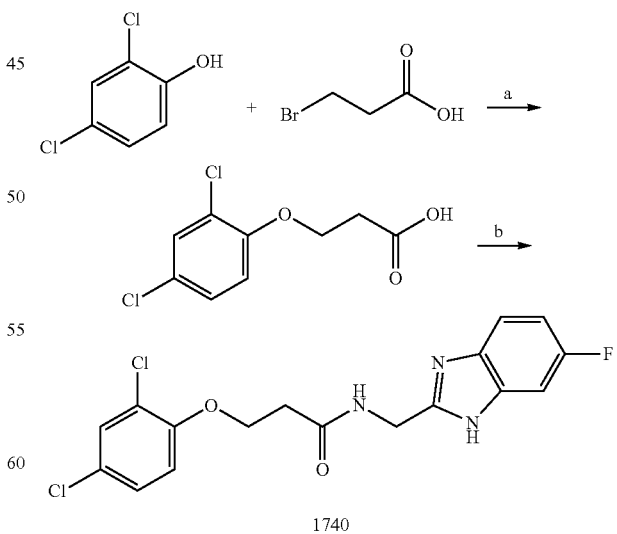

Scheme 9

Reagents and conditions (a) NaOH, H$_2$O, refluxing; (b) HBTU, DIPEA, DMF, (5-fluoro-1H-benzo[d]imidazol-2-yl)methanamine General Procedure 4 (1740, 1683, 1704, 1705, 1671, 1675, 1674, 1727):

A solution of 2,4-dichlorophenol (10 mmol) and NaOH (10 mmol) in 20 mL of water was heated at 100° C. for 20 min. A solution of 3-bromopropionic acid (20 mmol) and NaOH (20 mmol) in 10 ml of water was added slowly to the above hot solution. The mixture was heated at 100° C. overnight, cooling to room temperature. The reaction mixture was made acidic with concentrated HCl. The mixture was extracted into ether (3 times), and the combined organic layer was extracted with saturated NaHCO$_3$. The water layer was made acidic and extracted with ether (3 times). The combined organic layer was washed with brine, dried over Na$_2$SO$_4$. After solvent was removed, the residue was chromatographed via silica gel, eluted with MeOH/DCM to give 3-(2,4-dichlorophenoxy)propanoic acid in white solid. The solution of 3-(2,4-dichlorophenoxy)propanoic acid (20 mg, 0.085 mmol, DIPEA (0.25 mmol), EDC HCl (0.12 mmol) and DMAP (0.085 mmol) in DMF (20 mL) was stirred for 10 min. To this reaction mixture (5-fluoro-3H-imidazo[4,5-b]pyridin-2-yl)methanamine (0.085 mmol) was added. The reaction mixture was stirred at room temperature overnight. The organic layer was washed with aq NaHCO$_3$ and brine. It was then dried over anhydrous sodium sulfate and evaporated under vacuum. The residue was purified by flash column chromatography to afford 3-(2,4-dichlorophenoxy)-N-((6-fluoro-1H-benzo[d]imidazol-2-yl)methyl)propanamide (1740). LC/MS: (ESI) (M+H)$^+$=383.3.

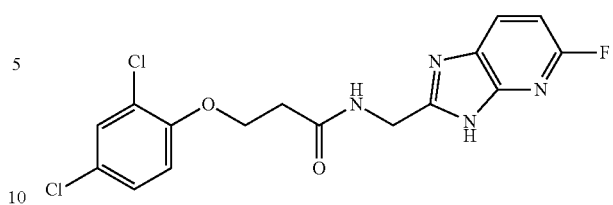

1705 was synthesized using (5-fluoro-3H-imidazo[4,5-b]pyridin-2-yl)methanamine in General Procedure 4. LC/MS: (ESI) (M+H)$^+$=384.7.

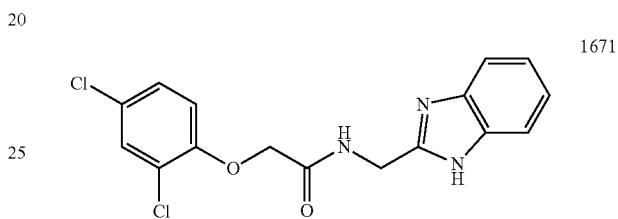

1671 was synthesized using 2-bromoacetyl bromide and (1H-benzo[d]imidazol-2-yl)methanamine in General Procedure 4. LC/MS: (ESI) (M+H)$^+$=351.4.

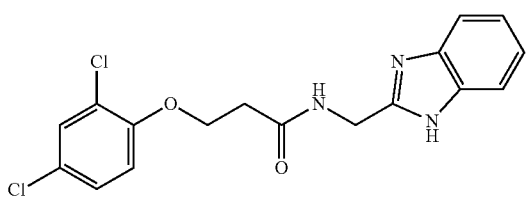

1683 was synthesized using (1H-benzo[d]imidazol-2-yl)methanamine in General Procedure 4. LC/MS: (ESI) (M+H)$^+$=385.6.

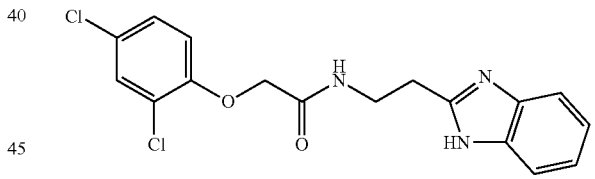

1675 was synthesized using 2-bromoacetyl bromide and 2-(1H-benzo[d]imidazol-2-yl)ethanamine in General Procedure 4. LC/MS: (ESI) (M+H)$^+$=365.4.

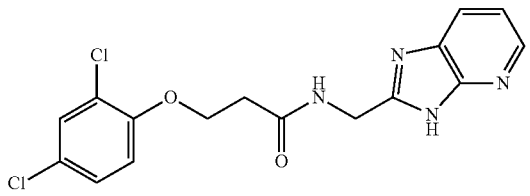

1704 was synthesized using (3H-imidazo[4,5-b]pyridin-2-yl)methanamine in General Procedure 4. LC/MS: (ESI) (M+H)$^+$=366.5.

1674 was synthesized using 2-bromoacetyl bromide and (1H-indol-2-yl)methanamine in General Procedure 4. LC/MS: (ESI) (M+H)$^+$=350.7.

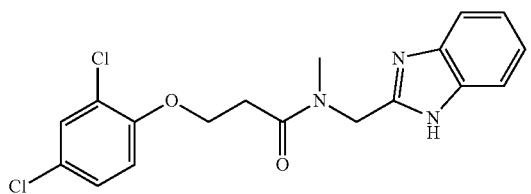

1727 was synthesized using (1H-benzo[d]imidazol-2-yl)-N-methylmethanamine in General Procedure 4. LC/MS: (ESI) (M+H)+=379.3.

Scheme 10

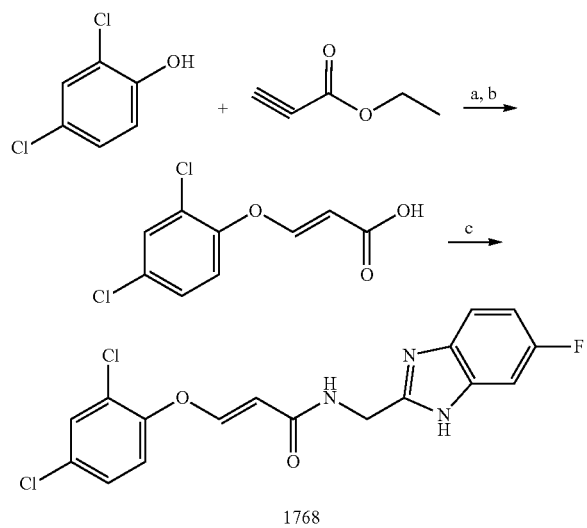

1768

Reagents and conditions (a) CH₃CN, NMM; (b) NaOH, Ethanol; (c) EDC, DIPEA, DCM, (5-fluoro-3H-imidazo[4,5-b]pyridin-2-yl)methanamine A solution of 2,4-dichloro-phenol (1 mmol), ethyl propiolate (1.2 mmol) and N-methylmorpholine (0.06 mmol) in CH₂Cl₂ (10 mL) was stirred at room temperature overnight. The solution was then washed with water and brine, and dried over anhydrous sodium sulfate. After removal of the solvent, the crude product was purified by column chromatography to give (E)-3-(2,4-Dichloro-phenoxy)-acrylic acid ethyl ester. To a solution of (E)-3-(2,4-Dichloro-phenoxy)-acrylic acid ethyl ester (30 mg, 0.115 mmol) in ethanol (2 mL) was added and 1 N NaOH (1 ml). The resultant mixture was microwave irradiated for 15 min at 80° C. After being cooled to room temperature, it was poured into ethyl acetate (50 mL), washed with 0.1 N HCl, water, brine dried over magnesium sulfate, and evaporated to dry to yield 3-(2,4-Dichloro-phenoxy)-acrylic acid. The solution of 3-(2,4-Dichloro-phenoxy)-acrylic acid (20 mg, 0.086 mmol, 1.0 equiv), DIPEA (3 equiv), EDC HCl (1.5 equiv) and DMAP (1.0 equiv) in DCM (20 mL) was stirred for 10 min. To this reaction mixture (5-fluoro-3H-imidazo[4,5-b]pyridin-2-yl)methanamine (1.0 equiv) was added. The reaction mixture was stirred at room temperature overnight. The organic layer was washed with sat. NaHCO₃ and brine. It was then dried over anhydrous sodium sulfate and evaporated under vacuum. The residue was purified by flash column chromatography to afford 3-(2,4-Dichloro-phenoxy)-N-(5-fluoro-3H-imidazo[4,5-b]pyridin-2-ylmethyl)-acrylamide (1768). LC/MS: (ESI) (M+H)+=382.2.

Scheme 11

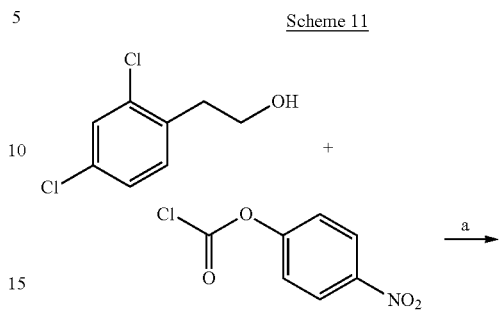

1741

Reagents and conditions (a) DCM, pyridine; (b) 5-fluoro-3H-imidazo[4,5-b]pyridin-2-yl)methanamine General Procedure 5(1741, 1701, 1706, 1707, 1699, 1728):

To a solution of 2-(2,4-dichloro-phenyl)-ethanol (200 mg, 1.04 mmol) in 5 ml of DCM was added 4-nitrophenol chloroformate (200 mg, 0.99 mmol) in 3 ml of DCM and pyridine (84.8µl, 1.05 mmol) at 0° C. The mixture was at 0° C. for 3 h. The solvent was removed and the residue was dissolved in ethyl acetate. The solution was washed with water, brine, dried over anhydrous sodium sulfate and evaporated under vacuum. The residue was purified by flash column chromatography to give carbonic acid 2-(2,4-dichloro-phenyl)-ethyl ester 4-nitro-phenyl ester. 5-fluoro-3H-imidazo[4,5-b]pyridin-2-yl)methanamine (0.06 mmol) was added into the solution of carbonic acid 2-(2,4-dichloro-phenyl)-ethyl ester 4-nitro-phenyl ester (0.06 mmol) in DCM (10 ml) at 0° C. with stirring. The mixture was stirred at room temperature overnight. The solution was diluted with 50 ml of DCM and washed with 0.1 N NaOH (50 ml), brine, dried over anhydrous sodium sulfate and evaporated under vacuum. The residue was purified by flash column chromatography to give (6-Fluoro-1H-benzoimidazol-2-ylmethyl)-carbamic acid 2-(2,4-dichloro-phenyl)-ethyl ester (1741). LC/MS: (ESI) (M+H)+=383.1.

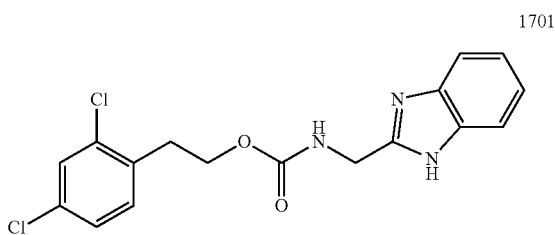 [SMILES: O=C(NCc1nc2ccccc2[nH]1)OCCc1ccc(Cl)cc1Cl]

1701 was synthesized using (1H-benzo[d]imidazol-2-yl)methanamine in General Procedure 5. LC/MS: (ESI) (M+H)⁺=365.7.

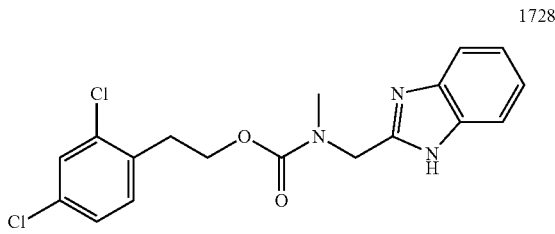 [SMILES: CN(Cc1nc2ccccc2[nH]1)C(=O)OCCc1ccc(Cl)cc1Cl]

1728 was synthesized using (1H-benzo[d]imidazol-2-yl)-N-methylmethanamine in General Procedure 5. LC/MS: (ESI) (M+H)⁺=379.5.

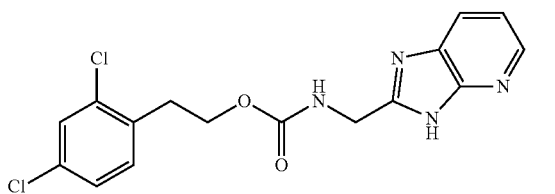

1706 was synthesized using (3H-imidazo[4,5-b]pyridin-2-yl)methanamine in General Procedure 5. LC/MS: (ESI) (M+H)⁺=366.6.

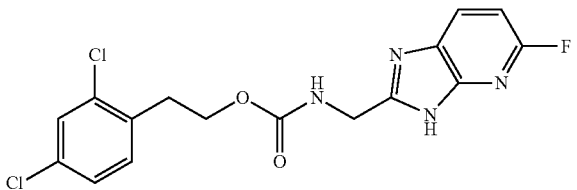

1707 was synthesized using (3H-imidazo[4,5-b]pyridin-2-yl)methanamine in General Procedure 5. LC/MS: (ESI) (M+H)⁺=384.5.

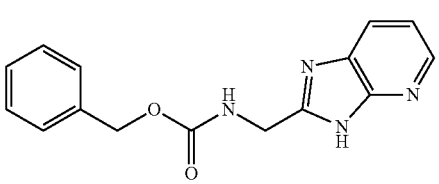

1699 was synthesized using phenylmethanol and (3H-imidazo[4,5-b]pyridin-2-yl)methanamine in General Procedure 5. LC/MS: (ESI) (M+H)⁺=283.4.

Scheme 12

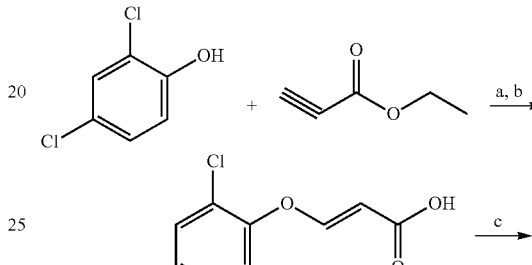

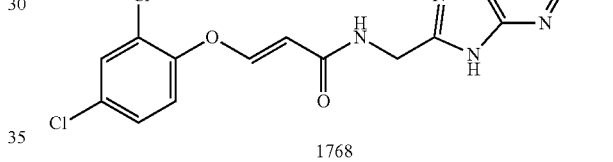

Reagents and conditions (a) CH₃CN, NMM; (b) NaOH, Ethanol; (c) EDC, DIPEA, DMAP, DCM, (5-fluoro-3H-imidazo[4,5-b]pyridin-2-yl)methanamine General Procedure 6 (1768, 1729, 1779, 1765, 1766):

A solution of 2,4-dichloro-phenol (1 mmol), ethyl propiolate (1.2 mmol) and N-methylmorpholine (0.06 mmol) in CH₂Cl₂ (10 mL) was stirred at room temperature overnight. The solution was then washed with water and brine, and dried over anhydrous sodium sulfate. After removal of the solvent, the crude product was purified by column chromatography to give (E)-3-(2,4-Dichloro-phenoxy)-acrylic acid ethyl ester. To a solution of (E)-3-(2,4-Dichloro-phenoxy)-acrylic acid ethyl ester (30 mg, 0.115 mmol) in ethanol (2 mL) was added and 1 N NaOH (1 ml). The resultant mixture was microwave irradiated for 15 min at 80° C. After being cooled to room temperature, it was poured into ethyl acetate (50 mL), washed with 0.1 N HCl, water, brine dried over magnesium sulfate, and evaporated to dry to yield 3-(2,4-Dichloro-phenoxy)-acrylic acid. The solution of 3-(2,4-Dichloro-phenoxy)-acrylic acid (20 mg, 0.086 mmol), DIPEA 0.26 mmol), EDC HCl (0.13 mmol) and DMAP (0.086 mmol) in DCM (20 mL) was stirred for 10 min. To this reaction mixture (5-fluoro-3H-imidazo[4,5-b]pyridin-2-yl)methanamine (0.086 mmol) was added. The reaction mixture was stirred at room temperature overnight. The organic layer was washed with sat. NaHCO₃ and brine. It was then dried over anhydrous sodium sulfate and evaporated under vacuum. The residue was purified by flash column chromatography to afford 3-(2,4-Dichloro-phenoxy)-N-(5-fluoro-3H-imidazo[4,5-b]pyridin-2-ylmethyl)-acrylamide (1768). LC/MS: (ESI) (M+H)⁺=382.2.

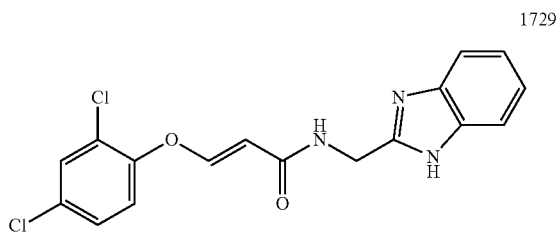 [SMILES: O=C(/C=C/Oc1ccc(Cl)cc1Cl)NCc1nc2ccccc2[nH]1]

1729 was synthesized using (1H-benzo[d]imidazol-2-yl)methanamine in General Procedure 6. LC/MS: (ESI) (M+H)$^+$=363.4.

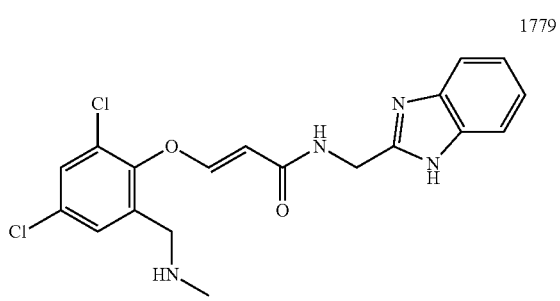 [SMILES: CNCc1cc(Cl)cc(Cl)c1O/C=C/C(=O)NCc1nc2ccccc2[nH]1]

1779 was synthesized using 2,4-dichloro-6-((methylamino)methyl)phenol and (1H-benzo[d]imidazol-2-yl)methanamine in General Procedure 6. LC/MS: (ESI) (M+H)$^+$=406.6.

Scheme 13

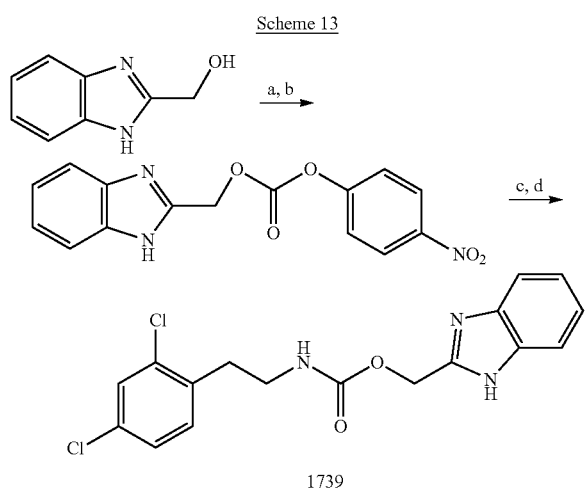

Reagents and conditions (a) Boc$_2$O, CH$_3$CN/MeOH, DIPEA, μW, 50° C., 10 min; (b) DCM, pyridine, 4-nitrophenol chloroformate; (c) 2-(2,4-dichloro-phenyl)-ethylamine; (d) TFA, CH$_2$Cl$_2$ The mixture of (1H-Benzoimidazol-2-yl)-methanol (71 mg, 0.48 mmol), DIPEA (0.17 ml) and Boc$_2$O (105 mg, 0.48 mmol) in CH$_3$CN (ml) and MeOH (0.5 ml) was microwave irradiated for 10 min at 50° C. After the solvents were removed, the residue was dissolved in 3 ml of DCM. 4-nitrophenol chloroformate (0.48 mmol) in 2 ml of DCM and pyridine (20 μl) was added at 0° C. and stirred for 2 h. The solvent was removed and the residue was dissolved in ethyl acetate. The solution was washed with water, brine, dried over anhydrous sodium sulfate and evaporated under vacuum. The residue was purified by flash column chromatography to give 2-(4-Nitro-phenoxycarbonyloxymethyl)-benzoimidazole-1-carboxylic acid tert-butyl ester. 2-(2,4-Dichloro-phenyl)-ethylamine (0.06 mmol) was added into the solution of 2-(4-Nitro-phenoxycarbonyloxymethyl)-benzoimidazole-1-carboxylic acid tert-butyl ester (0.06 mmol) in DCM (10 ml) at 0° C. with stirring. The mixture was stirred at room temperature overnight. The solution was diluted with 50 ml of DCM and washed with 0.1 N NaOH (50 ml), brine, dried over anhydrous sodium sulfate and evaporated under vacuum. The residue was purified by flash column chromatography and further de-protected with TFA/DCM to give [2-(2,4-Dichloro-phenyl)-ethyl]-carbamic acid 1H-benzoimidazol-2-ylmethyl ester (1739). LC/MS: (ESI) (M+H)$^+$=365.7.

Scheme 14

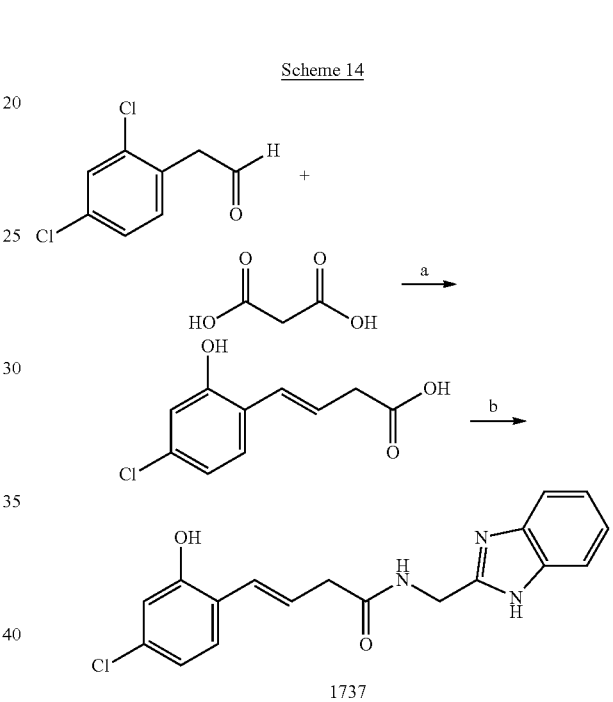

Reagents and conditions (a) NMM, μW 80° C., 15 min; (b) EDC, DIPEA, DCM, (1H-benzo[d]imidazol-2-yl)methanamine (2,4-Dichloro-phenyl)-acetaldehyde (38 mg, 0.2 mmol) and malonic acid (23 mg, 1.1 equiv) in 70 μl of NMM were mixed thoroughly and subjected to microwave irradiation at 80 C for 15 min. The mixture was diluted with ethyl acetate (50 ml) and washed with water, brine, dried over anhydrous sodium sulfate and evaporated under vacuum. The residue was purified by flash column chromatography to give (E)-4-(4-Chloro-2-hydroxy-phenyl)-but-3-enoic acid. The solution of (E)-4-(4-Chloro-2-hydroxy-phenyl)-but-3-enoic acid (20 mg, 0.094 mmol, 1.0 equiv), DIPEA (3 equiv), EDC HCl (1.5 equiv) and DMAP (1.0 equiv) in DCM (20 mL) was stirred for 10 min. To this reaction mixture (1H-benzo[d]imidazol-2-yl)methanamine (1.0 equiv) was added. The reaction mixture was stirred at room temperature overnight. The organic layer was washed with sat. NaHCO$_3$ and brine. It was then dried over anhydrous sodium sulfate and evaporated under vacuum. The residue was purified by flash column chromatography to afford 4-(4-Chloro-2-hydroxyphenyl)-but-3-enoic acid (1H-benzoimidazol-2-ylmethyl)-amide (1737). LC/MS: (ESI) (M+H)$^+$=342.3.

Scheme 15

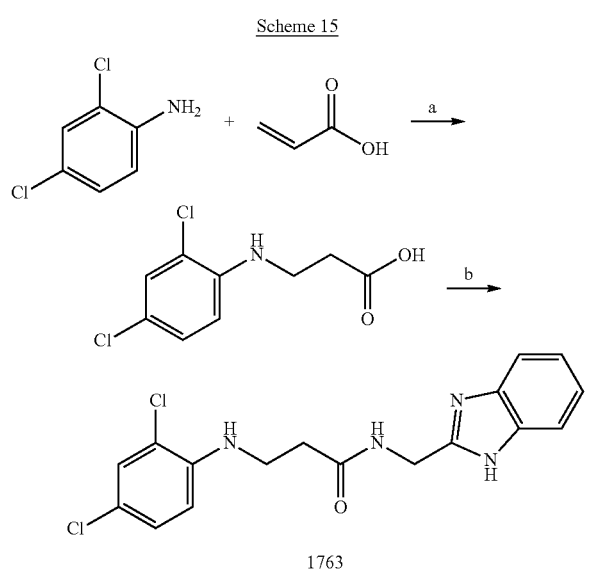

Reagents and conditions (a) 100° C. 2 h; (b) EDC, DIPEA, DCM, (1H-benzo[d]imidazol-2-yl)methanamine A mixture of 2,4-dichloroaniline (1.032 g), acrylic acid (2 ml) was heated at 100° C. for 2 h with stirring to give brownish solution. The hot solution was added dropwise into 500 ml of water with vigorously stirring. The precipitate was collected by filtration and washed with water. The solid was dissolved in ethyl acetate and washed with water, brine and dried over anhydrous sodium sulfate and evaporated under vacuum. The solid was directly used without further purification. The solution of (3-(2,4-dichlorophenylamino)propanoic acid (20 mg, 0.089 mmol, 1.0 equiv), DIPEA (3 equiv), EDC HCl (1.5 equiv) and DMAP (1.0 equiv) in DCM (20 mL) was stirred for 10 min. To this reaction mixture (1H-benzo[d]imidazol-2-yl)methanamine (1.0 equiv) was added. The reaction mixture was stirred at room temperature overnight. The organic layer was washed with aq NaHCO₃ and brine. It was then dried over anhydrous sodium sulfate and evaporated under vacuum. The residue was purified by flash column chromatography to afford N-(1H-Benzoimidazol-2-ylmethyl)-3-(2,4-dichloro-phenylamino)-propionamide (1763). LC/MS: (ESI) (M+H)⁺= 364.3.

Scheme 16

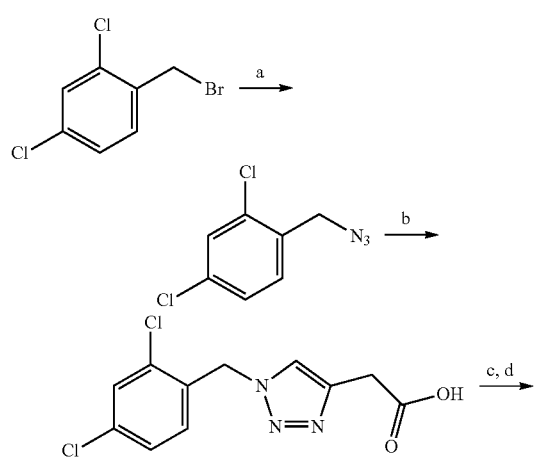

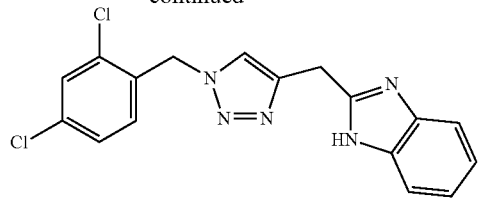

Reagents and conditions (a) NaN₃, water; (b) ethyl but-3-ynoate, CuSO4, sodium ascorbate; (c) EDC, DIPEA, DCM, (1H-benzo[d]imidazol-2-yl)methanamine; (d) AcOH, 60° C., 4 h.

General Procedure 7 (1752, 1753):

A solution of 2,4-dichlorobenzyl bromide (100 mg) in acetone was treated with excess NaN₃ and refluxed for 5 hours. The reactions was concentrated by 20% and diluted with saturated sodium chloride solution. The reaction was then extracted with ether, washed with brine, dried (Na₂SO₄) and concentrated to give 1-(azidomethyl)-2,4-dichlorobenzene. To the solution of 3-butynoic acid (0.4 mmol) in 2 ml MeOH and 2 ml water was added 1-(azidomethyl)-2,4-dichlorobenzene (0.4 mmol), CuSO₄(10 mol %), and sodium ascorbate (20 mol %). The resulting mixture was stirred at room temperature overnight. The mixture was extracted with ethyl acetate. The organic layers were washed once with brine, dried over Na₂SO₄, and evaporated under vacuum. The residue was purified by flash chromatography on silica gel with CH₂Cl₂/MeOH to give 2-(1-(2,4-dichlorobenzyl)-1H-1,2,3-triazol-4-yl)acetic acid. To a 10 mL DCM solution of 2-(1-(2,4-dichlorobenzyl)-1H-1,2,3-triazol-4-yl)acetic acid (50 mg, 0.175 mmol) were added N,N-diisopropylethylamine (3 equiv), EDC HCl (1.5 equiv), HOBt (1 equiv), 4-chlorobenzene-1,2-diamine (1 equiv). The reaction mixture was stirred at room temperature for 6 hr. The solution was diluted with 50 ml DCM, washed with water, sat. ammonium chloride, sat. sodium bicarbonate and brine, dried over anhydrous Na₂SO₄, filtered and concentrated. To the residue, 3 ml of acetic acid was added and this mixture was heated for 4 hrs at 60° C. After evaporation, the obtained mixture was purified by flash column chromatography (DCM/MeOH) to give 2-((1-(2,4-dichlorobenzyl)-1H-1,2,3-triazol-4-yl)methyl)-1H-benzo[d]imidazole (1752). LC/MS: (ESI) (M+H)⁺=359.8.

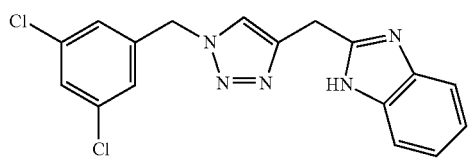

1753 was synthesized using 3,5-dichlorobenzyl bromide in General Procedure 7. LC/MS: (ESI) (M+H)⁺=359.8.

Scheme 17

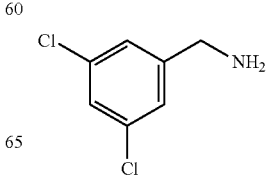

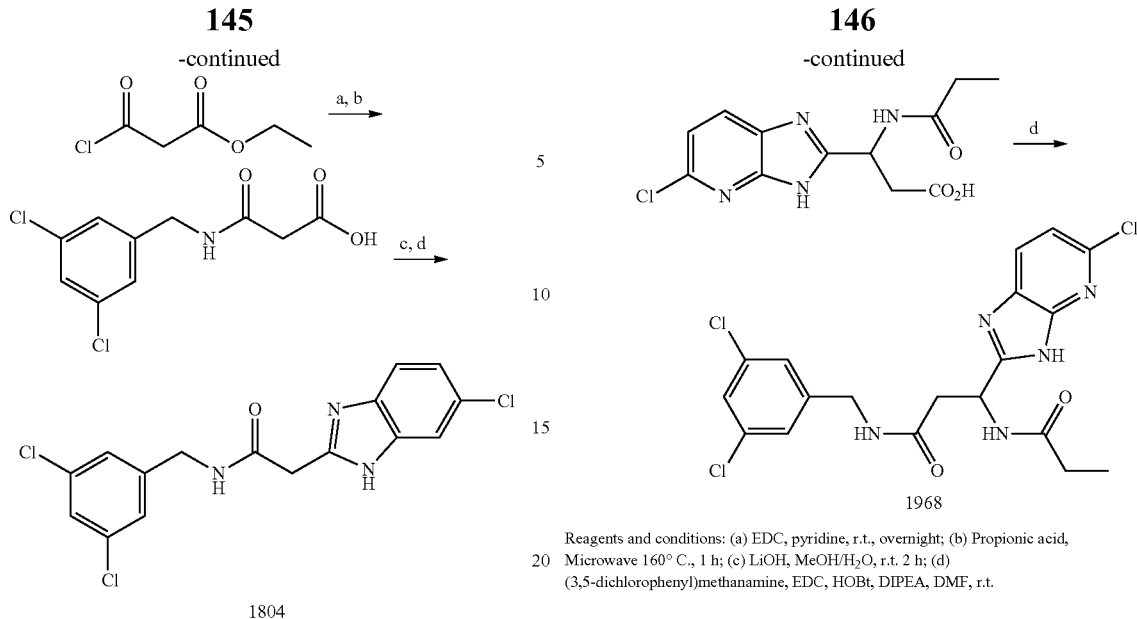

Reagents and conditions (a) DIPEA, DCM; (b) NaOH. Ethanol; (c) EDC, DIPEA, HOBt, 4-chlorobenzene-1,2-diamine; (d) AcOH, 60° C., 4 h.

To a solution of 3,5-dichlorobenzylamine (133 mg, 0.756 mmol) and DIPEA (0.756 mmol) in 10 ml of DCM was added ethyl malonyl chloride (0.756 mmol) in 3 ml of DCM at 0° C. with stirring. The reaction was performed at 0° C. for 2 h. The solvent was removed and the residue was dissolved in ethyl acetate. The solution was washed with water, brine, dried over anhydrous sodium sulfate and evaporated under vacuum. The residue was purified by flash column chromatography to give ethyl 2-(3,5-dichlorobenzylcarbamoyl)acetate. To a solution of ethyl 2-(3,5-dichlorobenzylcarbamoyl)acetate (30 mg, 0.103 mmol) in ethanol (2 mL) was added and 1 N NaOH (1 ml). The resultant mixture was microwave irradiated for 15 min at 80° C. After being cooled to room temperature, it was poured into ethyl acetate (50 mL), washed with 0.1 N HCl, water, brine dried over magnesium sulfate, and evaporated to dry to yield 2-(3,5-dichlorobenzylcarbamoyl)acetic acid. The solution of 2-(3,5-dichlorobenzylcarbamoyl) acetic acid (20 mg, 0.076 mmol, 1.0 equiv), DIPEA (3 equiv), EDC HCl (1.5 equiv) and HOBt (1.0 equiv) in DCM (20 mL) was stirred for 10 min. To this reaction mixture 4-chlorobenzene-1,2-diamine (1.0 equiv) was added. The reaction mixture was stirred at room temperature overnight. The organic layer was washed with aq NaHCO$_3$ and brine. It was then dried over anhydrous sodium sulfate and evaporated under vacuum. To the residue, 3 ml of acetic acid was added and this mixture was heated for 4 hrs at 60° C. After evaporation, the obtained mixture was purified by flash column chromatography (DCM/MeOH) to give N-(3,5-dichlorobenzyl)-2-(6-chloro-1H-benzo[d]imidazol-2-yl)acetamide (1804). LC/MS: (ESI) (M+H)$^+$=369.5.

Scheme 18

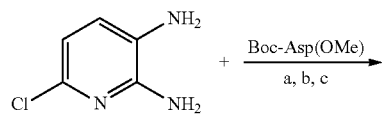

Reagents and conditions: (a) EDC, pyridine, r.t., overnight; (b) Propionic acid, Microwave 160° C., 1 h; (c) LiOH, MeOH/H$_2$O, r.t. 2 h; (d) (3,5-dichlorophenyl)methanamine, EDC, HOBt, DIPEA, DMF, r.t.

6-chloropyridine-2,3-diamine (1 eq) and Boc-Asp(OMe) (1 eq) in pyridine (2 ml) was added EDC (1.5 eq). The mixture was stirred at r.t. overnight, and pyridine was then removed under reduced pressure. After addition of saturated aqueous sodium bicarbonate to the residue, the mixture was extracted with DCM. The organic layer was dried over anhydrous sodium sulfate, and concentrated in vacuum. Purification through flash chromatography on silica gel eluted with MeOH-DCM (0.5% ammonia hydroxide) gave intermediate methyl 4-((3-amino-6-chloropyridin-2-yl) amino)-3-((tert-butoxycarbonyl)amino)-4-oxobutanoate.

Intermediate methyl 4-((3-amino-6-chloropyridin-2-yl) amino)-3-((tert-butoxycarbonyl)amino)-4-oxobutanoate was microwave irradiated in 3 mL propionic acid at 160° C. for 1 hours. The reaction was concentrated in vacuum and the residue partitioned between saturated sodium bicarbonate and DCM. The organic extract was dried over anhydrous sodium sulfate, and concentrated in vacuum. Purification through flash chromatography on silica gel eluted with MeOH-DCM (0.5% ammonia hydroxide) gave methyl 4-((3-amino-6-chloropyridin-2-yl) amino)-4-oxo-3-propionamidobutanoate.

The ethyl ester group of intermediate methyl 4-((3-amino-6-chloropyridin-2-yl)amino)-4-oxo-3-propionamidobutanoate was hydrolyzed using LiOH to get the free acid and used for the next step without purification.

3-(5-chloro-3H-imidazo[4,5-b]pyridin-2-yl)-3-propionamidopropanoic acid (1 eq), DIPEA (3 eq), (3,5-dichlorophenyl)methanamine (2 eq) were dissolved in DMF, then EDC (1.5 eq) and HOBt (1.5 eq) were added, the resulting mixture was stirred at r.t. for 3 h. The solvent was removed under vacuum and the residue was dissolved in DCM and washed with sat. sodium bicarbonate and brine. The organic layer was dried over Na$_2$SO$_4$ and concentrated under vacuum. The residue was purified by flash column chromatography (DCM/MeOH), yielding compound 1968. LC/MS: (ESI) (M+H)$^+$=455.5.

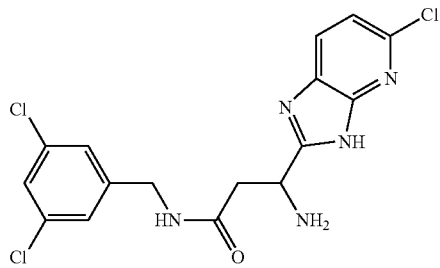

1969 3-amino-3-(5-chloro-3H-imidazo[4,5-b]pyridin-2-yl)-N-(3,5-dichlorobenzyl)propanamide was synthesized using 2-((((9H-fluoren-9-yl)methoxy)carbonyl)amino)-4-(tert-butoxy)-4-oxobutanoic acid in General Procedure with minor modifications. LC/MS: (ESI) (M+H)+=372.1.

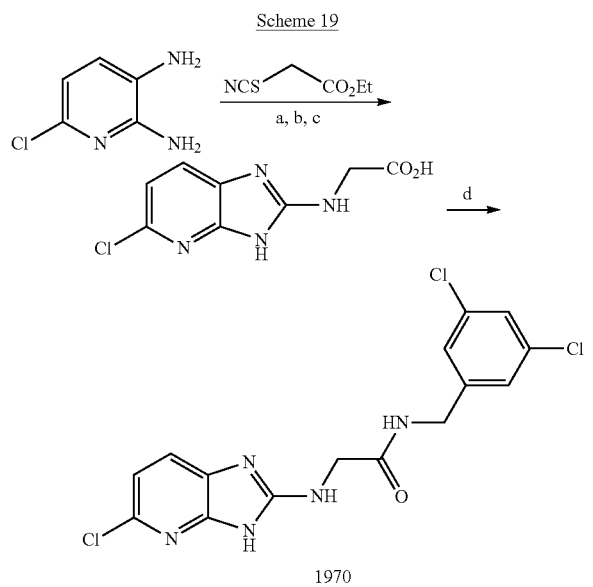

Reagents and conditions: (a) CH₃CN, r.t. - reflux; (b) DIC, reflux, overnight; (c) LiOH, CH₃OH/H₂O, r.t. overnight; (d) (3,5-dichlorophenyl)methanamine, EDC, HOBt, DIPEA, DMF, r.t.

6-chloropyridine-2,3-diamine (1 eq) was dissolved in CH₃CN, then ethyl 2-thiocyanatoacetate was added dropwise at r.t. After refluxed for 1 h, the solvent was removed under vacuum and the residue was dissolved in DCM and washed with sat. sodium bicarbonate and brine. The organic layer was dried over Na₂SO₄ and concentrated under vacuum. The residue was purified by flash column chromatography (DCM/MeOH), yielding compound ethyl 2-(3-(2-amino-6-chloropyridin-3-yl)thioureido)acetate.

Ethyl 2-(3-(2-amino-6-chloropyridin-3-yl)thioureido)acetate in anhydrous acetonitrile, was added DIC (2 eq). The solution was refluxed overnight. The solvent was removed under vacuum and residue was purified by flash column chromatography (DCM/MeOH), yielding compound ethyl 2-((5-chloro-3H-imidazo[4,5-b]pyridin-2-yl)amino)acetate.

LiOH.H₂ (3 eq) was added to the solution of ethyl 2-((5-chloro-3H-imidazo[4,5-b]pyridin-2-yl)amino)acetate in CH₃OH/H₂O (CH₃OH:H₂O=3:1). The reaction mixture was stirred at r.t. overnight. The solvent was removed under vacuum and residue was purified by flash column chromatography (DCM/MeOH), yielding 2-((5-chloro-3H-imidazo[4,5-b]pyridin-2-yl)amino)acetic acid.

A solution of 2-((5-chloro-3H-imidazo[4,5-b]pyridin-2-yl)amino)acetic acid (1 eq), (3,5-dichlorophenyl)methanamine (1 eq), EDC (1.5 eq), HOBt (1.5 eq) and DIPEA (2 eq) in DMF was stirred at room temperature overnight. The solvent was then removed under vacuum. The residue was dissolved in DCM. The organic layer was washed with brine, dried and concentrated under vacuum. Purification by chromatography afforded 1970: 2-((5-chloro-3H-imidazo[4,5-b]pyridin-2-yl)amino)-N-(3,5-dichlorobenzyl)acetamide. LC/MS: (ESI) (M+H)+=385.5.

Scheme 20

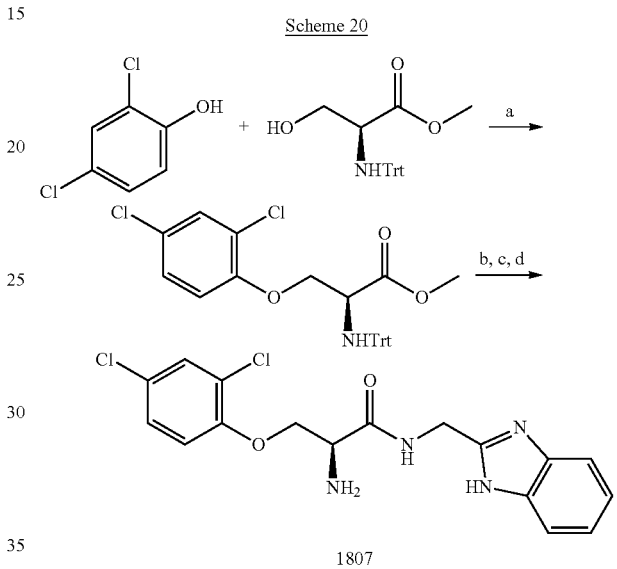

Reagents and conditions (a) PPh3, DIAD, THF; (b) NaOH. methanol; (c) EDC, DIPEA, DMAP, C-(1H-benzoimidazol-2-yl)-methylamine; (d) TFA, DCM, 4 h.

To a solution of N-trityl-L-serine methyl ester (110 mg, 0.303 mmol), 2,4-dichlorophenol (49.4 mg, 0.303 mmol), and triphenylphosphine (0.303 mmol) in anhydrous THF (5 mL) was added DIAD (0.303 mmol) dropwise at room temperature. The solution was microwave irradiated at 90° C. for 1 h. The crude product was purified with flash column chromatography to give (S)-methyl 3-(2,4-dichlorophenoxy)-2-(tritylamino)propanoate. To a solution of (S)-methyl 3-(2,4-dichlorophenoxy)-2-(tritylamino)propanoate (80 mg, 0.158 mmol) in ethanol (2 mL) was added and 1 N NaOH (1 ml). The resultant mixture was microwave irradiated for 10 min at 80° C. After being cooled to room temperature, it was poured into ethyl acetate (50 mL), washed with 0.1 N HCl, water, brine dried over magnesium sulfate, and evaporated. The crude product was purified with flash column chromatography. The solution of (S)-3-(2,4-dichlorophenoxy)-2-(tritylamino)propanoic acid (60 mg, 0.12 mmol, 1.0 equiv), DIPEA (3 equiv), EDC HCl (1.5 equiv) and DMAP (1.0 equiv) in DCM (20 mL) was stirred for 10 min. To this reaction mixture (1H-benzo[d]imidazol-2-yl)methanamine (1.0 equiv) was added. The reaction mixture was stirred at room temperature overnight. The organic layer was washed with aq NaHCO₃ and brine. It was then dried over anhydrous sodium sulfate and evaporated under vacuum. The residue was treated with TFA (1 ml) and DCM (3 ml) for 4 h. After the solvents was removed, the residue was dissolved in methanol and purified by preparative HPLC to give (S)—N-((1H-benzo[d]imidazol-2-yl)

methyl)-3-(2,4-dichlorophenoxy)-2-aminopropanamide (1807). LC/MS: (ESI) (M+H)$^+$=380.3.

Scheme 21

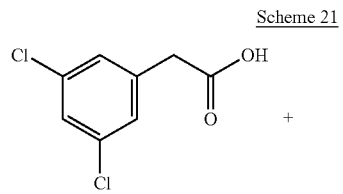

+

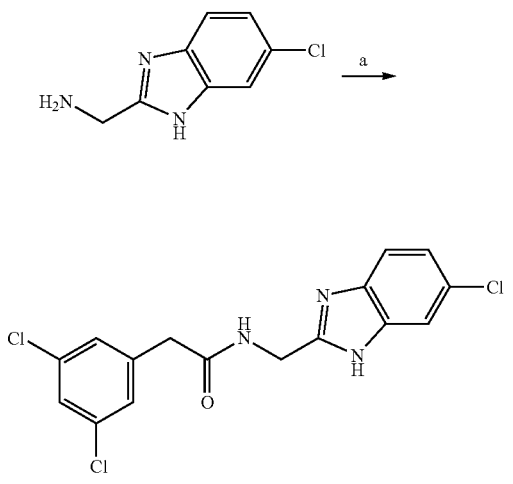

1851

Reagentss and conditions (a) EDC, DIPEA, DMAP, DCM

General Procedure 8 (1851, 1852, 1873-1880):

The solution of 2-(3,5-dichlorophenyl)acetic acid (30 mg, 0.146 mmol, 1.0 equiv), DIPEA (3 equiv), EDC HCl (1.5 equiv) and DMAP (1.0 equiv) in DCM (20 mL) was stirred for 10 min. To this reaction mixture (6-chloro-1H-benzo[d]imidazol-2-yl)methanamine was added. The reaction mixture was stirred at room temperature overnight. The reaction mixture was stirred at room temperature overnight. The organic layer was washed with sat. NaHCO$_3$ and brine. It was then dried over anhydrous sodium sulfate and evaporated under vacuum. The residue was purified by flash column chromatography to afford N-((6-chloro-1H-benzo[d]imidazol-2-yl)methyl)-2-(3,5-dichlorophenyl)acetamide (1851). LC/MS: (ESI) (M+H)$^+$=369.5.

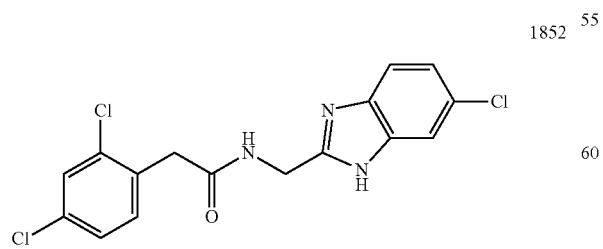

1852

1852 was synthesized using 2-(2,4-dichlorophenyl)acetic acid in General Procedure 8. LC/MS: (ESI) (M+H)$^+$=369.5.

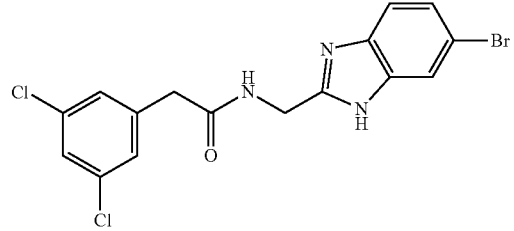

1873

1873 was synthesized using 2-(3,5-dichlorophenyl)acetic acid in General Procedure 8. LC/MS: (ESI) (M+H)$^+$=414.1.

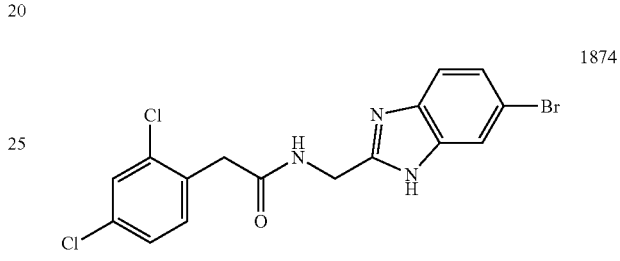

1874

1874 was synthesized using 2-(2,4-dichlorophenyl)acetic acid in General Procedure 8. LC/MS: (ESI) (M+H)$^+$=414.1.

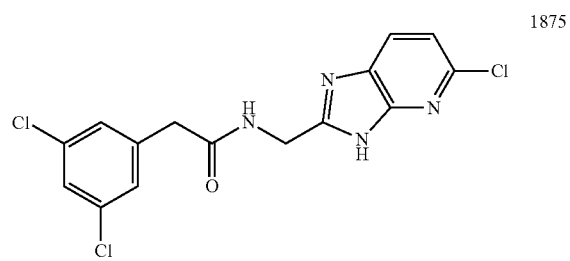

1875

1875 was synthesized using 2-(3,5-dichlorophenyl)acetic acid in General Procedure 8. LC/MS: (ESI) (M+H)$^+$=370.5.

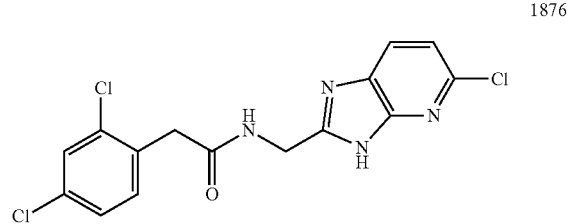 [SMILES: O=C(Cc1ccc(Cl)cc1Cl)NCc1nc2ccc(Cl)cc2[nH]1]

1876

1876 was synthesized using 2-(2,4-dichlorophenyl)acetic acid in General Procedure 8. LC/MS: (ESI) (M+H)$^+$=370.5.

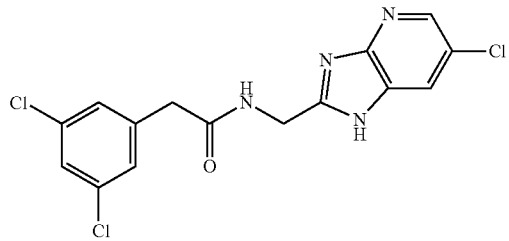

1877 was synthesized using 2-(3,5-dichlorophenyl)acetic acid in General Procedure 8. LC/MS: (ESI) (M+H)$^+$=370.5.

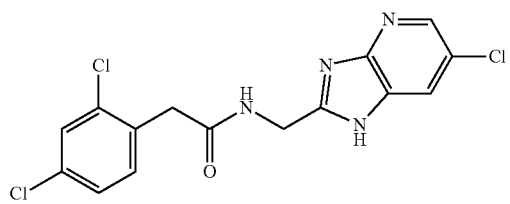

1878 was synthesized using 2-(2,4-dichlorophenyl)acetic acid in General Procedure 8. LC/MS: (ESI) (M+H)$^+$=370.5.

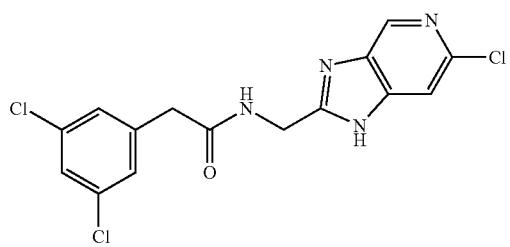

1879 was synthesized using 2-(3,5-dichlorophenyl)acetic acid in General Procedure 8. LC/MS: (ESI) (M+H)$^+$=370.5.

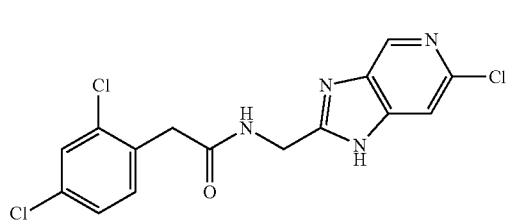

1880 was synthesized using 2-(2,4-dichlorophenyl)acetic acid in General Procedure 8. LC/MS: (ESI) (M+H)=370.5.

Scheme 22

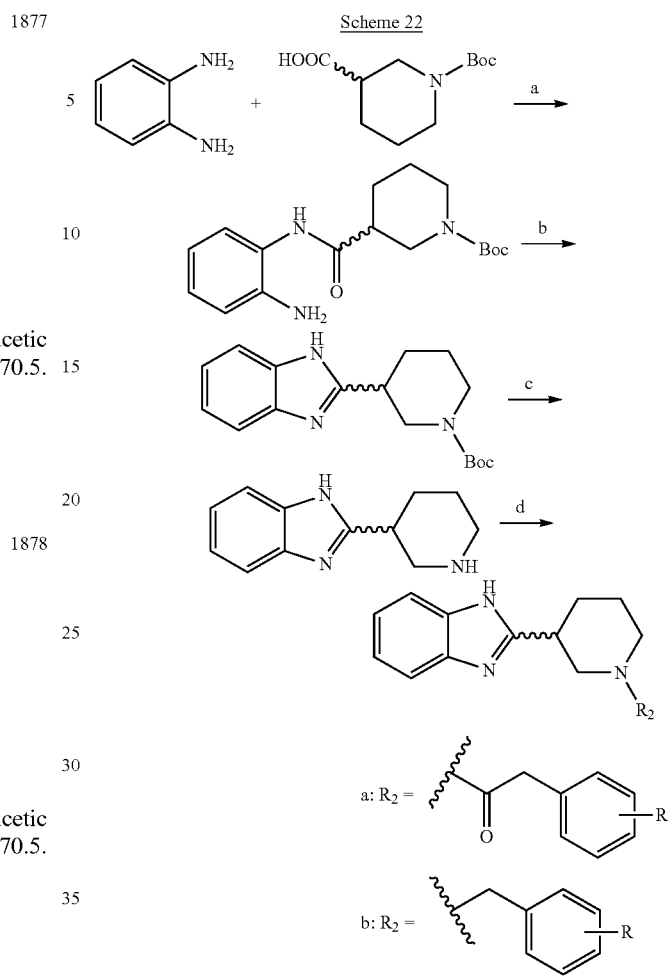

Reagents and conditions: (a) EDC, pyridine, r.t. overnight; (b) 4a: AcOH, 60° C., 3 h; (c) TFA, DCM, r.t., overnight; (d) 6a: EDC, HOBt, DIPEA, THF, r.t. 3 h; 6b: NaBH$_3$CN, AcOH, CH$_3$OH, r.t., overnight.

General Procedure 9:

(a) Benzene-1,2-diamine (0.5 mM) and 1-(tert-butoxycarbonyl)piperidine-3-carboxylic acid (0.5 mM) in pyridine (2 mL) was added EDC (144 mg, 0.75 mM). The mixture was stirred at r.t. overnight, and pyridine was then removed under reduced pressure. After addition of saturated aqueous sodium bicarbonate to the residue, the mixture was extracted with EA. The organic layer was dried over anhydrous sodium sulfate, and concentrated in vacuum. Purification through flash chromatography on silica gel eluted with MeOH-DCM (0.5% ammonia hydroxide) gave intermediate tert-butyl 3-((2-aminophenyl)carbamoyl)piperidine-1-carboxylate.

(b) tert-butyl 3-((2-aminophenyl)carbamoyl)piperidine-1-carboxylate was heated in 5 mL glacial acetic acid at 60° C. for 3 hours. The reaction was concentrated in vacuum and the residue partitioned between saturated sodium bicarbonate and DCM. The organic extract was dried over anhydrous sodium sulfate, and concentrated in vacuum. Purification through flash chromatography on silica gel eluted with MeOH-DCM (0.5% ammonia hydroxide) gave intermediate tert-butyl 3-(1H-benzo[d]imidazol-2-yl)piperidine-1-carboxylate.

(c) tert-butyl 3-(1H-benzo[d]imidazol-2-yl)piperidine-1-carboxylate was dissolved in DCM, the solution was cooled to 0° C., then TFA (5 eq) was added dropwise. The mixture was stirred at r.t. overnight, the solvent was removed in vacuum. HCl in Methanol was added to the residue, and the solvent was removed to give intermediate 2-(piperidin-3-yl)-1H-benzo[d]imidazole as HCl salt.

(d) a: Intermediate 2-(piperidin-3-yl)-1H-benzo[d]imidazole (0.2 mM) and substituted phenylacetic acid (0.2 mM) were dissolved in THF, EDC (mM), HOBt (mM) and DIPEA (0.24 mM) were added to the reaction solution. The mixture was stirred at r.t. for 3 hours. The solvent was removed under reduced pressure and the residue was extracted with DCM. The organic layer was dried over sodium sulfate, concentrated in vacuum, and the residue was purified through flash chromatography on silica gel eluted with MeOH-DCM (0.5% ammonia hydroxide) to give target compound a.

b: Intermediate 2-(piperidin-3-yl)-1H-benzo[d]imidazole (0.2 mM) and substituted benzaldehyde (0.2 mM) were dissolved in CH$_3$OH, AcOH (0.3 mM) and NaBH$_3$CN (0.4 mM) were added. The mixture was stirred at r.t. overnight. The solvent was removed under reduced pressure and the residue was extracted by DCM. The organic was dried over sodium sulfate. Remove solvent in vacuum and purify through flash chromatography on silica gel eluted with MeOH-DCM (0.5% ammonia hydroxide) to give target compound b.

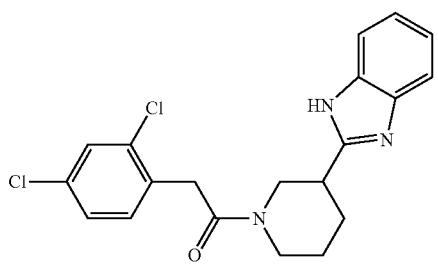

1731: 1-(3-(1H-benzo[d]imidazol-2-yl)piperidin-1-yl)-2-(2,4-dichlorophenyl) ethanone was synthesized using 2,4-dichlorophenyl)acetic acid, 1-(tert-butoxycarbonyl)piperidine-3-carboxylic acid and benzene-1,2-diamine following the general procedure 9. MS (ESI) (M+H)$^+$=389.1

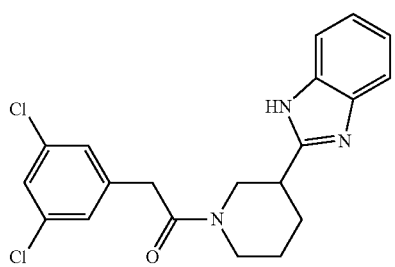

1732: 1-(3-(1H-benzo[d]imidazol-2-yl)piperidin-1-yl)-2-(3,5-dichlorophenyl)ethanone was synthesized using 3,5-dichlorophenyl)acetic acid, 1-(tert-butoxycarbonyl)piperidine-3-carboxylic acid and benzene-1,2-diamine following the general procedure 9. $^1$H NMR (500 MHz, MeOD) δ 7.85-7.71 (m, 2H), 7.67-7.54 (m, 2H), 7.34-7.28 (m, 1H), 7.27-7.21 (m, 2H), 4.74 (d, J=12.0 Hz, 0.81H), 4.55 (dd, J=35.4, 12.3 Hz, 0.53H), 4.03 (d, J=13.7 Hz, 0.72H), 3.96- 3.78 (m, 1.98H), 3.53 (dd, J=24.9, 12.4 Hz, 0.54H), 3.39 (dt, J=10.2, 6.8 Hz, 2.29H), 2.86 (t, J=11.6 Hz, 0.23H), 2.39 (d, J=9.4 Hz, 0.97H), 2.12 (dt, J=13.7, 7.0 Hz, 0.72H), 2.01 (dd, J=40.9, 12.5 Hz, 0.52H), 1.88 (d, J=13.6 Hz, 0.72H), 1.76-1.58 (m, 0.98H). MS (ESI) (M+H)$^+$=389.1

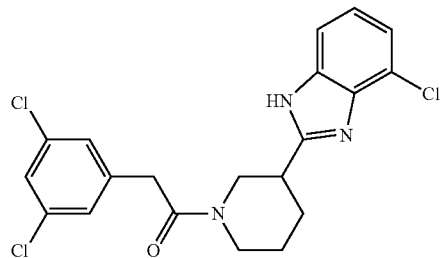

1733: 1-(3-(4-chloro-1H-benzo[d]imidazol-2-yl)piperidin-1-yl)-2-(3,5-dichlorophenyl) ethanone was synthesized using 3,5-dichlorophenyl)acetic acid, 1-(tert-butoxycarbonyl)piperidine-3-carboxylic acid and 3-chlorobenzene-1,2-diamine following the general procedure 9. MS (ESI) (M+H)$^+$=423.6

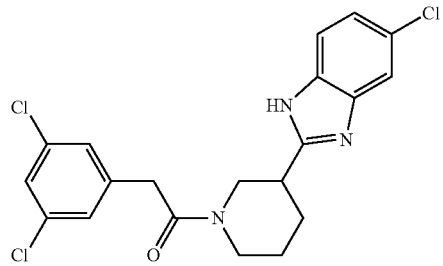

1734: 1-(3-(5-chloro-1H-benzo[d]imidazol-2-yl)piperidin-1-yl)-2-(3,5-dichlorophenyl) ethanone was synthesized using 3,5-dichlorophenyl)acetic acid, 1-(tert-butoxycarbonyl)piperidine-3-carboxylic acid and 4-chlorobenzene-1,2-diamine following the general procedure 9. $^1$H NMR (500 MHz, CDCl$_3$) 7.52 (s, 1H), 7.44 (d, J=7.3 Hz, 1H), 7.19-7.11 (m, 2H), 7.00 (s, 2H), 4.35 (d, J=11.2 Hz, 1H), 3.77-3.70 (m, 1H), 3.68 (d, J=6.9 Hz, 2H), 3.65-3.56 (m, 1H), 3.44 (t, J=11.2 Hz, 1H), 3.27 (s, 1H), 2.65-2.54 (m, 1H), 2.12 (dd, J=16.0, 7.0 Hz, 1H), 1.62-1.49 (m 1H) 1.44-1.34 (m, 1H). MS (ESI) (M+H)$^+$=423.6

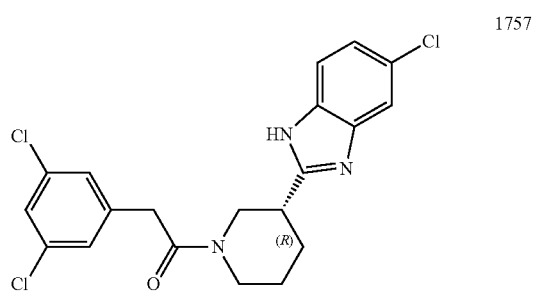

1757: (R)-1-(3-(5-chloro-1H-benzo[d]imidazol-2-yl)piperidin-1-yl)-2-(3,5-dichlorophenyl)ethanone was synthesized using 3,5-dichlorophenyl)acetic acid, (R)-1-(tert-butoxycarbonyl)piperidine-3-carboxylic acid and 4-chlorobenzene-1,2-diamine following the general procedure 9. MS (ESI) (M+H)⁺=423.6

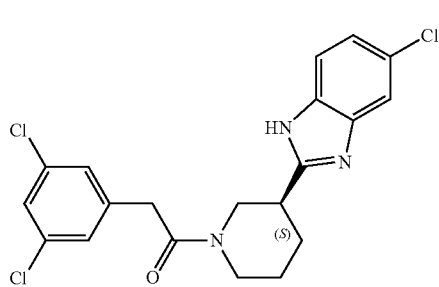

1758: (S)-1-(3-(5-chloro-1H-benzo[d]imidazol-2-yl)piperidin-1-yl)-2-(3,5-dichlorophenyl)ethanone was synthesized using 3,5-dichlorophenyl)acetic acid, (S)-1-(tert-butoxycarbonyl)piperidine-3-carboxylic acid and 4-chlorobenzene-1,2-diamine following the general procedure 9. MS (ESI) (M+H)⁺=423.5

1744: 2-(3,5-dichlorophenyl)-1-(3-(5-fluoro-1H-benzo[d]imidazol-2-yl)piperidin-1-yl)ethanone was synthesized using 3,5-dichlorophenyl)acetic acid, 1-(tert-butoxycarbonyl)piperidine-3-carboxylic acid and 4-fluorobenzene-1,2-diamine following the general procedure 9. MS (ESI) (M+H)⁺=407.8

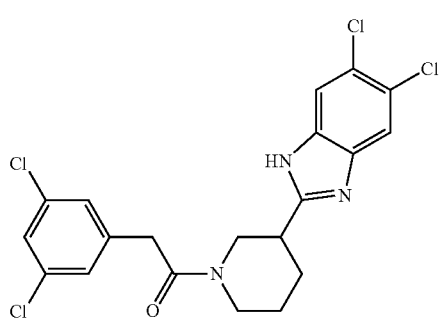

1745: 1-(3-(5,6-dichloro-1H-benzo[d]imidazol-2-yl)piperidin-1-yl)-2-(3,5-dichlorophenyl)ethanone was synthesized using 3,5-dichlorophenyl)acetic acid, 1-(tert-butoxycarbonyl)piperidine-3-carboxylic acid and 4,5-dichlorobenzene-1,2-diamine following the general procedure 9. ¹H NMR (500 MHz, CDCl₃) δ 8.02 (s, 0.29H), 7.66 (s, 2.00H), 7.16 (s, 0.79H), 7.01 (s, 1.87H), 4.36 (dd, J=13.3, 3.8 Hz, 1H), 3.76-3.70 (m, 1H), 3.70-3.67 (m, 1H), 3.64 (d, J=13.6 Hz, 1H), 3.46 (t, J=10.2 Hz, 1H), 3.38-3.27 (m, 1H), 2.64 (dd, J=13.4, 4.7 Hz, 1H), 2.15 (dd, J=13.5, 9.9 Hz, 1H), 1.66-1.54 (m, 1H), 1.43-1.31 (m, 1H). MS (ESI) (M+H)⁺=457.4

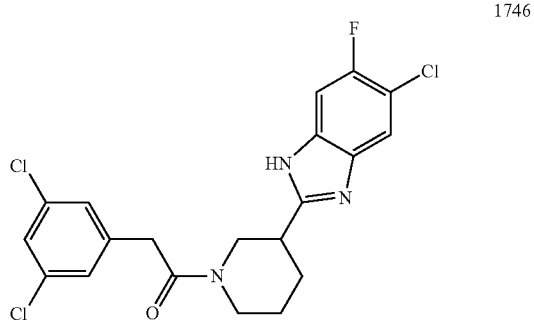 [SMILES: O=C(Cc1cc(Cl)cc(Cl)c1)N1CCCC(c2nc3cc(Cl)c(F)cc3[nH]2)C1]

1746: 1-(3-(5-chloro-6-fluoro-1H-benzo[d]imidazol-2-yl)piperidin-1-yl)-2-(3,5-dichlorophenyl)ethanone was synthesized using 3,5-dichlorophenyl)acetic acid, 1-(tert-butoxycarbonyl)piperidine-3-carboxylic acid and 4-chloro-5-fluorobenzene-1,2-diamine following the general procedure 9. MS (ESI) (M+H)⁺=441.6

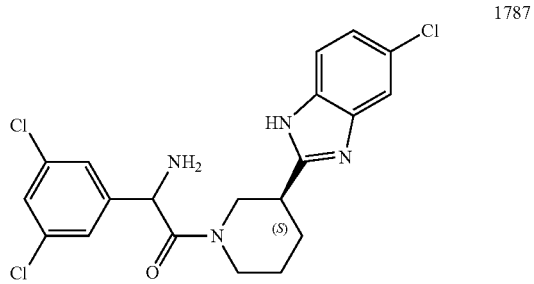

1787: 2-amino-1-((S)-3-(5-chloro-H-benzo[d]imidazol-2-yl)piperidin-1-yl)-2-(3,5-dichlorophenyl)ethanone was synthesized using 2-((tert-butoxycarbonyl)amino)-2-(3,5-dichlorophenyl)acetic acid, (S)-methyl piperidine-3-carboxy(S)-1-(tert-butoxycarbonyl)piperidine-3-carboxylic acid late and 4-chlorobenzene-1,2-diamine following the general procedure 9. MS (ESI) (M+H)⁺=439.8; HPLC analysis: 97.2% purity

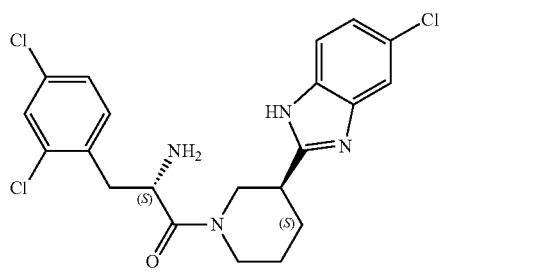

1799: (S)-2-amino-1-((S)-3-(5-chloro-1H-benzo[d]imidazol-2-yl)piperidin-1-yl)-3-(2,4-dichlorophenyl)propan-1-one was synthesized using (S)-2-((tert-butoxycarbonyl)amino)-3-(2,4-dichlorophenyl)propanoic acid, (S)-1-(tert-butoxycarbonyl)piperidine-3-carboxylic acid and 4-chlorobenzene-1,2-diamine following the general procedure 9. MS (ESI) (M+H)$^+$=453.8; HPLC analysis: 100% purity

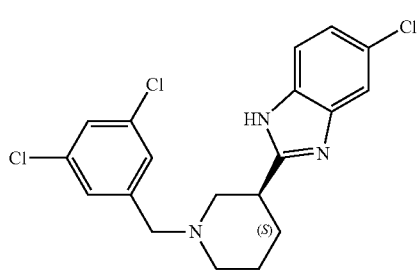

1813: (S)-5-chloro-2-(1-(3,5-dichlorobenzyl)piperidin-3-yl)-1H-benzo[d]imidazole was synthesized using 3,5-dichlorobenzaldehyde, (S)-1-(tert-butoxycarbonyl)piperidine-3-carboxylic acid and 4-chlorobenzene-1,2-diamine following the general procedure 9. MS (ESI) (M+H)$^+$=395.5; HPLC analysis: 94.3% purity

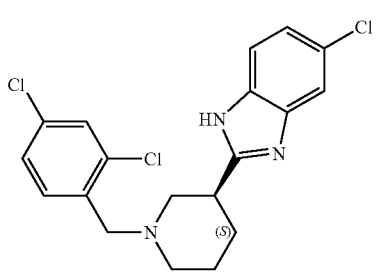

1837: (S)-5-chloro-2-(1-(2,4-dichlorobenzyl)piperidin-3-yl)-1H-benzo[d]imidazole was synthesized using 2,4-dichlorobenzaldehyde, (S)-1-(tert-butoxycarbonyl)piperidine-3-carboxylic acid and 4-chlorobenzene-1,2-diamine following the general procedure 9. MS (ESI) (M+H)$^+$=395.6; HPLC analysis: 99.0% purity

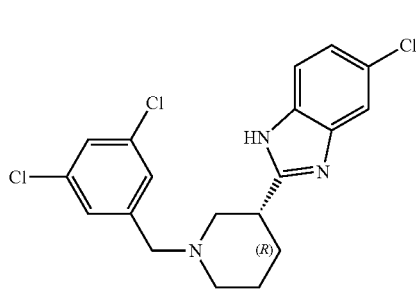

1838: (R)-5-chloro-2-(1-(3,5-dichlorobenzyl)piperidin-3-yl)-1H-benzo[d]imidazole was synthesized using 3,5-dichlorobenzaldehyde, (R)-1-(tert-butoxycarbonyl)piperidine-3-carboxylic acid and 4-chlorobenzene-1,2-diamine following the general procedure 9. MS (ESI) (M+H)$^+$=395.6; HPLC analysis: 100% purity.

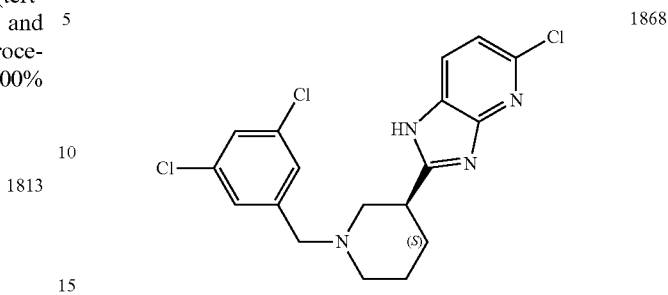

1868: (S)-5-chloro-2-(1-(3,5-dichlorobenzyl)piperidin-3-yl)-1H-imidazo[4,5-b]pyridine was synthesized using 3,5-dichlorobenzaldehyde, (S)-1-(tert-butoxycarbonyl)piperidine-3-carboxylic acid and 6-chloropyridine-2,3-diamine following the general procedure 9. MS (ESI) (M+H)$^+$=396.5; HPLC analysis: 95.4% purity

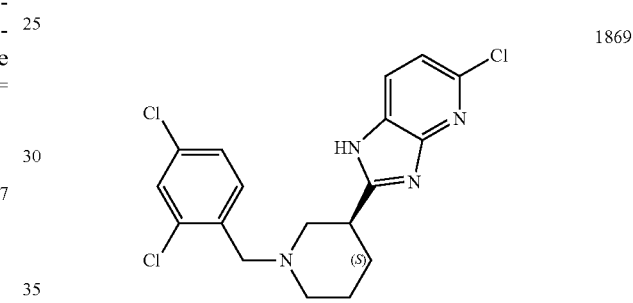

1869: (S)-5-chloro-2-(1-(2,4-dichlorobenzyl)piperidin-3-yl)-1H-imidazo[4,5-b]pyridine was synthesized using 2,4-dichlorobenzaldehyde, (S)-1-(tert-butoxycarbonyl)piperidine-3-carboxylic acid and 6-chloropyridine-2,3-diamine following the general procedure 9. MS (ESI) (M+H)$^+$=396.5; HPLC analysis: 98.8% purity

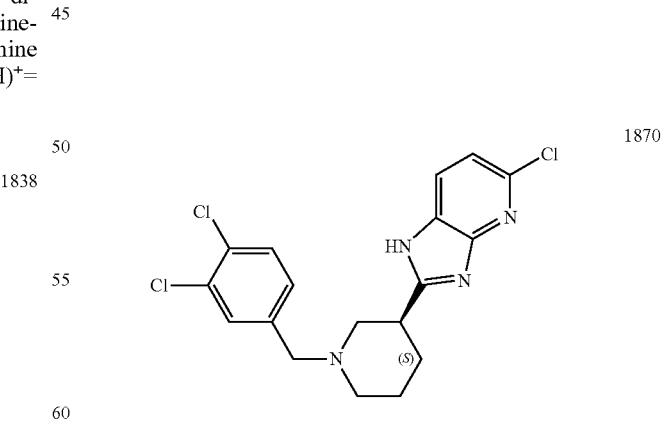

1870: (S)-5-chloro-2-(1-(3,4-dichlorobenzyl)piperidin-3-yl)-1H-imidazo[4,5-b]pyridine was synthesized using 3,4-dichlorobenzaldehyde, (S)-1-(tert-butoxycarbonyl)piperidine-3-carboxylic acid and 6-chloropyridine-2,3-diamine following the general procedure 9. MS (ESI) (M+H)$^+$=396.5; HPLC analysis: 100% purity

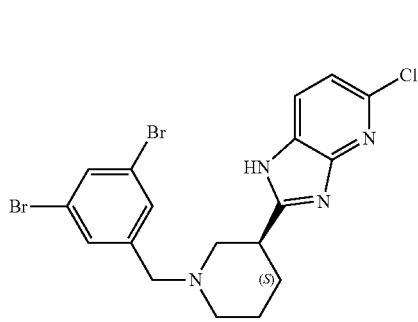

1871: (S)-5-chloro-2-(1-(3,4-dibromobenzyl)piperidin-3-yl)-1H-imidazo[4,5-b]pyridine was synthesized using 3,4-dibromobenzaldehyde, (S)-1-(tert-butoxycarbonyl)piperidine-3-carboxylic acid and 6-chloropyridine-2,3-diamine following the general procedure 9. MS (ESI) (M+H)$^+$= 485.3; HPLC analysis: 93.7% purity

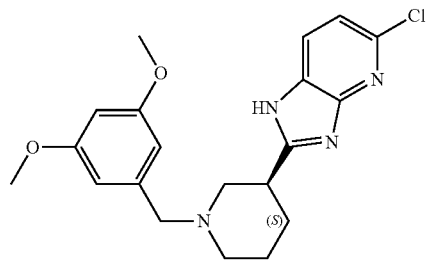

1872: (S)-5-chloro-2-(1-(3,5-dimethoxybenzyl)piperidin-3-yl)-1H-imidazo[4,5-b]pyridine was synthesized using 3,5-dimethoxybenzaldehyde, (S)-1-(tert-butoxycarbonyl)piperidine-3-carboxylic acid and 6-chloropyridine-2,3-diamine following the general procedure 9. MS (ESI) (M+H)$^+$= 387.7; HPLC analysis: 100% purity Scheme 23

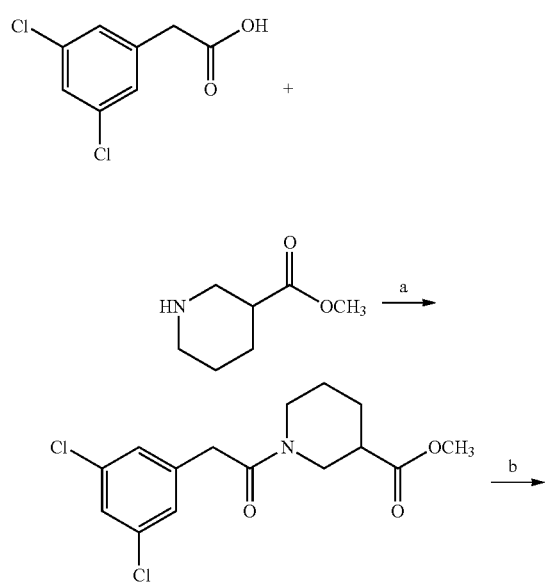

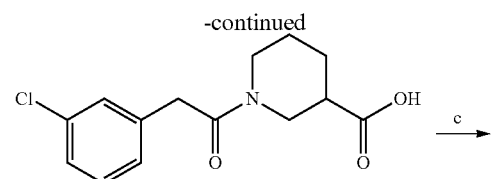

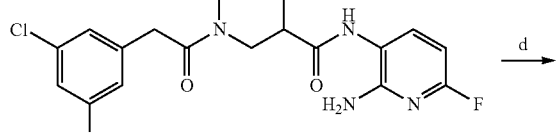

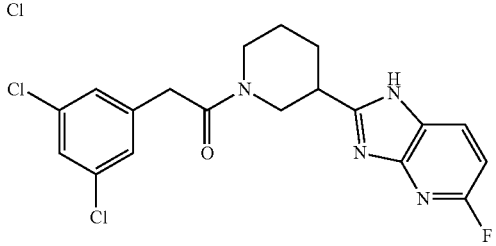

1761

Reagents and conditions: (a) triphosgen, DIPEA, DCM, 0° C. (b) EDC, HOBt, DIPEA, DMF, r.t. 3 H; (c) LiOH, CH$_3$OH/H$_2$O, r.t. overnight; (d) BH$_3$, THF, 0° C-r.t., overnight (e) 6-fluoropyridine-2,3-diamine, EDC, pyridine, r.t. overnight; (f) AcOH, POCl$_3$, Microwave 150° C., 1 h.

General Procedure 10:

(a) To a stirred solution of methyl piperidine-3-carboxylate (72 mg, 0.5 mmol) in DCM (10 mL) was added DIPEA (2 eq) and cooled to 0° C. A solution of triphosgene (59 mg, 0.2 mmol) in DCM (2 mL) was added dropwise to the reaction mixture and stirred at room temperature for 2 h. The solution was cooled to 0° C. and 3,5-dichloroaniline (81 mg, 0.5 mmol) in DCM (2 ml) was added. The reaction mixture was stirred at 0° C. for 30 min. The solution was washed with brine, dried over anhydrous sodium sulfate and evaporated under vacuum. The residue was purified by flash column chromatography to give methyl 1-((3,5-dichlorophenyl)carbamoyl)piperidine-3-carboxylate.

(b): 2-(3,5-dichlorophenyl)acetic acid (1 mM) and methyl piperidine-3-carboxylate (1 mM) were dissolved in DMF, EDC (1.2 mM), HOBt (1.2 mM) and DIPEA (1.5 mM) were added to the mixture. The reaction mixture was stirred at r.t. for 3 hours. The solvent was removed under reduced pressure and the residue was extracted with DCM. The organic layer was dried over sodium sulfate, concentrated in vacuum, and the residue was purified through flash chromatography on silica gel eluted with MeOH-DCM (0.5% ammonia hydroxide) to give intermediate methyl 1-(2-(3,5-dichlorophenyl)acetyl)piperidine-3-carboxylate.

(c) LiOH.H$_2$O (3 eq) was added to the solution of methyl 1-(2-(3,5-dichlorophenyl)acetyl)piperidine-3-carboxylate in CH$_3$OH/H$_2$O (CH$_3$OH:H$_2$O=3:1). The reaction mixture was stirred at r.t. overnight. The solvent was evaporated under reduced pressure, the residue was extracted with EA/1N HCl solution. The organic layer was dried over sodium sulfate, concentrated in vacuum to give 1-(2-(3,5-dichlorophenyl)acetyl)piperidine-3-carboxylic acid without further purification.

(d) Methyl 1-(2-(3,5-dichlorophenyl)acetyl)piperidine-3-carboxylate in anhydrous THF was added BH$_3$ (5 eq) in THF at 0° C. The mixture was stirred at r.t. overnight. The solvent was removed under reduced pressure, saturated NaHCO₃ was added and extracted with DCM. The organic layer was dried over sodium sulfate, concentrated in vacuum, and the residue was purified through flash chromatography on silica gel to give methyl 1-(3,5-dichlorophenethyl)piperidine-3-carboxylate.

(e) 1-(2-(3,5-dichlorophenyl)acetyl)piperidine-3-carboxylic acid (0.2 mM) and 6-fluoropyridine-2,3-diamine (0.2 mM) in pyridine (2 mL) was added EDC (0.3 mM). The mixture was stirred at r.t. overnight, and pyridine was then removed under reduced pressure. After addition of saturated aqueous sodium bicarbonate to the residue, the mixture was extracted with EA. The organic layer was dried over anhydrous sodium sulfate, and concentrated in vacuum. Purification through flash chromatography on silica gel eluted with MeOH-DCM (0.5% ammonia hydroxide) gave N-(2-amino-6-fluoropyridin-3-yl)-1-(2-(3,5-dichlorophenyl)acetyl)piperidine-3-carboxamide.

(f) N-(2-amino-6-fluoropyridin-3-yl)-1-(2-(3,5-dichlorophenyl)acetyl)piperidine-3-carboxamide was dissolved in 3 mL glacial acetic acid, POCl₃ (3 eq) was added, the mixture was microwave irradiated at 150° C. for 1 hour. The reaction was concentrated in vacuum and the residue partitioned between saturated sodium bicarbonate and DCM. The organic extract was dried over anhydrous sodium sulfate, and concentrated in vacuum. The residue was purified through flash chromatography on silica gel eluted with MeOH-DCM (0.5% ammonia hydroxide) to give target compound 1761: 2-(3,5-dichlorophenyl)-1-(3-(5-fluoro-1H-imidazo[4,5-b]pyridin-2-yl)piperidin-1-yl)ethanone MS (ESI) (M+H)⁺=408.6

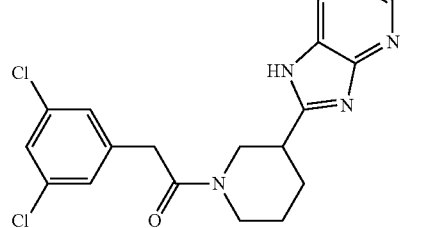

1762: 1-(3-(5-chloro-1H-imidazo[4,5-b]pyridin-2-yl)piperidin-1-yl)-2-(3,5-dichlorophenyl)ethanone was synthesized using 3,5-dichlorophenyl)acetic acid, methyl piperidine-3-carboxylate and 6-chloropyridine-2,3-diamine following the general procedure 10. MS (ESI) (M+H)⁺=424.5

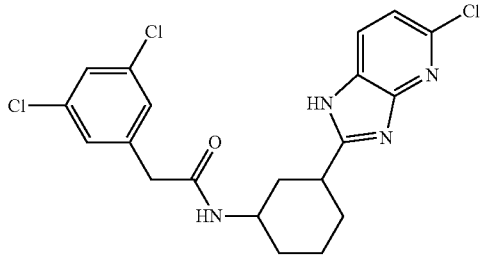

1786: N-(3-(5-chloro-1H-imidazo[4,5-b]pyridin-2-yl)cyclohexyl)-2-(3,5-dichlorophenyl)acetamide was synthesized using 3,5-dichlorophenyl)acetic acid, methyl 3-aminocyclohexanecarboxylate and 6-fluoropyridine-2,3-diamine following the general procedure 10. MS (ESI) (M+H)⁺=438.8; HPLC analysis: 91.0% purity

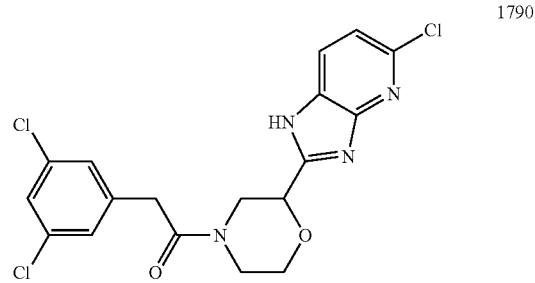 [SMILES: O=C(Cc1cc(Cl)cc(Cl)c1)N1CCOC(c2nc3nc(Cl)ccc3[nH]2)C1]

1790: 1-(2-(5-chloro-1H-imidazo[4,5-b]pyridin-2-yl)morpholino)-2-(3,5-dichlorophenyl)ethanone was synthesized using 3,5-dichlorophenyl)acetic acid, methyl morpholine-2-carboxylate and 6-chloropyridine-2,3-diamine following the general procedure 10. MS (ESI) (M+H)⁺= 427.4

1791: N-(2-amino-6-chloropyridin-3-yl)-4-(2-(3,5-dichlorophenyl)acetyl) piperazine-2-carboxamide was synthesized using 3,5-dichlorophenyl)acetic acid, 1-tert-butyl 2-methyl piperazine-1,2-dicarboxylate and 6-chloropyridine-2,3-diamine following the general procedure 10 with minor modifications. MS (ESI) (M+H)⁺=443.4

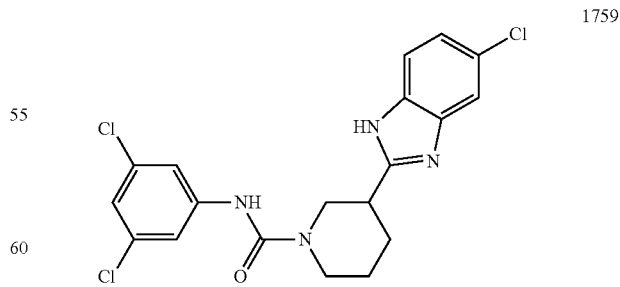

1759: 3-(5-chloro-1H-benzo[d]imidazol-2-yl)-N-(3,5-dichlorophenyl) piperidine-1-carboxamide was synthesized following the general procedure 10. MS (ESI) (M+H)⁺= 424.8

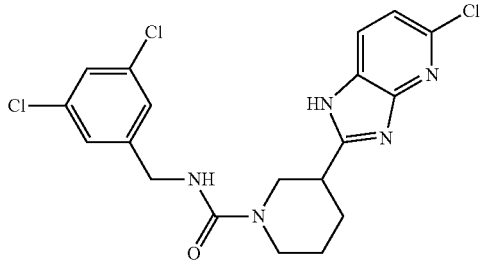

1785: 3-(5-chloro-1H-imidazo[4,5-b]pyridin-2-yl)-N-(3,5-dichlorobenzyl) piperidine-1-carboxamide was synthesized using (3,5-dichlorophenyl)methanamine and 6-chloropyridine-2,3-diamine following the general procedure 10. MS (ESI) (M+H)$^+$=435.6

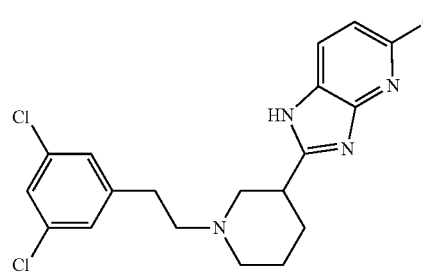

1812: 5-chloro-2-(1-(3,5-dichlorophenethyl)piperidin-3-yl)-1H-imidazo[4,5-b]pyridine was synthesized using (3,5-dichlorophenyl)methanamine and 6-chloropyridine-2,3-diamine following the general procedure 10. $^1$H NMR (500 MHz, MeOD) δ 8.08 (d, J=8.3 Hz, 0.65H), 8.00 (d, J=8.2 Hz, 0.34H), 7.47 (d, J=8.3 Hz, 0.62H), 7.44-7.35 (m, 3.38H), 4.21 (d, J=11.7 Hz, 0.33H), 4.10 (d, J=11.4 Hz, 0.60H), 3.86-3.71 (m, 1.64H), 3.61 (d, J=10.9 Hz, 0.42H), 3.56-3.47 (m, 2.29H), 3.43 (dd, J=20.3, 12.7 Hz, 0.98H), 3.26-3.14 (m, 2.60H), 2.42 (d, J=11.4 Hz, 0.61H), 2.29-2.18 (m, 1.30H), 2.13 (dd, J=26.5, 14.8 Hz, 1H), 2.04-1.90 (m, 1.00H), 1.89-1.75 (m, 0.35H). MS (ESI) (M+H)$^+$=410.5

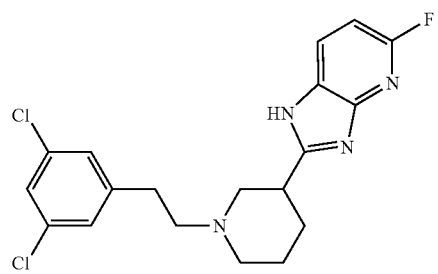

1798: 5-fluoro-2-(1-(3,5-dichlorophenethyl)piperidin-3-yl)-1H-imidazo[4,5-b]pyridine was synthesized using (3,5-dichlorophenyl)methanamine and 6-fluoropyridine-2,3-diamine following the general procedure 10. MS (ESI) (M+H)$^+$=394.3

Scheme 24

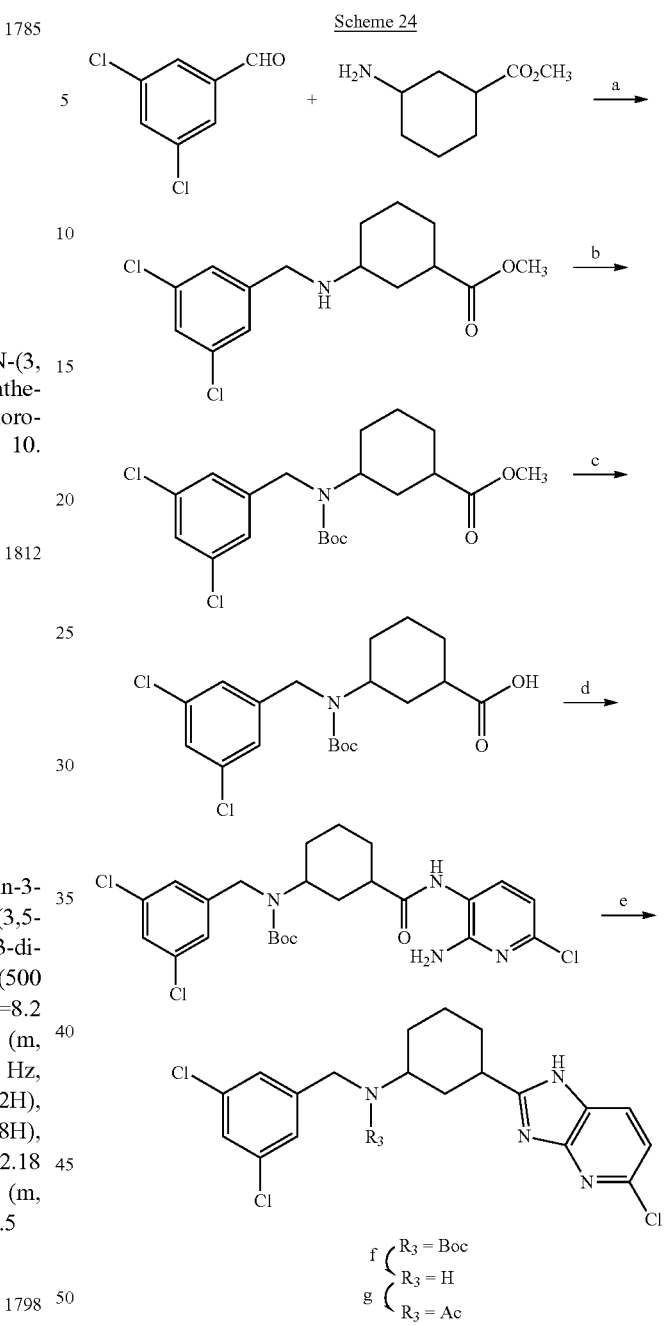

Reagents and conditions: (a) NaBH$_3$CN, AcOH, CH$_3$OH, r.t., overnight; (b) (Boc)$_2$O, DIPEA, DCM, r.t., 3 h; (c) LiOH, CH$_3$OH/H$_2$O, r.t. overnight; (d) 6-chloropyridine-2,3-diamine, EDC, pyridine, r.t. overnight; (e) (I) AcOH, 60° C., 3 h, (II) AcOH, POCl$_3$, Microwave 150° C., 1 h; (f) TFA, DCM, r.t., overnight, following condition (e) (I); (g) Ac$_2$O, DIPEA, DCM, r.t. 2 h, following conditions (e) (I) and f; (f) TFA, DCM, r.t. overnight; (g) Ac$_2$O, DIPEA, DCM, r.t. 3 h.

General Procedure 11:

(a) 3,5-dichlorobenzaldehyde (0.2 mM) and methyl 3-aminocyclohexanecarboxylate (0.2 mM) were dissolved in CH$_3$OH, AcOH (0.3 mM) and NaBH$_3$CN (0.4 mM) were added. The mixture was stirred at r.t. overnight. The solvent was removed under reduced pressure and the residue was extracted by EA. The organic phase was dried over sodium sulfate. Remove solvent in vacuum and purify through flash chromatography on silica gel eluted with MeOH-DCM (0.5% ammonia hydroxide) to give methyl 3-((3,5-dichlorobenzyl)amino)cyclohexanecarboxylate which was used for next step without further purification.

(b) methyl 3-((3,5-dichlorobenzyl)amino)cyclohexanecarboxylate was dissolved in DCM, DIPEA (1.5 eq) was added to the solution. (Boc)$_2$O was then added in portions at 0° C., and the mixture stirred at r.t. for 3 hours. The solvent was removed under reduced pressure and the residue was extracted by EA. The organic phase was dried over sodium sulfate. Remove solvent in vacuum and purify through flash chromatography on silica gel eluted with EA-hexane to give methyl 3-((tert-butoxycarbonyl)(3,5-dichlorobenzyl)amino) cyclohexanecarboxylate.

(c) LiOH.H$_2$O (3 eq) was added to the solution of methyl 3-((tert-butoxycarbonyl)(3,5-dichlorobenzyl)amino)cyclohexanecarboxylate in CH$_3$OH/H$_2$O (CH$_3$OH:H$_2$O=3:1). The reaction mixture was stirred at r.t. overnight. The solvent was evaporated under reduced pressure, the residue was extracted with EA/1N HCl solution. The organic layer was dried over sodium sulfate, concentrated in vacuum to give 3-((tert-butoxycarbonyl)(3,5-dichlorobenzyl) amino) cyclohexanecarboxylic acid which was used for the next step without further purification.

(d) 3-((tert-butoxycarbonyl)(3,5-dichlorobenzyl)amino) cyclohexanecarboxylic acid (0.2 mM) and 6-chloropyridine-2,3-diamine (0.2 mM) in pyridine (2 mL) was added EDC (0.3 mM). The mixture was stirred at r.t. overnight, and pyridine was then removed under reduced pressure. After addition of saturated aqueous sodium bicarbonate to the residue, the mixture was extracted with EA. The organic layer was dried over anhydrous sodium sulfate, and concentrated in vacuum. Purification through flash chromatography on silica gel eluted with MeOH-DCM (0.5% ammonia hydroxide) gave tert-butyl (3-((2-amino-6-chloropyridin-3-yl)carbamoyl)cyclohexyl)(3,5-dichlorobenzyl)carbamate.

(e I) tert-butyl (3-((2-amino-6-chloropyridin-3-yl)carbamoyl)cyclohexyl)(3,5-dichlorobenzyl)carbamate was heated in 5 mL glacial acetic acid at 60° C. for 3 hours. The reaction mixture was concentrated in vacuum and the residue partitioned between saturated sodium bicarbonate and DCM. The organic extract was dried over anhydrous sodium sulfate, and concentrated in vacuum. Purification through flash chromatography on silica gel eluted with MeOH-DCM (0.5% ammonia hydroxide) gave tert-butyl (3-(5-chloro-1H-imidazo[4,5-b]pyridin-2-yl)cyclohexyl)(3,5-dichlorobenzyl)carbamate.

(e II) tert-butyl (3-((2-amino-6-chloropyridin-3-yl)carbamoyl)cyclohexyl)(3,5-dichlorobenzyl)carbamate was dissolved in 3 mL glacial acetic acid, POCl$_{13}$ (3 eq) was added, the mixture was microwave irradiated at 150° C. for 1 hour. The reaction mixture was concentrated in vacuum and the residue partitioned between saturated sodium bicarbonate and DCM. The organic extract was dried over anhydrous sodium sulfate, and concentrated in vacuum. The residue was purified through flash chromatography on silica gel eluted with MeOH-DCM (0.5% ammonia hydroxide) to give target compounds 1788 3-(5-chloro-H-imidazo[4,5-b]pyridin-2-yl)-N-(3,5-dichlorobenzyl)cyclohexanamine. $^1$H NMR (500 MHz, MeOD) δ 8.21 (t, J=8.6 Hz, 1H), 7.67-7.60 (m, 3H), 7.60-7.54 (m, 1H), 4.34 (s, 2H), 3.59-3.52 (m, 1H), 3.51-3.41 (m, 1H), 2.83-2.73 (m, 1H), 2.35 (d, J=10.5 Hz, 1H), 2.27 (d, J=11.7 Hz, 1H), 2.16 (d, J=11.5 Hz, 1H), 2.07-1.93 (m, 1H), 1.71 (m, 3H). MS (ESI) (M+H)$^+$=410.5; HPLC analysis: 88.2% purity; and 1789 N-(3-(5-chloro-1H-imidazo[4,5-b]pyridin-2-yl)cyclohexyl)-N-(3,5-dichlorobenzyl)acetamide. MS (ESI) (M+H)$^+$=452.5; HPLC analysis: 98.0% purity.

(f) tert-butyl (3-(5-chloro-1H-imidazo[4,5-b]pyridin-2-yl)cyclohexyl)(3,5-dichlorobenzyl)carbamate was dissolved in DCM, the solution was cooled to 0° C., then TFA (5 eq) was added dropwise. The mixture was stirred at r.t. overnight, the solvent was removed in vacuum. The residue was partitioned between saturated sodium bicarbonate and DCM. The organic extract was dried over anhydrous sodium sulfate, and concentrated in vacuum. The residue was purified through flash chromatography on silica gel eluted with MeOH-DCM (0.5% ammonia hydroxide) to give target compound 1788 3-(5-chloro-1H-imidazo[4,5-b]pyridin-2-yl)-N-(3,5-dichlorobenzyl)cyclohexanamine.

(g) 1788 3-(5-chloro-1H-imidazo[4,5-b]pyridin-2-yl)-N-(3,5-dichlorobenzyl) cyclohexanamine was dissolved in DCM, DIPEA (1.5 eq) and Ac$_2$O (1.5 eq) were added, the mixture was stirred at r.t. for 3 hours. H$_2$O was added and extracted with DCM. The organic extract was dried over anhydrous sodium sulfate, and concentrated in vacuum. The residue was purified through flash chromatography on silica gel eluted with MeOH-DCM (0.5% ammonia hydroxide) to give target compound 1789 N-(3-(5-chloro-1H-imidazo[4,5-b]pyridin-2-yl)cyclohexyl)-N-(3,5-dichlorobenzyl)acetamide.

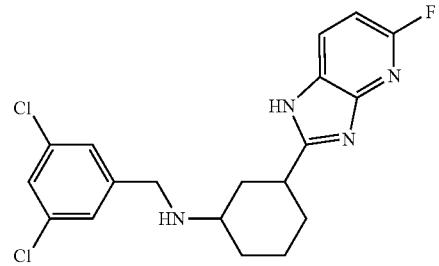 [SMILES: Fc1ccc2[nH]c(C3CCCC(NCc4cc(Cl)cc(Cl)c4)C3)nc2n1]

1800: N-(3,5-dichlorobenzyl)-3-(5-fluoro-1H-imidazo[4,5-b]pyridin-2-yl) cyclohexanamine was synthesized using 3,5-dichlorobenzaldehyde, methyl 3-aminocyclohexanecarboxylate and 6-fluoropyridine-2,3-diamine following the general procedure 11. MS (ESI) (M+H)$^+$=394.1; HPLC analysis: 95.5% purity

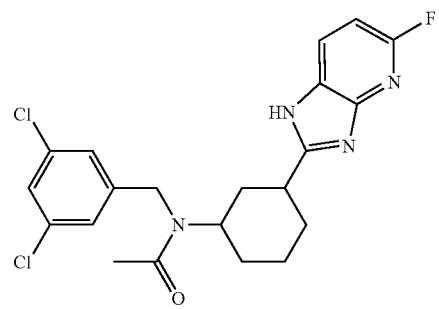 [SMILES: CC(=O)N(Cc1cc(Cl)cc(Cl)c1)C1CCCC(c2nc3nc(F)ccc3[nH]2)C1]

1801: N-(3,5-dichlorobenzyl)-N-(3-(5-fluoro-1H-imidazo[4,5-b]pyridin-2-yl) cyclohexyl)acetamide was obtained during the synthesis of ChemID: 1800. MS (ESI) (M+H)$^+$=436.2; HPLC analysis: 91.5% purity

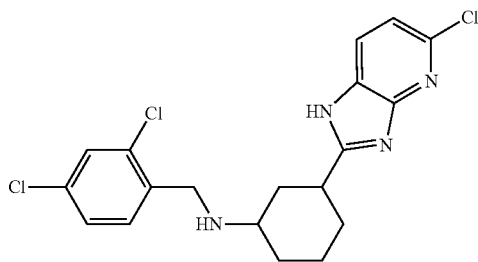 [SMILES: Clc1ccc(CNC2CCCC(c3nc4nc(Cl)ccc4[nH]3)C2)c(Cl)c1]

1809: 3-(5-chloro-1H-imidazo[4,5-b]pyridin-2-yl)-N-(2,4-dichlorobenzyl) cyclohexanamine was synthesized using 2,4-dichlorobenzaldehyde, methyl 3-aminocyclohexanecarboxylate and 6-chloropyridine-2,3-diamine following the general procedure 11. MS (ESI) (M+H)$^+$=411.3; HPLC analysis: 91.2% purity

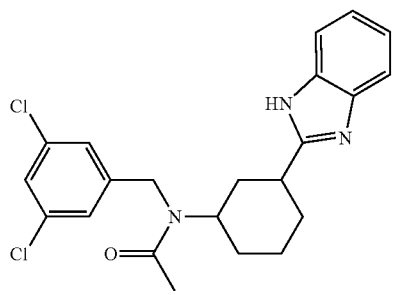

1816: N-(3-(1H-benzo[d]imidazol-2-yl)cyclohexyl)-N-(3,5-dichlorobenzyl) acetamide was obtained during the synthesis of ChemID: 1815. MS (ESI) (M+H)$^+$=417.0; HPLC analysis: 100% purity

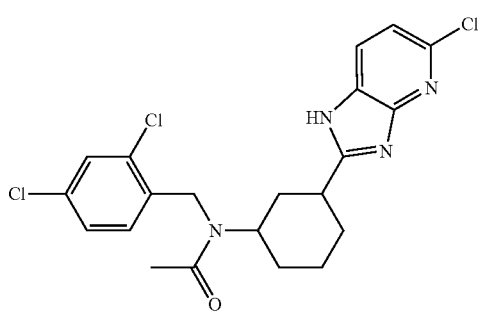 [SMILES: CC(=O)N(Cc1ccc(Cl)cc1Cl)C1CCCC(c2nc3nc(Cl)ccc3[nH]2)C1]

1810: N-(3-(5-chloro-1H-imidazo[4,5-b]pyridin-2-yl)cyclohexyl)-N-(2,4-dichlorobenzyl)acetamide was obtained during the synthesis of ChemID: 1809. MS (ESI) (M+H)$^+$=452.7; HPLC analysis: 95.0% purity

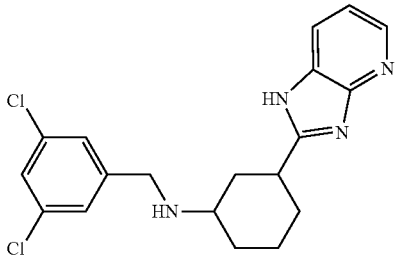

1817: N-(3,5-dichlorobenzyl)-3-(1H-imidazo[4,5-b]pyridin-2-yl) cyclohexanamine was synthesized using 3,5-dichlorobenzaldehyde, methyl 3-aminocyclohexanecarboxylate and pyridine-2,3-diamine following the general procedure 11. MS (ESI) (M+H)$^+$=376.1; HPLC analysis: 100% purity

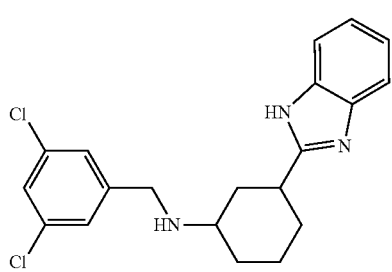 [SMILES: Clc1cc(Cl)cc(CNC2CCCC(c3nc4ccccc4[nH]3)C2)c1]

1815: 3-(1H-benzo[d]imidazol-2-yl)-N-(3,5-dichlorobenzyl)cyclohexanamine was synthesized using 3,5-dichlorobenzaldehyde, methyl 3-aminocyclohexanecarboxylate and benzene-1,2-diamine following the general procedure 11. MS (ESI) (M+H)$^+$=374.9; HPLC analysis: 96.1% purity

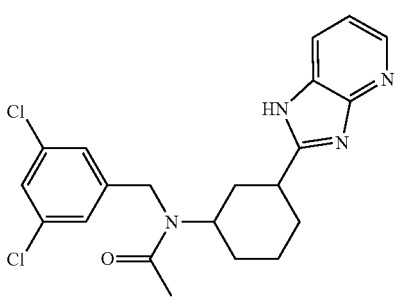 [SMILES: CC(=O)N(Cc1cc(Cl)cc(Cl)c1)C1CCCC(c2nc3ncccc3[nH]2)C1]

1818: N-(3-(1H-imidazo[4,5-b]pyridin-2-yl)cyclohexyl)-N-(3,5-dichlorobenzyl) acetamide was obtained during the synthesis of ChemID: 1817. MS (ESI) (M+H)$^+$=418.4; HPLC analysis: 98.2% purity

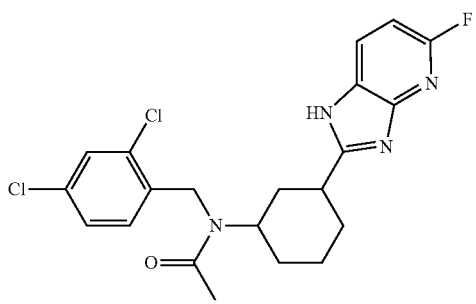 [SMILES: CC(=O)N(Cc1ccc(Cl)cc1Cl)C1CCCC(c2nc3nc(F)ccc3[nH]2)C1]

1836: N-(2,4-dichlorobenzyl)-N-(3-(5-fluoro-1H-imidazo[4,5-b]pyridin-2-yl) cyclohexyl)acetamide was synthesized using 2,4-dichlorobenzaldehyde, methyl 3-aminocyclohexanecarboxylate and 6-fluoropyridine-2,3-diamine following the general procedure. MS (ESI) (M+H)$^+$=436.3; HPLC analysis: 96.5% purity

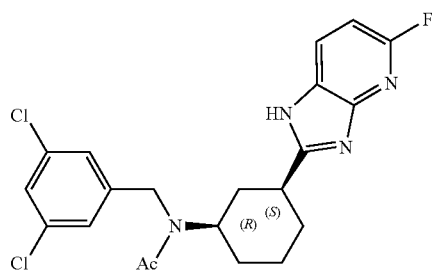

1932: N-(3,5-dichlorobenzyl)-N-((1R,3S)-3-(5-fluoro-1H-imidazo[4,5-b]pyridin-2-yl)cyclohexyl)acetamide was synthesized using 3,5-dichlorobenzaldehyde, (1S,3R)-methyl 3-aminocyclohexanecarboxylate and 4-fluorobenzene-1,2-diamine following the general procedure 11. MS (ESI) (M+H)$^+$=436.0

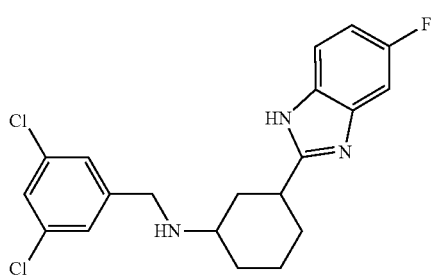 [SMILES: Fc1ccc2[nH]c(C3CCCC(NCc4cc(Cl)cc(Cl)c4)C3)nc2c1]

1839: N-(3,5-dichlorobenzyl)-3-(5-fluoro-1H-benzo[d]imidazol-2-yl) cyclohexanamine was synthesized using 3,5-dichlorobenzaldehyde, methyl 3-aminocyclohexanecarboxylate and 4-fluorobenzene-1,2-diamine following the general procedure 11. MS (ESI) (M+H)$^+$=392.9; HPLC analysis: 100% purity

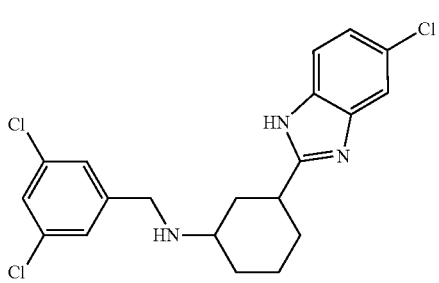

1840: 3-(5-chloro-1H-benzo[d]imidazol-2-yl)-N-(3,5-dichlorobenzyl) cyclohexanamine was synthesized using 3,5-dichlorobenzaldehyde, methyl 3-aminocyclohexanecarboxylate and 4-chlorobenzene-1,2-diamine following the general procedure 11. $^1$H NMR (500 MHz, CDCl$_3$) δ 7.50-7.43 (br, 1H), 7.38 (d, J=6.3 Hz, 1H), 7.42-7.35 (m, 3H), 7.16 (dd, J=8.5, 1.7 Hz, 1H), 3.85 (s, 2H), 3.10 (s, 1H), 2.85 (s, 1H), 2.33 (d, J=12.4 Hz, 2H), 2.01 (s, 2H), 2.00-1.90 (m, 1H), 1.87-1.78 (m, 1H), 1.74 (dd, J=21.6, 9.0 Hz, 1H), 1.63 (dd, J=21.6, 9.0 Hz, 1H), 1.51-1.37 (m, 2H). MS (ESI) (M+H)$^+$=409.5

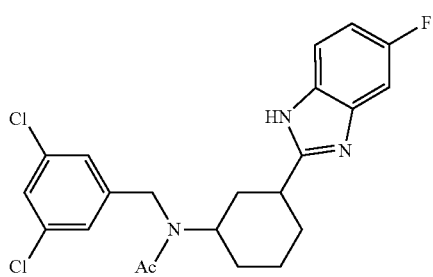 [SMILES: CC(=O)N(Cc1cc(Cl)cc(Cl)c1)C1CCCC(c2nc3cc(F)ccc3[nH]2)C1]

1860: N-(3,5-dichlorobenzyl)-N-(3-(5-fluoro-1H-benzo[d]imidazol-2-yl) cyclohexyl)acetamide was obtained during the synthesis of ChemID: 1839. MS (ESI) (M+H)$^+$=435.1

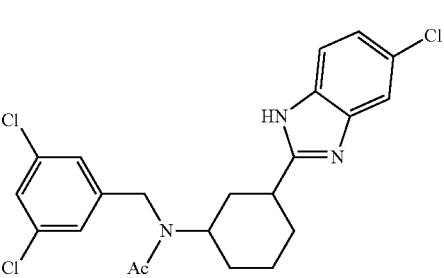 [SMILES: CC(=O)N(Cc1cc(Cl)cc(Cl)c1)C1CCCC(c2nc3cc(Cl)ccc3[nH]2)C1]

1861: N-(3-(5-chloro-1H-benzo[d]imidazol-2-yl)cyclohexyl)-N-(3,5-dichlorobenzyl)acetamide was obtained during the synthesis of ChemID: 1839. MS (ESI) (M+H)$^+$=452.9

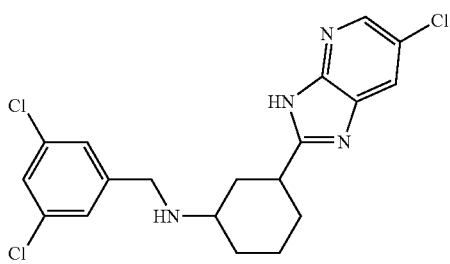 [SMILES: Clc1cc(Cl)cc(CNC2CCCC(c3nc4cc(Cl)cnc4[nH]3)C2)c1]

1841: 3-(6-chloro-3H-imidazo[4,5-b]pyridin-2-yl)-N-(3,5-dichlorobenzyl) cyclohexanamine was synthesized using 3,5-dichlorobenzaldehyde, methyl 3-aminocyclohexanecarboxylate and 5-chloropyridine-2,3-diamine following the general procedure 11. MS (ESI) (M+H)$^+$=410.4; HPLC analysis: 85.0% purity.

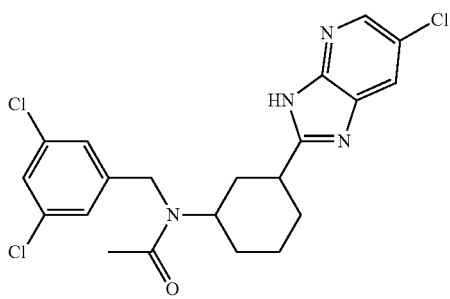 [SMILES: CC(=O)N(Cc1cc(Cl)cc(Cl)c1)C1CCCC(c2nc3cc(Cl)cnc3[nH]2)C1]

1842: N-(3-(6-chloro-3H-imidazo[4,5-b]pyridin-2-yl)cyclohexyl)-N-(3,5-dichlorobenzyl)acetamide was obtained during the synthesis of ChemID: 1841. MS (ESI) (M+H)$^+$= 452.6; HPLC analysis: 100% purity.

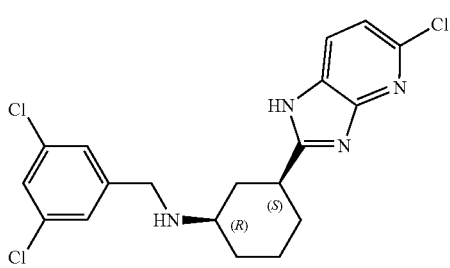

1854: (1R,3S)-3-(5-chloro-1H-imidazo[4,5-b]pyridin-2-yl)-N-(3,5-dichlorobenzyl)cyclohexanamine was synthesized using 3,5-dichlorobenzaldehyde, (1S,3R)-methyl 3-aminocyclohexanecarboxylate and 6-chloropyridine-2,3-diamine following the general procedure 11. $^1$H NMR (500 MHz, CDCl$_3$) δ 8.05-7.88 (br, 1H), 7.26 (s, 1H), 7.25-7.23 (m, 2H), 7.22 (s, 1H), 3.83 (dd, J=33.3, 13.8 Hz, 2H), 3.20 (t, J=10.4, 1H), 2.74 (t, J=10.4, 1H), 2.42 (d, J=12.5 Hz, 1H), 2.18-2.10 (m, 1H), 2.09-1.97 (m, 1H), 1.96-1.87 (m, 1H), 1.74-1.62 (m, 2H), 1.49 (td, J=12.0, 3.4 Hz, 1H), 1.27 (dd, J=16.4, 9.3 Hz, 1H). MS (ESI) (M+H)$^+$=410.5; HPLC analysis: 100% purity.

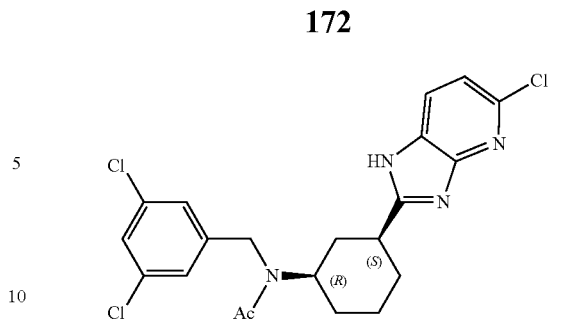

1859: N-((1R,3S)-3-(5-chloro-1H-imidazo[4,5-b]pyridin-2-yl)cyclohexyl)-N-(3,5-dichlorobenzyl)acetamide was obtained during the synthesis of ChemID: 1854. MS (ESI) (M+H)$^+$=453.2; HPLC analysis: 95.3% purity.

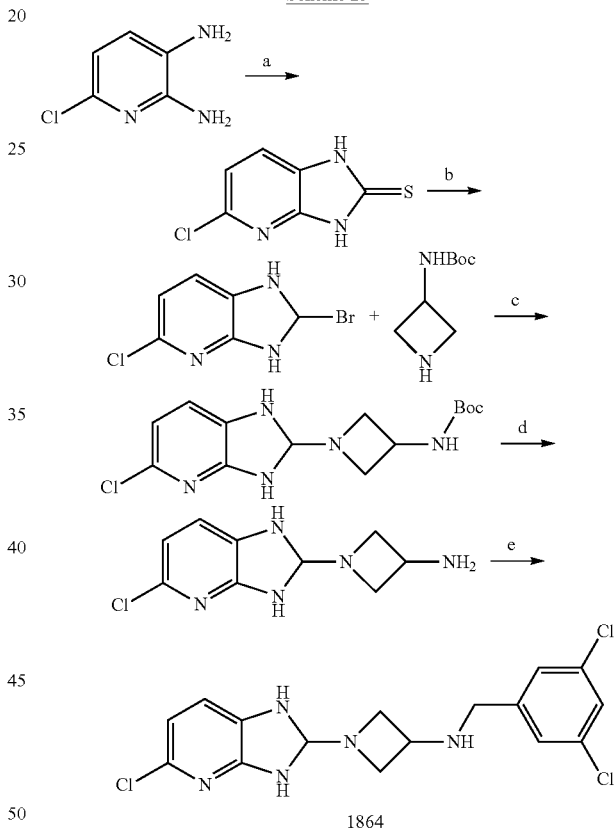

Scheme 25

1864

Reagents and conditions: (a) CS$_2$, EtOH/Pyridine, 40° C., overnight; (b) Br$_2$, HBr, AcOH, r.t. overnight; (c) Pyridine, 100° C., 30 min; (d) TFA, DCM, r.t., overnight; (e) 3,5-dichlorobenzaldehyde, DIPEA, NaBH$_3$CN, AcOH, CH$_3$OH, r.t., overnight.

General Procedure 12:

(a) To a solution of 6-chloropyridine-2,3-diamine (144 mg, 1 mM) in a mixture of EtOH (5 mL) and pyridine (2 mL) was added carbon disulfide (0.5 mL) at r.t. The mixture was stirred at 40° C. overnight. The mixture was cooled to r.t., the resulting solid was filtered and washed with ether to give light yellow solid 5-chloro-1H-imidazo[4,5-b]pyridine-2(3H)-thione.

(b) 5-chloro-1H-imidazo[4,5-b]pyridine-2(3H)-thione (92.5 mg, 0.5 mM) was dissolved in acetic acid (2 mL), 48% HBr (aq) (0.084 mL) was added and the mixture cooled under ice. Br$_2$ (0.1 mL) was added to the mixture under vigorous shaking. The mixture was vigorously stirred at r.t. over night. H₂O (2 mL) was added, and the resulting solution was cooled in an ice bath. The pH was adjusted to 4 with solid NaOH, and the precipitate was collected by filtration and washed by ether to get 2-bromo-5-chloro-1H-imidazo[4,5-b]pyridine.

(c) 2-bromo-5-chloro-1H-imidazo[4,5-b]pyridine (60 mg, 0.258 mM) was dissolved in pyridine (2 mL), tert-butyl azetidin-3-ylcarbamate (155 mg, 0.77 mM) was added and the reaction mixture was microwave irradiated at 100° C. for 30 min. The reaction mixture was concentrated in vacuum and the residue partitioned between saturated sodium bicarbonate and DCM. The organic extract was dried over anhydrous sodium sulfate, and concentrated in vacuum. The residue was purified through flash chromatography on silica gel eluted with MeOH-DCM (0.5% ammonia hydroxide) to give tert-butyl (1-(5-chloro-1H-imidazo[4,5-b]pyridin-2-yl) azetidin-3-yl)carbamate.

(d) tert-butyl (1-(5-chloro-1H-imidazo[4,5-b]pyridin-2-yl)azetidin-3-yl) carbamate was dissolved in DCM, the solution was cooled to 0° C., then TFA (5 eq) was added dropwise. The mixture was stirred at r.t. overnight, the solvent was removed in vacuum. HCl in Methanol was added to the residue, and the solvent was removed to give 1-(5-chloro-1H-imidazo[4,5-b]pyridin-2-yl)azetidin-3-amine as HCl salt.

(e) 1-(5-chloro-1H-imidazo[4,5-b]pyridin-2-yl)azetidin-3-amine was dissolved in CH₃OH, DIPEA (1.2 eq) was added and the solution stirred at r.t. for 10 min. Substituted benzaldehyde 8 (1.2 eq) was added, following by adding AcOH (2 eq) and NaBH₃CN (2 eq). The mixture was stirred at r.t. overnight. The solvent was removed under reduced pressure and the residue was extracted by DCM. The organic phase was dried over sodium sulfate. Remove solvent in vacuum and purify through flash chromatography on silica gel eluted with MeOH-DCM (0.5% ammonia hydroxide) to give 1864. ¹H NMR (500 MHz, CDCl₃) δ 7.80-7.43 (br, 1H), 7.35-7.21 (m, 3H), 7.13-6.76 (br, 1H), 4.37-3.97 (m, 2H), 3.81 (s, 2H), 3.29-3.06 (br, 2H), 2.78 (s, 1H), 2.00-1.92 (br, 2H), 1.53-1.40 (br, 2H). MS (ESI) (M+H)⁺=383.6; HPLC analysis: 100% purity.

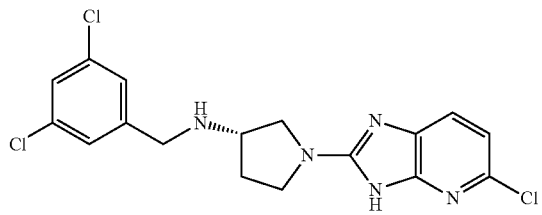

1845

1845 was synthesized using 3,5-dichlorobenzaldehyde and tert-butyl (S)-pyrrolidin-3-ylcarbamate following the general Procedure 12. LC/MS: (ESI) (M+H)⁺=397.7.

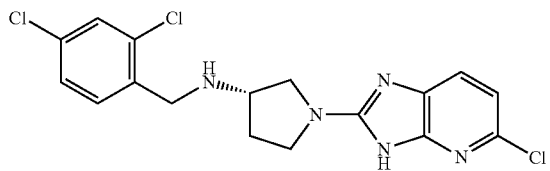

1846

1846 was synthesized using 2,4-dichlorobenzaldehyde following the general Procedure 12.

LC/MS: (ESI) (M+H)⁺=397.7.

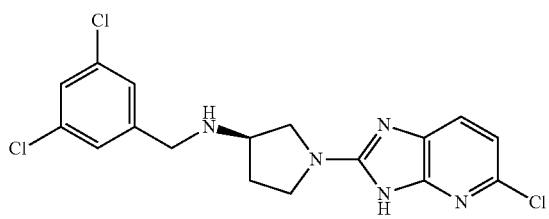

1847

1847 was synthesized using 3,5-dichlorobenzaldehyde and tert-butyl (R)-pyrrolidin-3-ylcarbamate following the general Procedure 12. LC/MS: (ESI) (M+H)⁺=397.7.

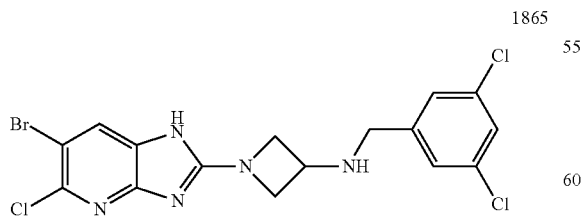

1865

1865 was synthesized using 3,5-dichlorobenzaldehyde, tert-butyl azetidin-3-ylcarbamate and 2,6-dibromo-5-chloro-1H-imidazo[4,5-b]pyridine following the general procedures 12. LC/MS: (ESI) (M+H)⁺=462.4.

1848

1848 was synthesized using 2,4-dichlorobenzaldehyde and tert-butyl (R)-pyrrolidin-3-ylcarbamate following the general Procedure 12. LC/MS: (ESI) (M+H)⁺=397.7.

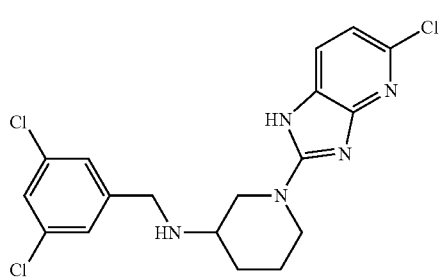

1811

1811: 1-(5-chloro-1H-imidazo[4,5-b]pyridin-2-yl)-N-(3,5-dichlorobenzyl) piperidin-3-amine was synthesized using 3,5-dichlorobenzaldehyde and tert-butyl piperidin-3-ylcarbamate following the general procedure 12. $^1$H NMR (500 MHz, CDCl$_3$) δ 7.65-7.37 (br, 1H), 7.19 (s, 1H), 7.12 (s, 2H), 7.08-6.84 (br, 1H), 4.20-3.95 (br, 1H), 3.91-3.77 (br, 1H), 3.71 (s, 2H), 3.34-2.87 (m, 1H), 2.77 (s, 1H), 2.02-1.91 (m, 1H), 1.90-1.77 (m, 1H), 1.68-1.50 (m, 1H), 1.50-1.33 (m, 2H). MS (ESI) (M+H)$^+$=411.7; HPLC analysis: 99.6% purity.

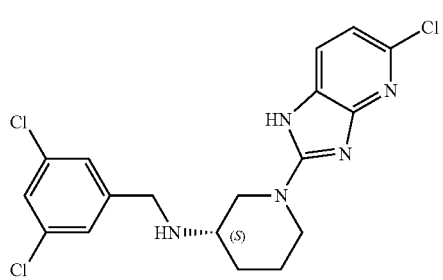

1856

1856: (S)-1-(5-chloro-1H-imidazo[4,5-b]pyridin-2-yl)-N-(3,5-dichlorobenzyl) piperidin-3-amine was synthesized using 3,5-dichlorobenzaldehyde and (S)-tert-butyl piperidin-3-ylcarbamate following the general procedure 12. $^1$H NMR (500 MHz, CDCl$_3$) δ 7.64-7.43 (br, 1H), 7.22-7.18 (m, 1H), 7.18-7.11 (m, 1H), 7.08-6.91 (br, 1H), 4.19-3.95 (br, 1H), 3.93-3.77 (br, 1H), 3.75 (s, 2H), 3.33-2.97 (m, 2H), 2.85-2.71 (br, 1H), 2.03-1.92 (m, 1H), 1.91-1.79 (m, 1H), 1.69-1.55 (m, 1H), 1.55-1.40 (m, 1H). MS (ESI) (M+H)$^+$=411.4; HPLC analysis: 95.6% purity.

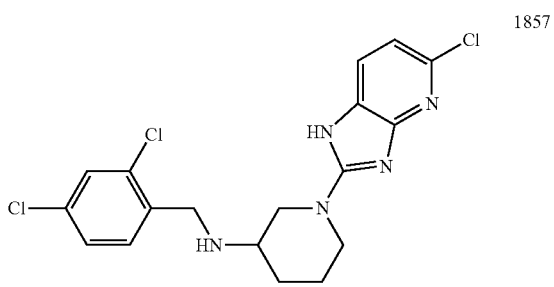 [SMILES: Clc1ccc(CNC2CCCN(c3nc4nc(Cl)ccc4[nH]3)C2)c(Cl)c1]

1857

1857: 1-(5-chloro-1H-imidazo[4,5-b]pyridin-2-yl)-N-(2,4-dichlorobenzyl) piperidin-3-amine was synthesized using 2,4-dichlorobenzaldehyde and tert-butyl piperidin-3-ylcarbamate following the general procedure 12. MS (ESI) (M+H)$^+$=411.6; HPLC analysis: 96.7% purity.

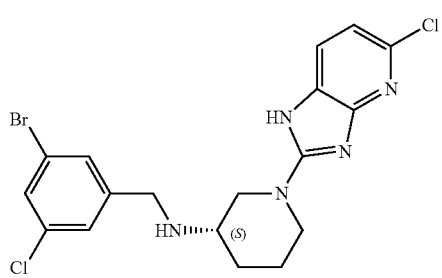

1912

1912: (S)—N-(3-bromo-5-chlorobenzyl)-1-(5-chloro-1H-imidazo[4,5-b]pyridin-2-yl)piperidin-3-amine was synthesized using 3-bromo-5-chlorobenzaldehyde and (S)-tert-butyl piperidin-3-ylcarbamate following the general procedure 12. MS (ESI) (M+H)$^+$=455.9

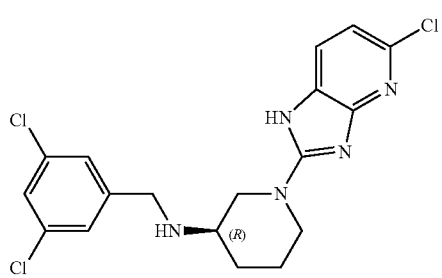

1855

1855: (R)-1-(5-chloro-1H-imidazo[4,5-b]pyridin-2-yl)-N-(3,5-dichlorobenzyl) piperidin-3-amine was synthesized using 3,5-dichlorobenzaldehyde and (R)-tert-butyl piperidin-3-ylcarbamate following the general procedure 12. MS(ESI) (M+H)$^+$=412.0; HPLC analysis: 100% purity

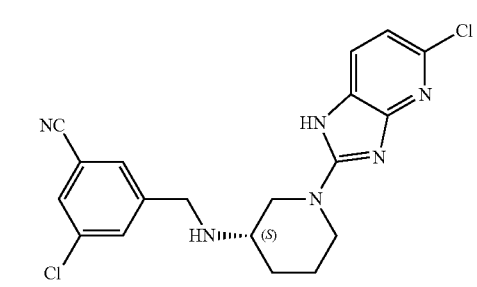

1992

1992: (S)-3-chloro-5-(((1-(5-chloro-1H-imidazo[4,5-b]pyridin-2-yl)piperidin-3-yl)amino)methyl)benzonitrile was synthesized using 3-chloro-5-formylbenzonitrile and (S)-tert-butyl piperidin-3-ylcarbamate following the general procedure 12. MS (ESI) (M+H)$^+$=402.2

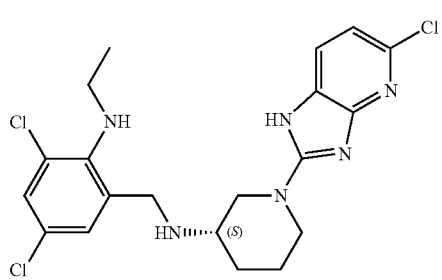

1940: (S)-1-(5-chloro-1H-imidazo[4,5-b]pyridin-2-yl)-N-(3,5-dichloro-2-(ethylamino)benzyl)piperidin-3-amine was synthesized using 3,5-dichloro-2-(ethylamino)benzaldehyde and (S)-tert-butyl piperidin-3-ylcarbamate following the general procedure 12. MS (ESI) (M+H)=454.6

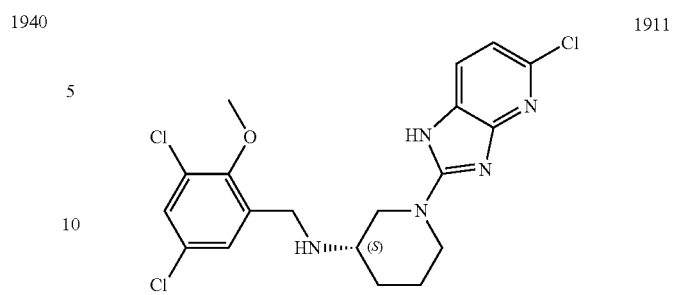

1911: (S)-1-(5-chloro-1H-imidazo[4,5-b]pyridin-2-yl)-N-(3,5-dichloro-2-methoxybenzyl)piperidin-3-amine was synthesized using 3,5-dichloro-2-methoxybenzaldehyde and (S)-tert-butyl piperidin-3-ylcarbamate following the general procedure 12. MS (ESI) (M+H)$^+$=441.8

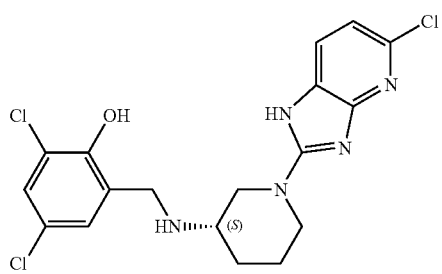

1921: (S)—N-(3-bromo-5-chloro-2-ethoxybenzyl)-1-(5-chloro-1H-imidazo[4,5-b]pyridin-2-yl)piperidin-3-amine was synthesized using 3,5-dichloro-2-hydroxybenzaldehyde and (S)-tert-butyl piperidin-3-ylcarbamate following the general procedure 12. MS (ESI) (M+H)$^+$=427.6

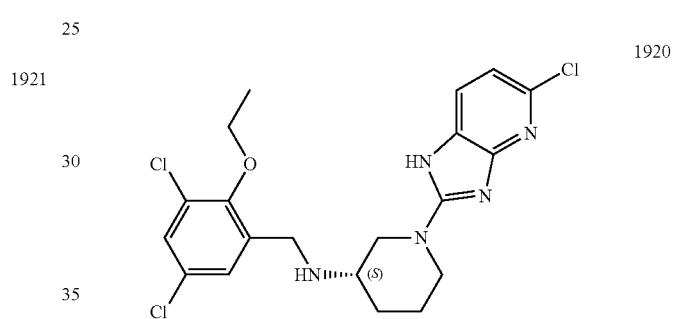

1920: (S)-1-(5-chloro-1H-imidazo[4,5-b]pyridin-2-yl)-N-(3,5-dichloro-2-ethoxybenzyl)piperidin-3-amine was synthesized using 3,5-dichloro-2-ethoxybenzaldehyde and (S)-tert-butyl piperidin-3-ylcarbamate following the general procedure 12. MS (ESI) (M+H)$^+$=455.7

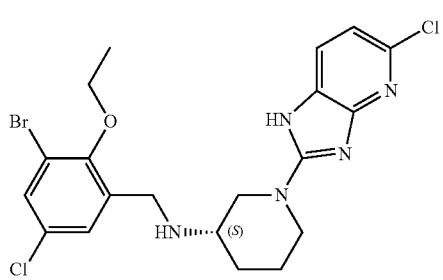

1937: (S)—N-(3-bromo-5-chloro-2-ethoxybenzyl)-1-(5-chloro-1H-imidazo[4,5-b]pyridin-2-yl)piperidin-3-amine was synthesized using 3-bromo-5-chloro-2-ethoxybenzaldehyde and (S)-tert-butyl piperidin-3-ylcarbamate following the general procedure 12. MS (ESI) (M+H)$^+$=500.2

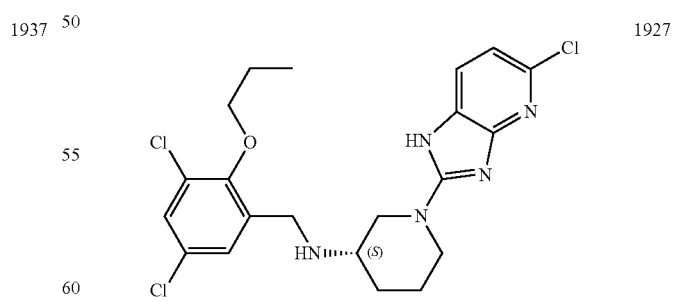

1927: (S)-1-(5-chloro-1H-imidazo[4,5-b]pyridin-2-yl)-N-(3,5-dichloro-2-propoxybenzyl)piperidin-3-amine was synthesized using 3,5-dichloro-2-propoxybenzaldehyde and (S)-tert-butyl piperidin-3-ylcarbamate following the general procedure 12. MS (ESI) (M+H)$^+$=469.8

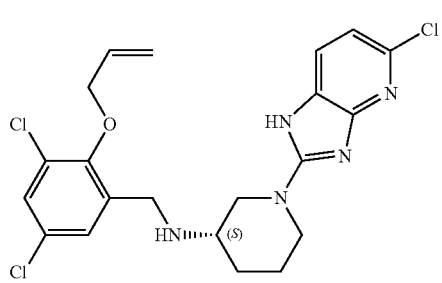

1928: (S)—N-(2-(allyloxy)-3,5-dichlorobenzyl)-1-(5-chloro-1H-imidazo[4,5-b]pyridin-2-yl)piperidin-3-amine was synthesized using 2-(allyloxy)-3,5-dichlorobenzaldehyde and (S)-tert-butyl piperidin-3-ylcarbamate following the general procedure 12. MS (ESI) (M+H)$^+$=467.7

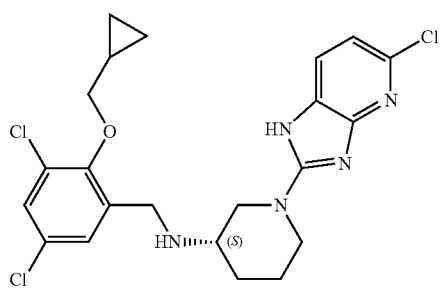

1929: (S)-1-(5-chloro-1H-imidazo[4,5-b]pyridin-2-yl)-N-(3,5-dichloro-2-(cyclopropylmethoxy)benzyl)piperidin-3-amine was synthesized using 3,5-dichloro-2-(cyclopropylmethoxy)benzaldehyde and (S)-tert-butyl piperidin-3-ylcarbamate following the general procedure 12. MS (ESI) (M+H)$^+$=481.7

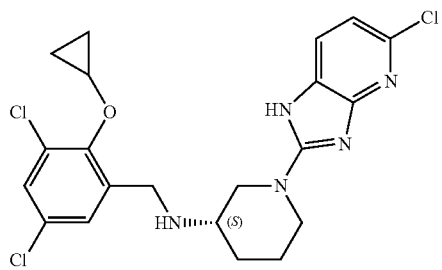

1930: (S)-1-(5-chloro-1H-imidazo[4,5-b]pyridin-2-yl)-N-(3,5-dichloro-2-cyclopropoxybenzyl)piperidin-3-amine was synthesized using 3,5-dichloro-2-cyclopropoxybenzaldehyde and (S)-tert-butyl piperidin-3-ylcarbamate following the general procedure 12. MS (ESI) (M+H)$^+$=467.7

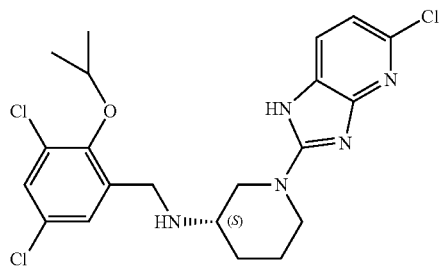

1931: (S)-1-(5-chloro-1H-imidazo[4,5-b]pyridin-2-yl)-N-(3,5-dichloro-2-isopropoxybenzyl)piperidin-3-amine was synthesized using 3,5-dichloro-2-isopropoxybenzaldehyde and (S)-tert-butyl piperidin-3-ylcarbamate following the general procedure 12. MS (ESI) (M+H)*-469.4

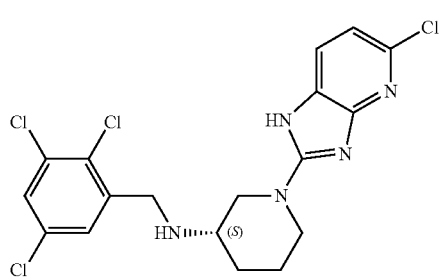

1902: (S)-1-(5-chloro-1H-imidazo[4,5-b]pyridin-2-yl)-N-(2,3,5-trichlorobenzyl)piperidin-3-amine was synthesized using 2,3,5-trichloro-2-benzaldehyde and (S)-tert-butyl piperidin-3-ylcarbamate following the general procedure 12. MS (ESI) (M+H)$^+$=445.8

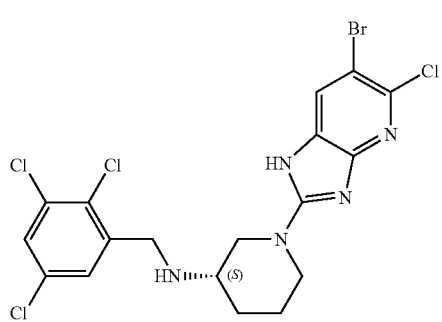

1905: (S)-1-(6-bromo-5-chloro-1H-imidazo[4,5-b]pyridin-2-yl)-N-(2,3,5-trichlorobenzyl)piperidin-3-amine was synthesized using 2,3,5-trichlorobenzaldehyde and (S)-tert-butyl piperidin-3-ylcarbamate and 2,6-dibromo-5-chloro-1H-imidazo[4,5-b]pyridine following the general procedure 12. MS (ESI) (M+H)$^+$=525.7

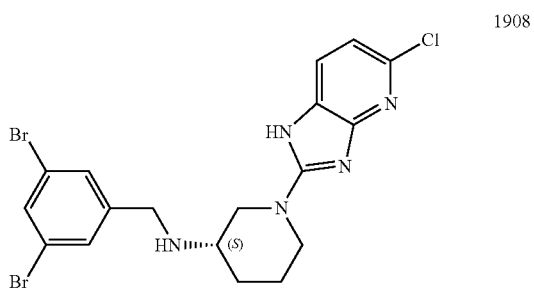

1908: (S)-1-(5-chloro-1H-imidazo[4,5-b]pyridin-2-yl)-N-(3,5-dibromobenzyl) piperidin-3-amine was synthesized using 3,5-dibromo-benzaldehyde and (S)-tert-butyl piperidin-3-ylcarbamate following the general procedure 12. MS (ESI) (M+H)$^+$=500.6

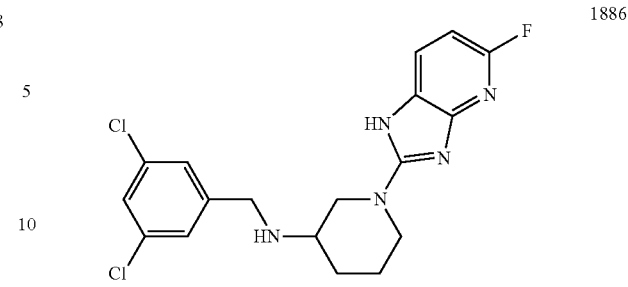

1886: N-(3,5-dichlorobenzyl)-1-(5-fluoro-1H-imidazo[4,5-b]pyridin-2-yl) piperidin-3-amine was synthesized using 3,5-dichlorobenzaldehyde and tert-butyl piperidin-3-ylcarbamate following the general procedure 12. MS (ESI) (M+H)$^+$=395.0; HPLC analysis: 96.7% purity.

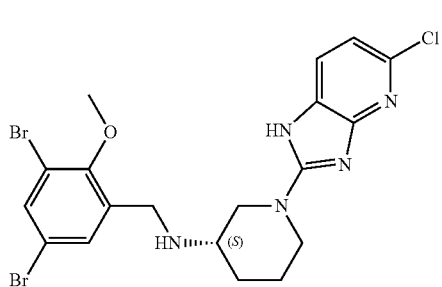

1909: (S)-1-(5-chloro-1H-imidazo[4,5-b]pyridin-2-yl)-N-(3,5-dibromo-2-methoxybenzyl)piperidin-3-amine was synthesized using 3,5-dibromo-2-methoxybenzaldehyde and (S)-tert-butyl piperidin-3-ylcarbamate following the general procedure 12. MS (ESI) (M+H)$^+$=530.3

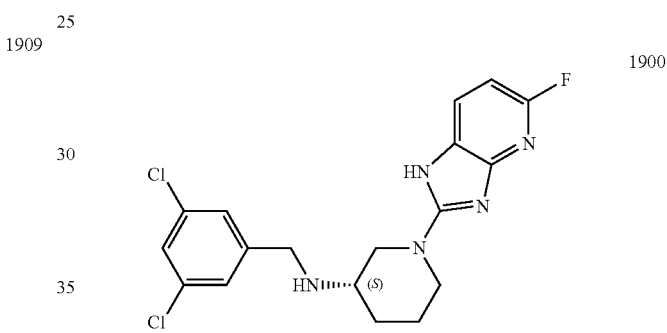

1900: (S)—N-(3,5-dichlorobenzyl)-1-(5-fluoro-1H-imidazo[4,5-b]pyridin-2-yl)piperidin-3-amine was synthesized using 3,5-dichlorobenzaldehyde and tert-butyl piperidin-3-ylcarbamate and 2-bromo-5-fluoro-1H-imidazo[4,5-b]pyridine following the general procedure 12. MS (ESI) (M+H)$^+$= 395.0; HPLC analysis: 96.7% purity.

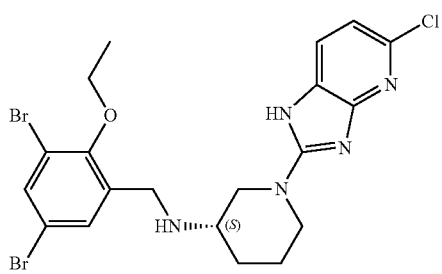

1910: (S)-1-(5-chloro-1H-imidazo[4,5-b]pyridin-2-yl)-N-(3,5-dibromo-2-ethoxybenzyl)piperidin-3-amine was synthesized using 3,5-dibromo-2-ethoxybenzaldehyde and (S)-tert-butyl piperidin-3-ylcarbamate following the general procedure 12. MS (ESI) (M+H)$^+$=544.4

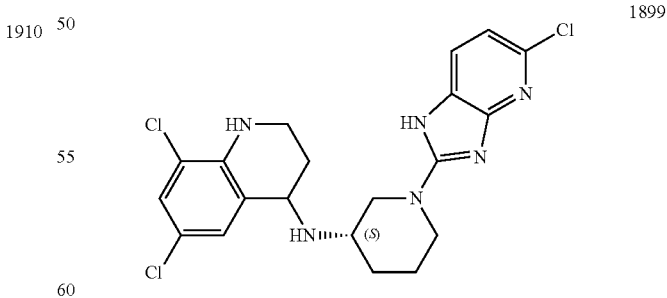

1899: 6,8-dichloro-N—((S)-1-(5-chloro-1H-imidazo[4,5-b]pyridin-2-yl) piperidin-3-yl)-1,2,3,4-tetrahydroquinolin-4-amine. In the case of compound 1899, intermediate 21 (1 eq) reacted with 6,8-dichloro-2,3-dihydroquinolin-4(1H)-one (1 eq) in EtOH under MW condition at 100° C. for 1 h to get the target compound 1899. MS (ESI) (M+H)$^+$=452.7

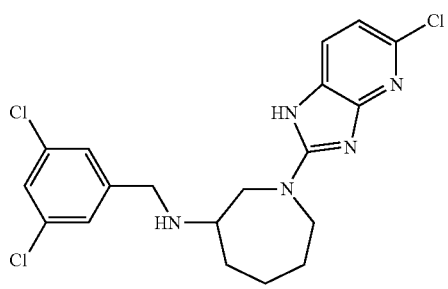

1903 1-(5-chloro-1H-imidazo[4,5-b]pyridin-2-yl)-N-(3,5-dichlorobenzyl) azepan-3-amine was synthesized using 3,5-dichlorobenzoic acid and tert-butyl azepan-3-ylcarbamate following the general procedure 12. MS (ESI) (M+H)$^+$=425.9

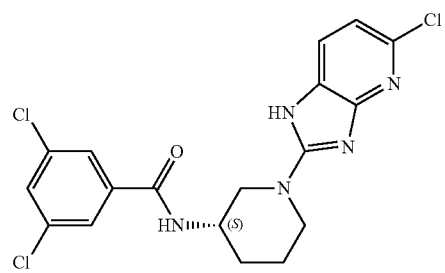

1889: (S)-3,5-dichloro-N-(1-(5-chloro-1H-imidazo[4,5-b]pyridin-2-yl) piperidin-3-yl benzamide was synthesized using 3,5-dichlorobenzoic acid and (S)-tert-butyl piperidin-3-ylcarbamate following the general procedure 12. MS (ESI) (M+H)$^+$=425.5; HPLC analysis: 95.3% purity.

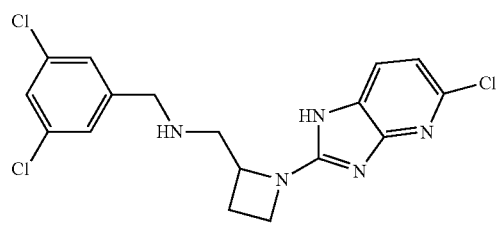

1915 1-(1-(5-chloro-1H-imidazo[4,5-b]pyridin-2-yl)azetidin-2-yl)-N-(3,5-dichlorobenzyl)methanamine was synthesized using 3,5-dichlorobenzoic acid and tert-butyl (azetidin-2-ylmethyl)carbamate following the general procedure 12. MS (ESI) (M+H)$^+$=397.5

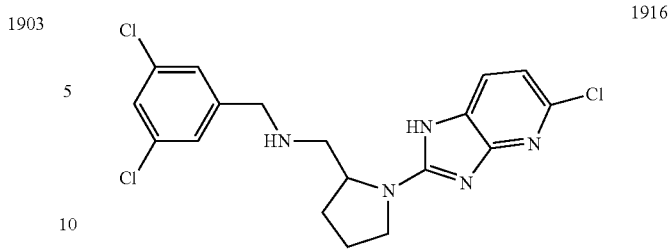

1916 1-(1-(5-chloro-1H-imidazo[4,5-b]pyridin-2-yl)pyrrolidin-2-yl)-N-(3,5-dichlorobenzyl)methanamine was synthesized using 3,5-dichlorobenzoic acid and tert-butyl (pyrrolidin-2-ylmethyl)carbamate following the general procedure 12. MS (ESI) (M+H)$^+$=411.9

Scheme 26

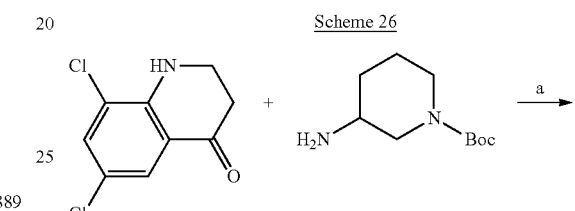

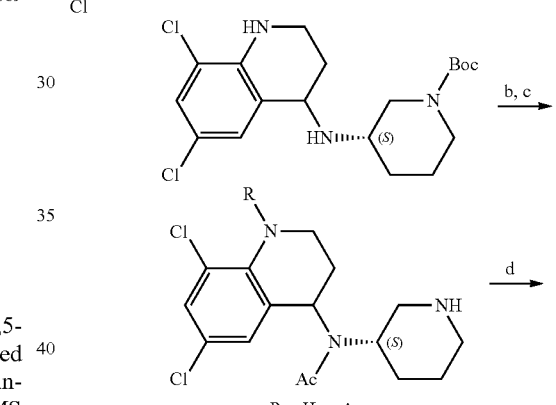

R = H or Ac

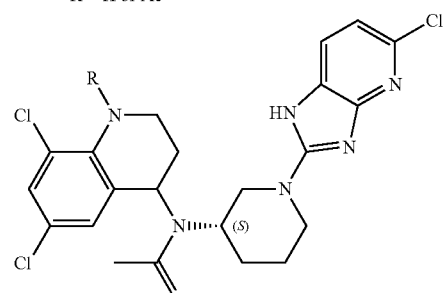

1943: R = H
1945: R = Ac

Reagents and conditions: (a) Ti(OEt)$_4$, NaBH$_3$CN, DCE, MW, 100° C., 30 min; (b) AcCl, K$_2$CO$_3$, CH$_3$CN, 60° C., 3 h; (c) TFA, DCM, r.t., overnight; (d) NaBH$_3$CN, CH$_3$OH/AcOH, r.t., 3 h.

6,8-dichloro-2,3-dihydroquinolin-4(1H)-one (1 eq) and tert-butyl 3-aminopiperidine-1-carboxylate (1.5 eq) were dissolved in DCE, Ti(OEt)$_4$ (3 eq) and NaBH$_3$CN (2 eq) were added, the mixture was then microwave irradiated at 100° C. for 30 min. Saturated NaHCO$_3$ was added, extracted with DCM, washed with brine, concentrated under vacuum and purified via flash column chromatography to yield intermediate N-(6,8-dichloro-1,2,3,4-tetrahydroquinolin-4-yl)-N—((S)-piperidin-3-yl)acetamide.

N-(6,8-dichloro-1,2,3,4-tetrahydroquinolin-4-yl)-N—((S)-piperidin-3-yl)acetamide was dissolved in CH$_3$CN, K$_2$CO$_3$ (6 ea) and AcCl (6 eq) were added. The mixture was stirred at 60° C. for 3 h. The solvent was evaporated off, extracted with DCM, washed with brine, concentrated under vacuum and purified via flash column chromatography to yield intermediates (3S)-tert-butyl 3-(N-(6,8-dichloro-1,2,3,4-tetrahydroquinolin-4-yl)acetamido)piperidine-1-carboxylate and N-(1-acetyl-6,8-dichloro-1,2,3,4-tetrahydroquinolin-4-yl)-N—((S)-piperidin-3-yl)acetamide, then follow the procedures of (d) and (e) in Scheme 25 to produce the products 1943 and 1945. 1943: MS (ESI) (M+H)$^+$=494.5; 1945: MS (ESI) (M+H)$^+$=536.5

Hz, 1H), 3.61 (ddd, J=13.6, 10.5, 3.0 Hz, 1H), 2.15-2.04 (m, 2H), 2.01-1.93 (m, 1H), 1.82-1.73 (m, 1H). MS (ESI) (M+H)$^+$=412.8

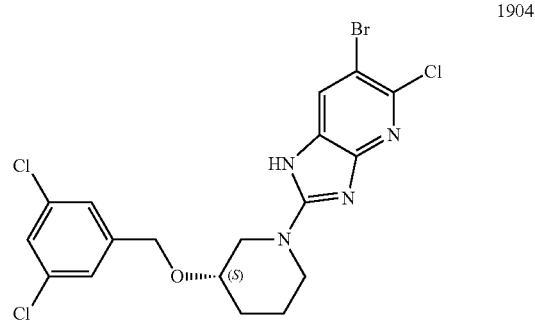

1904: (S)-6-bromo-5-chloro-2-(3-((3,5-dichlorobenzyl)oxy)piperidin-1-yl)-1H-imidazo[4,5-b]pyridine was synthesized using 2,6-dibromo-5-chloro-1H-imidazo[4,5-b]pyridine following the general procedure 13. MS (ESI) (M+H)$^+$= 491.2

Scheme 27

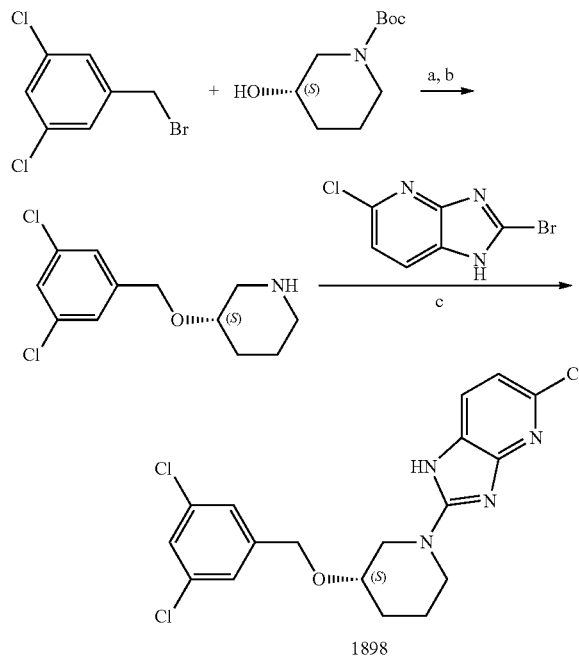

Reagents and conditions: (a) NaH, DMF, 0° C.-r.t., 2 h; (b) TFA, DCM, r.t. overnight; (c) Pyridine, 100° C., 30 min.

General Procedure 13

(S)-tert-butyl 3-hydroxypiperidine-1-carboxylate (1 eq) was dissolved in dry DMF, the solution was cooled to 0° C., NaH (2 eq) was added, stirred for 10 min, then 1-(bromomethyl)-3,5-dichlorobenzene (1 eq) in DMF was added dropwise. The solution was stirred at r.t for 2 h and the solvent was removed under vacuum. The residue was dissolved in DCM and washed with sat. sodium bicarbonate and brine. The organic layer was dried over Na$_2$SO$_4$ and concentrated under vacuum. The residue was dissolved in DCM, and TFA (5 eq) was added, the mixture was stirred at r.t. over night. The solvent was removed under vacuum to get the deprotedted intermediate which was used for next step without further purification.

Step C was conducted following the procedure of step (c) in Scheme 22 to get compound 1898: $^1$H NMR (500 MHz, MeOD) δ 7.69 (d, J=8.3 Hz, 1H), 7.34 (d, J=8.3 Hz, 1H), 7.24-7.21 (m, 1H), 7.17-7.14 (m, 2H), 4.67 (d, J=12.7 Hz, 1H), 4.55 (d, J=12.7 Hz, 1H), 4.56 (s, 1H), 4.54 (s, 1H), 3.99 (dd, J=14.0, 3.7 Hz, 1H), 3.95-3.86 (m, 2H), 3.78 (d, J=13.8

Scheme 28

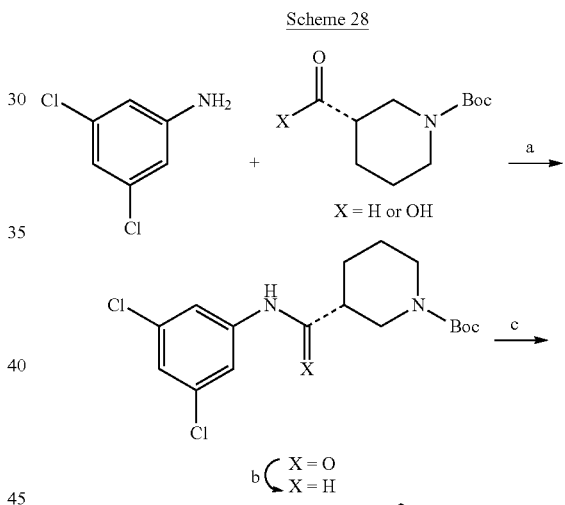

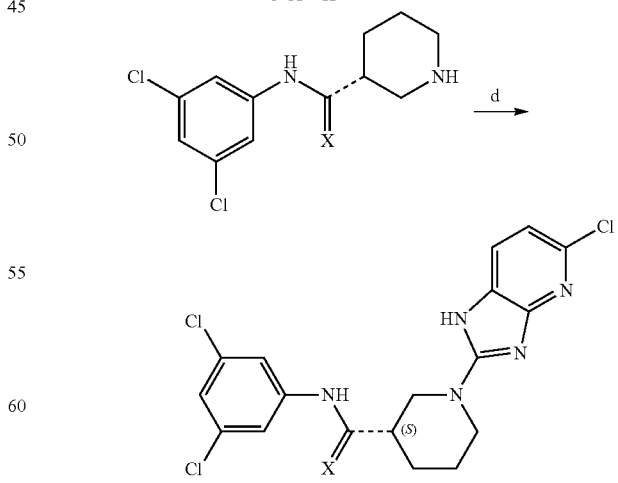

Reagents and conditions: (a) X = H: NaBH$_3$CN, AcOH, CH$_3$OH, r.t., overnight; X = O: EDC, pyridine, r.t. overnight; (b) BH$_3$ in THF, r.t., overnight; (c) 2-bromo-5-chloro-1H-imidazo[4,5-b]pyridine, Pyridine, 100° C., 30 min.

General Procedure 14

Compound 3,5-dichloroaniline reacted with tert-butyl 3-formylpiperidine-1-carboxylate under reductive amination condition to get intermediate tert-butyl 3-(((3,5-dichlorophenyl)amino)methyl)piperidine-1-carboxylate, then Boc protective group was removed using TFA to get 3,5-dichloro-N-(piperidin-3-ylmethyl)aniline which reacted with 2-bromo-5-chloro-1H-imidazo[4,5-b]pyridine following procedure of Scheme 22 to get target compound 1862 3,5-dichloro-N-((1-(5-chloro-1H-imidazo[4,5-b]pyridin-2-yl)piperidin-3-yl)methyl)aniline. $^1$H NMR (500 MHz, MeOD) δ 7.70 (d, J=7.8 Hz, 1H), 7.39-7.27 (m, 1H), 6.63-6.49 (m, 3H), 4.05 (d, J=9.2 Hz, 1H), 3.96-3.89 (m, 1H), 3.49-3.41 (m, 1H), 3.12 (dd, J=29.3, 15.1 Hz, 2H), 2.18-1.91 (m, 3H), 1.85-1.69 (m, 1H), 1.58-1.42 (m, 1H), 1.37-1.21 (s, 1H). MS (ESI) (M+H)$^+$=412.0; HPLC analysis: 85.0% purity.

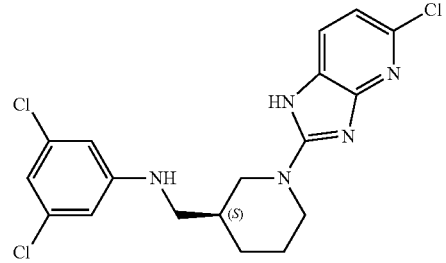

1923: (S)-3,5-dichloro-N-((1-(5-chloro-1H-imidazo[4,5-b]pyridin-2-yl)piperidin-3-yl)methyl)aniline was synthesized using (R)-piperidine-3-carboxylic acid following the General Procedure 14. MS (ESI) (M+H)$^+$=412.2

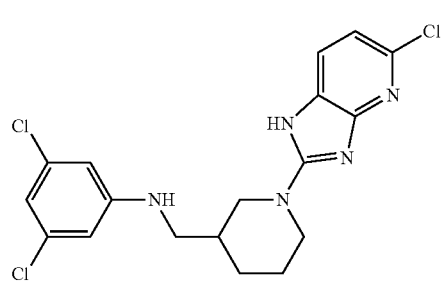

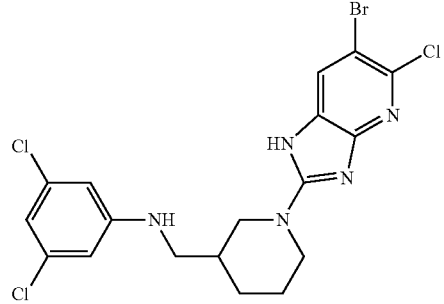

1863 N-((1-(6-bromo-5-chloro-1H-imidazo[4,5-b]pyridin-2-yl)piperidin-3-yl)methyl)-3,5-dichloroaniline was synthesized using piperidine-3-carboxylic acid following the General Procedure 14. MS (ESI) (M+H)$^+$=489.7

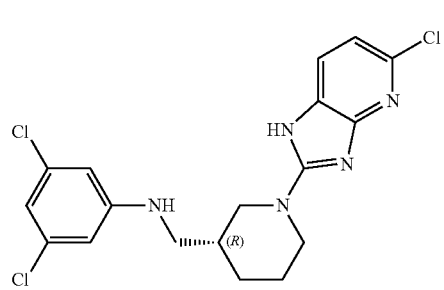

1922: (R)-3,5-dichloro-N-((1-(5-chloro-1H-imidazo[4,5-b]pyridin-2-yl)piperidin-3-yl)methyl)aniline was synthesized using (S)-piperidine-3-carboxylic acid following the General Procedure 14. MS (ESI) (M+H)$^+$=412.2

1888: (S)-1-(5-chloro-1H-imidazo[4,5-b]pyridin-2-yl)-N-(3,5-dichlorophenyl)piperidine-3-carboxamide was synthesized using 3,5-dichloroaniline reacted with (s)-1-(tert-butoxycarbonyl)piperidine-3-carboxylic acid to get intermediate (s)-tert-butyl 3-((3,5-dichlorophenyl)carbamoyl)piperidine-1-carboxylate, then following the procedure of synthesizing ChemID: 1862. MS (ESI) (M+H)$^+$=426.0; HPLC analysis: 100% purity.

Scheme 29

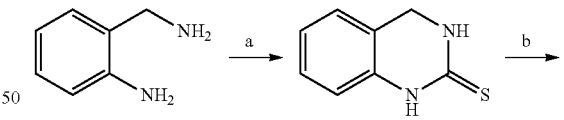

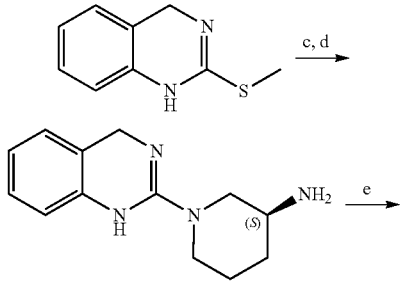

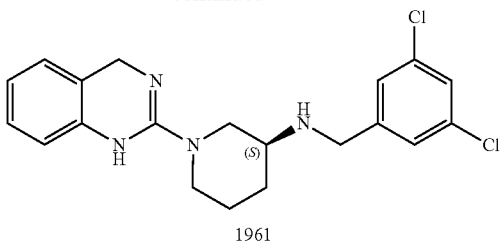

1961

Reagents and conditions: (a) CS₂, EtOH, 55° C., overnight; (b) CH₃I, K₂CO₃, CH₃CN, r.t. overnight; (c) (S)-tert-butyl piperidin-3-ylcarbamate, pyridine, 150° C., Microwave, overnight; (d) TFA, DCM, r.t. overnight; (e) 3,5-dichlorobenzaldehyde, MeOH, NaBH₃CN, r.t., 3 h (a) To a solution of 2-(aminomethyl)aniline (366 mg, 3 mM) in EtOH (5 mL) was added carbon disulfide (3 mL) at r.t. The mixture was stirred at 55° C. overnight. The solvent was evaporated off and the resulting solid was filtered and washed with ether to give light yellow solid 3,4-dihydroquinazoline-2(1H)-thione.

(b) 3,4-dihydroquinazoline-2(1H)-thione (1 eq) was suspended in CH₃CN, K₂CO₃ (4 eq) and CH₃I (3 eq) were added. The resulting mixture stirred at r.t. over night. The reaction was concentrated in vacuum and the residue was extracted with DCM. The organic extract was dried over anhydrous sodium sulfate, and concentrated in vacuum. Purification through flash chromatography on silica gel eluted with MeOH-DCM (0.5% ammonia hydroxide) to get (S)-tert-butyl (1-(1,4-dihydroquinazolin-2-yl)piperidin-3-yl)carbamate as brown solid.

(c) 2-(methylthio)-1,4-dihydroquinazoline was dissolved in pyridine, (S)-tert-butyl piperidin-3-ylcarbamate was added and the reaction mixture was microwave irradiated at 150° C. for 1 h. The reaction mixture was concentrated in vacuum and the residue partitioned between saturated sodium bicarbonate and DCM. The organic extract was dried over anhydrous sodium sulfate, and concentrated in vacuum. The residue was purified through flash chromatography on silica gel eluted with MeOH-DCM (0.5% ammonia hydroxide) to give intermediate (S)-tert-butyl (1-(1,4-dihydroquinazolin-2-yl)piperidin-3-yl).

(S)-tert-butyl (1-(1,4-dihydroquinazolin-2-yl)piperidin-3-yl) was deprotected the Boc protecting group under TFA/DCM condition, the resulting compound reacted with 3,5-dichlorobenzaldehyde under typical reductive amination conditions to yield target compound 1961 MS (ESI) (M+H)⁺= 390.1.

Scheme 30

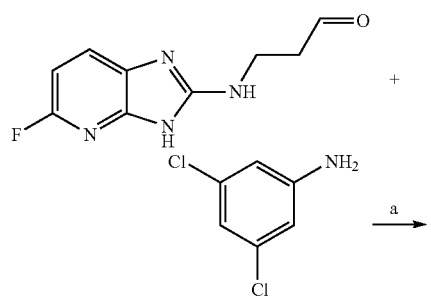

a →

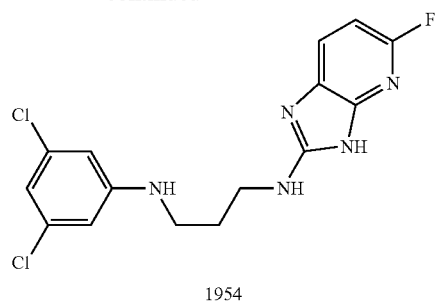

1954

Reagents and conditions: (a) NaBH₃CN, MeOH/AcOH, 60° C., overnight.

General Procedure 15 (1954, 1956 &1967): 3-((5-fluoro-3H-imidazo[4,5-b]pyridin-2-yl)amino)propanal (1.2 eq) and 3,5-dichloroaniline (1 eq) was dissolved in MeOH, AcOH (2 eq) and NaBH₃CN (2 eq) were added. The mixture was heated to 60° C. overnight. The solvent was removed under vacuum and the residue was dissolved in DCM and washed with sat. sodium bicarbonate and brine. The organic layer was dried over Na₂SO₄ and concentrated under vacuum. The residue was purified by flash column chromatography (DCM/MeOH), yielding compound 1954. MS (ESI) (M+H)⁺=355.6.

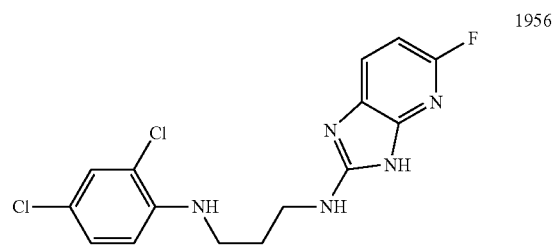 [SMILES: Fc1ccc2nc(NCCCNc3ccc(Cl)cc3Cl)[nH]c2n1]

1956

1956: N1-(2,4-dichlorophenyl)-N3-(5-fluoro-3H-imidazo[4,5-b]pyridin-2-yl)propane-1,3-diamine was synthesized using 2,4-dichloroaniline following the General Procedure 15. MS (ESI) (M+H)⁺=355.6.

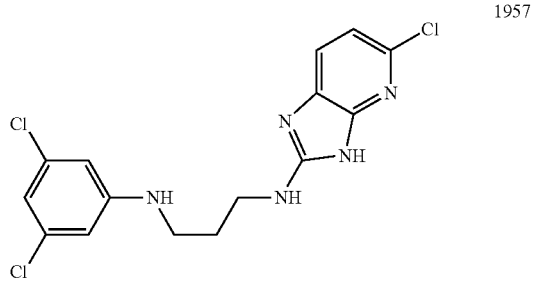 [SMILES: Clc1cc(Cl)cc(NCCCNc2nc3ccc(Cl)nc3[nH]2)c1]

1957

1957: N1-(2,4-dichlorophenyl)-N3-(5-chloro-3H-imidazo[4,5-b]pyridin-2-yl)propane-1,3-diamine was synthesized using 2,4-dichloroaniline following the General Procedure 15. MS (ESI) (M+H)⁺=355.5.

Scheme 31

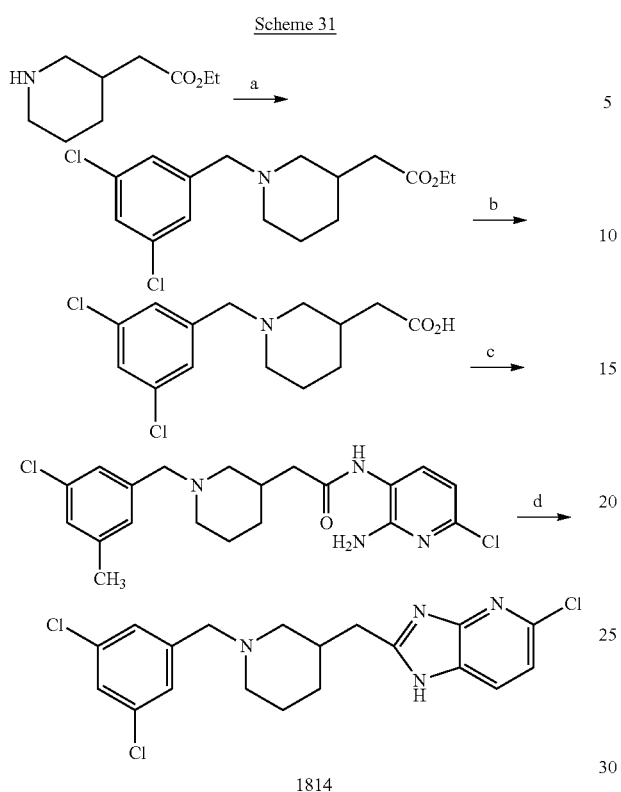

1814

Reagents and conditions: (a) 8, NaBH₃CN, AcOH, CH₃OH, r.t., overnight; (b) LiOH, CH₃OH/H₂O, r.t. overnight; (c) 5, EDC, pyridine, r.t. overnight; (d) AcOH, POCl₃, Microwave, 150° C., 1 h.

(a) ethyl 2-(piperidin-3-yl)acetate (88 mg, 0.5 mM) and 3,5-dichlorobenzaldehyde (86 mg, 0.5 mM) were dissolved in CH₃OH, AcOH (60 mg, 1 mM) and NaBH₃CN (63 mg, 1 mM) were added to the solution. The mixture was stirred at r.t. overnight. The solvent was removed under reduced pressure and the residue was extracted by EA. The organic phase was dried over sodium sulfate and the solvent was removed under reduced pressure. The residue was purify through flash chromatography on silica gel eluted with EA/hexane to give ethyl 2-(1-(3,5-dichlorobenzyl)piperidin-3-yl)acetate.

(b) LiOH.H₂O (3 eq) was added to the solution of methyl 3-((3,5-dichlorobenzyl)amino)cyclohexanecarboxylate in CH₃OH/H₂O (CH₃OH:H₂O=3:1). The reaction mixture was stirred at r.t. overnight. The solvent was evaporated under reduced pressure, the residue was used for the next step without further purification.

(c) 2-(1-(3,5-dichlorobenzyl)piperidin-3-yl)acetic acid obtained from above step was dissolved in pyridine (2 mL), EDC (1.5 eq) was added and the mixture was stirred at r.t. overnight. Pyridine was removed under reduced pressure, saturated aqueous sodium bicarbonate was added to the residue, and extracted with DCM. The organic layer was dried over anhydrous sodium sulfate, and concentrated in vacuum. Purification through flash chromatography on silica gel eluted with MeOH-DCM (0.5% ammonia hydroxide) gave N-(2-amino-6-chloropyridin-3-yl)-2-(1-(3-chloro-5-methylbenzyl)piperidin-3-yl)acetamide.

(d) N-(2-amino-6-chloropyridin-3-yl)-2-(1-(3-chloro-5-methylbenzyl)piperidin-3-yl)acetamide was dissolved in 3 mL glacial acetic acid, POCl₁.₃ (3 eq) was added, the mixture was microwave irradiated at 150° C. for 1 hour. The reaction mixture was concentrated in vacuum and the residue partitioned between saturated sodium bicarbonate and DCM. The organic extract was dried over anhydrous sodium sulfate, and concentrated in vacuum. The residue was purified through flash chromatography on silica gel eluted with MeOH-DCM (0.5% ammonia hydroxide) to give compound 1814:5-chloro-2-((1-(3,5-dichlorobenzyl)piperidin-3-yl)methyl)-1H-imidazo[4,5-b]pyridine, MS (ESI)(M+H)⁺= 411.5.

Scheme 32

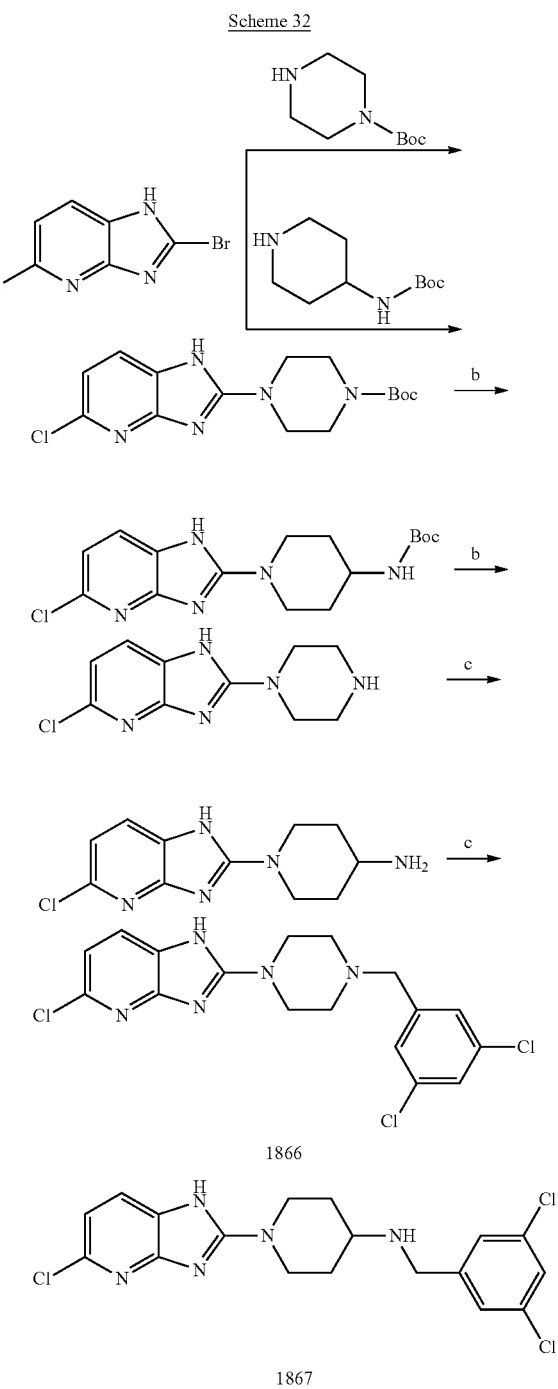

1866

1867

1866: 5-chloro-2-(4-(3,5-dichlorobenzyl)piperazin-1-yl)-1H-imidazo[4,5-b]pyridine was synthesized using 3,5-dichlorobenzaldehyde and tert-butyl piperazine-1-carboxylate following the general procedure as Scheme 22. MS(ESI) (M+H)⁺=397.4; HPLC analysis: 98.1% purity 1867: 1-(5-chloro-1H-imidazo[4,5-b]pyridin-2-yl)-N-(3,5-dichlorobenzyl)piperidin-4-amine was synthesized using 3,5-dichlorobenzaldehyde and tert-butyl piperidin-4-ylcarbamate following the general procedure as Scheme 22. $^1$H NMR (500 MHz, CDCl$_3$) δ 7.80-7.43 (br, 1H), 7.35-7.21 (m, 3H), 7.13-6.76 (br, 1H), 4.37-3.97 (m, 2H), 3.81 (s, 2H), 3.29-3.06 (br, 2H), 2.78 (s, 1H), 2.00-1.92 (br, 2H), 1.53-1.40 (br, 2H). MS(ESI) (M+H)⁺=411.7; HPLC analysis: 94.5% purity.

cyanuric chloride (1 equiv) in 0.3 ml acetone at 0° C. The mixture was stirred at 0° C. for 1 hour. Then C-(5-Fluoro-3H-imidazo[4,5-b]pyridin-2-yl)-methylamine (1 equiv) was added and the mixture was microwave irradiated at 80° C. for 20 min. After most solvents were removed, methanol was added. The solution was acidified and subject to HPLC purification to collect 1883, 1884 and 1885. LC/MS: (ESI) (M+H)⁺=566.2 for 1883; ESI) (M+H)⁺=559.4 for 1884; ESI) (M+H)⁺=418.5 for 1885.

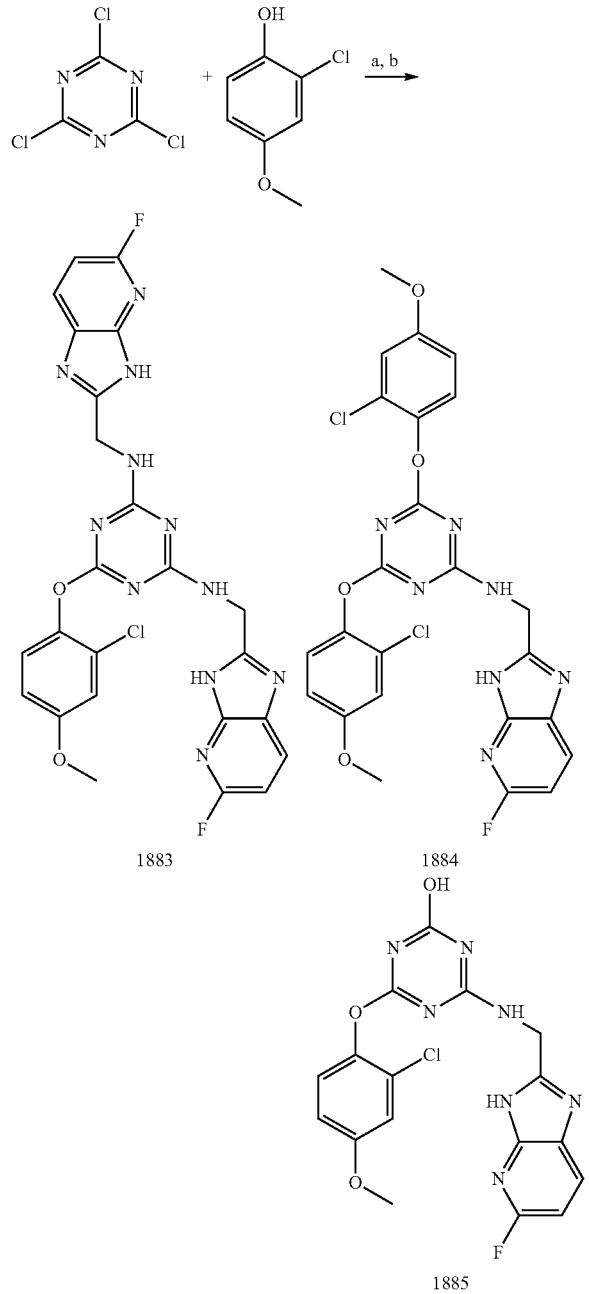

Scheme 33

1883  1884  1885

Reagents and conditions (a) NaOH, water, acetone, 0° C.; (b) C-(5-Fluoro-3H-imidazo[4,5-b]pyridin-2-yl)-methylamine, microwave irradiation, 80° C., 10 min.

A mixture of 2-chloro-4-methoxyphenol (45 mg, 0.285 mmol) and 0.5N NaOH (0.516 ml) was added slowly into

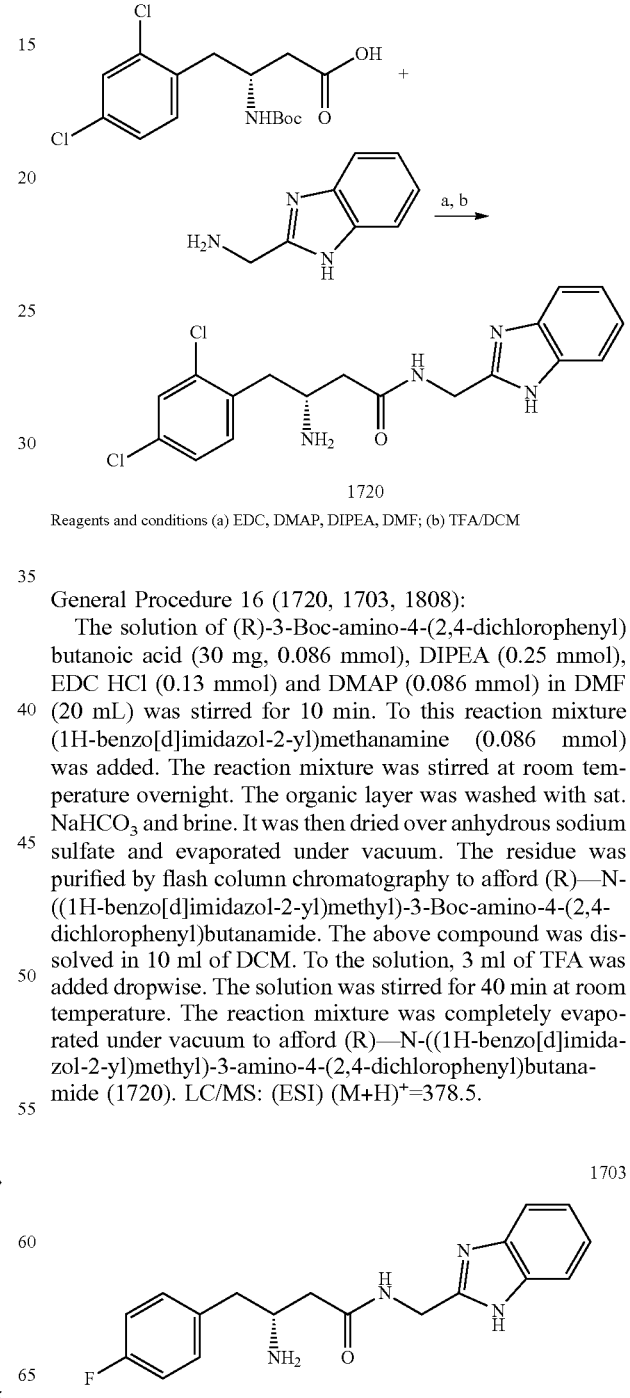

Scheme 34

1720

Reagents and conditions (a) EDC, DMAP, DIPEA, DMF; (b) TFA/DCM

General Procedure 16 (1720, 1703, 1808):

The solution of (R)-3-Boc-amino-4-(2,4-dichlorophenyl)butanoic acid (30 mg, 0.086 mmol), DIPEA (0.25 mmol), EDC HCl (0.13 mmol) and DMAP (0.086 mmol) in DMF (20 mL) was stirred for 10 min. To this reaction mixture (1H-benzo[d]imidazol-2-yl)methanamine (0.086 mmol) was added. The reaction mixture was stirred at room temperature overnight. The organic layer was washed with sat. NaHCO$_3$ and brine. It was then dried over anhydrous sodium sulfate and evaporated under vacuum. The residue was purified by flash column chromatography to afford (R)—N-((1H-benzo[d]imidazol-2-yl)methyl)-3-Boc-amino-4-(2,4-dichlorophenyl)butanamide. The above compound was dissolved in 10 ml of DCM. To the solution, 3 ml of TFA was added dropwise. The solution was stirred for 40 min at room temperature. The reaction mixture was completely evaporated under vacuum to afford (R)—N-((1H-benzo[d]imidazol-2-yl)methyl)-3-amino-4-(2,4-dichlorophenyl)butanamide (1720). LC/MS: (ESI) (M+H)⁺=378.5.

1703

1703 was synthesized using (R)-3-Boc-4-(4-fluorophenyl)butanoic acid in General Procedure 16. LC/MS: (ESI) (M+H)$^+$=327.5.

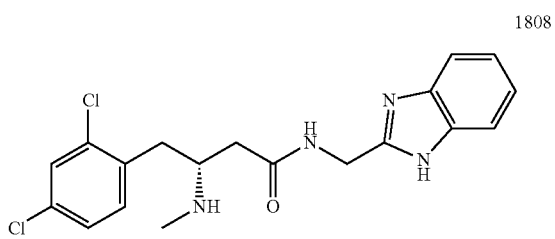 [SMILES: CN[C@@H](CC(=O)NCc1nc2ccccc2[nH]1)Cc1ccc(Cl)cc1Cl]

1808

1808 was synthesized using (R)-3-Boc-amino-4-(4-fluorophenyl)butanoic acid in General Procedure 16. LC/MS: (ESI) (M+H)$^+$=327.5.

Scheme 35

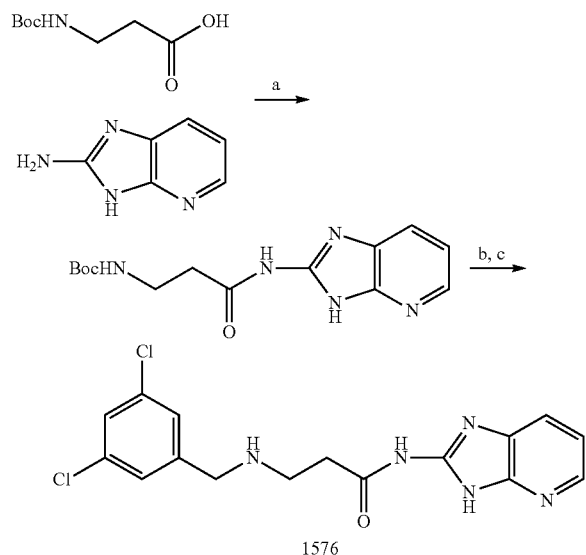

1576

Reagents and conditions (a) EDC, DIPEA, HOBt, DMF; (b) TFA, DCM; (c) 3,5-dichlorobenzaldehyde, MeOH, NaBH$_3$CN General Procedure 17 (1576, 1830, 1831):

The solution of Boc-β-Ala (16 mg, 0.086 mmol), DIPEA (0.26 mmol), EDC HCl (0.13 mmol) and HOBt (0.086 mmol) in DMF (20 mL) was stirred for 10 min. To this reaction mixture 3H-imidazo[4,5-b]pyridin-2-amine (0.086 mmol) was added. The reaction mixture was stirred at room temperature overnight. After the solvent was removed, the residue was dissolved in ethyl acetate and washed with water and brine. It was then dried over anhydrous sodium sulfate and evaporated under vacuum. The residue was purified by flash column chromatography to afford 3-Boc-amino-N-(3H-imidazo[4,5-b]pyridin-2-yl)propanamide.

The above compound was dissolved in 10 ml of DCM. To the solution, 3 ml of TFA was added dropwise. The solution was stirred for 40 min at room temperature. The solvent was evaporated off completely under vacuum, and the residue was co-distilled 2× with methylene chloride. The residue was dissolved in 3 ml MeOH, neutralized with DIPEA and 0.15 ml AcOH was added. 3,5-Dichlorobenzaldehyde (1.1 equiv) was added. After the mixture was stirred for 30 min, NaBH$_3$CN (0.17 mmol) was added. The mixture was stirred overnight and the solvent was removed under vacuum. The residue was dissolved in EtOAc (50 ml) and washed with sat. sodium bicarbonate and brine. The organic layer was dried over Na$_2$SO$_4$ and concentrated under vacuum. The residue was purified by flash column chromatography (DCM/MeOH), yielding 3-(3,5-dichlorobenzylamino)-N-(3H-imidazo[4,5-b]pyridin-2-yl)propanamide (1576). LC/MS: (ESI) (M+H)$^+$=365.5.

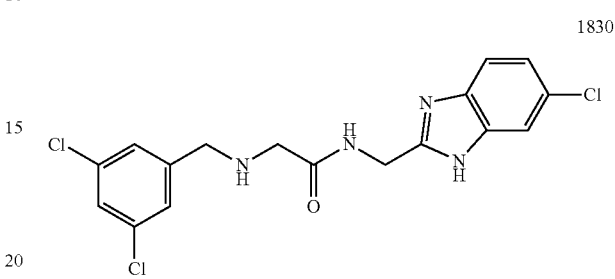

1830

1830 was synthesized using Boc-Gly and (6-chloro-1H-benzo[d]imidazol-2-yl)methanamine in General Procedure 17. LC/MS: (ESI) (M+H)$^+$=398.2.

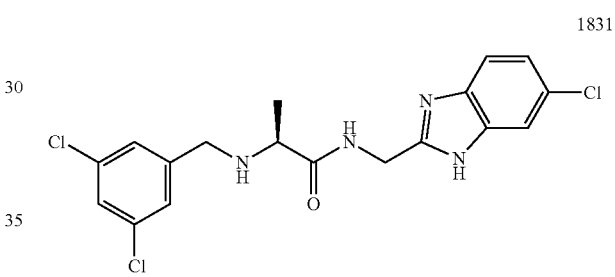

1831

1831 was synthesized using Boc-L-Ala and (6-chloro-1H-benzo[d]imidazol-2-yl)methanamine in General Procedure 17. LC/MS: (ESI) (M+H)$^+$=412.6.

Scheme 36

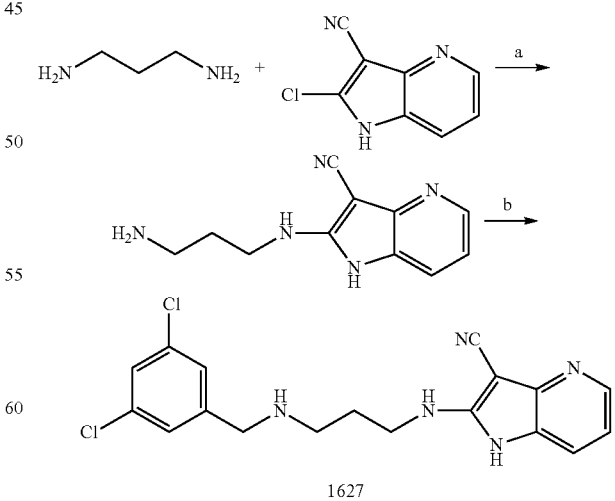

1627

Reagents and conditions (a) μw, 120° C. 2 h; (b) 3,5-dichlorobenzaldehyde, MeOH, NaBH$_3$CN Reagents and conditions (a) μw, 120° C. 2 h; (b) 3,5-dichlorobenzaldehyde, MeOH, NaBH₃CN 2-chloro-1H-pyrrolo[3,2-b]pyridine-3-carbonitrile (35 mg, 0.2 mmol) was dissolved in propane-1,3-diamine (1 ml). The mixture was microwave irradiated at 120° C. for 2 h. After the solvent was removed in vacuum. The residue was dissolved in ethyl acetate and washed with water three time, brine, dried over anhydrous sodium sulfate and evaporated under vacuum. The residue was purified by flash column chromatography to 2-(3-aminopropylamino)-1H-pyrrolo[3,2-b]pyridine-3-carbonitrile. 2-(3-aminopropylamino)-1H-pyrrolo[3,2-b]pyridine-3-carbonitrile (15 mg, 0.07 mmol) was dissolved in 5 ml of MeOH, 0.15 ml of AcOH. 3,5-dichlorobenzaldehyde (0.07 mmol) was added. After the mixture was stirred for 30 min, NaBH₃CN (0.14 mmol) was added. The mixture was stirred overnight and the solvent was removed under vacuum. The residue was dissolved in EtOAc (25 ml) and washed with sat. sodium bicarbonate and brine. The organic layer was dried over Na₂SO₄ and concentrated under vacuum. The residue was purified by flash column chromatography (DCM/MeOH), yielding 2-(3-(3,5-dichlorobenzylamino)propylamino)-1H-pyrrolo[3,2-b]pyridine-3-carbonitrile (1627). LC/MS: (ESI) (M+H)⁺=375.5.

night. The solution was diluted with 50 ml of DCM and washed with 0.1 N NaOH (50 ml), brine, dried over anhydrous sodium sulfate and evaporated under vacuum. The residue was purified by flash column chromatography to give (1-((1H-benzo[d]imidazol-2-yl)methyl)-3-(2,4-dichlorophenethyl)urea (1702). LC/MS: (ESI) (M+H)⁺=364.8.

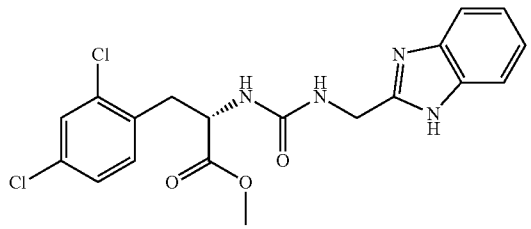

1755 was synthesized using (S)-methyl 2-amino-3-(2,4-dichlorophenyl)propanoate in General Procedure 18. LC/MS: (ESI) (M+H)⁺=422.5.

Scheme 37

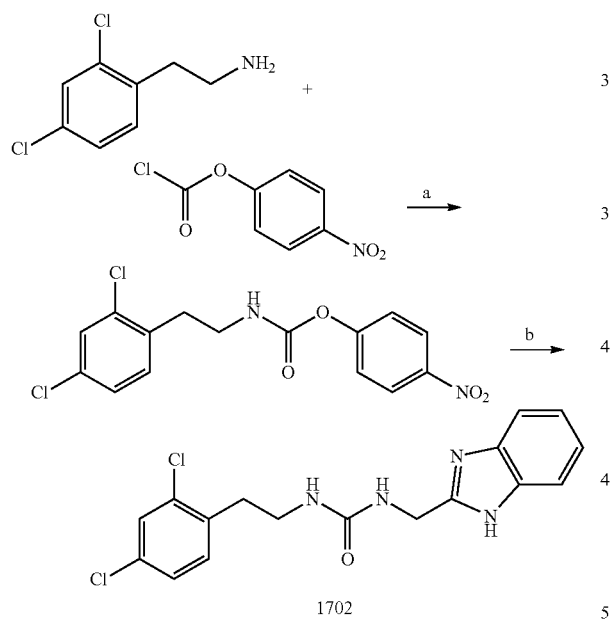

1702

Reagents and conditions (a) DCM, pyridine; (b) (1H-benzo[d]imidazol-2-yl)methanamine Scheme 38

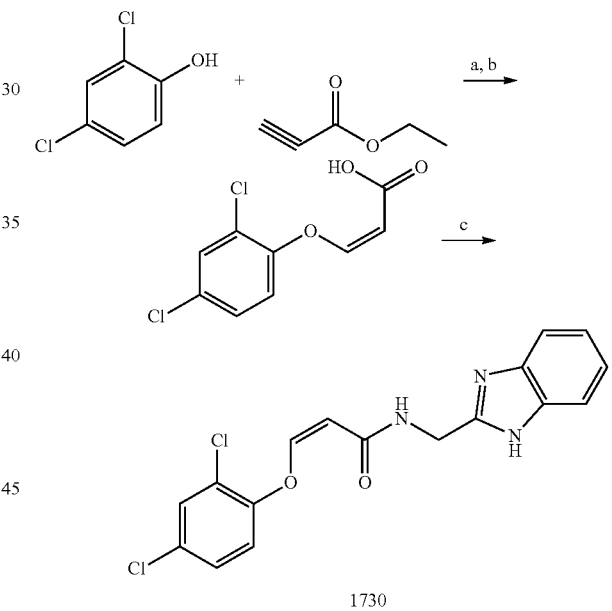

1730

Reagents and conditions (a) NaN₃, t-butanol; (b) NaOH, ethanol; (c) EDC, DIPEA, DCM, (1H-benzo[d]imidazol-2-yl)methanamine General Procedure 18 (1702, 1755): To a solution of 2-(2,4-dichlorophenyl)ethanamine (198 mg, 1.04 mmol) in 5 ml of DCM was added 4-nitrophenyl chloroformate (200 mg, 0.99 mmol) in 3 ml of DCM and pyridine (84.8 μl, 1.05 mmol) at 0° C. The mixture was at 0° C. for 3 h. The solvent was removed and the residue was dissolved in ethyl acetate. The solution was washed with water, brine, dried over anhydrous sodium sulfate and evaporated under vacuum. The residue was purified by flash column chromatography to give 4-nitrophenyl 2,4-dichlorophenethylcarbamate. (1H-benzo[d]imidazol-2-yl)methanamine (0.06 mmol) was added into the solution of 4-nitrophenyl 2,4-dichlorophenethylcarbamate (0.06 mmol) in DCM (10 ml) at 0° C. with stirring. The mixture was stirred at room temperature over- To a stirred solution of 2,4-dichlorophenol (163 mg, 1 mmol) and NaN₃ (0.1 mmol) in 10 ml of tert-butyl alcohol was added dropwise a mixture of ethyl propiolate (1 mmol) in 2 ml of tert-butyl alcohol at room temperature over 10 min. The reaction mixture was microwave irradiated at 80° C. for 15 min. After most of the solvent was removed, 50 ml of ethyl acetate was added. The organic was then washed with water and brine, and dried over anhydrous sodium sulfate. After removal of the solvent, the crude product was purified by column chromatography to give (Z)-3-(2,4-dichlorophenoxy)acrylic acid ethyl ester 6. To a solution of (Z)-3-(2,4-Dichloro-phenoxy)-acrylic acid ethyl ester (30 mg, 0.115 mmol) in ethanol (2 mL) was added and 1 N NaOH (1 ml). The resultant mixture was microwave irradiated for 15 min at 80° C. After being cooled to room temperature, it was poured into ethyl acetate (50 mL), washed with 0.1 N HC, water, brine dried over magnesium sulfate, and evaporated to dry to yield 3-(2,4-Dichlorophenoxy)-acrylic acid. The solution of (Z)-3-(2,4-Dichlorophenoxy)-acrylic acid (20 mg, 0.086 mmol), DIPEA (0.26 mmol), EDC HCl (0.13 mmol) and DMAP (0.086 mmol) in DCM (20 mL) was stirred for 10 min. To this reaction mixture (1H-benzo[d]imidazol-2-yl)methanamine (0.086 mmol) was added. The reaction mixture was stirred at room temperature overnight. The organic layer was washed with sat. NaHCO$_3$ and brine. It was then dried over anhydrous sodium sulfate and evaporated under vacuum. The residue was purified by flash column chromatography to afford (Z)—N-((1H-benzo[d]imidazol-2-yl)methyl)-3-(2,4-dichlorophenoxy)acrylamide (1730). LC/MS: (ESI) (M+H)$^+$=363.4.

Scheme 39

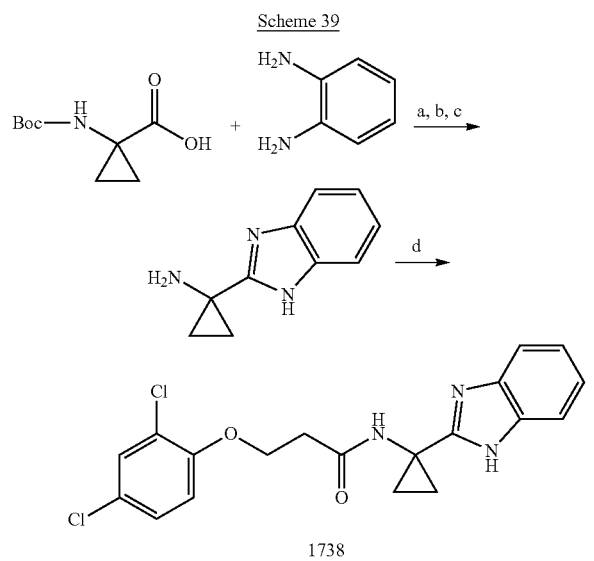

Reagents and conditions (a) HBTU, DIPEA, DMF; (b) HOAc, 60° C., 4 h; (c) TFA/DCM; (d) EDC, HOBt, DIPEA, DMF, 3-(2,4-dichlorophenoxy)propanoic acid.

To a 5 ml of DMF solution of 1-(Boc-amino)cyclopropanecarboxylic acid (100 mg, 0.50 mmol) were added N,N-diisopropylethylamine (1.5 mmol), HBTU (0.55 mmol), benzene-1,2-diamine (0.5 mmol). The reaction mixture was stirred at room temperature for 6 hr. After the solvent was removed, the residue was dissolved in ethyl acetate. The organic layer was washed water and brine. It was then dried over anhydrous sodium sulfate and evaporated under vacuum. To the residue, 3 ml of acetic acid was added and this mixture was heated for 4 hr at 60° C. After evaporation, the obtained mixture was purified by flash column chromatography (DCM/MeOH) to give 1-(1H-benzo[d]imidazol-2-yl)-Boc-N-cyclopropanamine. 1-(1H-benzo[d]imidazol-2-yl)-Boc-N-cyclopropanamine (27 mg, 0.1 mmol) was dissolved in DCM (4 ml) and TFA (2 ml) was added. The mixture was stirred at room temperature for 30 min. and the solvent was removed completely in vacuum. The residue was dissolved in DMF and 3-(2,4-dichlorophenoxy)propanoic acid (0.1 mmol), N,N-diisopropylethylamine (0.5 mmol), HBTU (0.15 mmol). The reaction mixture was stirred at room temperature for 6 hr. After the solvent was removed, the residue was dissolved in ethyl acetate. The organic layer was washed water, and brine. It was then dried over anhydrous sodium sulfate and evaporated under vacuum. The residue was purified by flash column chromatography to afford N-(1-(1H-benzo[d]imidazol-2-yl)cyclopropyl)-3-(2,4-dichlorophenoxy)propanamide (1738). LC/MS: (ESI) (M+H)$^+$=391.5.

Scheme 40

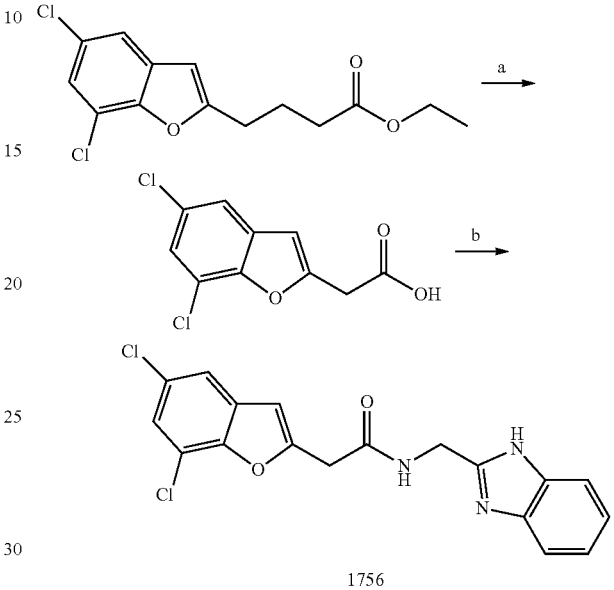

Reagents and conditions (a) NaOH, ethanol; (b) EDC, HOBt, DIPEA, DMF, (1H-benzo[d]imidazol-2-yl)methanamine Ethyl 2-(5,7-dichlorobenzofuran-2-yl) acetate was prepared from 3,5-dichloro-2-hydroxybenzaldehyde and ethyl propiolate according to the literature procedure[7]. Ethyl 2-(5,7-dichlorobenzofuran-2-yl) acetate (0.5 mmol) was dissolved in 1 ml of 2N NaOH and 1 ml of MeOH. The mixture was microwave irradiated at 80° C. for 8 min. After most of solvents were removed, the residue was neutralized with 1 N HCl and extracted with ethyl acetate (3×50 mL). The organic fractions were dried and concentrated under vacuum. The residue was dissolved in DMF and EDC (0.5 mmol), HOBt (0.5 mmol), DIPEA (1.0 mmol), (1H-benzo[d]imidazol-2-yl)methanamine (0.5 mmol) were added. The solution was stirred at room temperature overnight and then removed under vacuum. The residue was dissolved in EtOAc (25 mL). The organic layer was washed with water, brine (25 mL), dried and concentrated under vacuum. The residue was chromatographed to give N-((1H-benzo[d]imidazol-2-yl)methyl)-2-(5,7-dichlorobenzofuran-2-yl)acetamide (1756). LC/MS: (ESI) (M+H)$^+$=375.6.

Scheme 41

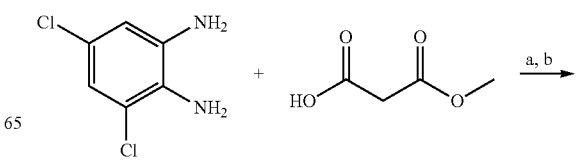

-continued

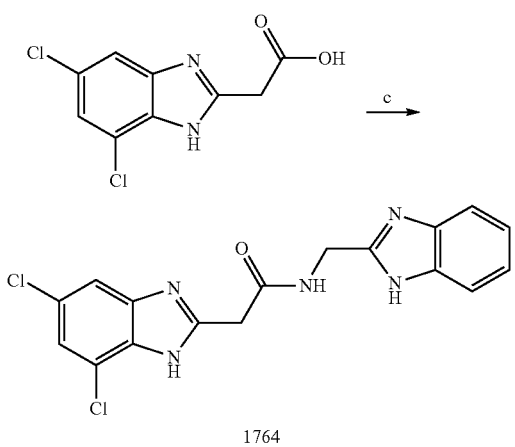

1764

Reagents and conditions (a) HBTU, DIPEA, DMF; (b) AcOH, 60° C., 4 h; (c), NaOH/MeOH; (d) EDC, HOBt, DIPEA, DMF, (1H-benzo[d]imidazol-2-yl)methanamine.

To a 5 ml of DMF solution of 2-(methoxycarbonyl)acetic acid (59 mg, 0.50 mmol) were added N,N-diisopropylethylamine (1.5 mmol), HBTU (0.55 mmol), 3,5-dichlorobenzene-1,2-diamine (0.5 mmol). The reaction mixture was stirred at room temperature for 6 hr. After the solvent was removed, the residue was dissolved in ethyl acetate. The organic layer was washed water and brine. It was then dried over anhydrous sodium sulfate and evaporated under vacuum. To the residue, 3 ml of acetic acid was added and this mixture was heated for 4 hrs at 60° C. After evaporation, the obtained mixture was purified by flash column chromatography (DCM/MeOH) to give methyl 2-(5,7-dichloro-1H-benzo[d]imidazol-2-yl)acetate. Methyl 2-(5,7-dichloro-1H-benzo[d]imidazol-2-yl)acetate (26 mg, 0.1 mmol) was dissolved in 1 ml of 2N NaOH and 1 ml of MeOH. The mixture was microwave irradiated at 80° C. for 8 min. After most of solvents were removed, the residue was neutralized with 1 N HCl and extracted with ethyl acetate (3×50 mL). The organic fractions were dried and concentrated under vacuum. The residue was dissolved in DMF and EDC (0.15 mmol), HOBt (0.1 mmol), DIPEA (0.25 mmol), (1H-benzo[d]imidazol-2-yl)methanamine (0.1 mmol) were added. The solution was stirred at room temperature overnight and then removed under vacuum. The residue was dissolved in EtOAc (25 mL). The organic layer was washed with water, brine (25 mL), dried and concentrated under vacuum. The residue was chromatographed to give N-((1H-benzo[d]imidazol-2-yl)methyl)-2-(5,7-dichloro-1H-benzo[d]imidazol-2-yl)acetamide (1764). LC/MS: (ESI) (M+H)$^+$=375.6.

Scheme 42

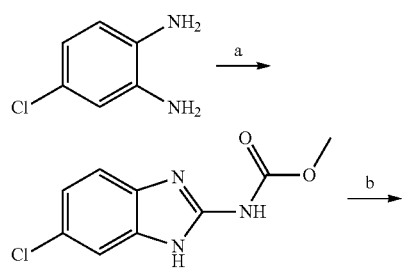

-continued

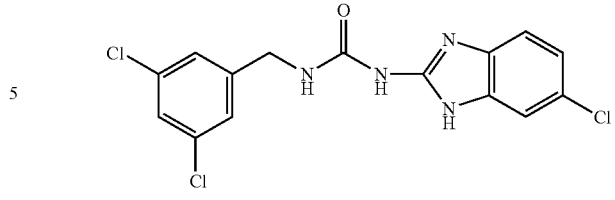

1793

Reagents and conditions (a) 1,3-bis(methoxycarbonyl)-2-methyl-2-thiopseudourea, EtOH, HCl; (b) pyridine, •6-chloro-1H-benzo[d]imidazol-2-amine, μW, 120° C., 40 min.

A mixture of 4-chlorobenzene-1,2-diamine (71 mg, 0.5 mmol) and 1,3-bis(methoxycarbonyl)-2-methyl-2-thiopseudourea (0.5 mmol) in EtOH (3 mL) was refluxed overnight. After cooling, the solid was formed when diethyl ether was added. The solid was treated with 10 ml of 1N HCl and heated for 2 h. After cooling, the precipitate was formed with addition of NH$_4$OH. The collected solid was dissolved in 3 ml of pyridine and 6-chloro-1H-benzo[d]imidazol-2-amine (5 mmol) was added. The mixture was microwave irradiated at 120° C. for 40 min. After the solvent was removed, the residue was dissolved in ethyl acetate. The organic layer was washed water and brine. It was then dried over anhydrous sodium sulfate and evaporated under vacuum. The residue was purified by flash column chromatography to give 1-(3,5-dichlorobenzyl)-3-(6-chloro-1H-benzo[d]imidazol-2-yl)urea (1793). LC/MS: (ESI) (M+H)$^+$= 370.3.

Scheme 43

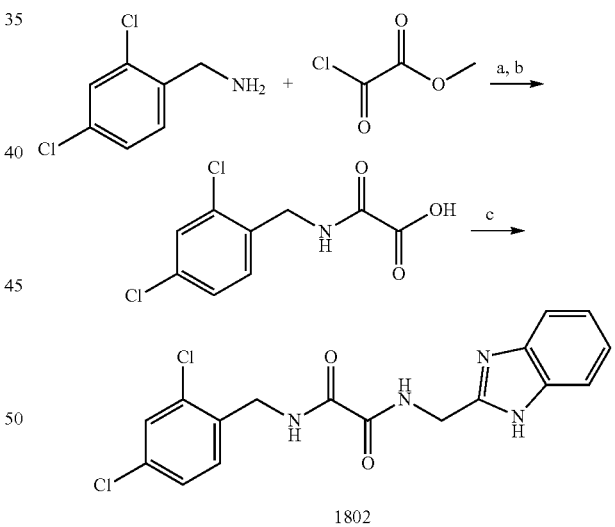

1802

Reagents and conditions (a) DCM; (b) NaOH/MeOH; (c) EDC, HOBt, DIPEA, DMF, (1H-benzo[d]imidazol-2-yl)methanamine To a solution of (2,4-dichlorophenyl)methanamine (88 mg, 0.5 mmol) in DCM was added methyl (chlorocarbonyl)formate (0.5 mmol) at 0° C. Then the solution was stirred at room temperature for 2 h. After the solvent was removed, the residue was dissolved in 1 ml of 2N NaOH and 1 ml of MeOH. The mixture was microwave irradiated at 80° C. for 8 min. After most of solvents were removed, the residue was neutralized with 1 N HCl and extracted with ethyl acetate (3×50 mL). The organic fractions were dried and concentrated under vacuum. The residue was dissolved in DMF and EDC (0.5 mmol), HOBt (0.5 mmol), DIPEA (1.0 mmol), (1H-benzo[d]imidazol-2-yl)methanamine (0.5 mmol) were added. The solution was stirred at room temperature overnight and then removed under vacuum. The residue was dissolved in EtOAc (25 mL). The organic layer was washed with water, brine (25 mL), dried and concentrated under vacuum. The residue was chromatographed to give N1-((1H-benzo[d]imidazol-2-yl)methyl)-N2-(2,4-dichlorobenzyl)oxalamide (1802). LC/MS: (ESI)(M+H)$^+$=378.6.

Scheme 44

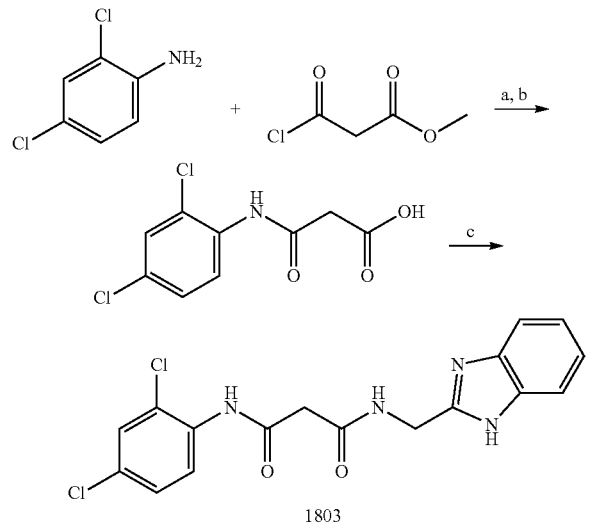

Reagents and conditions (a) DCM; (b) NaOH/MeOH; (c) EDC, HOBt, DIPEA, DMF, (1H-benzo[d]imidazol-2-yl)methanamine.

To a solution of 2,4-dichlorobenzenamine (81 mg, 0.5 mmol) in DCM was added methyl 2-(chlorocarbonyl)acetate (0.5 mmol) at 0° C. Then the solution was stirred at room temperature for 2 h. After the solvent was removed, the residue was dissolved in 1 ml of 2N NaOH and 1 ml of MeOH. The mixture was microwave irradiated at 80° C. for 8 min. After most of solvents were removed, the residue was neutralized with 1 N HCl and extracted with ethyl acetate (3×50 mL). The organic fractions were dried and concentrated under vacuum. The residue was dissolved in DMF and EDC (0.5 mmol), HOBt (0.5 mmol), DIPEA (1.0 mmol), (1H-benzo[d]imidazol-2-yl)methanamine (0.5 mmol) were added. The solution was stirred at room temperature overnight and then removed under vacuum. The residue was dissolved in EtOAc (25 mL). The organic layer was washed with water, brine (25 mL), dried and concentrated under vacuum. The residue was chromatographed to give N1-((1H-benzo[d]imidazol-2-yl)methyl)-N3-(2,4-dichlorophenyl)malonamide (1803). LC/MS: (ESI) (M+H)$^+$=378.6.

Scheme 45

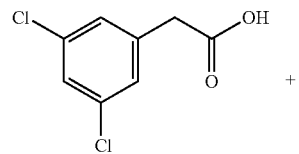

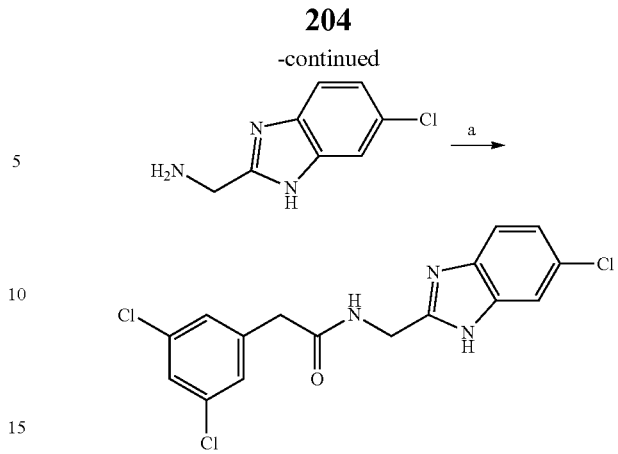

1851

Reagents and conditions (a) EDC, DMAP, DIPEA, DMF

General Procedure 19 (1851, 1852, 1874, 1873, 1876, 1878, 1880, 1875, 1877, 1879): The solution 2-(3,5-dichlorophenyl)acetic acid (30 mg, 0.15 mmol), DIPEA (0.45 mmol), EDC HCl (0.20 mmol) and DMAP (0.15 mmol) in DMF (10 mL) was stirred for 10 min. To this reaction mixture (6-chloro-1H-benzo[d]imidazol-2-yl)methanamine (0.15 mmol) was added. The reaction mixture was stirred at room temperature overnight. After the solvent was removed, the residue was dissolved in ethyl acetate. The organic layer was washed water and brine. It was then dried over anhydrous sodium sulfate and evaporated under vacuum. The residue was purified by flash column chromatography to give N-((6-chloro-1H-benzo[d]imidazol-2-yl)methyl)-2-(3,5-dichlorophenyl)acetamide (1851). LC/MS: (ESI) (M+H)$^+$=369.6.

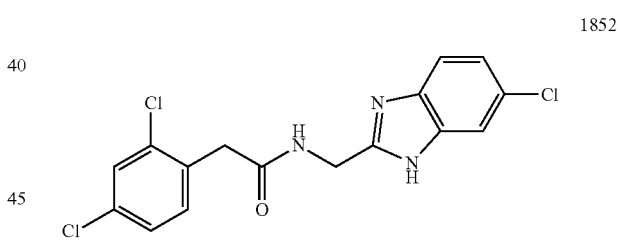

1852

1852 was synthesized using 2-(2,4-dichlorophenyl)acetic acid in General Procedure 19. LC/MS: (ESI) (M+H)$^+$=369.6.

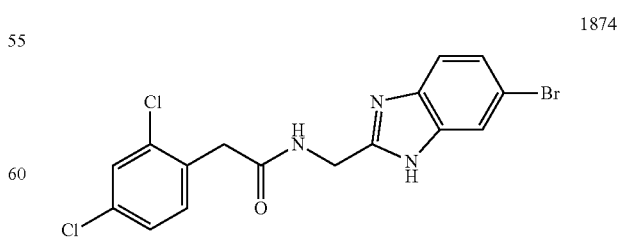

1874

1874 was synthesized using 2-(2,4-dichlorophenyl)acetic acid and (5-bromo-1H-benzo[d]imidazol-2-yl)methanamine in General Procedure 19. LC/MS: (ESI) (M+H)=414.2.

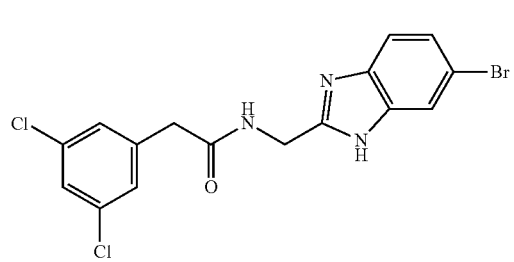

1873

1873 was synthesized using (5-bromo-H-benzo[d]imidazol-2-yl)methanamine in General Procedure 19. LC/MS: (ESI) (M+H)$^+$=414.1.

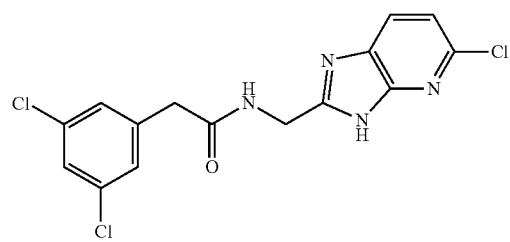

1875

1875 was synthesized using (5-chloro-3H-imidazo[4,5-b]pyridin-2-yl)methanamine in General Procedure 19. LC/MS: (ESI) (M+H)$^+$=370.5.

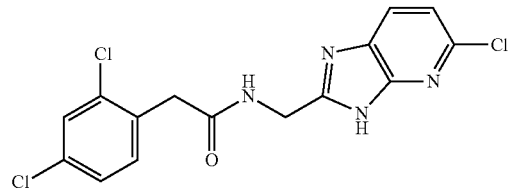

1876

1876 was synthesized using 2-(2,4-dichlorophenyl)acetic acid and (5-chloro-3H-imidazo[4,5-b]pyridin-2-yl)methanamine in General Procedure 19. LC/MS: (ESI) (M+H)$^+$=370.6.

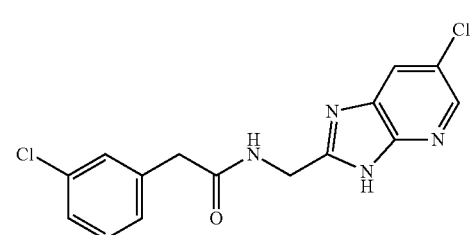

1877

1877 was synthesized using (6-chloro-3H-imidazo[4,5-b]pyridin-2-yl)methanamine in General Procedure 19. LC/MS: (ESI) (M+H)$^+$=370.5.

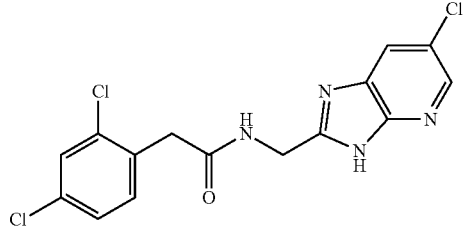

1878

1878 was synthesized using 2-(2,4-dichlorophenyl)acetic acid and (6-chloro-3H-imidazo[4,5-b]pyridin-2-yl)methanamine in General Procedure 19. LC/MS: (ESI) (M+H)$^+$=370.6.

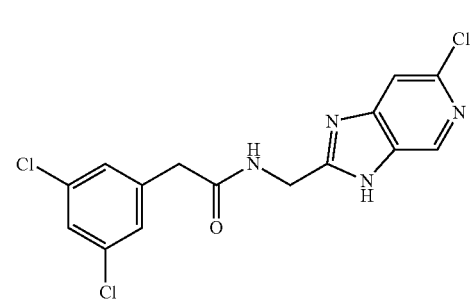

1879

1879 was synthesized using (6-chloro-3H-imidazo[4,5-c]pyridin-2-yl)methanamine in General Procedure 19. LC/MS: (ESI) (M+H)$^+$=370.5.

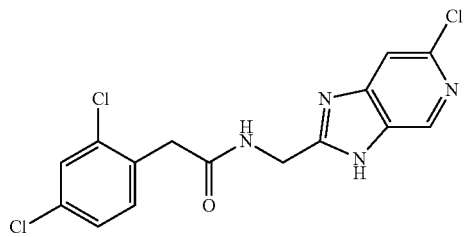

1880

1880 was synthesized using 2-(2,4-dichlorophenyl)acetic acid and (6-chloro-3H-imidazo[4,5-c]pyridin-2-yl)methanamine in General Procedure 19. LC/MS: (ESI) (M+H)$^+$=370.6.

Scheme 46

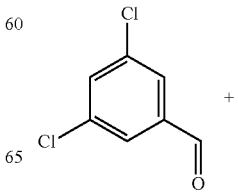

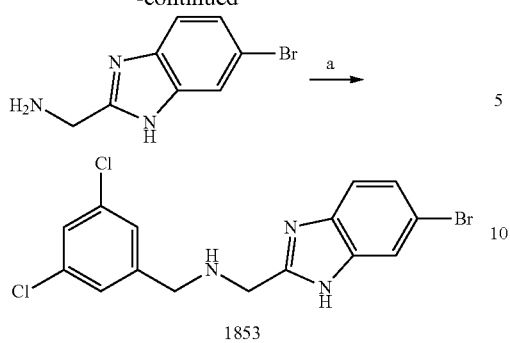

1853

Reagents and conditions (a) MeOH, HOAc, NaBH₃CN

General Procedure 20 (1853, 1881, 1882, 1892): (6-bromo-1H-benzo[d]imidazol-2-yl)methanamine (30 mg, 0.13 mmol) was dissolved in 5 ml of MeOH, 0.15 ml of AcOH. 3,5-dichlorobenzaldehyde (0.15 mmol) was added. After the mixture was stirred for 30 min, NaBH₃CN (0.30 mmol) was added. The mixture was stirred overnight and the solvent was removed under vacuum. The residue was dissolved in EtOAc (50 ml) and washed with sat. sodium bicarbonate and brine. The organic layer was dried over Na₂SO₄ and concentrated under vacuum. The residue was purified by flash column chromatography (DCM/MeOH), yielding N-(3,5-dichlorobenzyl)(6-bromo-1H-benzo[d]imidazol-2-yl)methanamine (1853). LC/MS: (ESI) (M+H)⁺=385.9.

1881

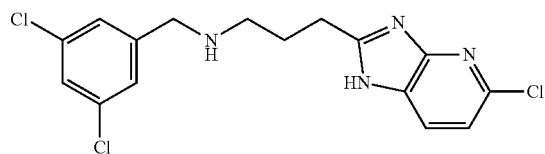

1881 was synthesized using 3-(5-chloro-H-imidazo[4,5-b]pyridin-2-yl)propan-1-amine in General Procedure 20. LC/MS: (ESI) (M+H)⁺=370.5.

1882

1882 was synthesized using 2-(5-chloro-1H-imidazo[4,5-b]pyridin-2-yl)ethanamine in General Procedure 20. LC/MS: (ESI) (M+H)⁺=356.6.

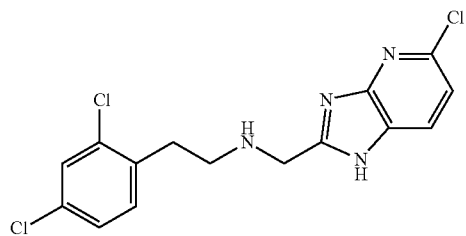

1892

1892 was synthesized using 2-(2,4-dichlorophenyl)acetaldehyde and 2-(5-chloro-1H-imidazo[4,5-b]pyridin-2-yl)ethanamine in General Procedure 20. LC/MS: (ESI) (M+H)⁺= 356.6.

Scheme 47

1716

Reagents and conditions (a) EtMgBr, Ti(O-i-Pr)₄, BF₃, OEt₂; (b) MeOH, HOAc, NaBH₃CN.

To a solution of 3,5-dichlorobenzonitrile (86 mg, 0.5 mmol) and Ti(Oi-Pr)₄ (0.6 mmol) in Et2O (5 mL) was added ethylmagnesium bromide (1.1 mmol) in ether at −78° C. The yellow solution was stirred for 10 min. After the solution was warmed to rt in 1 h, BF₃, OEt₂ (0.13 mL, 1 mmol) was added. After the mixture was stirred for 1 h, 1 N HCl (2 mL) and ether (10 mL) were added. The ether layer was washed with 0.2 N NaOH, and brine. It was then dried over anhydrous sodium sulfate and evaporated under vacuum. The residue was purified by flash column chromatography to give -(3,5-dichlorophenyl)cyclopropanamine[8]. The above purified compound (30 mg, 0.15 mmol) was dissolved in 5 ml of MeOH, 0.15 ml of AcOH. 3-(5-fluoro-3H-imidazo[4,5-b]pyridin-2-ylamino)propanal (0.15 mmol) was added. After the mixture was stirred for 30 min, NaBH₃CN (0.30 mmol) was added. The mixture was stirred overnight and the solvent was removed under vacuum. The residue was dissolved in EtOAc (50 ml) and washed with sat. sodium bicarbonate and brine. The organic layer was dried over Na₂SO₄ and concentrated under vacuum. The residue was purified by flash column chromatography (DCM/MeOH), yielding N-(3-(1-(3,5-dichlorophenyl) cyclopropylamino) propyl)-5-fluoro-3H-imidazo[4,5-b]pyridin-2-amine (1716). LC/MS: (ESI) (M+H)⁺=395.6

Scheme 48

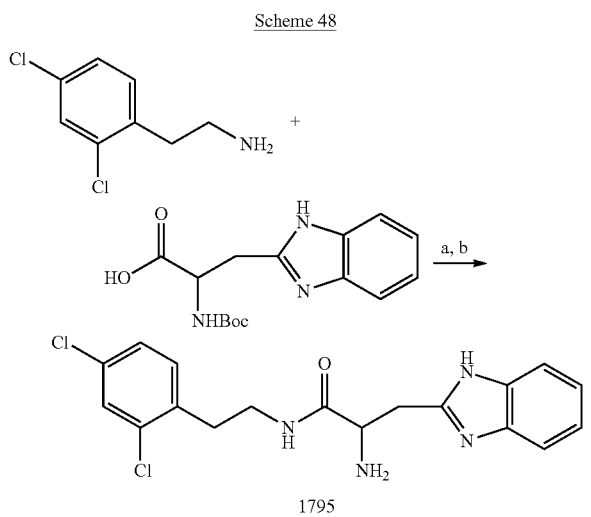

1795

Reagents and conditions (a) EDC, DMAP, DMF; (b) TFA, DCM.

The solution 2-Boc-amino-3-(1H-benzo[d]imidazol-2-yl) propanoic acid (46 mg, 0.15 mmol), DIPEA (0.45 mmol), EDC HCl (0.20 mmol) and DMAP (0.15 mmol) in DMF (10 mL) was stirred for 10 min. To this reaction mixture 2-(2, 4-dichlorophenyl)ethanamine (0.15 mmol) was added. The reaction mixture was stirred at room temperature overnight. After the solvent was removed, the residue was dissolved in ethyl acetate. The organic layer was washed water and brine. It was then dried over anhydrous sodium sulfate and evaporated under vacuum. The residue was purified by flash column chromatography. The above purified compound was dissolved in 3 ml of DCM. To the solution, 1 ml of TFA was added dropwise. The solution was stirred for 40 min at room temperature. The reaction mixture was evaporated under vacuum, neutralized with aq NaHCO$_3$ and extracted with ethyl acetate. The ethyl acetate layer was dried over anhydrous sodium sulfate and concentrated give N-(2,4-dichlorophenethyl)-2-amino-3-(1H-benzo[d]imidazol-2-yl)propanamide (1795). LC/MS: (ESI) (M+H)$^+$=378.3.

Scheme 49

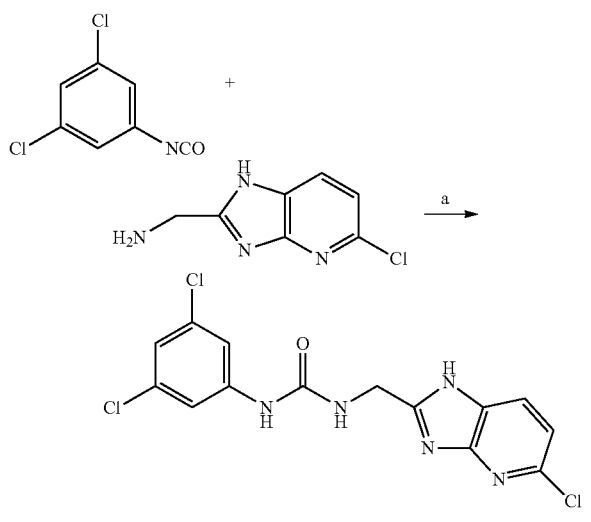

1890

Reagents and conditions (a) DIPEA, acetonitrile, DMF

General Procedure 21(1890, 1891, 1991):

To a solution of 1,3-dichloro-5-isocyanatobenzene (18 mg, 0.1 mmol) in acetronile (5 mL) and DMF (0.1 ml) was slowly added (5-chloro-1H-imidazo[4,5-b]pyridin-2-yl) methanamine 2HCl (0.11 mmol) and DIPEA (0.22 mmol) at 0° C. The mixture was stirred at room temperature for 30 min and then diluted with 25 ml of DCM. The organic phase was washed with water, brine, dried over Na$_2$SO$_4$. After solvent was removed, the residue was chromatographed via silica gel, eluted with MeOH/DCM to give 1-((5-chloro-1H-imidazo[4,5-b]pyridin-2-yl)methyl)-3-(3,5-dichlorophenyl) urea (1890), LC/MS: (ESI) (M+H)$^+$=371.6.

1891

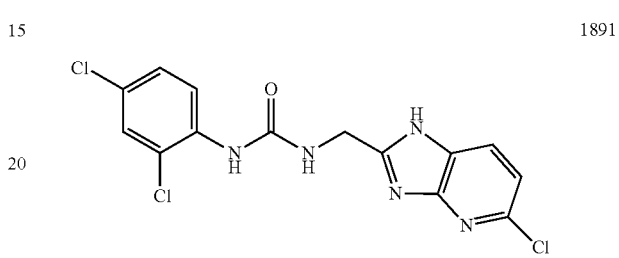

1891 was synthesized using 2,4-dichloro-1-isocyanatobenzene in General Procedure 21. LC/MS: (ESI) (M+H)$^+$=371.6.

1991

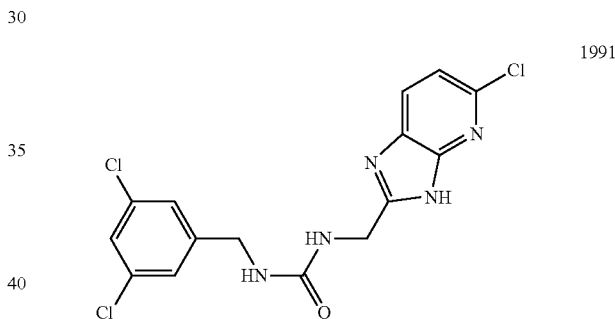

1991 was synthesized using (3,5-dichlorophenyl)methanamine in General Procedure 21. LC/MS: (ESI) (M+H)$^+$=385.1.

Scheme 50

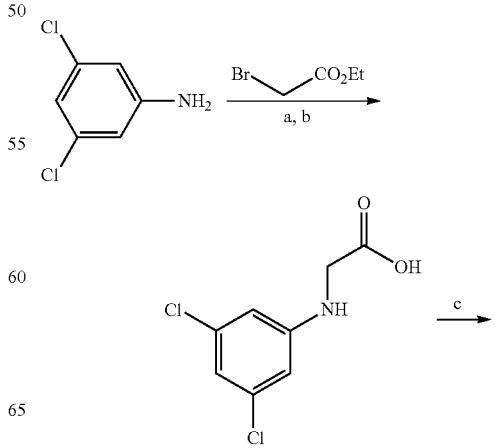

211
-continued

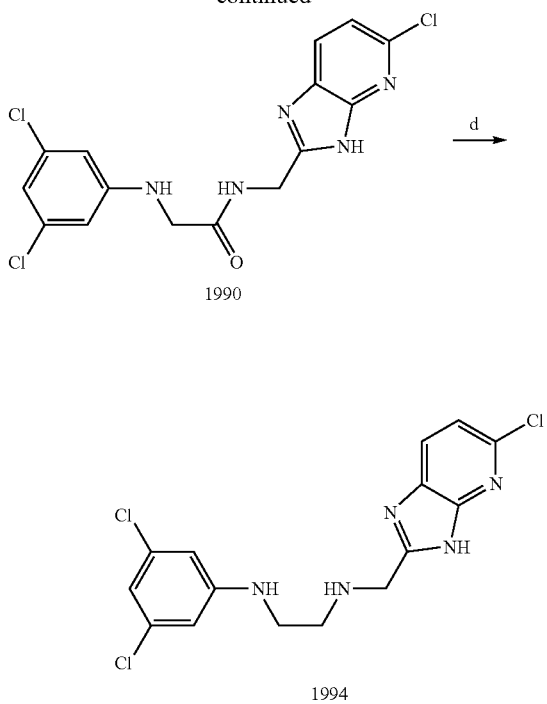

1990

1994

Reagents and conditions (a) NaOAc, EtOH, reflux, overnight; (b) LiOH, CH₃OH/H₂O, r.t., overnight; (c) EDC, pyridine, r.t.; (d) BH₃ in THF, r.t.

3,5-dichloroaniline (1 eq), ethyl 2-bromoacetate (3 eq) and NaOAc (3 eq) in EtOH was refluxed overnight. The solvent was removed under reduced pressure and the residue was extracted with DCM. The organic layer was dried over sodium sulfate, concentrated in vacuum, and the residue was purified through flash chromatography on silica gel eluted with EA-Hexane to give ethyl 2-((3,5-dichlorophenyl)amino)acetate.

LiOH.H₂O (3 eq) was added to the solution of ethyl 2-((3,5-dichlorophenyl)amino)acetate in CH₃OH/H₂O (CH₃OH:H₂O=3:1). The reaction mixture was stirred at r.t. overnight. The solvent was evaporated under reduced pressure, the residue was used for next step without further purification.

2-((3,5-dichlorophenyl)amino)acetic acid (1 eq) and (5-chloro-1H-imidazo[4,5-b]pyridin-2-yl)methanamine 2HC (1 eq) in pyridine (2 mL) was added EDC (1.5 eq). The mixture was stirred at r.t. overnight, and pyridine was then removed under reduced pressure. After addition of saturated aqueous sodium bicarbonate to the residue, the mixture was extracted with DCM. The organic layer was dried over anhydrous sodium sulfate, and concentrated in vacuum. Purification through flash chromatography on silica gel eluted with MeOH-DCM (0.5% ammonia hydroxide) gave compound 1990. LC/MS: (ESI) (M+H)⁺=385.5

Compound 1990 dissolved in anhydrous THF was added BH₃ (5 eq) in THF at r.t. The mixture was stirred at r.t. for 5 h. The solvent was removed under reduced pressure, saturated NaHCO₃ was added and extracted with DCM. The organic layer was dried over sodium sulfate, concentrated in vacuum, and the residue was purified through flash chromatography on silica gel to give compound 1994. LC/MS: (ESI) (M+H)⁺=371.9

212

Scheme 51

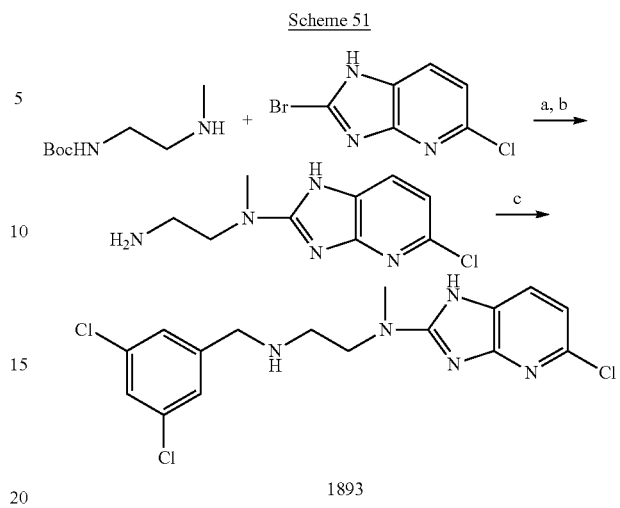

1893

Reagents and conditions (a) pyridine, heating; (b) TFA, DCM; (c) MeOH, HOAc, NaBH₃CN General Procedure 22(1893, 1894, 1925, 1949, 1757, 1599, 1634, 1641):

2-bromo-5-chloro-1H-imidazo[4,5-b]pyridine (30 mg, 0.13 mmol) was dissolved in pyridine (2 mL), tert-butyl 2-(methylamino)ethylcarbamate (0.52 mmol) was added and the reaction mixture was heated at 110° C. overnight or microwave irradiated at 120° C. for 1 h. The reaction mixture was concentrated in vacuum and the residue partitioned between saturated sodium bicarbonate and DCM. The organic extract was dried over anhydrous sodium sulfate, and concentrated in vacuum. The residue was purified through flash chromatography on silica gel eluted with MeOH-DCM (0.5% ammonia hydroxide) to give tert-butyl 2-(5-chloro-N-methyl-1H-imidazo[4,5-b]pyridin-2-ylamino)ethylcarbamate. Tert-butyl 2-(5-chloro-N-methyl-1H-imidazo[4,5-b]pyridin-2-ylamino)ethylcarbamate (32.5 mg, 0.1 mmol) was dissolved in DCM (4 ml) and TFA (2 ml) was added. The mixture was stirred at room temperature for 30 min. and the solvent was removed completely in vacuum. The residue was dissolved in methanol (4 ml) and neutralized with DIPEA (0.2 mmol). The solution was added HOAc (0.12 ml) and 3,5-dichlorobenzaldehyde (0.1 mml), following by adding NaBH₃CN (0.2 mmol). The mixture was stirred at r.t. overnight. The solvent was removed under reduced pressure and the residue was extracted by DCM. The organic phase was dried over sodium sulfate. Remove solvent in vacuum and purify through flash chromatography on silica gel eluted with MeOH-DCM (0.5% ammonia hydroxide) to give N-(2-(3,5-dichlorobenzylamino)ethyl)-5-chloro-N-methyl-1H-imidazo[4,5-b]pyridin-2-amine (1893). LC/MS: (ESI) (M+H)⁺=385.2.

1894

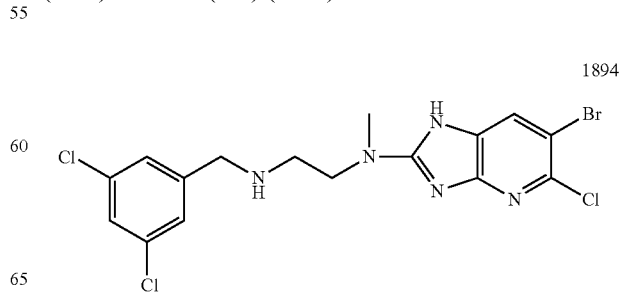

1894 was synthesized using 2,6-dibromo-5-chloro-H-imidazo[4,5-b]pyridine in General Procedure 22. LC/MS: (ESI) (M+H)+=464.6.

Procedure 22. $^1$H NMR (500 MHz, MeOD) δ 7.98 (d, J=6.2 Hz, 1H), 7.88 (d, J=7.7 Hz, 1H), 7.61-7.45 (m, 3H), 7.26 (m, 1H), 4.25 (s, 2H), 3.65 (t, J=6.6 Hz, 2H), 3.20 (m, 2H), 2.13 (m, 2H). LC/MS: (ESI) 351.6 [M+H]+.

1925

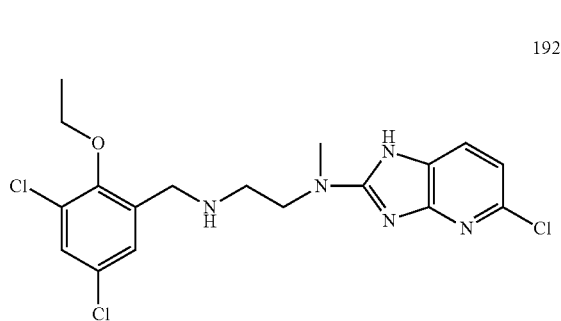

1925 was synthesized using 3,5-dichloro-2-ethoxybenzaldehyde in General Procedure 22. LC/MS: (ESI) (M+H)+=429.7.

1599

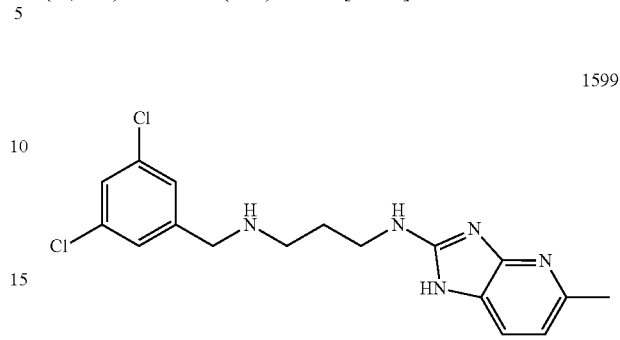

1599 was synthesized using 2-bromo-5-methyl-1H-imidazo[4,5-b]pyridine and tert-butyl 3-aminopropylcarbamate in General Procedure 22. LC/MS: (ESI) 365.4 [M+H]+.

1949

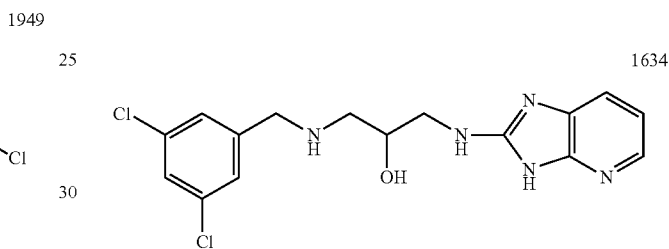

1634

1949 was synthesized using tert-butyl 2-(ethylamino)ethylcarbamate in General Procedure 22. LC/MS: (ESI) (M+H)+=399.5.

1634 was synthesized using 2-bromo-1H-imidazo[4,5-b]pyridine and tert-butyl 3-amino-2-hydroxypropylcarbamate in General Procedure 22. LC/MS: (ESI) 367.3 [M+H]+.

1913

1641

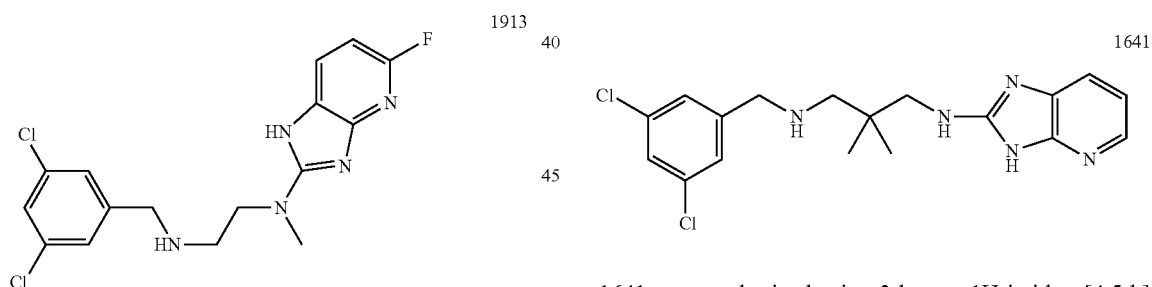

1913 was synthesized using 2-bromo-5-fluoro-1H-imidazo[4,5-b]pyridine in General Procedure 22. LC/MS: (ESI) (M+H)+=369.3.

1641 was synthesized using 2-bromo-1H-imidazo[4,5-b]pyridine and tert-butyl 3-amino-2,2-dimethylpropylcarbamate in General Procedure 22. LC/MS: (ESI) 379.2 [M+H]+.

Scheme 52

1575

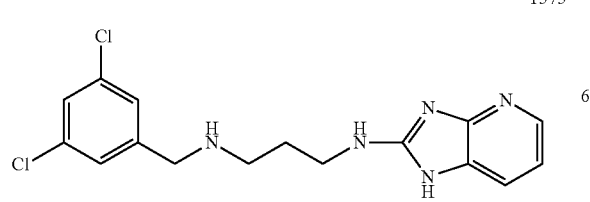

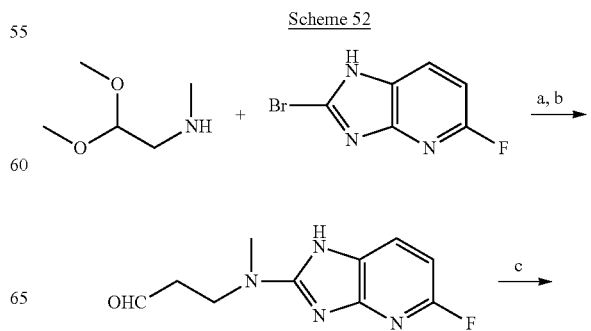

1575 was synthesized using 2-bromo-1H-imidazo[4,5-b]pyridine and tert-butyl 3-aminopropylcarbamate in General -continued

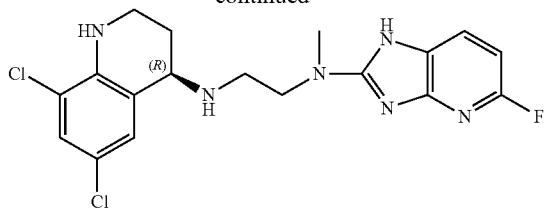

1919

Reagents and conditions (a) pyridine, Microwave 100° C., 1 h; (b) HCl (2M), Acetone, reflux, 1 h; (c) (R)-6,8-dichloro-1,2,3,4-tetrahydroquinolin-4-amine, MeOH, HOAc, NaBH₃CN General Procedure 23 (1919, 1939, 1917):

2-bromo-5-fluoro-1H-imidazo[4,5-b]pyridine (1 eq) was dissolved in pyridine (2 mL), 2,2-dimethoxy-N-methylethanamine (1.5 eq) was added and the reaction mixture was microwave irradiated at 100° C. for 1 h. The reaction mixture was concentrated in vacuum and the residue partitioned between saturated sodium bicarbonate and DCM. The organic extract was dried over anhydrous sodium sulfate, and concentrated in vacuum. The residue was purified through flash chromatography on silica gel eluted with MeOH-DCM (0.5% ammonia hydroxide) to give N-(2,2-dimethoxyethyl)-5-fluoro-N-methyl-1H-imidazo[4,5-b]pyridin-2-amine. N-(2,2-dimethoxyethyl)-5-fluoro-N-methyl-1H-imidazo[4,5-b]pyridin-2-amine (32.5 mg, 0.1 mmol) was dissolved in Acetone (4 ml) and HCl (2 M) was added, The mixture was refluxed for 1 h and the solvent was removed completely in vacuum. The residue was dissolved in methanol (4 ml) and neutralized with DIPEA (0.2 mmol). The solution was added HOAc (0.12 ml) and 3(R)-6,8-dichloro-1,2,3,4-tetrahydroquinolin-4-amine (0.1 mml), following by adding NaBH₃CN (0.2 mmol). The mixture was stirred at r.t. overnight. The solvent was removed under reduced pressure and the residue was extracted by DCM. The organic phase was dried over sodium sulfate. Remove solvent in vacuum and purify through flash chromatography on silica gel eluted with MeOH-DCM (0.5% ammonia hydroxide) to give (R)—N1-(6,8-dichloro-1,2,3,4-tetrahydroquinolin-4-yl)-N2-(5-fluoro-1H-imidazo[4,5-b]pyridin-2-yl)-N2-methylethane-1,2-diamine (1919). LC/MS: (ESI) (M+H)⁺=410.3

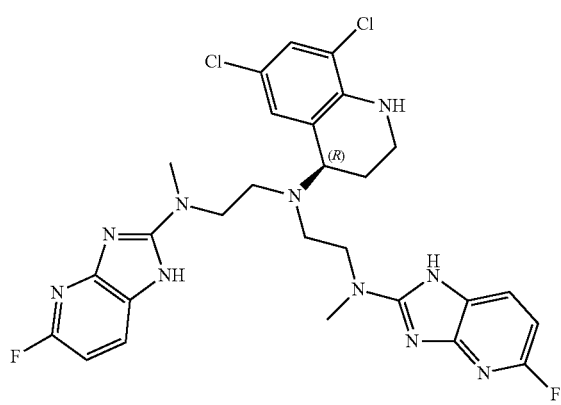

1939

1939: (R)—N1-(6,8-dichloro-1,2,3,4-tetrahydroquinolin-4-yl)-N2-(5-fluoro-1H-imidazo[4,5-b]pyridin-2-yl)-N1-(2-((5-fluoro-1H-imidazo[4,5-b]pyridin-2-yl)(methyl)amino)ethyl)-N2-methylethane-1,2-diamine was synthesized using 0.5 eq of 3(R)-6,8-dichloro-1,2,3,4-tetrahydroquinolin-4-amine following the General Procedure 23. LC/MS: (ESI) (M+H)⁺=601.9

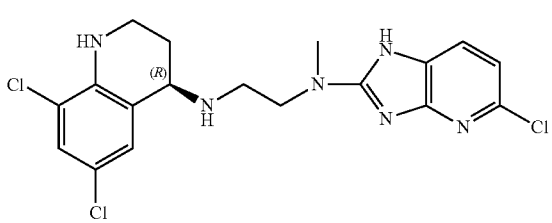

1917

1917 was synthesized using 2-bromo-5-chloro-1H-imidazo[4,5-b]pyridine in General Procedure 23. LC/MS: (ESI) (M+H)⁺=426.5.

Scheme 44

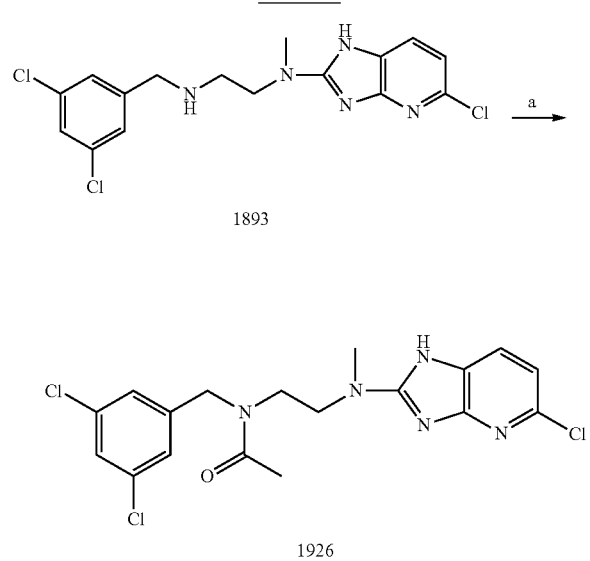

Reagents and conditions (a) DCM, Ac₂O, DIPEA, 0° C.

General Procedure 24 (1926, 1914, 1938):

To a solution of compound 1893 (17 mg, 0.045 mmol) in DCM (5 mL) was slowly added DIPEA (0.2 mmol) and acetic anhydride (0.045 mmol) in DCM at 0° C. The mixture was stirred overnight and then diluted with 25 ml of DCM. The organic phase was washed with water, brine, dried over Na₂SO₄. After solvent was removed, the residue was chromatographed via silica gel, eluted with MeOH/DCM to give N-(3,5-dichlorobenzyl)-N-(2-(5-chloro-N-methyl-1H-imidazo[4,5-b]pyridin-2-ylamino)ethyl)acetamide (1926), LC/MS: (ESI) (M+H)⁺=427.4.

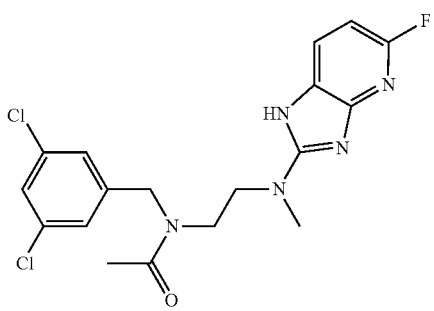

1914 was synthesized using 1913 in General Procedure 24. LC/MS: (ESI) (M+H)⁺=411.1

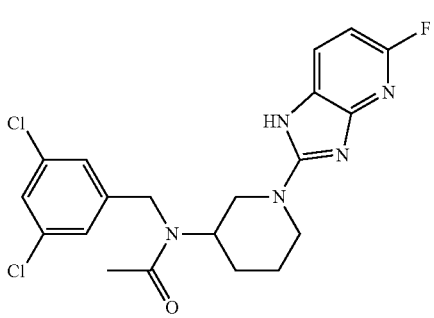

1887: N-(3,5-dichlorobenzyl)-N-(1-(5-fluoro-1H-imidazo[4,5-b]pyridin-2-yl)piperidin-3-yl)acetamide was synthesized using 1886 in General Procedure 24. MS (ESI) (M+H)⁺=437.3; HPLC analysis: 100% purity.

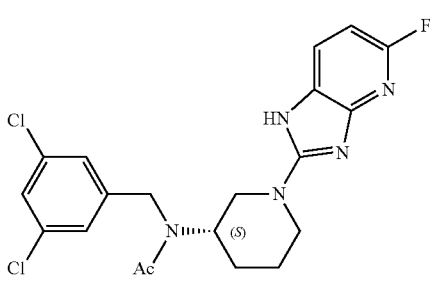

1901: (S)—N-(3,5-dichlorobenzyl)-N-(1-(5-fluoro-1H-imidazo[4,5-b]pyridin-2-yl)piperidin-3-yl)acetamide was synthesized following the procedure 24. MS (ESI) (M+H)⁺=437.3

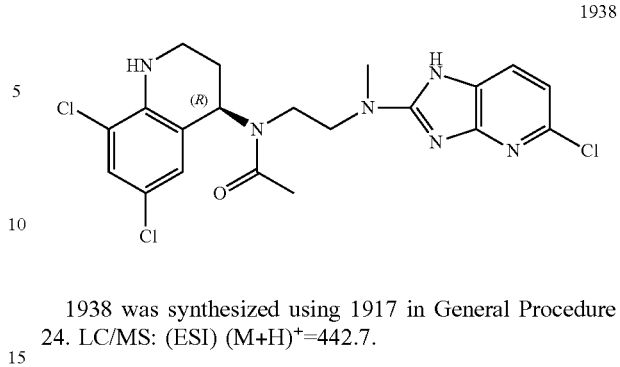

1938 was synthesized using 1917 in General Procedure 24. LC/MS: (ESI) (M+H)⁺=442.7.

Scheme 53

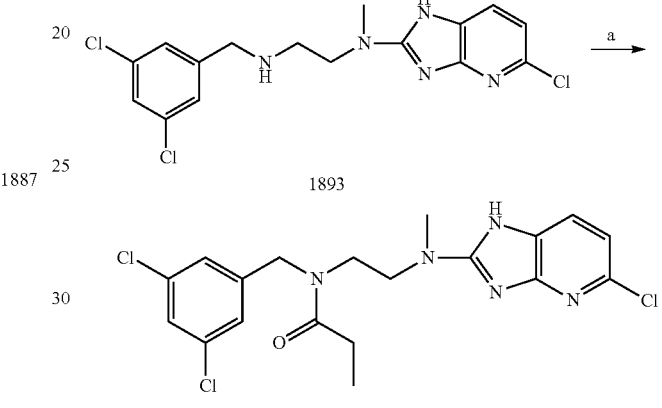

Reagents and conditions (a) DCM, propionic acid, EDC, DMAP, DIPEA

General Procedure 25 (1942, 1957, 1958):

The solution of propanoic acid (10 mg 0.135 mmol), DIPEA (0.4 mmol), EDC HCl (0.2 mmol) and DMAP (0.135 mmol) in DCM (20 mL) was stirred for 10 min. To this reaction mixture compound 1893 (0.135 mmmol) was added. The reaction mixture was stirred at room temperature overnight and diluted with 20 ml of DCM. The organic layer was washed with water and brine. It was then dried over anhydrous sodium sulfate and evaporated under vacuum. The residue was purified by flash column chromatography to afford N-(3,5-dichlorobenzyl)-N-(2-(5-chloro-N-methyl-1H-imidazo[4,5-b]pyridin-2-ylamino)ethyl)propionamide (1942). LC/MS: (ESI) (M+H)⁺=441.3.

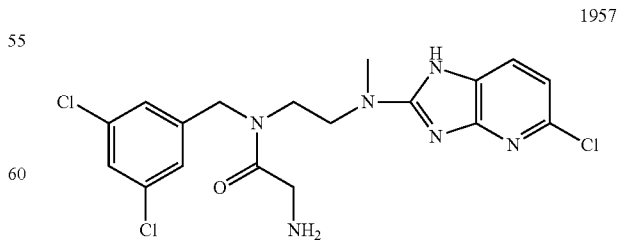

1957 was synthesized using Boc-Gly and following the Boc deprotection with TFA in DCM in General Procedure 25. LC/MS: (ESI) (M+H)⁺=442.7.

1958

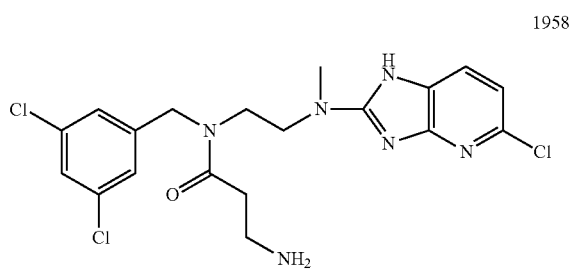 [SMILES: CN(CCN(Cc1cc(Cl)cc(Cl)c1)C(=O)CCN)c1nc2nc(Cl)ccc2[nH]1]

1958 was synthesized using Boc-β-Ala and following the Boc deprotection with TFA in DCM in General Procedure. LC/MS: (ESI) (M+H)+=456.7.

Scheme 54

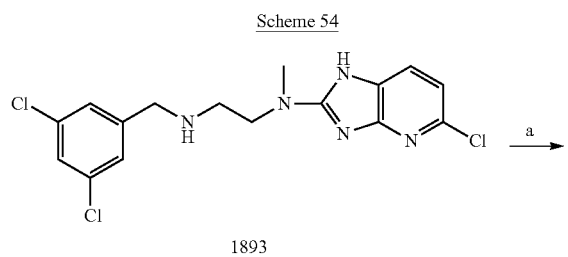

To a solution of compound 1893 (17 mg, 0.045 mmol) in DCM (5 mL) was slowly added DIPEA (0.2 mmol) and methyl chloroformate (0.045 mmol) in DCM at 0° C. The mixture was stirred overnight and then diluted with 25 ml of DCM. The organic phase was washed with water, brine, dried over Na$_2$SO$_4$. After solvent was removed, the residue was chromatographed via silica gel, eluted with MeOH/DCM to give methyl 3,5-dichlorobenzyl2-(5-chloro-N-methyl-1H-imidazo[4,5-b]pyridin-2-ylamino)ethylcarbamate (1963), LC/MS: (ESI) (M+H)+=443.5.

Scheme 55

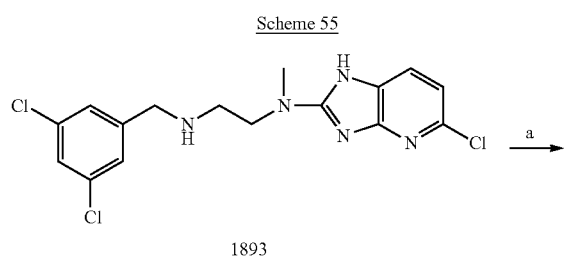

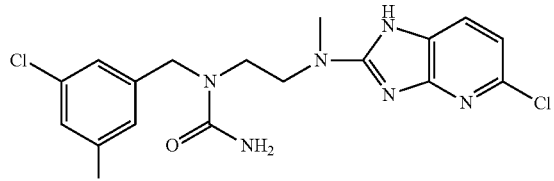

Reagents and conditions (a) DCM, trimethylsilylisocyanate, DIPEA, 0° C.

To a solution of compound 1893 (17 mg, 0.045 mmol) in DCM (5 mL) was slowly added DIPEA (0.2 mmol) and trimethylsilylisocyanate (0.045 mmol) in DCM at 0'C. The mixture was stirred overnight and then diluted with 25 ml of DCM. The organic phase was washed with water, brine, dried over Na$_2$SO$_4$. After solvent was removed, the residue was chromatographed via silica gel, eluted with MeOH/DCM to give 1-(3,5-dichlorobenzyl)-1-(2-(5-chloro-N-methyl-1H-imidazo[4,5-b]pyridin-2-ylamino)ethyl)urea (1972), LC/MS: (ESI) (M+H)+=428.4.

Scheme 56

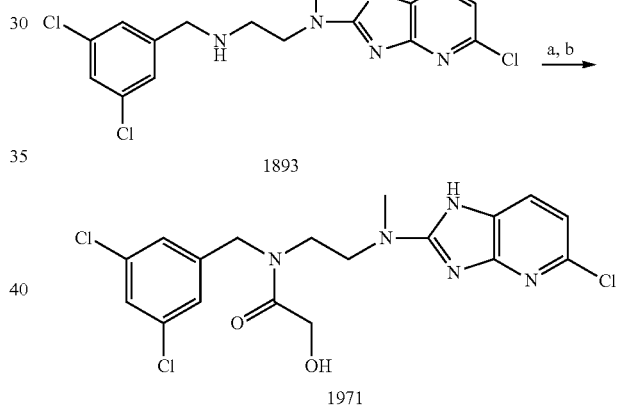

To a solution of compound 1893 (17 mg, 0.045 mmol) in DCM (5 mL) was slowly added DIPEA (0.05 mmol) and acetoxyacetyl chloride (0.045 mmol) in DCM at 0° C. The mixture was stirred overnight and then diluted with 25 ml of DCM. The organic phase was washed with water, brine, dried over Na$_2$SO$_4$. After solvent was removed, the residue was chromatographed via silica gel, eluted with MeOH/DCM to give ((N-(3,5-dichlorobenzyl)-N-(2-(5-chloro-N-methyl-1H-imidazo[4,5-b]pyridin-2-ylamino)ethyl)carbamoyl)methyl acetate. ((N-(3,5-dichlorobenzyl)-N-(2-(5-chloro-N-methyl-1H-imidazo[4,5-b]pyridin-2-ylamino)ethyl)carbamoyl)methyl acetate (19 mg, 0.04 mmol) in MeOH was added K$_2$CO$_3$ (0.16 mmol), and stirred at room temperature for 1 hour. The mixture was concentrated, and water (10 mL) was added and extracted with CH$_2$Cl$_2$ (3×35 mL). The combined organic extracts were dried (Na$_2$SO$_4$), filtered, and concentrated to give N-(3,5-dichlorobenzyl)-N-(2-(5-chloro-N-methyl-1H-imidazo[4,5-b]pyridin-2-ylamino)ethyl)-2-hydroxyacetamide (1971), LC/MS: (ESI) (M+H)+=443.5.

Scheme 57

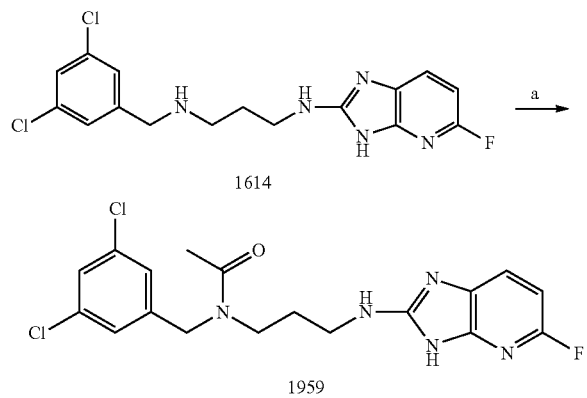

Reagents and conditions (a) DCM, Ac₂O, DIPEA, 0° C.

To a solution of compound 1614 HCl salt (20 mg, 0.045 mmol) in DCM (5 mL) was slowly added DIPEA (0.2 mmol) and acetic anhydride (0.045 mmol) in DCM at 0° C. The mixture was stirred overnight and then diluted with 25 ml of DCM. The organic phase was washed with water, brine, dried over Na$_2$SO$_4$. After solvent was removed, the residue was chromatographed via silica gel, eluted with MeOH/DCM to give N-(3,5-dichlorobenzyl)-N-(3-(5-fluoro-3H-imidazo[4,5-b]pyridin-2-ylamino)propyl)acetamide (1959), LC/MS: (ESI) (M+H)$^+$=411.5.

Scheme 58

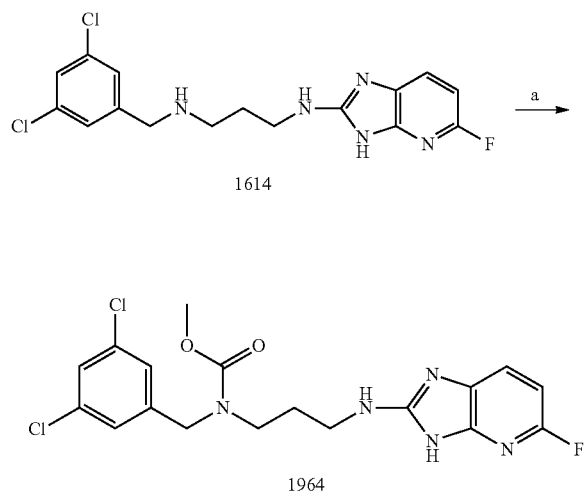

Reagents and conditions (a) DCM, methyl chloroformate, DIPEA, 0° C.

To a solution of compound 1614 HCl salt (20 mg, 0.045 mmol) in DCM (5 mL) was slowly added DIPEA (0.2 mmol) and methyl chloroformate (0.045 mmol) in DCM at 0° C. The mixture was stirred overnight and then diluted with 25 ml of DCM. The organic phase was washed with water, brine, dried over Na$_2$SO$_4$. After solvent was removed, the residue was chromatographed via silica gel, eluted with MeOH/DCM to give methyl 3,5-dichlorobenzyl3-(5-fluoro-3H-imidazo[4,5-b]pyridin-2-ylamino)propylcarbamate (1964), LC/MS: (ESI) (M+H)$^+$=427.6.

Scheme 59

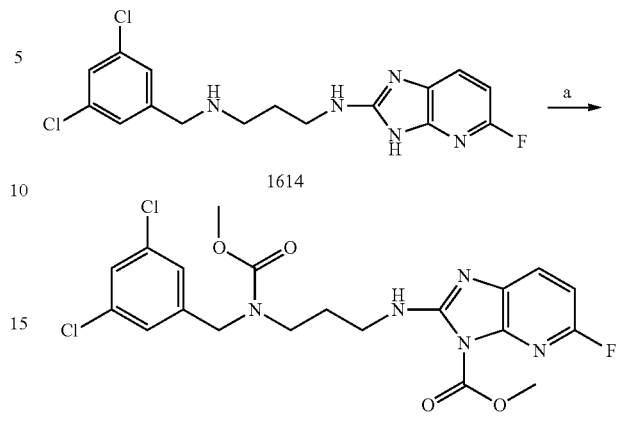

Reagents and conditions (a) DCM, methyl chloroformate, DIPEA, 0° C.

To a solution of compound 1614 HCl salt (20 mg, 0.045 mmol) in DCM (5 mL) was slowly added DIPEA (0.4 mmol) and methyl chloroformate (0.090 mmol) in DCM at 0° C. The mixture was stirred overnight and then diluted with 25 ml of DCM. The organic phase was washed with water, brine, dried over Na$_2$SO$_4$. After solvent was removed, the residue was chromatographed via silica gel, eluted with MeOH/DCM to give methyl 3,5-dichlorobenzyl3-(3-(methoxycarbonyl)-5-fluoro-3H-imidazo[4,5-b]pyridin-2-ylamino)propylcarbamate (1965), LC/MS: (ESI) (M+H)$^+$=484.4.

Scheme 60

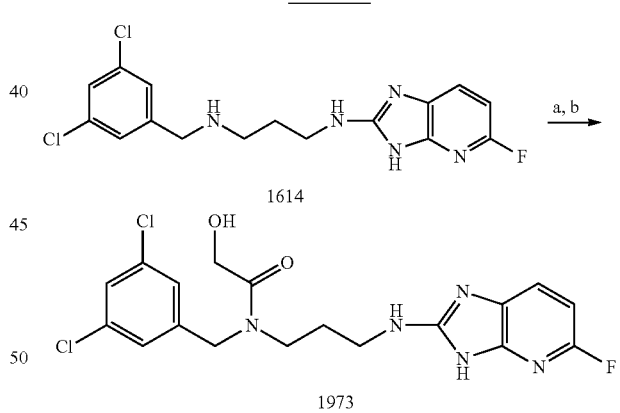

Reagents and conditions (a) DCM, acetoxyacetyl chloride, DIPEA, 0° C.; (b) K$_2$CO$_3$, MeOH To a solution of compound 1614 HCl salt (20 mg, 0.4 mmol) in DCM (5 mL) was slowly added DIPEA (0.2 mmol) and acetoxyacetyl chloride (0.045 mmol) in DCM at 0° C. The mixture was stirred overnight and then diluted with 25 ml of DCM. The organic phase was washed with water, brine, dried over Na$_2$SO$_4$. After solvent was removed, the residue was chromatographed via silica gel, eluted with MeOH/DCM to give (N-(3,5-dichlorobenzyl)-N-(3-(5-fluoro-3H-imidazo[4,5-b]pyridin-2-ylamino)propyl)carbamoyl)methyl acetate. (N-(3,5-dichlorobenzyl)-N-(3-(5-fluoro-3H-imidazo[4,5-b]pyridin-2-ylamino)propyl)carbamoyl)methyl acetate (18.8 mg, 0.04 mmol) in MeOH was added K₂CO₃ (0.16 mmol), and stirred at room temperature for 1 hour. The mixture was concentrated, and water (10 mL) was added and extracted with CH₂Cl₂ (3×35 mL). The combined organic extracts were dried (Na₂SO₄), filtered, and concentrated to give N-(3,5-dichlorobenzyl)-N-(3-(5-fluoro-3H-imidazo[4,5-b]pyridin-2-ylamino)propyl)-2-hydroxyacetamide (1973), LC/MS: (ESI) (M+H)⁺=427.4.

Scheme 61

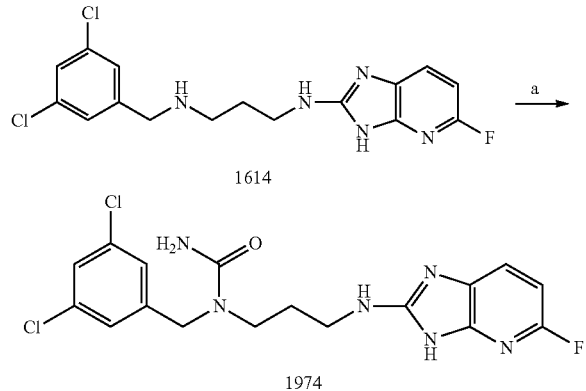

Reagents and conditions (a) DCM, trimethylsilylisocyanate, DIPEA, 0° C.

To a solution of compound 1614 HCl salt (20 mg, 0.045 mmol) in DCM (5 mL) was slowly added DIPEA (0.2 mmol) and trimethylsilylisocyanate (0.045 mmol) in DCM at 0° C. The mixture was stirred overnight and then diluted with 25 ml of DCM. The organic phase was washed with water, brine, dried over Na₂SO₄. After solvent was removed, the residue was chromatographed via silica gel, eluted with MeOH/DCM to give 1-(3,5-dichlorobenzyl)-1-(3-(5-fluoro-3H-imidazo[4,5-b]pyridin-2-ylamino)propyl)urea (1974), LC/MS: (ESI) (M+H)⁺=412.6.

General Procedure 26 (1933, 1960):

A solution of 4-bromo-2-fluoropyridine (17.6 mg, 0.1 mmol), (1H-benzo[d]imidazol-2-yl)methanamine HCl salt (26.4 mg, 0.12 mmol), cesium carbonate (0.25 mmol) in DMF (1.0 mL) was microwave irradiated at 90° C. for 10 min. The solvent was then removed under vacuum. The residue was dissolved in EtOAc (25 mL), filtered. The organic layer was washed with brine (25 mL), dried and concentrated under vacuum. Purification by chromatography afforded the N-((1H-benzo[d]imidazol-2-yl)methyl)-4-bromopyridin-2-amine. The solution of N-((1H-benzo[d]imidazol-2-yl)methyl)-4-bromopyridin-2-amine (0.08 mmol), 2-chloro-4-methoxyphenol (0.12 mmol) and cesium carbonate (0.16 mmol) in DMF (1.0 mL) was microwave irradiated at 120° C. for 1 h. The solvent was then removed under vacuum. The residue was dissolved in EtOAc (25 mL), filtered. The organic layer was washed with brine (25 mL), dried and concentrated under vacuum. Purification by chromatography afforded N-((1H-benzo[d]imidazol-2-yl)methyl)-4-(2-chloro-4-methoxyphenoxy)pyridin-2-amine (1933). LC/MS: (ESI) (M+H)⁺=381.7.

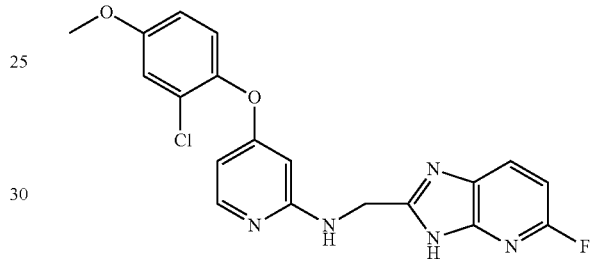

1960

1960 was synthesized using (5-fluoro-3H-imidazo[4,5-b]pyridin-2-yl)methanamine in General Procedure 26. LC/MS: (ESI) (M+H)⁺=400.6.

Scheme 62

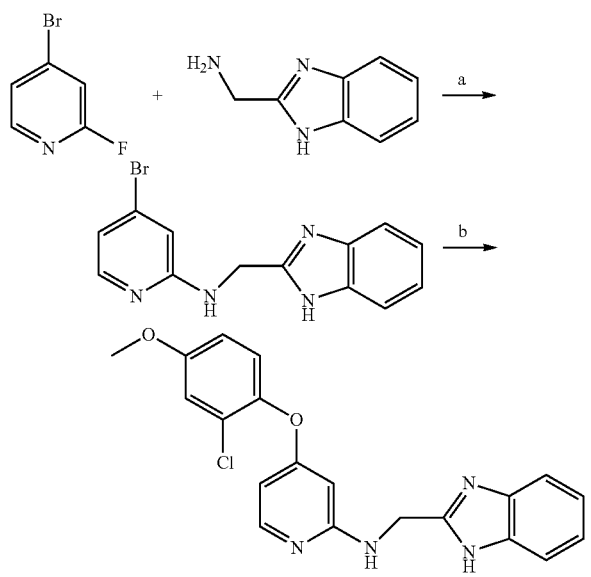

Reagents and conditions (a) DMF, Cs₂CO₃, µW, 90° C., 10 min; (b) 2-chloro-4-methoxyphenol, DMF, Cs₂CO₃, µW, 120° C., 1 h.

Scheme 63

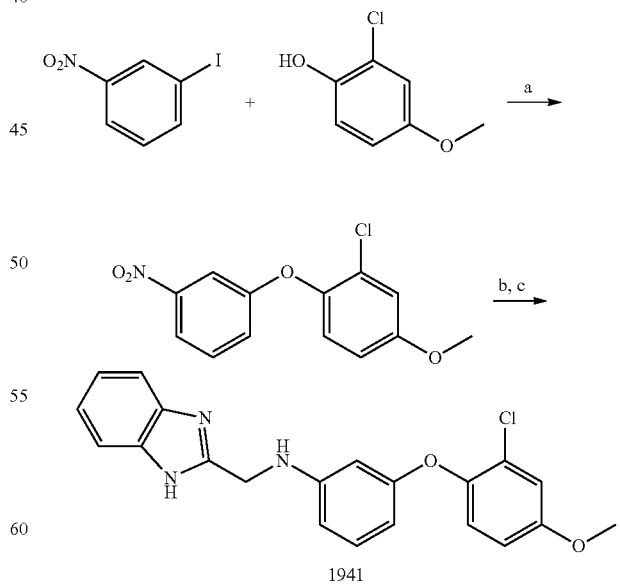

Reagents and conditions (a) CuI, Cs₂CO₃, dioxane, µw, 100° C., 1 h; (b) Fe, AcOH (c) KI, EtOH, benzimidazole.

A solution of 1-iodo-3-nitrobenzene (24.8 mg, 0.1 mmol), 2-chloro-4-methoxyphenol (31.7 mg, 0.2 mmol), CuI (1.91 mg, 0.01 mmol), cesium carbonate (65.2 mg, 0.2 mmol) in 1,4-dioxane (1.0 mL) was heated at 100° C. for 1 h under microwave. The solvent was then removed under vacuum. The residue was dissolved in EtOAc (5 mL), filtered. The organic layer was washed with brine (25 mL), dried and concentrated under vacuum. Purification by chromatography (5-10% ethyl acetate in hexane) afforded the biaryl ether. The biaryl ether (13.6 mg, 0.05 mmol) was treated with Fe (11.2 g, 0.2 mmol), NH$_4$CL (11.0 mg, 0.2 mmol) in 1 mL EtOH, and 0.5 mL H$_2$O was heated at 75° C. for 4 h. After the reaction completed, the mixture was filtered, neutralized with 1 M NaOH and extracted with ethyl acetate (3×50 mL). The organic fractions were dried and concentrated under vacuum. The residue was chromatographed (10-15% ethyl acetate in hexane) to afford the amine as a yellow solid. A mixture of benzimidazoles (7.5 mg, 0.045 mmol), substituted aniline (7.5 mg, 0.03 mmol) and KI (9.9 mg, 0.06 mmol) in 1.0 mL of ethanol was heated under reflux. After 6 h, KOH (0.1 mmol in 1.0 L of water) was added with continuous stirring and heating for 2 h. After the reaction completed, the mixture was extracted with ethyl acetate. The organic fractions were dried and concentrated under vacuum. The residue was chromatographed to give 1941 as a yellow solid. $^1$H NMR (500 MHz, CD$_3$OD): δ=7.50 (dd, J=8.5 Hz, 3.0 Hz, 2H), 7.20-7.24 (m, 2H), 7.02 (t, J=8.0 Hz, 1H), 6.91 (d, J=3.0 Hz, 1H), 6.85 (d, J=9.0 Hz, 1H), 6.63 (dd, J=9.0 Hz, 3.0 Hz, 1H), 6.37 (dd, J=8.0 Hz, 3.0 Hz, 1H), 6.16 (dd, J=8.0 Hz, 2.0 Hz, 1H), 6.06-6.07 (m, 1H), 4.53 (s, 2H), 3.78 (s, 3H) ppm.

A solution of 2-bromo-4-fluoropyridine (35 mg, 0.2 mmol), methyl 2-aminoacetate (0.4 mmol), cesium carbonate (0.50 mmol) in DMF (2.0 mL) was heated at 80° C. for 20 min under microwave. The solvent was then removed under vacuum. The residue was dissolved in EtOAc (25 mL), filtered. The organic layer was washed with brine (25 mL), dried and concentrated under vacuum. Purification by chromatography afforded methyl 2-(2-bromopyridin-4-ylamino)acetate. The solution of the methyl 2-(2-bromopyridin-4-ylamino)acetate (24.6 mg, 0.1 mmol), 2-chloro-4-methoxyphenol (0.2 mmol), CuI (0.01 mmol) and cesium carbonate (0.3 mmol) in dioxane (2 ml) was heated at 160° C. for 2 h under microwave. The solvent was then removed under vacuum. The residue was dissolved in EtOAc (25 mL), filtered. The organic layer was washed with brine (25 mL), dried and concentrated under vacuum. Purification by chromatography afforded methyl 2-(2-(2-chloro-4-methoxyphenoxy)pyridin-4-ylamino)acetate.

The solution of methyl 2-(2-(2-chloro-4-methoxyphenoxy)pyridin-4-ylamino)acetate (0.1 mmol) in 1 ml of 2N NaOH and 1 ml of MeOH was microwave irradiated at 80° C. for 8 min.

After most of solvents were removed, the residue was neutralized with 1 N HCl and extracted with ethyl acetate (3×50 mL). The organic fractions were dried and concentrated under vacuum. The residue was dissolved in pyridine and EDC (0.12 mmol), benzene-1,2-diamine (1.2 mmol) were added. The solution was stirred at room temperature overnight. The residue was dissolved in acetic acid (1 ml). The solution was heated at 60° C. for 3 h. The solvent was then removed under vacuum. The residue was dissolved in EtOAc (25 mL). The organic layer was washed with brine (25 mL), dried and concentrated under vacuum.

The residue was chromatographed to give N-((1H-benzo[d]imidazol-2-yl)methyl)-2-(2-chloro-4-methoxyphenoxy)pyridin-4-amine (190 L S/: (ESI) (M+H)$^+$=381.7.

Scheme 64

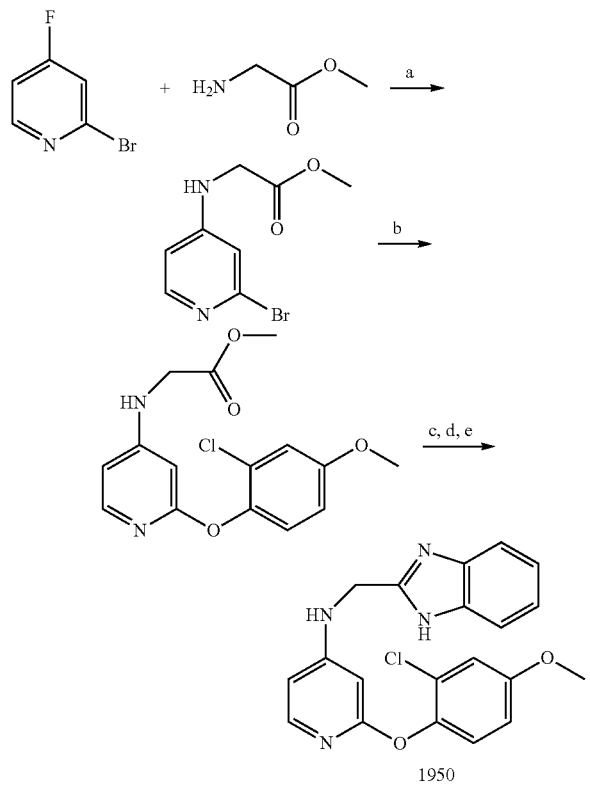

Reagents and conditions (a) DMF, Cs$_2$CO$_3$, μW, 80° C., 20 min; (b) 2-chloro-4-methoxyphenol, CuI, Cs$_2$CO$_3$, dioxane, μw, 160° C., 2 h; (c), NaOH, MeOH, μw, 80° C., 8 min; (d) EDC, pyridine; (e) HOAc, 60° C.

Scheme 65

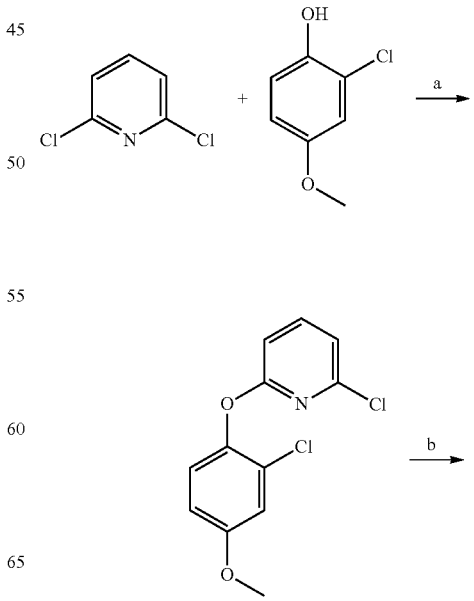

-continued

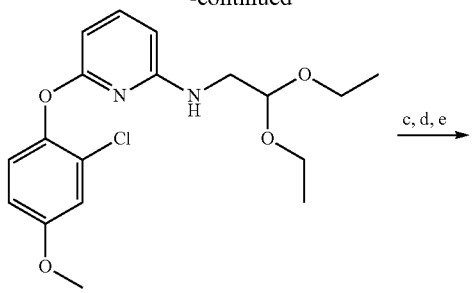

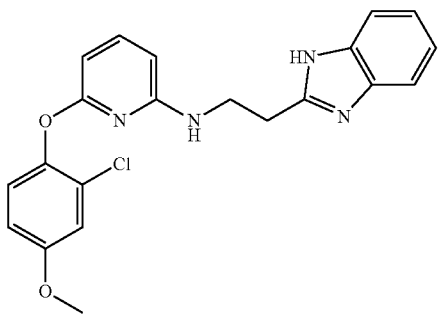

1918

1918 was synthesized using 3,3-diethoxypropan-1-amine in General Procedure 27. LC/MS: (ESI) (M+H)$^+$=395.6.

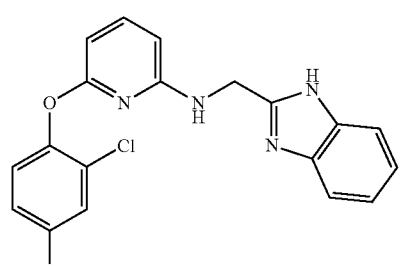

1924

Reagents and conditions (a) acetonile, K$_2$CO$_3$, μW, 100° C., 1 h; (b) 2,2-diethoxyethanamine, MW 120° C., 10 min; (c), NaOH, MeOH, μW 80° C., 8 min; (d) benzene-1,2-diamine, EDC, pyridine; (e) HOAc, 60° C.

General Procedure 27(1924, 1918):

A solution of 2,6-dichloropyridine (29 mg, 0.2 mmol), 2-chloro-4-methoxyphenol (0.4 mmol), potassium carbonate (0.60 mmol) in acetonitrile (2.0 mL) was heated at 100° C. for 1 h under microwave. The solvent was then removed under vacuum. The residue was dissolved in EtOAc (25 mL), filtered. The organic layer was washed with brine (25 mL), dried and concentrated under vacuum. Purification by chromatography afforded 2-(2-chloro-4-methoxyphenoxy)-6-chloropyridine. The solution of 2-(2-chloro-4-methoxyphenoxy)-6-chloropyridine (20 mg, 0.075 mmol) in 2,2-diethoxyethanamine (1 ml) was heated at 120° C. for 10 min under microwave. The solvent was then removed under vacuum. The residue was dissolved in EtOAc (25 mL), filtered. The organic layer was washed with brine (25 mL), dried and concentrated under vacuum. Purification by chromatography afforded 6-(2-chloro-4-methoxyphenoxy)-N-(2,2-diethoxyethyl)pyridin-2-amine. The solution of 6-(2-chloro-4-methoxyphenoxy)-N-(2,2-diethoxyethyl)pyridin-2-amine (0.05 mmol) in 0.4 ml of acetone and 1 ml of 2 N HCl was stirred at room temperature for 3 h. After most of solvents were removed, the residue was neutralized with 1 N NaOH and extracted with ethyl acetate. The organic fractions were dried and concentrated under vacuum. The residue was dissolved in 1 ml of DMF and NaHSO$_3$ (0.05 mmol), benzene-1,2-diamine (0.05 mmol) were added. The solution was stirred at 100° C. for 3 h. The solvent was then removed under vacuum. The residue was dissolved in EtOAc (25 mL). The organic layer was washed with brine (25 mL), dried and concentrated under vacuum. The residue was chromatographed to give N-((1H-benzo[d]imidazol-2-yl)methyl)-6-(2-chloro-4-methoxyphenoxy)pyridin-2-amine (1924). LC/MS: (ESI) (M+H)$^+$=381.7.

Scheme 66

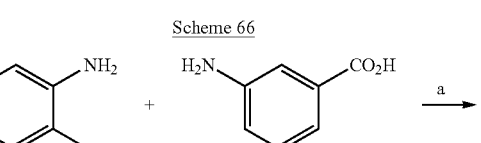

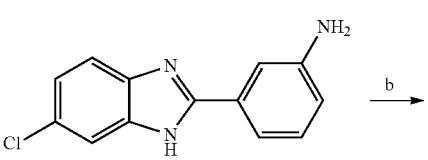

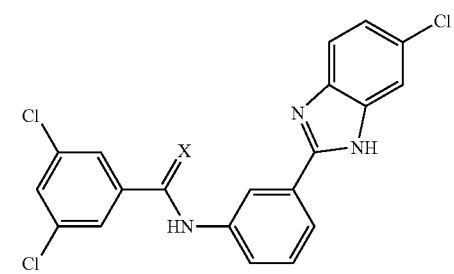

1952: X = H
1953: X = O

Reagents and conditions: (a) PPA, 180° C., 4 h; (b) 3,5-dichlorobenzaldehyde, MeOH, NaBH$_3$CN, r.t., 3 h.

4-chlorobenzene-1,2-diamine (1 eq) and 3-aminobenzoic acid (1 eq) in PPA was heated to 180° C. for 4 h. Cold NaOH aq (5 M) was added to the reaction mixture to adjust the pH to 10.0. Extracted with DCM, washed with brine, concentrated under vacuum and purified via flash column chromatography to yield 3-(6-chloro-1H-benzo[d]imidazol-2-yl) aniline. 3-(6-chloro-1H-benzo[d]imidazol-2-yl)aniline reacted with 3,5-dichlorobenzaldehyde following the general reductive amination condition in Scheme 1 yields 1952. LC/MS: (ESI) (M+H)$^+$=403.5

3-(6-chloro-1H-benzo[d]imidazol-2-yl)aniline reacted with 3,5-dichlorobenzoic acid to produce product 1953. LC/MS: (ESI) (M+H)$^+$=417.6

Scheme 67

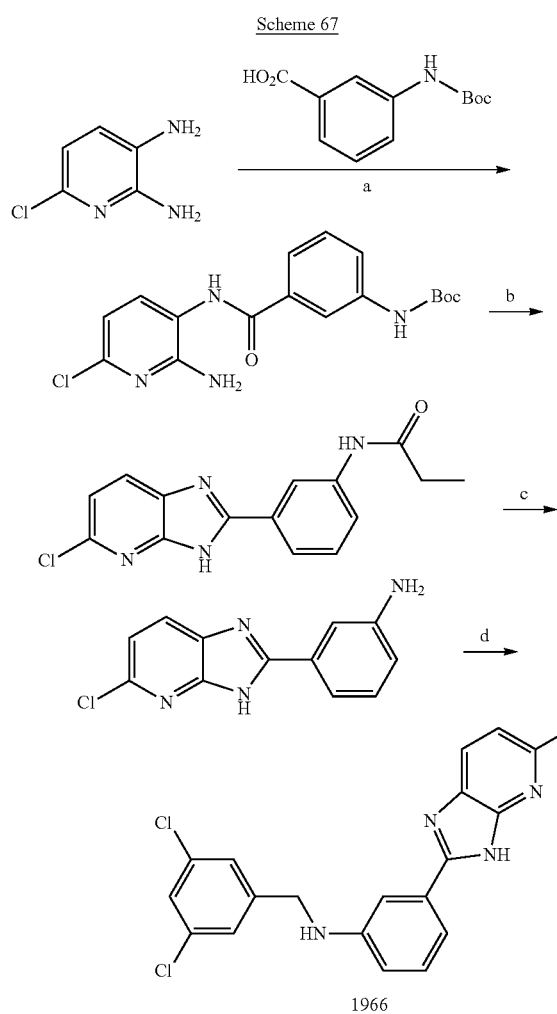

Reagents and conditions:
(a) EDC, pyridine, r.t. overnight;
(b) Propionic acid, Microwave 180° C., 1 h;
(c) HCl (aq), Microwave 120° C., 1 h;
(d) 3,5-dichlorobenzaldehyde, MeOH, NaBH₃CN, r.t., 3 h.

6-chloropyridine-2,3-diamine (0.5 mM) and 3-((tert-butoxycarbonyl)amino) benzoic acid (0.5 mM) in pyridine (2 mL) was added EDC (144 mg, 0.75 mM). The mixture was stirred at r.t. overnight, and pyridine was then removed under reduced pressure. After addition of saturated aqueous sodium bicarbonate to the residue, the mixture was extracted with DCM. The organic layer was dried over anhydrous sodium sulfate, and concentrated in vacuum. Purification through flash chromatography on silica gel eluted with MeOH-DCM (0.5% ammonia hydroxide) gave intermediate tert-butyl (3-((2-amino-6-chloropyridin-3-yl)carbamoyl) phenyl)carbamate.

Intermediate tert-butyl (3-((2-amino-6-chloropyridin-3-yl)carbamoyl) phenyl) carbamate was microwave irradiated in 3 mL propionic acid at 180° C. for 1 hours. The reaction was concentrated in vacuum and the residue partitioned between saturated sodium bicarbonate and DCM. The organic extract was dried over anhydrous sodium sulfate, and concentrated in vacuum. Purification through flash chromatography on silica gel eluted with MeOH-DCM (0.5% ammonia hydroxide) gave N-(3-(5-chloro-3H-imidazo[4,5-b]pyridin-2-yl)phenyl) propionamide.

The suspension of N-(3-(5-chloro-3H-imidazo[4,5-b]pyridin-2-yl)phenyl) propionamide in concentrated HCl was microwave irradiated at 120° C. for 1 h. Evaporated off the solvent got 3-(5-chloro-3H-imidazo[4,5-b]pyridin-2-yl)aniline as yellow solid, which was used for the next step directly.

3-(5-chloro-3H-imidazo[4,5-b]pyridin-2-yl)aniline reacted with 3,5-dichlorobenzaldehyde following the general reductive amination condition in Scheme 1 yields 1966.
LC/MS: (ESI) (M+H)⁺=404.7

Scheme 68

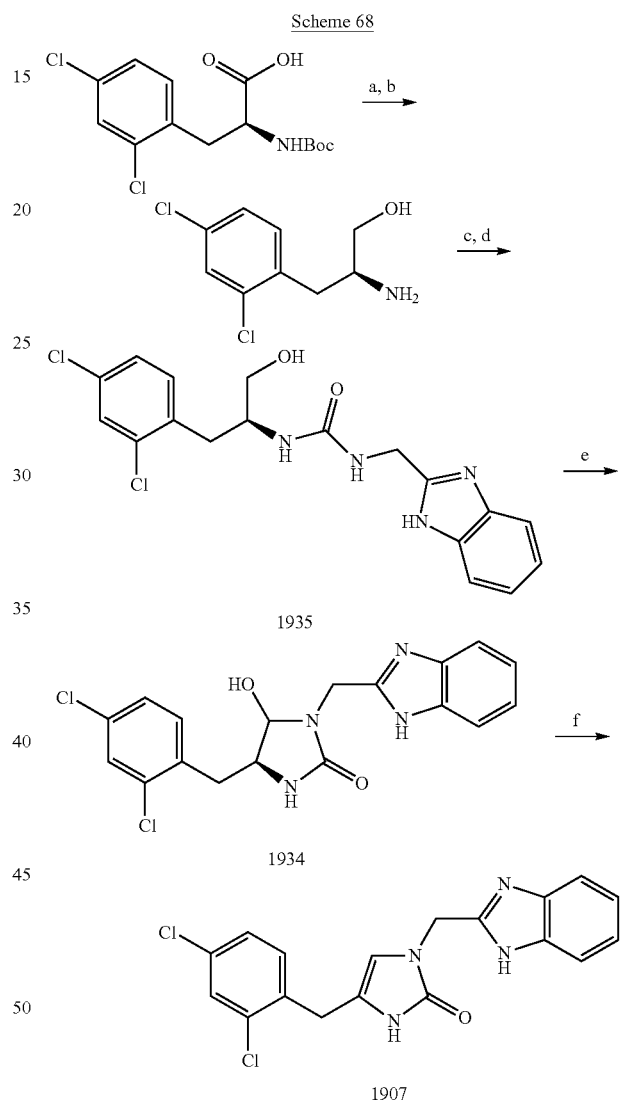

Reagents and condition
(a) HOBt, EDC; (b) DCM, TFA;
(c) tert-butyl 2-(isocyanatomethyl)-1-Boc-1H-benzo[d]imidazole-1-carboxylate, DCM;
(d) DCM, TFA; (e) Des-Martin reagent; (f) HCOOH, 50° C.

To a solution of (S)-2-Boc-amino-3-(2,4-dichlorophenyl) propanoic acid (245 mg, 0.735 mmol) in DCM (15 mL) was added HOBt (123 mg, 0.8 mmol) and EDC (154 mg, 0.8 mmol). The mixture was stirred for 30 min and then concentrated under vacuum. The residue was dissolved in THF (15 mL) and NaBH₄ (56 mg, 1.47 mmol) was added at 0° C. Then the mixture was added 0.5 ml of water. The resulting mixture was stirred at 0° C. for 30 min and quenched with MeOH (5 mL). After most solvents were removed, EtOAc (25 mL) was added. The organic phase was washed with 10% citric, saturated NaHCO$_3$, brine, dried over Na$_2$SO$_4$. After solvent was removed, the residue was chromatographed via silica gel, eluted with MeOH/DCM to give (S)-2-Boc-amino-3-(2,4-dichlorophenyl)propan-1-ol[8]. (S)-2-Boc-amino-3-(2,4-dichlorophenyl)propan-1-ol (96 mg, 0.3 mmol) was dissolved in 10 ml of DCM. To the solution, 3 ml of TFA was added dropwise. The solution was stirred for 40 min at room temperature. The reaction mixture was completely evaporated under vacuum. The residue was dissolved in anhydrous DCM containing DIPEA (0.4 mmol). The solution was cooled to 0° C. and tert-butyl 2-(isocyanatomethyl)-1H-benzo[d]imidazole-1-carboxylate (0.3 mmol) in DCM was added slowly. The reaction was performed at room temperature for 1 h. The solution was diluted with DCM and washed with water, brine, dried over Na$_2$SO$_4$. After solvent was removed, the residue was chromatographed via silica gel, eluted with MeOH/DCM to give 1-((1-Boc-1H-benzo[d]imidazol-2-yl)methyl)-3-((S)-3-(2,4-dichlorophenyl)-1-hydroxypropan-2-yl)urea. 1-((1-Boc-1H-benzo[d]imidazol-2-yl)methyl)-3-((S)-3-(2,4-dichlorophenyl)-1-hydroxypropan-2-yl)urea was dissolved in 10 ml of DCM. To the solution, 3 ml of TFA was added dropwise. The solution was stirred for 40 min at room temperature. The reaction mixture was completely evaporated under vacuum to give 1-((1H-benzo[d]imidazol-2-yl)methyl)-3-((S)-3-(2,4-dichlorophenyl)-1-hydroxypropan-2-yl)urea (1935) LC/MS: (ESI) (M+H)$^+$=394.5. Compound 1935 (50 mg, 0.127 mmol) was dissolved in THF and Des-Martin reagent (0.15 mmol) was added. The mixture was stirred at room temperature overnight. The solvent was then removed under vacuum. The residue was dissolved in EtOAc (25 mL). The organic layer was washed with saturated NaHCO$_3$, brine, dried and concentrated under vacuum. Purification by chromatography afforded (S)-2-Fmoc-amino-3-(2,4-dichlorophenyl)-N-methoxy-N-methylpropanamide to give (4S)-1-((1H-benzo[d]imidazol-2-yl)methyl)-4-(2,4-dichlorobenzyl)-5-hydroxyimidazolidin-2-one (1934) LC/MS: (ESI) (M+H)$^+$=392.4. Compound 1934 was dissolved in formic acid and heated at 50° C. overnight to give 3-((1H-benzo[d]imidazol-2-yl)methyl)-5-(2,4-dichlorobenzyl)-1H-imidazol-2(3H)-one (1907). LC/MS: (ESI) (M+H)$^+$= 374.5.

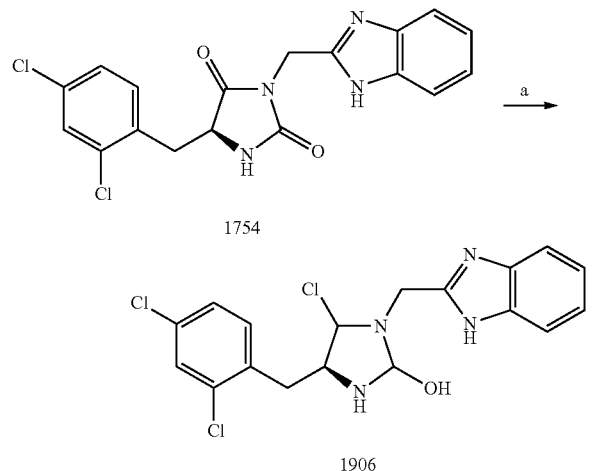

Scheme 69

1754

1906

Reagents and conditions (a) NaBH$_4$, EtOH

To a solution of compound 1754 (58 mg, 0.15 mmol) in ethanol (15 mL) was added NaBH$_4$ (1.5 mmol). The mixture was stirred at room temperature overnight. After most solvents were removed, EtOAc (25 mL) was added. The organic phase was washed with water, brine, dried over Na$_2$SO$_4$. After solvent was removed, the residue was chromatographed via silica gel, eluted with MeOH/DCM to give 1906 (5S)-3-((H-benzo[d]imidazol-2-yl)methyl)-5-(2,4-dichlorobenzyl)imidazolidine-2,4-diol, LC/MS: (ESI) (M+H)$^+$=395.5.

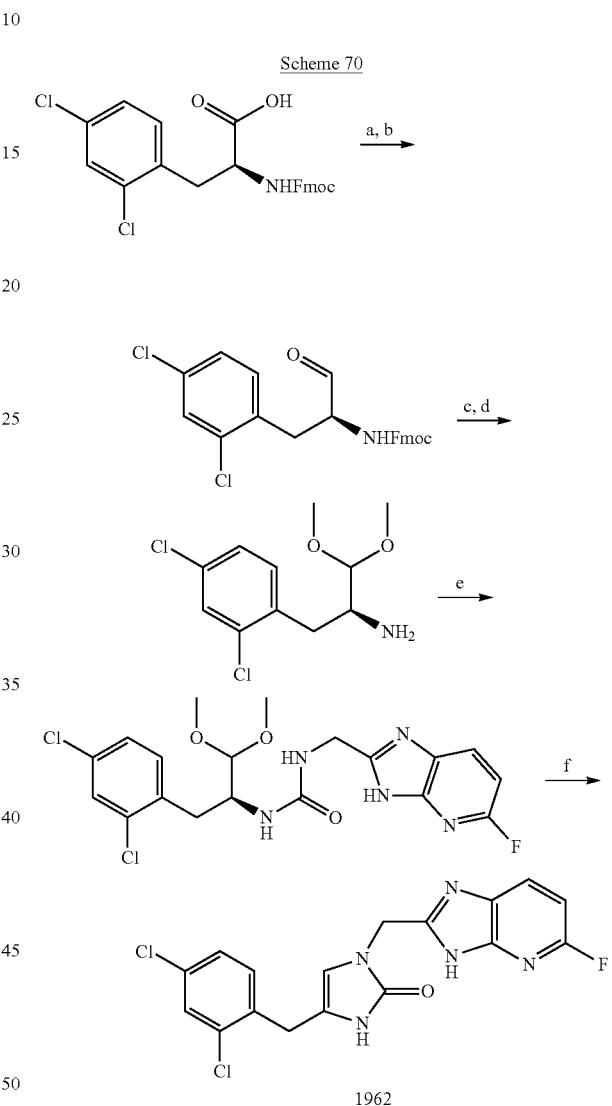

Scheme 70

1962

Reagents and conditions (a) HATU, methoxymethanamine, DMF (b) LiAlH$_4$, THF, 0° C.; (c) MeOH, HCl, µw, 80° C., 10 min; (d) DBU, ethyl acetate; (e) triphosgene, DIPEA, DCM, (5-fluoro-3H-imidazo[4,5-b]pyridin-2-yl)methanamine; (f) 2N HCl, 80° C., 10 min A solution of (S)-2-Fmoc-amino-3-(2,4-dichlorophenyl) propanoic acid (228 mg, 0.5 mmol), N-methoxymethanamine HCl (58 mg, 0.6 mmol), HATU (0.6 mmol) and DIPEA (1.2 mmol) in 5 ml of DMF was stirred at room temperature overnight. The solvent was then removed under vacuum. The residue was dissolved in EtOAc (25 mL). The organic layer was washed with brine (25 mL), dried and concentrated under vacuum. Purification by chromatography afforded (S)-2-Fmoc-amino-3-(2,4-dichlorophenyl)-N-methoxy-N-methyl propanamide. (S)-2-Fmoc-amino-3-(2, 4-dichlorophenyl)-N-methoxy-N-methylpropanamide (200 mg, 0.4 mmol) in anhydrous THF was slowly added LiAlH4 (0.5 mmol) at OC. The mixture was stirred for 1 h, then water was added slowly. The mixture was extracted into ether (3 times), and the combined organic layer was washed with brine, dried over Na$_2$SO$_4$. After solvent was removed, the residue was chromatographed via silica gel, eluted with MeOH/DCM to give (S)-2-Fmoc-amino-3-(2,4-dichlorophenyl)propanal. (S)-2-Fmoc-amino-3-(2,4-dichlorophenyl) propanal (150 mg, 0.34 mmol) was dissolved and concentrated HCl (30 μl) was added. The solution was microwave irradiated at 80° C. for 10 min. After the solvent was removed, the residue was dissolved in ethyl acetate and washed with saturated NaHCO$_3$. The organic layer was treated with DBU (0.35 mmol) for 10 min with stirring. The organic layer was washed with, water, brine, dried over Na$_2$SO$_4$. After solvent was removed, the residue was dissolved in anhydrous DCM. The solution was added DIPEA (0.4 mmol) and triphosgene (0.12 mmol at OC. The solution was stirred at OC for 1 h and room temperature for 2 h, then (5-fluoro-3H-imidazo[4,5-b]pyridin-2-yl)methanamine (0.35 mmol) was added. The reaction was performed at room temperature for 1 h. The solution was diluted with DCM and washed with water, brine, dried over Na$_2$SO$_4$. After solvent was removed, the residue was chromatographed via silica gel, eluted with MeOH/DCM to give 1-((S)-3-(2,4-dichlorophenyl)-1,1-dimethoxypropan-2-yl)-3-((5-fluoro-3H-imidazo[4,5-b]pyridin-2-yl)methyl)urea. 1-((S)-3-(2,4-dichlorophenyl)-1,1-dimethoxypropan-2-yl)-3-((5-fluoro-3H-imidazo[4,5-b]pyridin-2-yl)methyl)urea (50 mg, 0.11 mmol) was dissolved in 2 ml of acetone and 4 ml of 2N HCl. The solution was microwave irradiated at 80° C. for 10 min. After the solvent was removed, the residue was dissolved in ethyl acetate and washed with saturated NaHCO$_3$, brine, dried over Na$_2$SO$_4$. After solvent was removed, the residue was chromatographed via silica gel, eluted with MeOH/DCM to 5-(2,4-dichlorobenzyl)-3-((5-fluoro-3H-imidazo[4,5-b]pyridin-2-yl)methyl)-1H-imidazol-2(3H)-one (1962). $^1$H NMR (500 MHz, MeOD) δ 8.04 (t, J=7.8 Hz, 1H), 7.47 (s, 1H), 7.31 (m, 2H), 6.93 (dd, J=18.1, 8.8 Hz, 1H), 6.23 (s, 1H), 5.04 (s, 2H), 3.83 (s, 2H). LC/MS: (ESI) (M+H)$^+$=393.5.

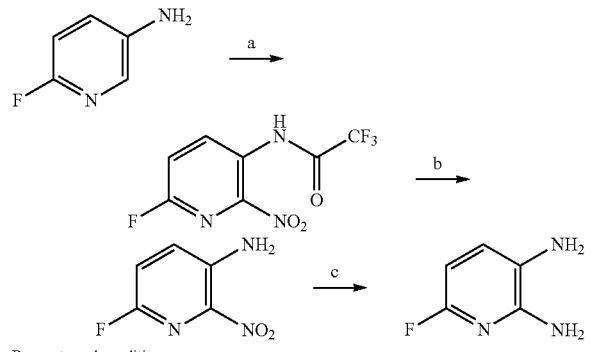

Scheme 71

Reagents and conditions
(a) CF$_3$COOH/(CF$_3$CO)$_2$O, NH$_4$NO$_3$;
(b) NH$_3$/MeOH; (c) H$_2$/Pd, MeOH Synthesis of 6-fluoropyridine-2,3-diamine. Trifluoroacetic anhydride (8.8 ml) was slowly added to a solution of 5-amino-2-fluoropyridine (1.0 g) dissolved in trifluoroacetic acid (15.2 ml) at 0° C. After stirred in 5 min, the clear solution was added ammonium nitrate (1.43 g) portionally. The mixture was stirred at 0° C. for 4 h. After solvents were removed, the residue was dissolved in EtOAc, washed with brine three times, dried over Na$_2$SO$_4$. The orange residue was purified via silica gel column with EtOAc/hexane elution to obtain 1.4 g of 2,2,2-trifluoro-N-(6-fluoro-2-nitropyridin-3-yl)acetamide in yellow oil. $^1$H NMR (500 MHz, MeOD) δ 8.60 (t, J=10.5 Hz, 1H), 7.61 (d, J=3.4 Hz, 1H).

Ammonia (7 N solution in methanol, 2.0 eq.) was slowly added to a solution of 2,2,2-trifluoro-N-(6-fluoro-2-nitropyridin-3-yl)acetamide (0.82 g) in 10 ml of methanol. After stirred at rt for overnight, the solvent was removed. The residue was purified via silica gel column (30-50% EtOAc in hexane) to afford the 6-fluoro-2-nitropyridin-3-amine as yellow solid. LC/MS: (ESI)(M+H)$^+$=159.2.

6-fluoro-2-nitropyridin-3-amine (157 mg, 1.0 mmol) was dissolved in 5 ml of MeOH and reduced with H$_2$ balloon in the presence of 0.2 eq of 10% Pd/C for 2 h at rt. The solution was filtered through a celite pad. After the solvent was removed, the residue was purified via silica gel column (30-50% EtOAc in hexane) to obtain 6-fluoropyridine-2,3-diamine as pink solid. $^1$H NMR (500 MHz, MeOD) δ 7.00 (dd, J=7.9, 7.2 Hz, 1H), 6.07 (dd, J=8.0, 2.2 Hz, 1H). LC/MS: (ESI) (M+H)$^+$=128.8.

Scheme 72

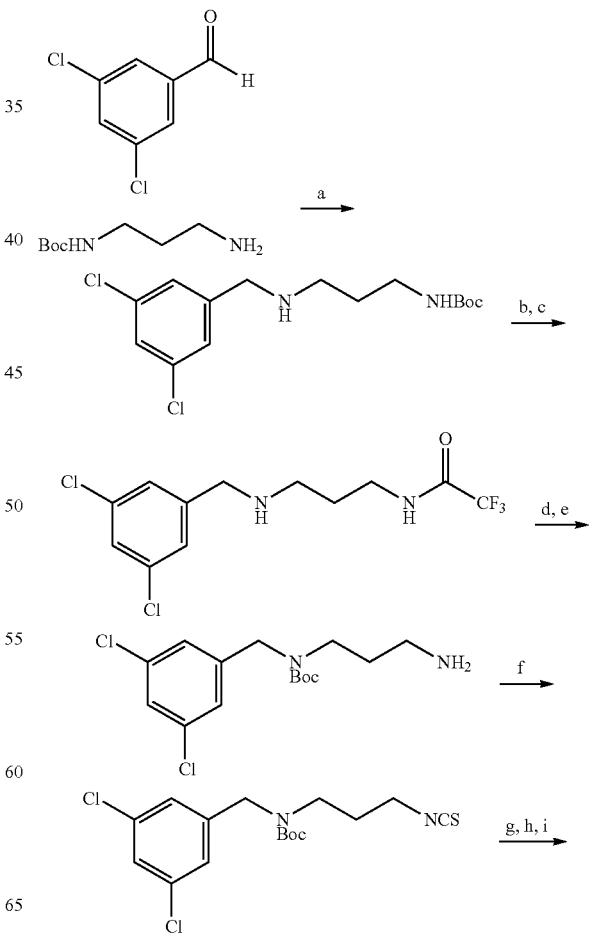

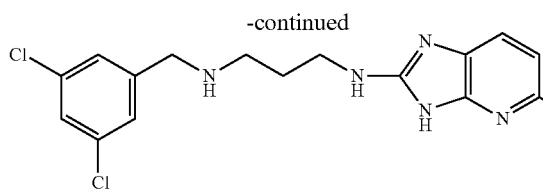

1614

Reagents and conditions
(a) MeOH, HOAc, NaBH₃CN; (b) TFA/DCM;
(c) ethyl 2,2,2-trifluoroacetate; (d) Boc₂O;
(e) NaOH, MeOH; (f) CS₂, Boc₂O;
(g) 6-fluoropyridine-2,3-diamine;
(h) DIC; (i) HCl, dioxane General Procedure 28 (1614, 1708, 1829, 1849, 1850):

Tert-butyl 3-aminopropylcarbamate (1.29 g, 7.42 mmol) was dissolved in 20 ml of MeOH, 1.0 ml of AcOH and 3,5-dichlorobenzaldehyde (1.3 g, 7.42 mmol) was added. After the mixture was stirred for 30 min, NaBH₃CN (14.8 mmol) was added. The mixture was stirred overnight and the solvent was removed under vacuum. The residue was dissolved in EtOAc (50 ml) and washed with sat. sodium bicarbonate and brine. The organic layer was dried over Na₂SO₄ and concentrated under vacuum. The residue was purified by flash column chromatography (DCM/MeOH) to give 1.6 g of tert-butyl 3-(3,5-dichlorobenzylamino)propylcarbamate. Tert-butyl 3-(3,5-dichlorobenzylamino)propylcarbamate (1.0 g, 3.0 mmol) was dissolved in DCM (20 ml) and TFA (10 ml) was added. The mixture was stirred at room temperature for 1 h and the solvent was removed completely in vacuum. The residue was added anhydrous DCM (50 ml) and treated with DIPEA to basic. The solution was added ethyl 2,2,2-trifluoroacetate (3.6 mmol) in 10 ml of DCM over 30 min at 0° C. The solution was stirred at room temperature overnight, following by adding Boc₂O (4.5 mmol) and DIPEA (4.5 mmol). The mixture was stirred at room temperature overnight, then washed water, and brine. It was then dried over anhydrous sodium sulfate and evaporated under vacuum. The residue was purified by flash column chromatography to afford tert-butyl 3-(2,2,2-trifluoroacetamido)propyl3,5-dichlorobenzylcarbamate. To the solution of tert-butyl 3-(2,2,2-trifluoroacetamido)propyl3,5-dichlorobenzylcarbamate (1.0 g, 2.33 mmol) in 20 ml of MeOH, NaOH (466 mg, 11.65 mmol) in 10 ml of water was added. The solution was stirred at room temperature overnight. After the solvent was removed, the residue was dissolved in ethyl acetate. The organic layer was washed water, and brine. It was then dried over anhydrous sodium sulfate and evaporated under vacuum. The residue was purified by flash column chromatography (MeOH/NH₄OH/DCM) to afford tert-butyl 3,5-dichlorobenzyl3-aminopropylcarbamate.

The synthetic procedure was based on the reference[10]. To the solution of tert-butyl 3,5-dichlorobenzyl-3-aminopropylcarbamate (0.71 g, 2.13 mmol) in 5 ml of anhydrous EtOH, 1.283 ml CS₂ (20.13 mmol) and DIPEA (2.13 mmol) were added. The solution was stirred at room temperature for 1 h. At 0° C., BOc₂O (2.024 mmol) in 1 ml of ethanol was added, following immediately adding DMAP (0.0426 mmol) in ethanol. The solution was stirred at 0° C. for 5 min, then room temperature for 2 h. After the solvent was removed, the residue was purified by flash column chromatography (MeOH/NH₄OH/DCM) to afford tert-butyl 3,5-dichlorobenzyl3-isothiocyanatopropylcarbamate in 84% yield. To the solution of tert-butyl 3,5-dichlorobenzyl3-isothiocyanatopropylcarbamate (0.733 g, 1.95 mmol) in 20 ml anhydrous acetonitrile was added 6-fluoropyridine-2,3-diamine (1.95 mmol). The mixture was refluxed for 20 h. After the solvent was removed, the residue was recrystallized in EtOAc/hexane twice to give tert-butyl 3,5-dichlorobenzyl3-(3-(2-amino-6-fluoropyridin-3-yl)thioureido) propylcarbamate. To solution of tert-butyl 3,5-dichlorobenzyl3-(3-(2-amino-6-fluoropyridin-3-yl)thioureido)propylcarbamate (487 mg 0.98 mmol) in 25 ml of anhydrous acetonitrile (warm to dissolve), DIC (19.6 mmol) was added. The solution was refluxed for 10 h. After cooling down, the white precipitate was collected by filtration to give tert-butyl 3,5-dichlorobenzyl3-(5-fluoro-3H-imidazo[4,5-b]pyridin-2-ylamino)propylcarbamate. To the solution of tert-butyl 3,5-dichlorobenzyl3-(5-fluoro-3H-imidazo[4,5-b]pyridin-2-ylamino) propylcarbamate (0.15 mmol) in dioxane (20 ml), excess 4 N HCl in dioxane was added. The precipitate was formed in 5 min. The mixture was continued to stir overnight. The solid was collected and washed with dioxane to obtain the white solid of 1614 in HCl form. ¹H NMR (500 MHz, MeOD) δ 7.87 (m, 1H), 7.59 (s, 2H), 7.56 (s, 1H), 6.97 (s, 1H), 4.27 (s, 2H), 3.59 (t, J=6.9 Hz, 2H), 3.24 (m, 2H), 2.16 (m, 2H). LC/MS: (ESI) 369.5 [M+H]⁺.

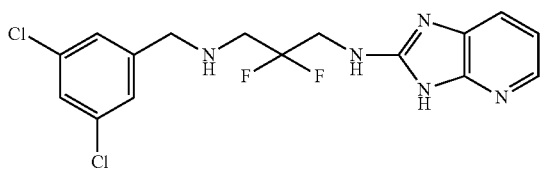

1708

1708 was synthesized using tert-butyl 3-amino-2,2-difluoropropylcarbamate and pyridine-2,3-diamine in General Procedure 28. ¹H NMR (500 MHz, MeOD) δ 7.96 (d, J=4.0 Hz, 1H), 7.49 (d, J=7.6 Hz, 1H), 7.28 (s, 2H), 7.25 (s, 1H), 6.99 (m, 1H), 3.93 (t, J=13.6 Hz, 2H), 3.81 (s, 2H), 2.95 (t, J=13.9 Hz, 2H). LC/MS: (ESI) 386.9 [M+H]⁺. LC/MS: (ESI) (M+H)⁺=387.6.

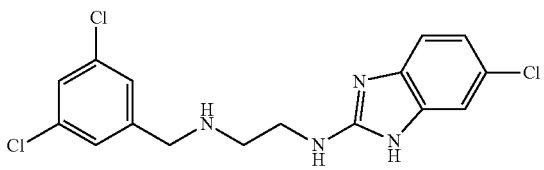

1829

1829 was synthesized using tert-butyl 2-aminoethylcarbamate and 4-chlorobenzene-1,2-diamine in General Procedure 28. LC/MS: (ESI) (M+H)⁺=370.5.

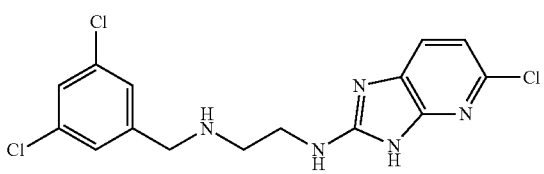

1849

1849 was synthesized using tert-butyl 2-aminoethylcarbamate and 6-chloropyridine-2,3-diamine in General Procedure 28. LC/MS: (ESI) (M+H)$^+$=371.5.

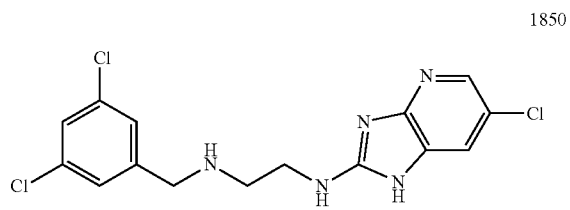 [SMILES: Clc1cc(Cl)cc(CNCCNc2nc3ncc(Cl)cc3[nH]2)c1]

1850

1850 was synthesized using tert-butyl 2-aminoethylcarbamate and 5-chloropyridine-2,3-diamine in General Procedure 28. LC/MS: (ESI) (M+H)$^+$=371.5.

Scheme 73

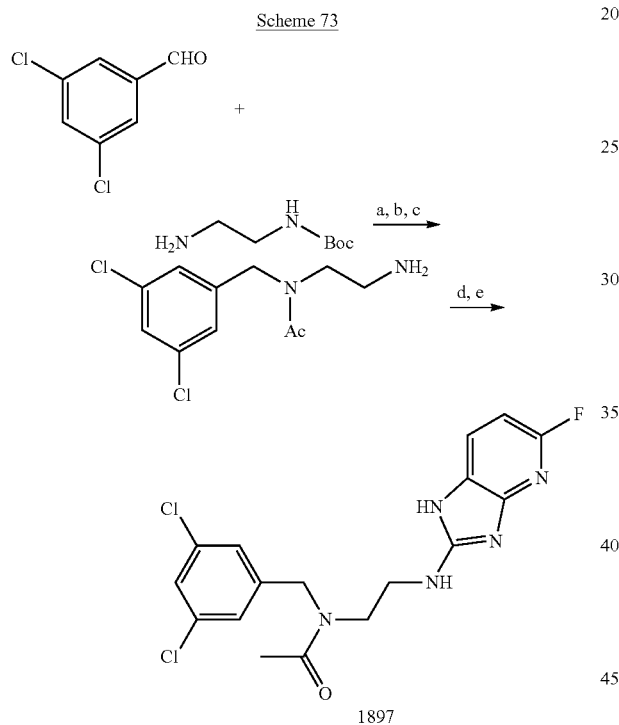

1897

Reagents and conditions: (a) NaBH$_3$CN, MeOH/AcOH, r.t., overnight; (b) Ac$_2$O, DIPEA, DCM, r.t., 2 h; (c) TFA, DCM, r.t., overnight; (d) CS$_2$, Boc$_2$O; then 6-fluoropyridine-2,3-diamine; (e) DIC, reflux, overnight.

3,5-dichlorobenzaldehyde (1 eq) and tert-butyl (2-aminoethyl)carbamate (1 eq) were dissolved in MeOH, AcOH (2 eq) and NaBH$_3$CN (2 eq) were added. The mixture was stirred overnight and the solvent was removed under vacuum. The residue was dissolved in EtOAc and washed with sat. sodium bicarbonate and brine. The organic layer was dried over Na$_2$SO$_4$ and concentrated under vacuum. The residue was purified by flash column chromatography (DCM/MeOH) to give tert-butyl (2-((3,5-dichlorobenzyl)amino) ethyl)carbamate.

To a solution of tert-butyl (2-((3,5-dichlorobenzyl)amino) ethyl)carbamate (1 eq) in DCM was slowly added DIPEA (1.5 eq) and acetic anhydride (1.2 eq) in DCM at 0° C. The mixture was stirred overnight and then diluted with DCM. The organic phase was washed with water, brine, dried over Na$_2$SO$_4$. After solvent was removed, the residue was chromatographed via silica gel, eluted with EA/hexane to give tert-butyl (2-(N-(3,5-dichlorobenzyl)acetamido)ethyl)carbamate.

Tert-butyl (2-(N-(3,5-dichlorobenzyl)acetamido)ethyl) carbamate was dissolved in DCM, and TFA (5 eq) was added, the mixture was stirred at r.t. over night. The solvent was removed under vacuum to get the deprotedted intermediate N-(2-aminoethyl)-N-(3,5-dichlorobenzyl)acetamide which was used for next step without further purification.

Steps d and e were conducted following General Procedures 28 to get the final product N-(3,5-dichlorobenzyl)-N-(2-((5-fluoro-1H-imidazo[4,5-b]pyridin-2-yl)amino)ethyl) acetamide (1897) LC/MS: (ESI) (M+H)$^+$=397.2.

Scheme 74

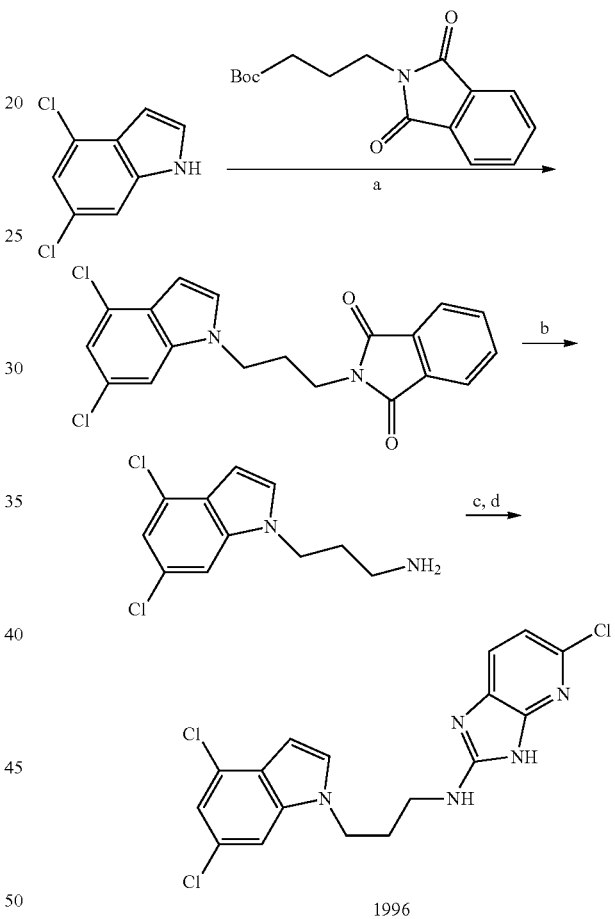

1996

Reagents and conditions: (a) K$_2$CO$_3$, DMF, 60° C., 3 h; (b) hydrazine, MeOH, reflux, 3 h; (c) CS$_2$, Boc$_2$O; then 6-fluoropyridine-2,3-diamine; (d) DIC, reflux, overnight.

4,6-dichloro-1H-indole (1 eq) was dissolved in DMF, K$_2$CO$_3$ (3 eq) and 2-(3-bromopropyl)isoindoline-1,3-dione (1.1 eq) was added and the mixture stirred at 60° C. for 3 h. Solvent was removed and extracted with DCM. The organic extract was washed with water, brine and dried over Na$_2$SO$_4$. The residue was purified via flash chromatography on silica gel to obtain 2-(3-(4,6-dichloro-1H-indol-1-yl) propyl)isoindoline-1,3-dione.

2-(3-(4,6-dichloro-1H-indol-1-yl)propyl)isoindoline-1,3-dione was dissolved in MeOH, hydrazine (3 eq) was added and the mixture refluxed for 3 h. Solvent was removed and the residue was purified via flash chromatography on silica gel to get 3-(4,6-dichloro-1H-indol-1-yl)propan-1-amine.

3-(4,6-dichloro-1H-indol-1-yl)propan-1-amine reacted with 6-chloropyridine-2,3-diamine following the general procedure for making benzimidazole ring to get compound 1996. LC/MS: (ESI) (M+H)+=395.0

Scheme 75

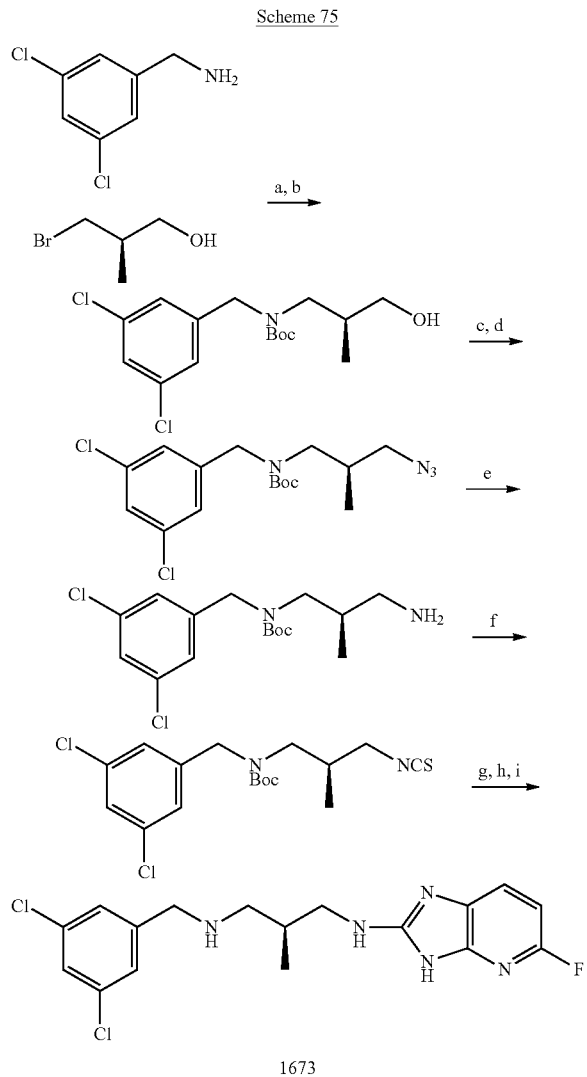

1673

Reagents and conditions
(a) KI, EtOH; (b) Boc₂O;
(c) CH₃SO₂Cl; (d) NaN₃;
(e) PPh₃/H₂O; (f) CS₂, Boc₂O;
(g) 6-fluoropyridine-2,3-diamine;
(h) DIC, acetonitrile; (i) HCl, dioxane General Procedures 29(1673, 1655)

A mixture of 3,5-dichlorobenzylamine (1.5 mmol) and (R)-(−)-3-bromo-2-methyl-1-propanol (0.5 mmol), DIPEA (0.5 mmol) and trace amount of KI in ethanol (1.0 ml) was microwave irradiated at 90° C. for 30 min. The solution was added (Boc)₂O (1.25 mmol) and DIPEA (1.5 mmol) in 2 ml of acetonitrile at room temperature overnight. After solvents were removed, the residues were dissolved in ethyl acetate, washed with water, brine and dried over Na₂SO₄. The organic extract was purified via flash chromatography on silica gel to obtain (S)-3-(N-(3,5-dichlorobenzyl)-N-Boc-amino)-2-methylpropan-1-ol in 50% yield. m/z: 371.0 ([M+Na]+

The solution of(S)-3-(N-(3,5-dichlorobenzyl)-N-Boc-amino)-2-methylpropan-1-ol (0.25 mmol) in 20 ml of dry DCM at −10° C. was added DIPEA (0.45 mmol) and methanesulfonyl chloride (0.38 mmol). The mixture was stirred at −10° C. for 30 min. After solvent was removed, the residue was dissolved in 5 ml of DMF and NaN₃ (0.50 mmol) was added. The mixture was stirred at 40-45° C. overnight. Solvent was removed and extracted with ethyl acetate. The organic extract was washed with water, brine and dried over Na₂SO₄. The residue was purified via flash chromatography on silica gel to obtain tert-butyl 3,5-dichlorobenzyl(S)-3-azido-2-methylpropylcarbamate. ¹H NMR (500 MHz, CDCl₃) δ 7.28 (m, 1H), 7.10 (s, 2H), 4.37 (s, 2H), 3.24 (m, 4H), 2.04 (br, 1H), 1.48 (m, 9H), 0.97 (d, J=6.7 Hz, 3H). m/z: 395.8 [M+Na]−

A mixture of tert-butyl 3,5-dichlorobenzyl(S)-3-azido-2-methylpropylcarbamate (0.083 mmol), PPh₃ (0.25 mmol) in 1 ml of THF and 15 µl of water was stirred at room temperature overnight. Purification was performed via flash chromatography on silica gel to obtain (R)—N1-(3,5-dichlorobenzyl)-N1-Boc-2-methylpropane-1,3-diamine. m/z: 347.8 [M+H]+

Following the general synthetic procedure of 1614, compound 1673 was synthesized using (R)—N1-(3,5-dichlorobenzyl)-N1-Boc-2-methylpropane-1,3-diamine. ¹H NMR (500 MHz, MeOD) δ 7.93-7.83 (m, 1H), 7.64 (s, 2H), 7.56 (s, 1H), 6.97 (d, J=8.4 Hz, 1H), 4.30 (q, J=13.3 Hz, 2H), 3.58-3.38 (m, 2H), 3.28 (m, 1H), 3.10-2.96 (m, 1H), 2.42 (s, 1H), 1.20 (d, J=6.7 Hz, 3H). m/z: 383.5 ([M+H]+.

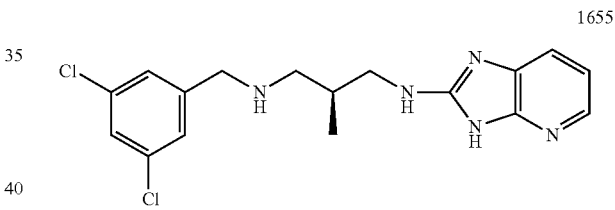

1655

1655 was synthesized using pyridine-2,3-diamine in General Procedure 29. ¹H NMR (500 MHz, MeOD) δ 8.03 (m, 1H), 7.56 (s, 2H), 7.46 (s, 1H), 7.32 (m, 1H), 7.00 (m, 1H), 4.59 (m, 2H), 3.63 (m, 2H), 3.40 (m, 2H, 2.20 (m, 1H), 1.28 (m 3H). LC/MS: (ESI) 365.5 [M+H]+.

Scheme 76

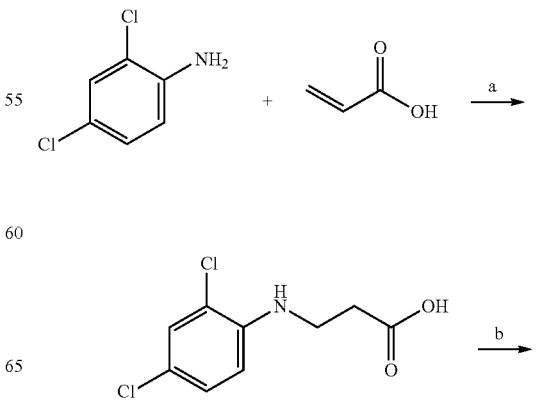

-continued

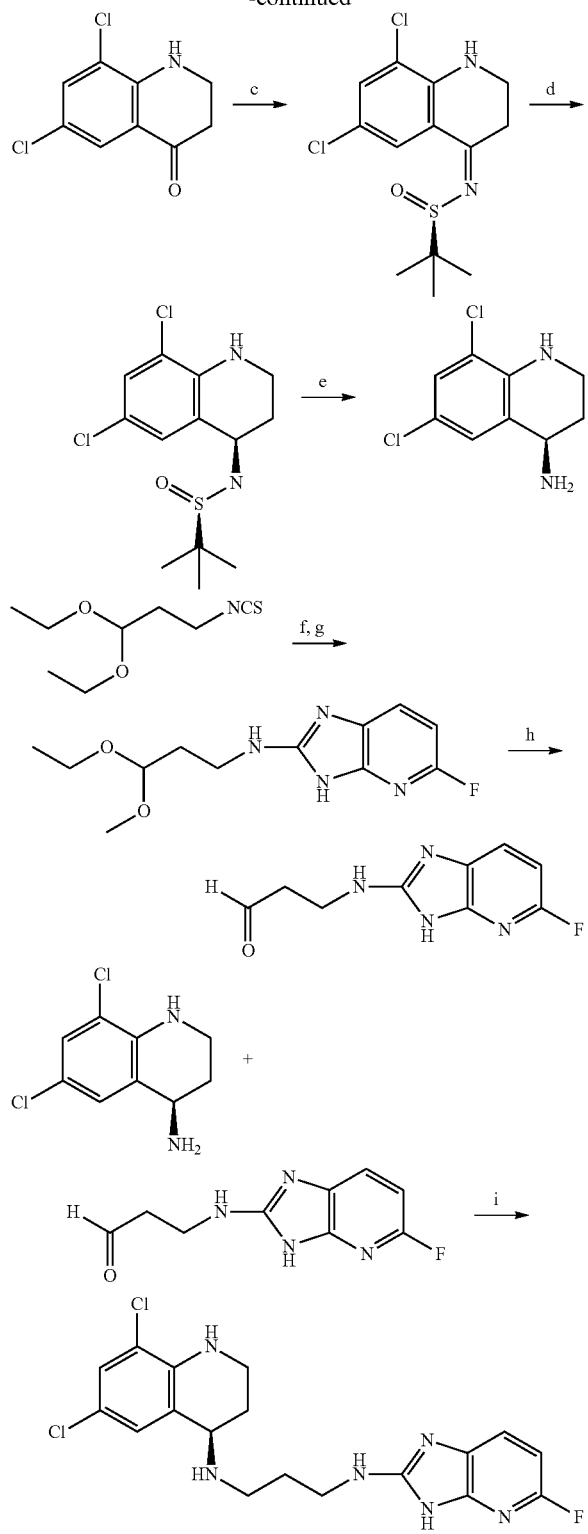

Reagents and conditions
(a) 100° C., 2 h; (b) PPA, CH₃SO₃H;
(c) (R)-(+)-tert-butylsulfinamide, Ti(OEt)₄;
(d) NaBH₄; (e) HCl, dioxane;
(f) 6-fluoropyridine-2,3-diamine, acetonitrile, heating;
(g) DIC, acetonitrile, heating; (h) HCl, acetone;
(i) MeOH, HOAc, NaBH₃CN A mixture of 2,4-dichloroaniline (1.032 g) and acrylic acid (2 ml) was heated to 100° C. for 2 h. After the reaction was completed, the reaction mixture was slowly added into 500 ml of water with strongly stirring. The solid was collected by filtration and dissolved in ethyl acetate. The organic layer was washed with water three time, brine and dried over Na₂SO₄. After solvent was removed, 3-(2,4-dichlorophenylamino)propanoic acid was obtained and directly used.

A mixture of 3-((2,4-dichlorophenyl)amino)propanoic acid (1.0 mmol) in polyphosphoric acid (PPA) (3 mL) and CH₃SO₃H (1.0 mL) was mechanically stirred at 100° C. for 10 h. After cooling to 0° C., ice-water was added into the reaction mixture. The aqueous phase was basified to pH=12 with solid NaOH at 0° C. The aqueous layer was extracted with ethyl acetate. The organic layer were dried over anhydrous Na₂SO₄, filtered, and evaporated under reduced pressure to give a crude product which was purified by column chromatography (petroleum ether: ethyl acetate=5:1) to give 6,8-dichloro-2,3-dihydroquinolin-4(1H)-one as yellow solid. m/z: 217.4 ([M+H]⁺

To a stirred solution of 6,8-dichloro-2,3-dihydroquinolin-4(1H)-one (0.3 mmol) in DCE (5 mL) was added Ti(OEt)₄ (2.0 eq.), and (R)-(+)-tert-butylsulfinamide (0.33 mmol then heated to 80° C. for 12 hours[11]. The reaction mixture was cooled and concentrated under vacuum, diluted with EtOAc (80 mL) and brine (100 mL) then the mixture was filtered through a pad of celite. The organic phase was separated, dried (Na₂SO₄) and concentrated under vacuum. The residue was subjected to flash silica chromatography, gradient elution (0 to 50%) hexane/ethyl acetate to furnish N—((R)-(+)-tert-butylsulfyl)-6,8-dichloro-2,3-dihydroquinolin-4(1H)-imine.

A solution of N—((R)-(+)-tert-butylsulfyl)-6,8-dichloro-2,3-dihydroquinolin-4(1H)-imine (0.1 mmol) in THF (2 mL) and water (20 µL) was cooled in an CH₃COCH₃/dry ice bath to −50° C. Upon equilibration to bath temperature, solid sodium borohydride (4.0 eq.) was added[12]. The resulting mixture was allowed to warm to rt over 4 h. The solvent was evaporated and the residue taken up in DCM, dried over anhydrous MgSO₄, the insoluble material was removed via filtration and the solvent was evaporated to afford colorless oil. The residue was purified by chromatography on silica using ethyl acetate/hexane as the eluent to give (R)—N-(tert-butylsulfyl)-6,8-dichloro-1,2,3,4-tetrahydroquinolin-4-amine. H¹ NMR (500 MHz, CDCl₃) δ 7.32 (m, 1H), 4.57 (br, 1H), 4.42-4.46 (m, 1H), 4.30-4.35 (m, 1H), 3.34 (s, 1H), 2.13-2.17 (m, 2H), 1.26 (s, 9H). m/z: 323.0 ([M+H]⁺

To a solution of (R)—N-(tert-butylsulfyl)-6,8-dichloro-1,2,3,4-tetrahydroquinolin-4-amine (0.05 mmol) in methanol (2 mL) was added 4.0 M of hydrochloric acid in 1,4-dioxane (5.0 eq.). The reaction mixture was stirred at rt for 2 h. The reaction mixture was concentrated to give (R)-6,8-dichloro-1,2,3,4-tetrahydroquinolin-4-amine and used without further purification.

A solution of (R)-6,8-dichloro-1,2,3,4-tetrahydroquinolin-4-amine HCl salt (0.1 mmol) in 5 ml of methanol was added DIPEA (0.1 mmol), 0.15 ml of HOAc and 3-(5-fluoro-3H-imidazo[4,5-b]pyridin-2-ylamino)propanal (0.12 mmol). The mixture was stirred at room temperature for 30 min, NaBH₃CN (0.2 mmol) was added. The reaction mixture was stirred at 50° C. for 2 days. After solvent was removed, the residue was chromatographed via silica gel, eluted with MeOH/DCM and further purified by using preparative HPLC to give compound 1717 in TFA salt. Conversion of TFA salt to HCl was performed via adding HCl in methanol and removing solvent to give a white solid.

m/z: $^1$H NMR (500 MHz, MeOD) δ 7.43 (m, 1H), 7.15 (m, 2H), 6.48 (d, J=8.2 Hz, 1H), 3.92 (m, 1H), 3.47 (m, 4H), 2.85 (m, 2H), 2.20 (d, J=17.5 Hz, 1H), 1.97 (m, 3H). LC/MS: (ESI) 410.4 [M+H]$^+$.

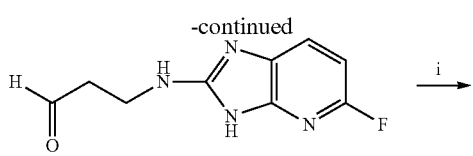

Scheme 77

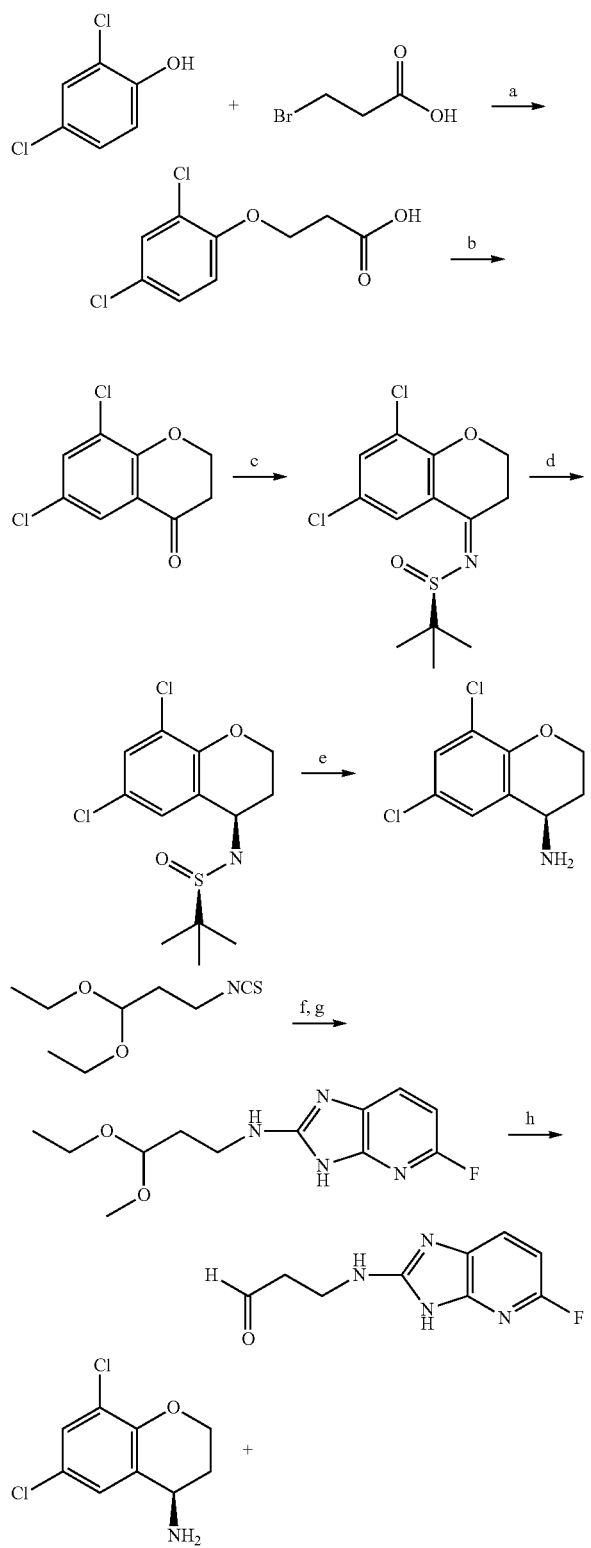

1709

Reagents and conditions
(a) NaOH, H$_2$O 100° C.; (b) oxalyl chloride, AlCl$_3$;
(c) (R)-(+)-tert-butylsulfinamide, Ti(OEt)$_4$;
(d) NaBH$_4$; (e) HCl, dioxane;
(f) 6-fluoropyridine-2,3-diamine, acetonitrile, heating;
(g) DIC, acetonitrile, heating; (h) HCl, acetone;
(i) MeOH, HOAc, NaBH$_3$CN A solution of 2,4-dichlorophenol (10 mmol) and NaOH (10 mmol) in 20 mL of water was heated at 100° C. for 20 min. A solution of 3-bromopropionic acid (20 mmol) and NaOH (20 mmol) in 10 ml of water was added slowly to the above hot solution. The mixture was heated at 100° C. overnight, cooling to room temperature. The reaction mixture was made acidic with concentrated HC. The mixture was extracted into ether (3 times), and the combined organic layer was extracted with saturated NaHCO$_3$. The water layer was made acidic and extracted with ether (3 times). The combined organic layer was washed with brine, dried over Na$_2$SO$_4$. After solvent was removed, the residue was chromatographed via silica gel, eluted with MeOH/DCM to give 3-(2,4-dichlorophenoxy)propanoic acid in white solid.

Oxalyl chloride (5.2 mmol)) was added to the solution of 3-(2,4-dichlorophenoxy)propanoic acid (2.6 mmol) in 20 mL of anhydrous DCM followed by a drop of DMF. After 1.5 hours, the solution was cooled in an ice-water bath. AlCl$_3$ (2.86 mmol) was added and the dark red solution was allowed to slowly reach room temperature and stirred overnight. The mixture was poured into ice and the organic layer was separated. The aqueous layer was extracted with ethyl acetate twice. The combined organic layers were washed with 1 N NaOH, brine, dried over Na$_2$SO$_4$ and concentrated. Flash chromatography of this residue eluted with hexane and EtOAc provided 6,8-dichloro-2,3-dihydrochromen-4-one in white solid. m/z: 218.2 ([M+H]$^+$ Following the synthetic procedure of compound 1717, compound 1709 was synthesized using (R)-6,8-dichloro-2,3-dihydrochromen-4-one. $^1$H NMR (500 MHz, MeOD) δ 7.91 (m, 1H), 7.62 (d, J=1.9 Hz, 1H), 7.54 (d, J=1.8 Hz, 1H), 7.00 (d, J=8.3 Hz, 1H), 4.68 (m, 1H), 4.51 (m, 2H), 3.66 (m, 2H), 3.45 (m, 2H), 2.54 (m, 1H), 2.51 (m, 1H), 2.25 (m, 2H). LC/MS: (ESI) 411.3 [M+H]$^+$.

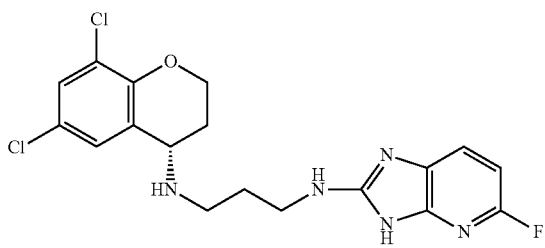

1711

Following the synthetic procedure of compound 1717, compound 1711 was synthesized using (S)-6,8-dichloro-2,3-dihydrochromen-4-one produced by L-Selectride[12]. LC/MS: (ESI) 411.3 [M+H]+.

Scheme 78

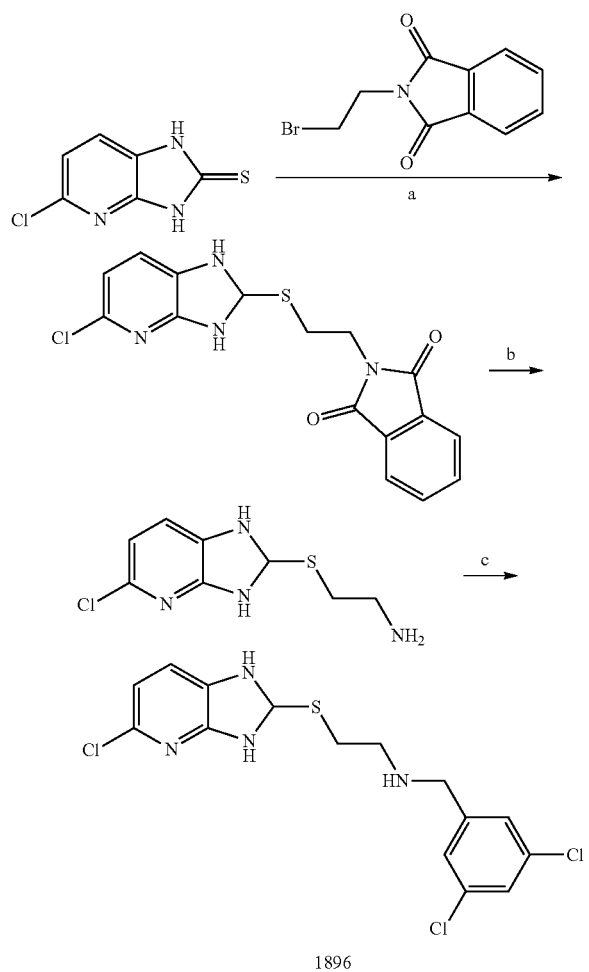

1896

Reagents and conditions:
(a) K₂CO₃, CH₃CN, r.t. overnight;
(b) H₂NNH₂, CH₃OH, MW, 70° C., 20 min,
(c) 3,5-dichlorobenzaldehyde, MeOH, NaBH₃CN.

5-chloro-1H-imidazo[4,5-b]pyridine-2(3H)-thione (1 eq), 2-(2-bromoethyl)isoindoline-1,3-dione (1 eq) were dissolved in CH₃CN, K₂CO₃ (4 eq) was added and the resulting mixture was stirred at room temperature over night. After the mixture was extracted with DCM, washed with brine, concentrated under vacuum and purified via flash column chromatography (10% MeOH in DCM) to yield the intermediate 2-(2-((5-chloro-1H-imidazo[4,5-b]pyridin-2-yl)thio)ethyl)isoindoline-1,3-dione.

2-(2-((5-chloro-1H-imidazo[4,5-b]pyridin-2-yl)thio) ethyl)isoindoline-1,3-dione was dissolved in MeOH, hydrazine (2 eq) was added, the mixture was then microwave irradiated at 70° C. for 20 min. The solvent was evaporated off and residue was purified via flash column chromatography directly eluting with 20% MeOH in DCM to yield the deprotected intermediate.

2-((5-chloro-1H-imidazo[4,5-b]pyridin-2-yl)thio) ethanamine was dissolved in MeOH, 3,5-Dichlorobenzaldehyde (1.1 equiv) was added, then AcOH was added (2 eq). After the mixture was stirred for 30 min, NaBH₃CN (2 equiv) was added. The mixture was stirred overnight and the solvent was removed under vacuum. The residue was dissolved in DCM and washed with sat. sodium bicarbonate and brine. The organic layer was dried over Na₂SO₄ and concentrated under vacuum. The residue was purified by flash column chromatography (DCM/MeOH), yielding compound 1896 as white solid. LC/MS: (ESI) 388.8 [M+H]+.

Scheme 79

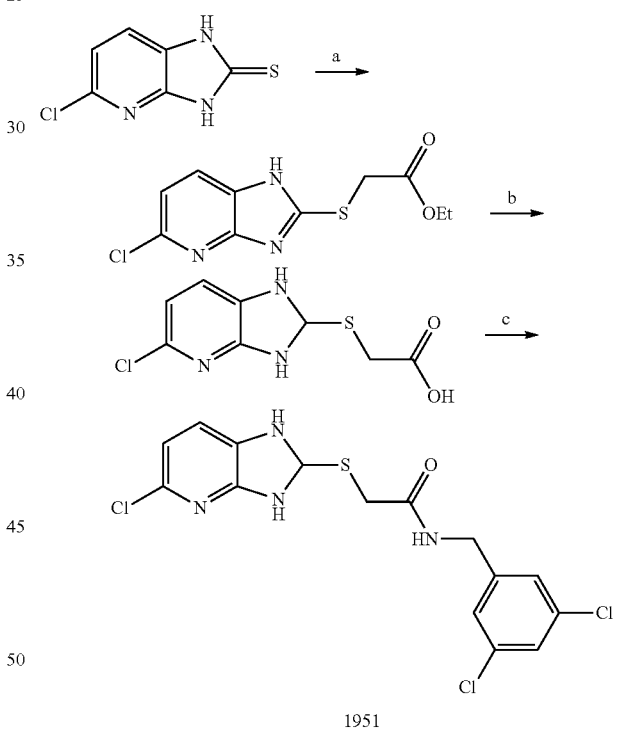

1951

Reagents and conditions:
(a) ethyl 2-bromoacetate, K₂CO₃, CH₃CN, r.t. overnight;
(b) LiOH, CH₃OH/H₂O, r.t. overnight,
(c) (3,5-dichlorophenyl)methanamine, HATU, DIPEA, DMF, r.t. 3 h.

5-chloro-1H-imidazo[4,5-b]pyridine-2(3H)-thione (1 eq) was dissolved in CH₃CN, K₂CO₃ (4 eq) was added and the resulting mixture was stirred at r.t. for 10 min. Ethyl 2-bromoacetate (1 eq) dissolved in CH₃CN was added dropwise. After the mixture was stirred at r.t. overnight, the solvent was evaporated off under reduced pressure. The residue was extracted with DCM, washed with brine, concentrated under vacuum to produce the product ethyl 2-((5-chloro-1H-imidazo[4,5-b]pyridin-2-yl)thio)acetate which was used for the next step without further purification.

The ethyl ester group of intermediate ethyl 2-((5-chloro-1H-imidazo[4,5-b]pyridin-2-yl)thio)acetate was hydrolyzed following the procedure of step b in Scheme 2 to get the free acid and used for the next step without purification.

2-((5-chloro-1H-imidazo[4,5-b]pyridin-2-yl)thio)acetic acid (1 eq), DIPEA (3 eq), (3,5-dichlorophenyl)methanamine (2 eq) were dissolved in DMF, then HBTU (2 eq) was added, the resulting mixture was stirred at r.t. for 3 h. The solvent was removed under vacuum and the residue was dissolved in DCM and washed with sat. sodium bicarbonate and brine. The organic layer was dried over $Na_2SO_4$ and concentrated under vacuum. The residue was purified by flash column chromatography (DCM/MeOH), yielding compound 1951. m/z: 402.8 ([M+H]$^+$ HOBt (1.5 eq), DIPEA (2.0 mmol), (3,5-dichlorophenyl)methanamine (1 eq) were added. The solution was stirred at room temperature overnight and then removed solvent under vacuum. The residue was dissolved in DCM. The organic layer was washed with water, brine (25 mL), dried and concentrated under vacuum. The residue was chromatographed to give 2-((5-chloro-3H-imidazo[4,5-b]pyridin-2-yl)amino)-N-(3,5-dichlorobenzyl)acetamide (1970). LC/MS: (ESI) (M+H)$^+$=385.5.

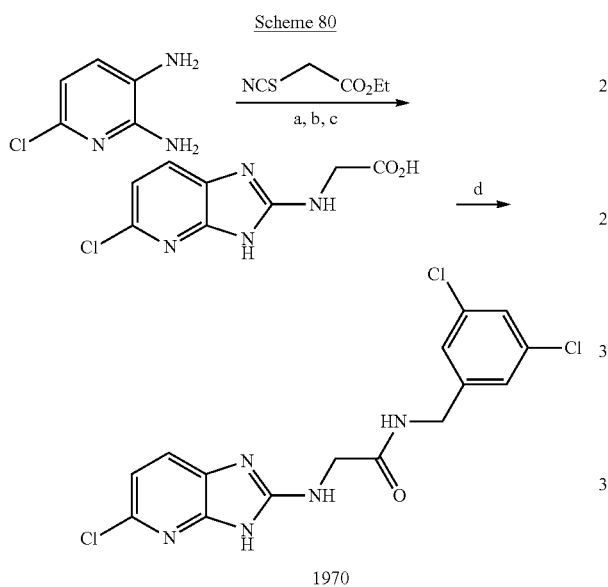

1970

Reagents and conditions:
(a) $CH_3CN$, reflux, overnight;
(b) HgO, S, EtOH, reflux, overnight;
(c) LiOH, MeOH/$H_2O$, r.t., 3 h;
(d) (3,5-dichlorophenyl)methanamine, EDC, HOBt, DIPEA, DMF.

6-chloropyridine-2,3-diamine (1 eq), ethyl 2-thiocyanatoacetate (1 eq) in $CH_3CN$ was refluxed over night. The solvent was removed under vacuum and the residue was dissolved in DCM and washed with brine. The organic layer was dried over $Na_2SO_4$ and concentrated under vacuum. The residue was purified by flash column chromatography (DCM/MeOH), yielding ethyl 2-(3-(2-amino-6-chloropyridin-3-yl)ureido)acetate.

To solution of ethyl 2-(3-(2-amino-6-chloropyridin-3-yl)ureido)acetate in EtOH, HgO (2 ep) and cat. S were added. The solution was refluxed overnight. The reaction mixture filtered through celite, washed with MeOH. The filtrate was collected, dried, purified by flash column chromatography (DCM/MeOH), yielding ethyl 2-((5-chloro-3H-imidazo[4,5-b]pyridin-2-yl)amino)acetate.

LiOH.$H_2O$ (3 eq) was added to the solution of ethyl 2-((5-chloro-3H-imidazo[4,5-b]pyridin-2-yl)amino)acetate in $CH_3OH$/$H_2O$ ($CH_3OH$:$H_2$=3:1). The reaction mixture was stirred at r.t. overnight. The solvent was evaporated under reduced pressure, the residue was used for next step without further purification.

2-((5-chloro-3H-imidazo[4,5-b]pyridin-2-yl)amino)acetic acid (1 eq) was dissolved in DMF and EDC (1.5 eq),

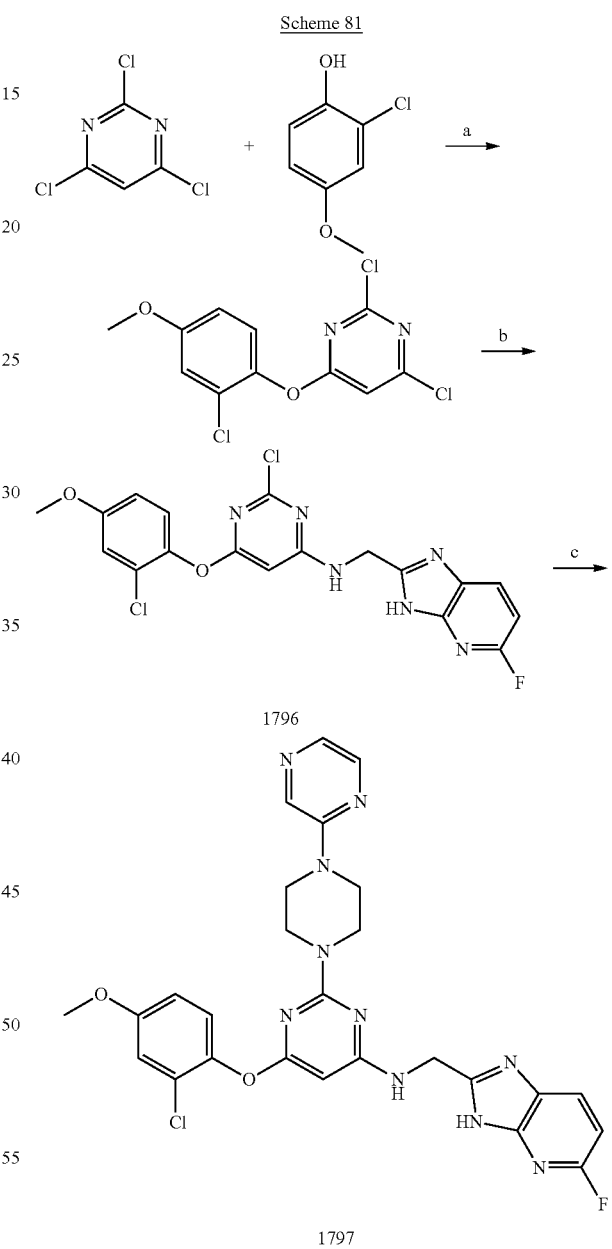

Reagents and conditions:
(a) acetone, NaOH, 0° C.;
(b) DMF, (5-fluoro-3H-imidazo[4,5-b]pyridin-2-yl)methanamine, 110° C., 30 min; (c) DMF, 3-(piperazin-1-yl)pyrazine, 110° C., 15 min Compound 1796 was synthesized according to the reference[13]. To a solution of 2,4,6-trichloropyrimidine (76 m g, 0.42 mmoles) in 2 mL of acetone at 0° C., was slowly added a solution of 2-chloro-4-methoxyphenoxide (0.46 mmoles)

and stirred at rt for 3 hours. After the solvent was removed, the residue was extracted with ethyl acetate. The organic layer was washed with water, brine (25 mL), dried and concentrated under vacuum. The residue was chromatographed to give 4-(2-chloro-4-methoxyphenoxy)-2,6-dichloropyrimidine. The solution of 4-(2-chloro-4-methoxyphenoxy)-2,6-dichloropyrimidine (0.2 mmol), (5-fluoro-3H-imidazo[4,5-b]pyridin-2-yl)methanamine (0.24 mmol) and DIPEA (0.4 mmol) in 1 ml of DMF was microwave irradiated at 110° C. for 30 min. After the solvent was removed, the residue was extracted with ethyl acetate. The organic layer was washed with water, brine (25 mL), dried and concentrated under vacuum. The residue was chromatographed to give 6-(2-chloro-4-methoxyphenoxy)-2-chloro-N-((5-fluoro-3H-imidazo[4,5-b]pyridin-2-yl)methyl)pyrimidin-4-amine (1796). LC/MS: (ESI) (M+H)$^+$=436.4.

To a solution of 6-(2-chloro-4-methoxyphenoxy)-2-chloro-N-((5-fluoro-3H-imidazo[4,5-b]pyridin-2-yl)methyl)pyrimidin-4-amine (0.1 mmoles), 2-(piperazin-1-yl)pyrazine (0.2 mmol) and DIPEA (0.2 mmol) in 1 ml of DMF was microwave irradiated at 110° C. for 15 min. After the solvent was removed, the residue was extracted with ethyl acetate. The organic layer was washed with water, brine (25 mL), dried and concentrated under vacuum. The residue was chromatographed to 6-(2-chloro-4-methoxyphenoxy)-N-((5-fluoro-3H-imidazo[4,5-b]pyridin-2-yl)methyl)-2-(4-(pyrazin-2-yl)piperazin-1-yl)pyrimidin-4-amine (1797). LC/MS: (ESI) (M+H)$^+$=564.1.

Scheme 82

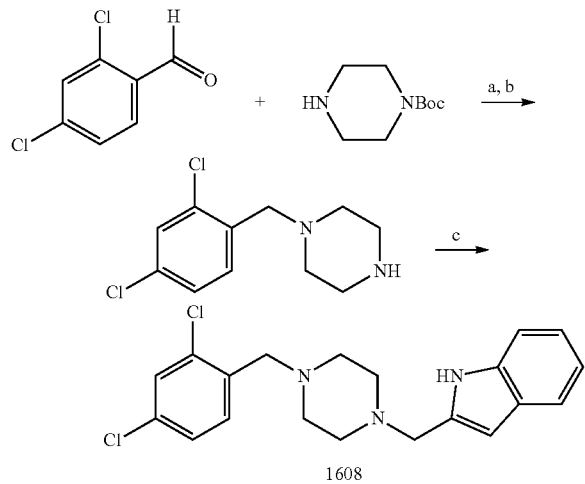

1608

Reagents and conditions:
(a) MeOH, HOAc, NaBH$_3$CN;
(b) TFA/DCM;
(c) MeOH, HOAc, NaBH$_3$CN, indole-3-carboxaldehyde 1-Boc-piperazine (50 mg, 0.269 mmol) was dissolved in 2 ml of MeOH, 0.1 ml of AcOH and 2,4-dichlorobenzaldehyde (47 mg, 0.269 mmol) was added. After the mixture was stirred for 30 min, NaBH$_3$CN (0.54 mmol) was added. The mixture was stirred overnight and the solvent was removed under vacuum. The residue was dissolved in EtOAc (50 ml) and washed with sat. sodium bicarbonate and brine. The organic layer was dried over Na$_2$SO$_4$ and concentrated under vacuum. The residue was purified by flash column chromatography (DCM/MeOH) to give 1-(2,4-dichlorobenzyl)-4-Boc-piperazine. 1-(2,4-dichlorobenzyl)-4-Boc-piperazine (60 mg, 0.174 mmol) was dissolved in DCM (4 ml) and TFA (2 ml) was added. The mixture was stirred at room temperature for 1 h and the solvent was removed completely in vacuum and the residue was co-distilled 2× with methylene chloride. The residue was dissolved in 3 ml MeOH, neutralized with DIPEA, and 0.15 ml AcOH, indole-3-carboxaldehyde (1.1 equiv) were added. After the mixture was stirred for 30 min, NaBH$_3$CN (2 equiv) was added. The mixture was stirred overnight and the solvent was removed under vacuum. The residue was dissolved in EtOAc (50 ml) and washed with sat. sodium bicarbonate and brine. The organic layer was dried over Na$_2$SO$_4$ and concentrated under vacuum. The residue was purified by flash column chromatography (DCM/MeOH), yielding 2-((4-(2,4-dichlorobenzyl)piperazin-1-yl)methyl)-1H-indole (1608). LC/MS: (ESI) (M+H)$^+$=375.5.

Scheme 83

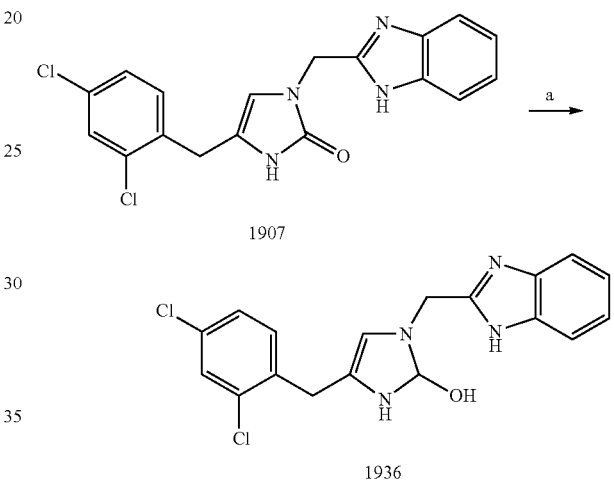

Reagents and conditions (a) LiAlH$_4$, THF

To a solution of 1907 (50 mg, 0.134 mmol) in anhydrous THF at 0° C. was added LiAlH$_4$ (5 mg, 0.134 mmol). After the mixture was stirred at 0° C. overnight, then water was added slowly. The mixture was extracted into ether (3 times), and the combined organic layer was washed with brine, dried over Na$_2$SO$_4$. After solvent was removed, the residue was chromatographed via silica gel, eluted with MeOH/DCM to give 3-((1H-benzo[d]imidazol-2-yl)methyl)-5-(2,4-dichlorobenzyl)-2,3-dihydro-1H-imidazol-2-ol (1936). LC/MS: (ESI) (M+H)$^+$=376.3.

Scheme 84

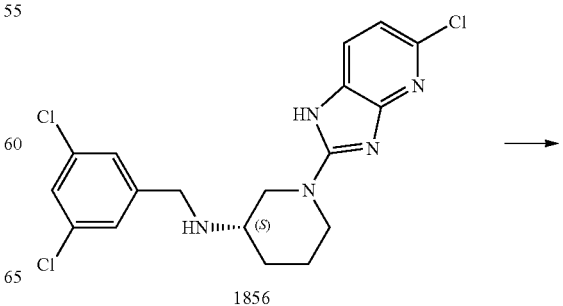

1856

251

-continued

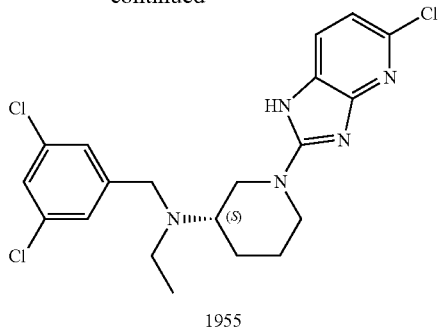

1955

Reagent and conditions: acetaldehyde, NaBH₃CN, AcOH, CH₃OH, r.t. overnight.

Compound 1856 (4.1 mg, 0.01 mmol) was dissolved in 1 ml of MeOH, 5 uL AcOH and acetaldehyde (4 mg, 0.03 mmol) was added. After the mixture was stirred for 30 min, NaBH₃CN (1.4 mg, 0.02 mmol) was added. The mixture was stirred at r.t. overnight and the solvent was removed under vacuum. The residue was dissolved in DCM and washed with sat. sodium bicarbonate and brine. The organic layer was dried over Na₂SO₄ and concentrated under vacuum. The residue was purified by flash column chromatography (DCM/MeOH) to give the target compound (S)-1-(5-chloro-1H-imidazo[4,5-b]pyridin-2-yl)-N-(3,5-dichlorobenzyl)-N-ethylpiperidin-3-amine (1955). LC/MS: (ESI) (M+H)⁺=439.8.

Scheme 85

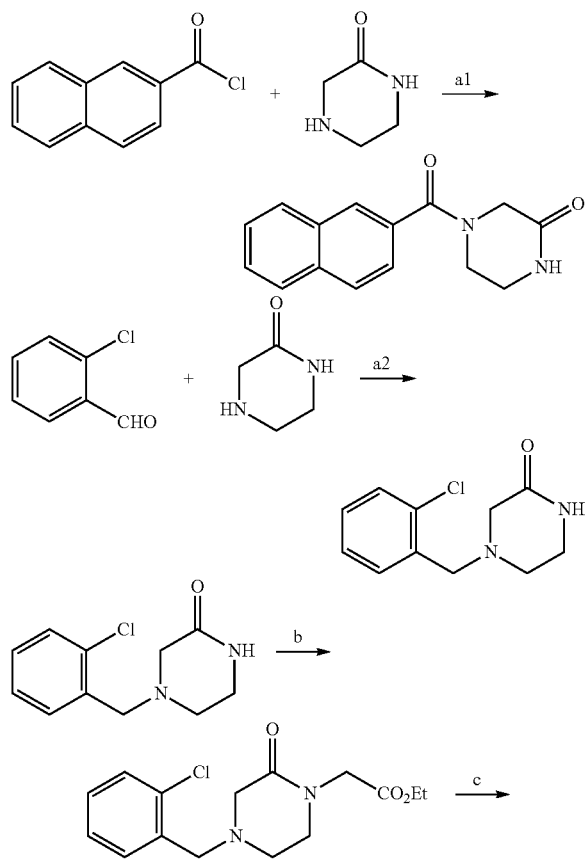

252

-continued

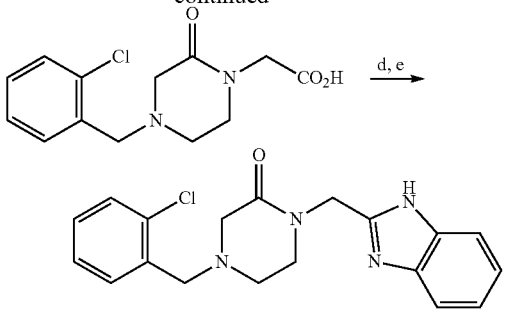

1735

Reagents and conditions: (a1) (a2) NaBH₃CN, AcOH, CH₃OH, r.t. overnight; (b) ethyl 2-bromoacetate, NaH, DMF, 0° C. r.t., 2 h; (c) LiOH, CH₃OH/H₂O, r.t. overnight; (d) benzene-1,2-diamine, EDC, pyridine, r.t. overnight; (e) (I) AcOH, 60° C., 3 h, General Procedures 30:

(a) 2-chlorobenzaldehyde (0.2 mM) and piperazin-2-one (0.2 mM) were dissolved in CH₃OH, then AcOH (0.3 mM) and NaBH₃CN (0.4 mM) were added. The mixture was stirred at r.t. overnight. The solvent was removed under reduced pressure and the residue was extracted by EA. The organic phase was dried over sodium sulfate. Remove solvent in vacuum and purify through flash chromatography on silica gel eluted with MeOH-DCM (0.5% ammonia hydroxide) to give 4-(2-chlorobenzyl)piperazin-2-one.

(b) The solution of 4-(2-chlorobenzyl)piperazin-2-one (1 eq) in DMF was cooled to 0° C., NaH (1.2 eq) was added and the resulting solution stirred at 0° C. for 10 min. Ethyl 2-bromoacetate (1.2 eq) was then added in dropwisely at 0° C., and the mixture stirred at r.t. for 2 hours. The solvent was removed under reduced pressure and the residue was extracted by EA. The organic phase was dried over sodium sulfate. Remove solvent in vacuum and purify through flash chromatography on silica gel eluted with EA-hexane to give ethyl 2-(4-(2-chlorobenzyl)-2-oxopiperazin-1-yl)acetate.

(c) LiOH.H₂O (3 eq) was added to the solution of ethyl 2-(4-(2-chlorobenzyl)-2-oxopiperazin-1-yl)acetate in CH₃OH/H₂O (CH₃OH:H₂O=3:1). The reaction mixture was stirred at r.t. overnight. The solvent was evaporated under reduced pressure, the residue 2-(4-(2-chlorobenzyl)-2-oxopiperazin-1-yl)acetic acid was used for the next step without further purification.

(d) 2-(4-(2-chlorobenzyl)-2-oxopiperazin-1-yl)acetic acid (1 eq) and benzene-1,2-diamine (1 eq) in pyridine was added EDC (1.5 eq). The mixture was stirred at r.t. overnight, and pyridine was then removed under reduced pressure. After addition of saturated aqueous sodium bicarbonate to the residue, the mixture was extracted with DCM. The organic layer was dried over anhydrous sodium sulfate, and concentrated in vacuum. Purification through flash chromatography on silica gel eluted with MeOH-DCM (0.5% ammonia hydroxide) gave N-(2-aminophenyl)-2-(4-(2-chlorobenzyl)-2-oxopiperazin-1-yl)acetamide.

(e) N-(2-aminophenyl)-2-(4-(2-chlorobenzyl)-2-oxopiperazin-1-yl)acetamide in glacial acetic acid was heated at 60° C. for 3 hours. The reaction mixture was concentrated in vacuum and the residue partitioned between saturated sodium bicarbonate and DCM. The organic extract was dried over anhydrous sodium sulfate, and concentrated in vacuum. Purification through flash chromatography on silica gel eluted with MeOH-DCM (0.5% ammonia hydroxide) gave in 5 mL glacial acetic acid (1735). LC/MS: (ESI) (M+H)⁺=356.0.

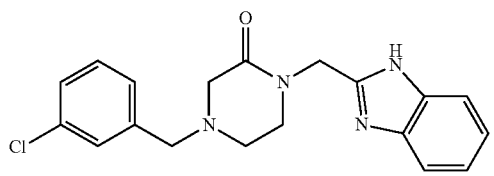

1736: 1-((1H-benzo[d]imidazol-2-yl)methyl)-4-(3-chlorobenzyl)piperazin-2-one was synthesized using 3-chlorobenzaldehyde in General Procedure 30. LC/MS: (ESI) (M+H)$^+$=355.8.

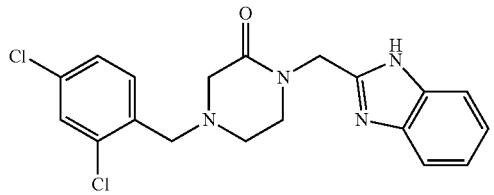

1747: 1-((1H-benzo[d]imidazol-2-yl)methyl)-4-(2,4-dichlorobenzyl)piperazin-2-one was synthesized using 2,4-dichlorobenzaldehyde in General Procedure 30. LC/MS: (ESI) (M+H)$^+$=390.5.

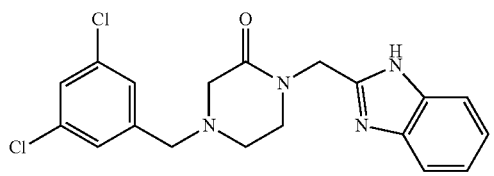

1748: 1-((1H-benzo[d]imidazol-2-yl)methyl)-4-(3,5-dichlorobenzyl)piperazin-2-one was synthesized using 3,5-dichlorobenzaldehyde in General Procedure 30. LC/MS: (ESI) (M+H)$^+$=390.4.

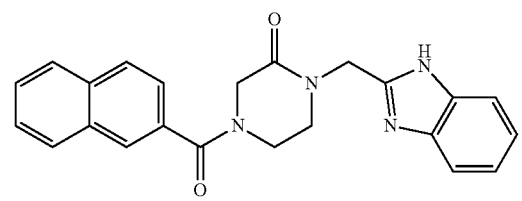

1760: 1-((1H-benzo[d]imidazol-2-yl)methyl)-4-(3,5-dichlorobenzyl)piperazin-2-on1-((1H-benzo[d]imidazol-2-yl)methyl)-4-(2-naphthoyl)piperazin-2-one was synthesized using 2-naphthoyl chloride in General Procedure 30. LC/MS: (ESI) (M+H)$^+$=385.5.

T. brucei MetRS Aminoacylation Assay.

Test compounds (assayed in triplicate in serial 3 dilutions) were pre-incubated for 15 minutes at room temperature with 10 nM of T. brucei MetRS (PMID: 21282428), 0.1 mM ATP, 240 nM $^3$H[L]-methionine (83 Ci/mmol) 0.1 U/mL pyrophosphatase (I1643; Sigma-Aldrich), 0.2 mM spermine, 0.1 mg/mL bovine serum albumin, 2.5 mM dithiothreitol, 25 mM HEPES-KOH (pH 7.9), 10 mM MgCl$_2$, 50 mM KCl, and 2% DMSO (PMID: 22720744, PMID: 25163684, PMID: 21282428). Reactions (75 µL/well) were started with the addition of 400 µg/mL bulk E. coli tRNA (R4251; Sigma-Aldrich or the equivalent activity of 10109550001; Roche) and incubated at room temperature for 120 minutes in 96-well filter plates with Durapore membranes (MSHVN4B10; Millipore). Reactions were quenched by adding 100 µL/well of ice cold 10% trichloroacetic acid and washed three times with 300 µL/well of ice cold 10% trichloroacetic acid. The plates were dried, 25 µL/well of scintillation fluid added, and the counts quantified using a scintillation plate reader. Percent inhibition was calculated by comparing the signal of wells with test compounds to that of wells without test compounds. Every assay also included wells without bulk E. coli tRNA and test compounds to measure background signal. IC$_{50}$ values were calculated in Prism 3.0.

Growth Inhibition Assays of T. brucei Cell Cultures.

T. brucei (bloodstream form strain 427 from K. Stuart, Seattle Biomedical Research Institute, Seattle, Wash.) was cultured in HMI-9 medium containing 10% fetal bovine serum, penicillin, and streptomycin at 37° C. with 5% CO. Drug sensitivity of the T. brucei strain was determined in 96 well microtiter plates in triplicate with an initial inoculum of 1×10$^4$ trypomastigotes per well. Compound stock solutions were prepared in DMSO at 20 mM and added in serial dilutions for a final volume of 200 µL/well. Parasite growth was quantified at 48 h by the addition of Alamar Blue (Alamar Biosciences, Sacramento, Calif. Pentamidine isethionate (Aventis, Dagenham, UK) was included in each assay as a positive control. Standard errors within assays were consistently less than 15%.

Biological Data

The compounds of the present disclosure were tested against A) MetRS (T. brucei) ATP depletion assay using Kinase-Glo, IC50 (nM); B) T. brucei EC50 (nM); C) T. cruzi EC50 (nM); D) MetRS (Giardia) aminoacylation assay with modified cpd dilution method IC50 (nM); E) Giardia intestinalis (ATCC 50580) EC50 (nM); F) L. amaz EC50 (nM); G) P. fal (3D37) EC50 (nM); H) MetRS (S. aureus) ATP depletion assay using Kinase-Glo with modified cpd dilution method, IC50 (nM); I) S. aureus (ATCC 29213) MIC/EC50, MIC (ug/ml); J) S. aureus MRSA (ATCC 43300) MIC/EC50, MIC (ug/ml); K) E. faecalis (ATCC 29212) MIC/EC50, MIC (ug/ml); L) E. faecium (ATCC 51559) MIC/EC50, MIC (ug/ml); M) MetRS (Brucella) ATP depletion assay using Kinase-Glo, IC50 (nM). The results are listed in Tables 1 and 2:

TABLE 1

| No. | A | B | C | D | E | F |
|---|---|---|---|---|---|---|
| 1575 | 9 | 9.36, 7.64 | 192.96 | 36 | >10000.0, 4500.0, 8000.0 | >10000.0 |
| 1576 | 109 | 402.68 | | | | |
| 1599 | 45.00, 59.00 | 661.89 | 2912.02 | | | |
| 1608 | >1000 | 4234.73 | | | | |
| 1614 | 16 | 6.22, 4.43, 1.81 | 39.45, 35.68 | 9 | 3423.0, 1978.0 | >1000, >1000 |
| 1627 | 61 | >9.08, 4.60 | 623.09 | | | |

TABLE 1-continued

| No. | A | B | C | D | E | F |
|---|---|---|---|---|---|---|
| 1634 | 133 | 121.06 | 9759.25 | | | |
| 1641 | <49.00, 138.00 | 7654.28, 8351.62 | | | | |
| 1655 | 43 | 11.34, 7.97 | 709.29 | | | 6740.1 |
| 1671 | 1271 | >20000 | | | | |
| 1673 | 11 | 7.58, 1.23 | 1536.16 | | | 7862.9, 5711.0, 8284.6 |
| 1674 | 23019 | >20000 | | | | |
| 1675 | 8228 | >20000 | | | | |
| 1683 | 74 | 8831.12 | >10000 | >1000 | >2000, >2000 | >1000 |
| 1699 | 13100 | >10000 | | | | |
| 1701 | 5 | 1293.71 | 8747.24 | | | |
| 1702 | 9.00, 11.00 | 4974.05 | | | | |
| 1703 | 12068 | >10000 | | | | |
| 1704 | 280 | 8610.96 | | | | |
| 1705 | 100 | 8839.47 | | | | |
| 1706 | 38 | 2761.15 | | | | |
| 1708 | 11 | 1561.50, 892.78 | >5000 | | | >1000 |
| 1707 | 26 | 1608.28 | >10000 | | | >1000 |
| 1709 | 8 | 1.70, 0.18, 0.05 | >4.57, 5.05 | 2 | 664.0, 492.0 | 1301.2, 1134.2 |
| 1711 | 752 | 2822.86 | | | | |
| 1716 | 51 | 373.64 | 1048.87 | | | >1000 |
| 1717 | 28 | >0.91, 0.67, 0.06, 0.41 | >4.57, 3.72 | 3 | 590.0, 316.0 | 2852.4 |
| 1720 | 70 | 848.39 | 3704.39 | | | |
| 1726 | 2378 | 8023.6 | | | | |
| 1727 | 5088 | >20000 | | | | |
| 1728 | >10000 | >20000 | | | | |
| 1729 | 17 | 119.43 | >5000 | | | >1000 |
| 1730 | 142 | 722.52 | | | | |
| 1731 | 5000 | >20000 | | | | |
| 1732 | 288 | >5000 | | | | |
| 1733 | 926 | 8810.04 | | | | |
| 1734 | 60 | 1396.88 | 4909.57 | | | |
| 1735 | >10000 | >20000 | | | | |
| 1736 | >10000 | >20000 | | | | |
| 1737 | 47 | >1000 | | | | |
| 1738 | >10000 | >20000 | | | | |
| 1739 | 1452 | >10000 | | | | |
| 1740 | 549 | >10000 | | | | |
| 1741 | 132 | 4223.16 | | | | |
| 1744 | 184 | 3260.27 | | | | |
| 1745 | 812 | 4602.62 | | | | |
| 1746 | 138 | 3333.74 | | | | |
| 1747 | >10000 | >10000 | | | | |
| 1748 | >10000 | >10000 | | | | |
| 1752 | 1364 | >10000 | | | | |
| 1753 | 73 | 2328.63 | >5000 | | | |
| 1754 | >10000 | 5894.39 | >5000 | | | |
| 1755 | 1390 | >10000 | | | | |
| 1756 | 3718 | >10000 | | | | |
| 1757 | 3500 | >10000 | | | | |
| 1758 | 31 | 4645.85 | | | | |
| 1759 | >10000 | >10000 | | | | |
| 1760 | >10000 | >10000 | | | | |
| 1761 | 54 | 995.78 | >5000 | | | |
| 1762 | 28 | 1058.06 | | | | |
| 1763 | 168 | 12657.66 | | | | |
| 1764 | >10000 | >20000 | | | | |
| 1765 | >10000 | >20000 | | | | |
| 1766 | 297 | 3525.77 | >5000 | | | |
| 1767 | 51 | 626.61 | 2929.69 | | | |
| 1768 | 18 | 70.23 | 1689.02 | | | >1000 |
| 1769 | 11 | 1071.12 | >5000 | | | |
| 1779 | >10000 | >20000 | | | | |
| 1780 | 67.00, 36.00 | 1162.97, 1061.52 | | | | |
| 1785 | >10000 | >20000 | | | | |
| 1786 | 310 | 5673.64 | | | | |
| 1787 | 267 | 2683.83 | | | | |
| 1788 | 124 | 358.76 | 4174.3 | | | |
| 1789 | 89 | 2810.59 | 4985.76 | | | |
| 1790 | 105 | 2695.33 | | | | |
| 1791 | 8477 | >20000 | | | | |
| 1792 | 150 | 2682.05 | | | | |
| 1793 | >10000 | 6375.52 | | | | |
| 1794 | 31.00, 17.00, 72.00, 70.00 | 1332.84, 1873.14, 1840.56 | 5229.23 | | | |
| 1795 | >10000 | 12335.27 | | | | |
| 1796 | 17 | 49.85, >9.08 | 521.12 | | | >1000 |
| 1797 | 23 | 22.23, >9.08 | 432.26 | | | >1000 |
| 1798 | >10000 | 1228.86 | | | | |
| 1799 | 2063 | 8308.97 | | | | |
| 1800 | 663 | 961.47 | | | | |
| 1801 | 533.00, 569.00 | 27.16, 11.92 | 252.47 | | | |
| 1802 | 4291 | >20000 | | | | |
| 1803 | >10000 | >20000 | | | | |
| 1804 | 389 | 14979.7 | | | | |
| 1805 | 56.00, 27.00 | 1692.64 | 5614.27 | | | |
| 1806 | 7628.00, 9885.00 | 3330.66 | | | | |
| 1807 | 1553 | 3729.23 | | | | |
| 1808 | >10000 | 17417.37 | | | | |
| 1809 | 43 | 821.2 | 3461.75 | | | |
| 1810 | 361 | 4526.85 | | | | |
| 1811 | 8 | 81.76 | 2512.78 | | | |
| 1812 | >10000 | 3762.72 | | | | |
| 1813 | 747 | 1375.15 | | | | |
| 1814 | 3397 | 7213.32 | | | | |
| 1815 | >10000 | 4086.56 | | | | |
| 1816 | >10000 | 8786.35 | | | | |
| 1817 | >10000 | 2055.91 | | | | |
| 1818 | 7951 | >20000 | | | | |
| 1819 | 7233 | 8903.31 | | | | |
| 1820 | 290 | 3142.7 | | | | |
| 1821 | 54 | 1670.28 | | | | |
| 1822 | 1493 | 3574.4 | | | | |
| 1823 | 2294 | 4557.37 | | | | |
| 1824 | 160 | 2240.02 | | | | |
| 1825 | 1558 | 3645.45 | | | | |
| 1826 | 454 | 7937.6 | | | | |
| 1827 | 390 | 5021.49 | | | | |
| 1828 | >10000 | 7405.91 | | | | |
| 1829 | 85 | 538.71 | 3042.29 | | | |
| 1830 | >10000 | >20000 | | | | |
| 1831 | >10000 | 8002.72 | | | | |
| 1832 | 243 | 2154.33 | | | | |
| 1833 | >10000 | >20000 | | | | |
| 1835 | 23 | 873.42 | >20000 | | | |
| 1836 | 1433 | 7630.29 | | | | |
| 1837 | 119 | 1336.92 | | | | |
| 1838 | >10000 | 8567.89 | | | | |
| 1839 | 3677 | 2318.59 | | | | |
| 1840 | 580 | 1952.34 | | | | |
| 1841 | 6301 | 3687.05 | | | | |
| 1842 | >10000 | 8577.61 | | | | |
| 1844 | 60 | 597.58 | 5424.02 | | | |
| 1845 | 47 | 1538.61 | | | | |
| 1846 | 1637 | 11030.23 | | | | |
| 1847 | 696 | 9012.74 | | | | |
| 1848 | 847 | 10588.34 | | | | |
| 1849 | 33 | 60.73 | 1812.42 | | | |
| 1850 | 385 | 3868.81 | | | | |
| 1851 | 81 | 3375.75 | | | | |
| 1852 | 75 | 5543.34 | | | | |
| 1853 | >10000 | >20000 | | | | |
| 1854 | 106 | 580.1 | | | | |
| 1855 | 192 | 998.64 | | | | |
| 1856 | 19 | 38.73 | 1471.8 | | | 4347.7 |
| 1857 | 72 | 1475.76 | | | | |
| 1858 | 340 | 1888.4 | | | | |

TABLE 1-continued

| No. | A | B | C | D | E | F |
|---|---|---|---|---|---|---|
| 1859 | 1429 | >20000 | | | | |
| 1860 | 6900 | 8565.45 | | | | |
| 1861 | 1471 | 4439.75 | | | | |
| 1862 | 31 | 343.15 | 4924.81 | | | |
| 1863 | >10000 | 3289.78 | | | | |
| 1864 | 2166 | >20000 | | | | |
| 1865 | >10000 | 6633.56 | | | | |
| 1866 | >10000 | >20000 | | | | |
| 1867 | 4970 | >20000 | | | | |
| 1868 | 77 | 1081.21 | | | | |
| 1869 | 52 | 1699.67 | | | | |
| 1870 | 54 | 457.53 | 2608.61 | | | |
| 1871 | 447 | 5435.64 | | | | |
| 1872 | >10000 | 8341.99 | | | | |
| 1873 | 98 | 5498.13 | | | | |
| 1874 | 51 | 3653.7 | | | | |
| 1875 | 38 | 1895.51 | 13103.6 | | | |
| 1876 | 375 | >20000 | | | | |
| 1877 | 191 | 8678.69 | | | | |
| 1878 | 195 | 7516.95 | | | | |
| 1879 | 416 | 11214.45 | | | | |
| 1880 | 214 | 8397.97 | | | | |
| 1881 | 35 | 306.67 | 5870.45 | | | |
| 1882 | 87 | 1024.25 | | | | |
| 1883 | 39 | 5620.25, 3665.62 | 17446.4 | | | |
| 1884 | 24 | 55.94 | 772.85 | | | |
| 1885 | 1510 | 5871.08 | | | | |
| 1886 | 14 | 299.07 | 5157.74 | | | |
| 1887 | 6657 | >20000 | | | | |
| 1888 | >10000 | >20000 | | | | |
| 1889 | >10000 | >20000 | | | | |
| 1890 | 78 | 6221.13 | | | | |
| 1891 | 3904 | >20000 | | | | |
| 1892 | 33 | 1547.62 | | | | |
| 1893 | 8 | 14.84, 28.19 | 339.9 | | | 3784.3 |
| 1894 | 179 | 2892.72 | | | | |
| 1895 | 17 | 569.06 | | | | |
| 1896 | 1054 | 1399.07 | | | | |
| 1897 | 16 | 652.55 | | | | |
| 1898 | 196 | 8801.76 | | | | |
| 1899 | 89 | >9.08, 56.50 | 259.67 | | | |
| 1900 | 27 | 127.66, >200.00 | 2237.11 | | | |
| 1901 | 692 | 5097.58 | | | | |
| 1902 | 18 | 354.05 | | | | |
| 1903 | 682 | 1813.45 | | | | |
| 1904 | >10000 | >20000 | | | | |
| 1905 | 4308 | >20000 | | | | |
| 1906 | 2942 | 6228.96 | | | | |
| 1907 | 19 | 346.06 | 7668.95 | | | >1000 |
| 1908 | 15 | 85.21 | | | | |
| 1909 | 20 | 333.54 | | | | |
| 1910 | 19 | 39.52 | 934.37 | | | |
| 1911 | 21 | 356.93 | | | | 5146.6 |
| 1912 | 8 | 70.6 | 2248.41 | | | 7726.2 |
| 1913 | 26 | 113.02 | | | | >1000 |
| 1914 | 18 | 252.1 | | | | |
| 1915 | 170 | 3104.67 | | | | |
| 1916 | 58 | 479.71 | | | | 9546.3 |
| 1917 | 21 | >0.91, 4.02 | 15.66 | | | 663.2 |
| 1918 | 1114 | 9556.51 | | | | |
| 1919 | 15 | 6.31, 9.45 | 88.77 | | | 1639.4 |
| 1920 | 16 | 110.76 | | | | |
| 1921 | 25 | 240.64 | | | | |
| 1922 | 140 | 2762.19 | | | | |
| 1923 | 32 | 566.36 | | | | |
| 1924 | 165 | 3284.35 | | | | |
| 1925 | 15 | 314.17 | | | | |
| 1926 | 20 | 75.52 | 1332.62 | | | |
| 1927 | 47 | 826.99 | | | | |
| 1928 | 21 | 325.55 | | | | |
| 1929 | 29 | 510.83 | | | | |
| 1930 | 389 | 3115.19 | | | | |
| 1931 | 305 | 1703.03 | | | | |
| 1932 | 518 | 8908.51 | | | | |
| 1933 | 22 | 102.11 | 1709.13 | | | |
| 1934 | 118 | 2001.52 | | | | |
| 1935 | >10000 | 9358.82 | | | | |
| 1936 | 65 | 1827.98 | | | | |
| 1937 | 19 | 229.79 | | | | |
| 1938 | 36 | >9.08, 30.53 | 266.04 | | | |
| 1939 | 73 | 29.64, 68.14 | 175.74 | | | |
| 1940 | 42 | 359.36 | | | | |
| 1941 | 273 | 3132.75 | | | | |
| 1942 | 20 | 145.42 | | | | |
| 1943 | 2130.00, 3540.00 | 418.74, 388.60 | | | | |
| 1944 | 535 | 11671.86 | | | | |
| 1945 | >10000 | 13696.23 | | | | |
| 1949 | 18 | 79.92, 85.47 | 1305.66 | | | |
| 1950 | 50 | 867.21, >200.00 | | | | |
| 1951 | 288 | 663.62 | | | | |
| 1952 | 2283.00, 1737.00 | 186.83, 367.34 | | | | |
| 1953 | >10000, >10000 | 903.42, 812.43 | | | | |
| 1954 | 61 | 368.97, 564.94 | | | | |
| 1955 | 286 | 1736.37 | | | | |
| 1956 | 325 | 1549.17 | | | | |
| 1957 | 11 | 14.52, 30.10 | | | | |
| 1958 | 13 | 62.37, 33.09 | | | | |
| 1959 | 16 | 39.30, 51.15 | | | | |
| 1960 | 21 | 21.52, >9.08 | | | | |
| 1961 | 121 | 3763.17 | | | | |
| 1962 | 19 | 12.92 | | | | |
| 1963 | 21 | 97.37 | | | | |
| 1964 | 17 | 36.65 | | | | |
| 1965 | 345.00, 322.00 | 96.2 | | | | |
| 1966 | 72 | 1034.47 | | | | |
| 1967 | 88 | 2301.41 | | | | |
| 1968 | 1856 | >20000 | | | | |
| 1969 | 782 | 7959.94 | | | | |
| 1970 | 69 | 2979.12 | | | | |
| 1971 | 13 | 62.28, 40.40 | | | | |
| 1972 | 27 | 58.00, 25.21 | | | | |
| 1973 | 11 | 90.99, 43.27 | | | | |
| 1974 | 7 | 38.82, 10.52 | | | | |
| 1990 | 17 | 2040.3 | | | | |
| 1991 | 18 | 2066.58 | | | | |
| 1992 | 14 | 110.82 | 2130.39 | | | |
| 1994 | 59 | 1414.46 | | | | |
| 1996 | | 5299.9 | | | | |

TABLE 2

| No. | G | H | I | J | K | L | M |
|---|---|---|---|---|---|---|---|
| 1575 | 7005.6 | 35 | | | | 0.625 | |
| 1614 | 7710.9 | 37 | 1.25 | | 0.625 | 1.25 | 490 |
| 1655 | | 171 | 10 | 10 | | | |
| 1673 | | 113 | 5 | 5 | | | |
| 1701 | | 67 | >10 | >10 | | | |
| 1705 | 1693 | | | | | | |
| 1706 | | 83 | | | | | |

TABLE 2-continued

| No. | G | H | I | J | K | L | M |
|---|---|---|---|---|---|---|---|
| 1708 | | 88 | | | | | |
| 1707 | | 37 | | | | | |
| 1709 | | 19 | | | | >0.04 | |
| 1711 | | 368 | | | >10, >10 | >10 | |
| 1716 | | | | | | | |
| 1717 | | 28 | 0.157 | 0.157 | >0.04, 0.079 | >0.04 | |
| 1720 | | 181 | >10 | >10 | | | |
| 1729 | | 27 | | | | >10 | |
| 1734 | | 2443 | >10 | >10 | | | |
| 1753 | | 1095 | | | | >10 | |
| 1758 | | 1041 | >10 | >10 | | | |
| 1761 | | 1912 | >10 | >10 | | | |
| 1762 | | 2884 | >10 | >10 | | | |
| 1767 | | >1000 | >10 | 10 | | | |
| 1768 | | 30 | >10 | >10 | | | |
| 1769 | | 95 | >10 | >10 | | | |
| 1794 | | 22581 | | | | | |
| 1796 | | 55 | | | | | |
| 1797 | | 2 | | | | | |
| 1805 | | >1000 | | | | | |
| 1811 | | 709 | | | | | |
| 1849 | | 3109 | | | | | |
| 1856 | | 365 | | | | | |
| 1862 | | 754 | | | | | |
| 1870 | | 837 | | | | | |
| 1883 | | 333 | | | | | |
| 1884 | | 122 | | | | | |
| 1886 | | 505 | | | | | |
| 1893 | | 296 | | | | | |
| 1895 | | 445 | | | | | |
| 1897 | | 606 | | | | | |
| 1899 | | 323 | | | | | |
| 1900 | | 303 | | | | | |
| 1907 | | 54 | | | | | |
| 1908 | | 155 | | | | | |
| 1910 | | 22 | | | | | |
| 1913 | | 691 | | | | | |
| 1914 | | 303 | | | | | |
| 1917 | | 137 | | | | | |
| 1919 | | 328 | | | | | |
| 1921 | | 1575 | | | | | |
| 1923 | | 504 | | | | | |
| 1925 | | 266 | | | | | |
| 1926 | | 172 | | | | | |
| 1933 | | 40 | | | | | |
| 1938 | | 1260 | | | | | |
| 1939 | | 271 | | | | | |
| 1942 | | 104 | | | | | |
| 1949 | | 606 | | | | | |
| 1950 | | 797 | | | | | |
| 1954 | | 928 | | | | | |
| 1957 | | 424 | | | | | |
| 1958 | | 381 | | | | | |
| 1959 | | 12 | | | | | |
| 1960 | | 12 | | | | | |
| 1962 | | 17 | | | | | |
| 1963 | | 348 | | | | | |
| 1966 | | 5734 | | | | | |
| 1967 | | >1000 | | | | | |
| 1970 | | 1078 | | | | | |
| 1971 | | 85 | | | | | |
| 1972 | | 140 | | | | | |

What is claimed is:

1. A compound that is:

[(3,5-dichlorophenyl)methyl][2,2-difluoro-3-({3H-imidazo[4,5-b]pyridin-2-yl}amino)propyl]amine;

N-(3-{[1-(3,5-dichlorophenyl)cyclopropyl]amino}propyl)-5-fluoro-3H-imidazo[4,5-b]pyridin-2-amine;

1-[3-(1H-1,3-benzodiazol-2-yl)piperidin-1-yl]-2-(2,4-dichlorophenyl)ethan-1-one;

1-[3-(1H-1,3-benzodiazol-2-yl)piperidin-1-yl]-2-(3,5-dichlorophenyl)ethan-1-one;

1-[3-(4-chloro-1H-1,3-benzodiazol-2-yl)piperidin-1-yl]-2-(3,5-dichlorophenyl)ethan-1-one;

1-[3-(5-chloro-1H-1,3-benzodiazol-2-yl)piperidin-1-yl]-2-(3,5-dichlorophenyl)ethan-1-one;

2-(3,5-dichlorophenyl)-1-[3-(5-fluoro-1H-1,3-benzodiazol-2-yl)piperidin-1-yl]ethan-1-one;

1-[3-(5,6-dichloro-1H-1,3-benzodiazol-2-yl)piperidin-1-yl]-2-(3,5-dichlorophenyl)ethan-1-one;

1-[3-(5-chloro-6-fluoro-1H-1,3-benzodiazol-2-yl)piperidin-1-yl]-2-(3,5-dichlorophenyl)ethan-1-one;

1-(1H-1,3-benzodiazol-2-ylmethyl)-4-[(2,4-dichlorophenyl)methyl]piperazin-2-one;

1-(1H-1,3-benzodiazol-2-ylmethyl)-4-[(3,5-dichlorophenyl)methyl]piperazin-2-one;

(5S)-3-(1H-1,3-benzodiazol-2-ylmethyl)-5-[(2,4-dichlorophenyl)methyl]imidazolidine-2,4-dione;

1-[(3R)-3-(5-chloro-1H-1,3-benzodiazol-2-yl)piperidin-1-yl]-2-(3,5-dichlorophenyl)ethan-1-one;

1-[(3S)-3-(5-chloro-1H-1,3-benzodiazol-2-yl)piperidin-1-yl]-2-(3,5-dichlorophenyl)ethan-1-one;

1-(1H-1,3-benzodiazol-2-ylmethyl)-4-(naphthalene-2-carbonyl)piperazin-2-one;

2-(3,5-dichlorophenyl)-1-(3-{5-fluoro-1H-imidazo[4,5-b]pyridin-2-yl}piperidin-1-yl)ethan-1-one;

1-(3-{5-chloro-1H-imidazo[4,5-b]pyridin-2-yl}piperidin-1-yl)-2-(3,5-dichlorophenyl)ethan-1-one;

N-(3-{5-chloro-1H-imidazo[4,5-b]pyridin-2-yl}cyclohexyl)-2-(3,5-dichlorophenyl)acetamide;

2-amino-1-[(3S)-3-{5-chloro-1H-imidazo[4,5-b]pyridin-2-yl}piperidin-1-yl]-2-(3,5-dichlorophenyl)ethan-1-one;

3-{5-chloro-1H-imidazo[4,5-b]pyridin-2-yl}-N-[(3,5-dichlorophenyl)methyl]cyclohexan-1-amine;

N-(3-{5-chloro-1H-imidazo[4,5-b]pyridin-2-yl}cyclohexyl)-N-[(3,5-dichlorophenyl)methyl]acetamide;

1-(2-{5-chloro-1H-imidazo[4,5-b]pyridin-2-yl}morpholin-4-yl)-2-(3,5-dichlorophenyl)ethan-1-one;

(4S)-1-(1H-1,3-benzodiazol-2-ylmethyl)-4-[(2,4-dichlorophenyl)methyl]imidazolidin-2-one;

1-[2-(3,5-dichlorophenyl)ethyl]-3-{5-fluoro-1H-imidazo[4,5-b]pyridin-2-yl}piperidine;

(2S)-2-amino-1-[(3S)-3-{5-chloro-1H-imidazo[4,5-b]pyridin-2-yl}piperidin-1-yl]-3-(2,4-dichlorophenyl)propan-1-one;

N-[(3,5-dichlorophenyl)methyl]-3-{5-fluoro-1H-imidazo[4,5-b]pyridin-2-yl}cyclohexan-1-amine;

N-[(3,5-dichlorophenyl)methyl]-N-(3-{5-fluoro-1H-imidazo[4,5-b]pyridin-2-yl}cyclohexyl)acetamide;

3-{5-chloro-1H-imidazo[4,5-b]pyridin-2-yl}-N-[(2,4-dichlorophenyl)methyl]cyclohexan-1-amine;

N-(3-{5-chloro-1H-imidazo[4,5-b]pyridin-2-yl}cyclohexyl)-N-[(2,4-dichlorophenyl)methyl]acetamide;

1-{5-chloro-1H-imidazo[4,5-b]pyridin-2-yl}-N-[(3,5-dichlorophenyl)methyl]piperidin-3-amine;

3-{5-chloro-1H-imidazo[4,5-b]pyridin-2-yl}-1-[2-(3,5-dichlorophenyl)ethyl]piperidine;

5-chloro-2-[(3S)-1-[(3,5-dichlorophenyl)methyl]piperidin-3-yl]-1H-1,3-benzodiazole;

3-({5-chloro-1H-imidazo[4,5-b]pyridin-2-yl}methyl)-1-[(3,5-dichlorophenyl)methyl]piperidine;

3-(1H-1,3-benzodiazol-2-yl)-N-[(3,5-dichlorophenyl)methyl]cyclohexan-1-amine;

N-[3-(1H-1,3-benzodiazol-2-yl)cyclohexyl]-N-[(3,5-dichlorophenyl)methyl]acetamide;

N-[(3,5-dichlorophenyl)methyl]-3-{1H-imidazo[4,5-b]pyridin-2-yl}cyclohexan-1-amine;
N-[(3,5-dichlorophenyl)methyl]-N-(3-{1H-imidazo[4,5-b]pyridin-2-yl}cyclohexyl)acetamide;
{2-[(6-chloro-1H-1,3-benzodiazol-2-yl)amino]ethyl}[(3,5-dichlorophenyl)methyl]amine;
N-(6-chloro-1H-1,3-benzodiazol-2-yl)-2-{[(3,5-dichlorophenyl)methyl]amino}acetamide;
(2S)—N-(6-chloro-1H-1,3-benzodiazol-2-yl)-2-{[(3,5-dichlorophenyl)methyl]amino}propanamide;
N-[(3,5-dichlorophenyl)methyl]-N-[3-(5-fluoro-1H-1,3-benzodiazol-2-yl)piperidin-1-yl]acetamide;
N-[(2,4-dichlorophenyl)methyl]-N-(3-{5-fluoro-1H-imidazo[4,5-b]pyridin-2-yl}cyclohexyl)acetamide;
5-chloro-2-[(3S)-1-[(2,4-dichlorophenyl)methyl]piperidin-3-yl]-1H-1,3-benzodiazole;
5-chloro-2-[(3R)-1-[(3,5-dichlorophenyl)methyl]piperidin-3-yl]-1H-1,3-benzodiazole;
N-[(3,5-dichlorophenyl)methyl]-3-(5-fluoro-1H-1,3-benzodiazol-2-yl)cyclohexan-1-amine;
3-(5-chloro-1H-1,3-benzodiazol-2-yl)-N-[(3,5-dichlorophenyl)methyl]cyclohexan-1-amine;
3-{6-chloro-3H-imidazo[4,5-b]pyridin-2-yl}-N-[(3,5-dichlorophenyl)methyl]cyclohexan-1-amine;
N-(3-{6-chloro-3H-imidazo[4,5-b]pyridin-2-yl}cyclohexyl)-N-[(3,5-dichlorophenyl)methyl]acetamide;
(3S)-1-{5-chloro-3H-imidazo[4,5-b]pyridin-2-yl}-N-[(3,5-dichlorophenyl)methyl]pyrrolidin-3-amine;
(3S)-1-{5-chloro-3H-imidazo[4,5-b]pyridin-2-yl}-N-[(2,4-dichlorophenyl)methyl]pyrrolidin-3-amine;
(3R)-1-{5-chloro-3H-imidazo[4,5-b]pyridin-2-yl}-N-[(3,5-dichlorophenyl)methyl]pyrrolidin-3-amine;
(3R)-1-{5-chloro-3H-imidazo[4,5-b]pyridin-2-yl}-N-[(2,4-dichlorophenyl)methyl]pyrrolidin-3-amine;
[2-({5-chloro-3H-imidazo[4,5-b]pyridin-2-yl}amino)ethyl][(3,5-dichlorophenyl)methyl]amine;
[2-({6-chloro-1H-imidazo[4,5-b]pyridin-2-yl}amino)ethyl][(3,5-dichlorophenyl)methyl]amine;
(1R,3S)-3-{5-chloro-1H-imidazo[4,5-b]pyridin-2-yl}-N-[(3,5-dichlorophenyl)methyl]cyclohexan-1-amine;
(3R)-1-{5-chloro-1H-imidazo[4,5-b]pyridin-2-yl}-N-[(3,5-dichlorophenyl)methyl]piperidin-3-amine;
(3S)-1-{5-chloro-1H-imidazo[4,5-b]pyridin-2-yl}-N-[(3,5-dichlorophenyl)methyl]piperidin-3-amine;
1-{5-chloro-1H-imidazo[4,5-b]pyridin-2-yl}-N-[(2,4-dichlorophenyl)methyl]piperidin-3-amine;
N-[(1R,3S)-3-{5-chloro-1H-imidazo[4,5-b]pyridin-2-yl}cyclohexyl]-N-[(3,5-dichlorophenyl)methyl]acetamide;
N-[(3,5-dichlorophenyl)methyl]-N-[3-(5-fluoro-1H-1,3-benzodiazol-2-yl)cyclohexyl]acetamide;
N-[3-(5-chloro-1H-1,3-benzodiazol-2-yl)cyclohexyl]-N-[(3,5-dichlorophenyl)methyl]acetamide;
1-{5-chloro-1H-imidazo[4,5-b]pyridin-2-yl}-4-[(3,5-dichlorophenyl)methyl]piperazine;
1-{5-chloro-1H-imidazo[4,5-b]pyridin-2-yl}-N-[(3,5-dichlorophenyl)methyl]piperidin-4-amine;
(3S)-3-{5-chloro-1H-imidazo[4,5-b]pyridin-2-yl}-1-[(3,5-dichlorophenyl)methyl]piperidine;
(3S)-3-{5-chloro-1H-imidazo[4,5-b]pyridin-2-yl}-1-[(2,4-dichlorophenyl)methyl]piperidine;
(3S)-3-{5-chloro-1H-imidazo[4,5-b]pyridin-2-yl}-1-[(3,4-dichlorophenyl)methyl]piperidine;
(3S)-3-{5-chloro-1H-imidazo[4,5-b]pyridin-2-yl}-1-[(3,5-dibromophenyl)methyl]piperidine;
(3S)-3-{5-chloro-1H-imidazo[4,5-b]pyridin-2-yl}-1-[(3,5-dimethoxyphenyl)methyl]piperidine;
N-[(3,5-dichlorophenyl)methyl]-1-{5-fluoro-1H-imidazo[4,5-b]pyridin-2-yl}piperidin-3-amine;
N-[(3,5-dichlorophenyl)methyl]-N-(1-{5-fluoro-1H-imidazo[4,5-b]pyridin-2-yl}piperidin-3-yl)acetamide;
3,5-dichloro-N-[(3S)-1-{5-chloro-1H-imidazo[4,5-b]pyridin-2-yl}piperidin-3-yl]benzamide;
5-chloro-N-(2-{[(3,5-dichlorophenyl)methyl]amino}ethyl)-N-methyl-3H-imidazo[4,5-b]pyridin-2-amine;
6-bromo-5-chloro-N-(2-{[(3,5-dichlorophenyl)methyl]amino}ethyl)-N-methyl-3H-imidazo[4,5-b]pyridin-2-amine;
N-[(3,5-dichlorophenyl)methyl]-N-[2-({5-fluoro-1H-imidazo[4,5-b]pyridin-2-yl}amino)ethyl]acetamide;
(3S)—N-[(3,5-dichlorophenyl)methyl]-1-{5-fluoro-1H-imidazo[4,5-b]pyridin-2-yl}piperidin-3-amine;
N-[(3,5-dichlorophenyl)methyl]-N-[(3S)-1-{5-fluoro-1H-imidazo[4,5-b]pyridin-2-yl}piperidin-3-yl]acetamide;
(3S)-1-{5-chloro-1H-imidazo[4,5-b]pyridin-2-yl}-N-[(2,3,5-trichlorophenyl)methyl]piperidin-3-amine;
(3S)-1-{6-bromo-5-chloro-1H-imidazo[4,5-b]pyridin-2-yl}-N-[(2,3,5-trichlorophenyl)methyl]piperidin-3-amine;
(5S)-3-(1H-1,3-benzodiazol-2-ylmethyl)-5-[(2,4-dichlorophenyl)methyl]imidazolidine-2,4-diol;
1-(1H-1,3-benzodiazol-2-ylmethyl)-4-[(2,4-dichlorophenyl)methyl]-2,3-dihydro-1H-imidazol-2-one;
(3S)-1-{5-chloro-1H-imidazo[4,5-b]pyridin-2-yl}-N-[(3,5-dibromophenyl)methyl]piperidin-3-amine;
(3S)-1-{5-chloro-1H-imidazo[4,5-b]pyridin-2-yl}-N-[(3,5-dibromo-2-methoxyphenyl)methyl]piperidin-3-amine;
(3S)-1-{5-chloro-1H-imidazo[4,5-b]pyridin-2-yl}-N-[(3,5-dibromo-2-ethoxyphenyl)methyl]piperidin-3-amine;
(3S)-1-{5-chloro-1H-imidazo[4,5-b]pyridin-2-yl}-N-[(3,5-dichloro-2-methoxyphenyl)methyl]piperidin-3-amine;
(3S)—N-[(3-bromo-5-chlorophenyl)methyl]-1-{5-chloro-1H-imidazo[4,5-b]pyridin-2-yl}piperidin-3-amine;
N-(2-{[(3,5-dichlorophenyl)methyl]amino}ethyl)-5-fluoro-N-methyl-1H-imidazo[4,5-b]pyridin-2-amine;
N-[(3,5-dichlorophenyl)methyl]-N-[2-({5-fluoro-1H-imidazo[4,5-b]pyridin-2-yl}(methyl)amino)ethyl]acetamide;
(3S)-1-{5-chloro-1H-imidazo[4,5-b]pyridin-2-yl}-N-[(3,5-dichloro-2-ethoxyphenyl)methyl]piperidin-3-amine;
2,4-dichloro-6-({[(3S)-1-{5-chloro-1H-imidazo[4,5-b]pyridin-2-yl}piperidin-3-yl]amino}methyl)phenol;
5-chloro-N-(2-{[(3,5-dichloro-2-ethoxyphenyl)methyl]amino}ethyl)-N-methyl-3H-imidazo[4,5-b]pyridin-2-amine;
N-[2-({5-chloro-3H-imidazo[4,5-b]pyridin-2-yl}(methyl)amino)ethyl]-N-[(3,5-dichlorophenyl)methyl]acetamide;
(3S)-1-{5-chloro-1H-imidazo[4,5-b]pyridin-2-yl}-N-[(3,5-dichloro-2-propoxyphenyl)methyl]piperidin-3-amine;
(3S)-1-{5-chloro-1H-imidazo[4,5-b]pyridin-2-yl}-N-{[3,5-dichloro-2-(prop-2-en-1-yloxy)phenyl]methyl}piperidin-3-amine;
(3S)-1-{5-chloro-1H-imidazo[4,5-b]pyridin-2-yl}-N-{[3,5-dichloro-2-(cyclopropylmethoxy)phenyl]methyl}piperidin-3-amine;

(3S)-1-{5-chloro-1H-imidazo[4,5-b]pyridin-2-yl}-N-[(3,5-dichloro-2-cyclopropoxyphenyl)methyl]piperidin-3-amine;

(3S)-1-{5-chloro-1H-imidazo[4,5-b]pyridin-2-yl}-N-{[3,5-dichloro-2-(propan-2-yloxy)phenyl]methyl}piperidin-3-amine;

N-[(3,5-dichlorophenyl)methyl]-N-[(1R,3S)-3-{5-fluoro-1H-imidazo[4,5-b]pyridin-2-yl}cyclohexyl]acetamide;

(4S)-1-(1H-1,3-benzodiazol-2-ylmethyl)-4-[(2,4-dichlorophenyl)methyl]-5-hydroxyimidazolidin-2-one;

1-(1H-1,3-benzodiazol-2-ylmethyl)-4-[(2,4-dichlorophenyl)methyl]-2,3-dihydro-1H-imidazol-2-ol;

(3S)—N-[(3-bromo-5-chloro-2-ethoxyphenyl)methyl]-1-{5-chloro-1H-imidazo[4,5-b]pyridin-2-yl}piperidin-3-amine;

(3S)-1-{5-chloro-1H-imidazo[4,5-b]pyridin-2-yl}-N-{[3,5-dichloro-2-(ethylamino)phenyl]methyl}piperidin-3-amine;

N-[2-({5-chloro-1H-imidazo[4,5-b]pyridin-2-yl}(methyl)amino)ethyl]-N-[(3,5-dichlorophenyl)methyl]propanamide;

5-chloro-N-(2-{[(3,5-dichlorophenyl)methyl]amino}ethyl)-N-ethyl-3H-imidazo[4,5-b]pyridin-2-amine;

(3S)-1-{5-chloro-3H-imidazo[4,5-b]pyridin-2-yl}-N-[(3,5-dichlorophenyl)methyl]-N-ethylpiperidin-3-amine;

2-amino-N-[2-({5-chloro-1H-imidazo[4,5-b]pyridin-2-yl}(methyl)amino)ethyl]-N-[(3,5-dichlorophenyl)methyl]acetamide;

3-amino-N-[2-({5-chloro-1H-imidazo[4,5-b]pyridin-2-yl}(methyl)amino)ethyl]-N-[(3,5-dichlorophenyl)methyl]propanamide;

N-[(3,5-dichlorophenyl)methyl]-N-[3-({5-fluoro-3H-imidazo[4,5-b]pyridin-2-yl}amino)propyl]acetamide;

4-[(2,4-dichlorophenyl)methyl]-1-({5-fluoro-3H-imidazo[4,5-b]pyridin-2-yl}methyl)-2,3-dihydro-1H-imidazol-2-one;

methyl N-[2-({5-chloro-1H-imidazo[4,5-b]pyridin-2-yl}(methyl)amino)ethyl]-N-[(3,5-dichlorophenyl)methyl]carbamate;

methyl N-[(3,5-dichlorophenyl)methyl]-N-[3-({5-fluoro-3H-imidazo[4,5-b]pyridin-2-yl}amino)propyl]carbamate;

methyl 2-[(3-{[(3,5-dichlorophenyl)methyl](methoxycarbonyl)amino}propyl)amino]-5-fluoro-3H-imidazo[4,5-b]pyridine-3-carboxylate;

N-[2-({5-chloro-3H-imidazo[4,5-b]pyridin-2-yl}(methyl)amino)ethyl]-N-[(3,5-dichlorophenyl)methyl]-2-hydroxyacetamide;

1-[2-({5-chloro-3H-imidazo[4,5-b]pyridin-2-yl}(methyl)amino)ethyl]-1-[(3,5-dichlorophenyl)methyl]urea;

N-[(3,5-dichlorophenyl)methyl]-N-[3-({5-fluoro-3H-imidazo[4,5-b]pyridin-2-yl}amino)propyl]-2-hydroxyacetamide;

1-[(3,5-dichlorophenyl)methyl]-1-[3-({5-fluoro-3H-imidazo[4,5-b]pyridin-2-yl}amino)propyl]urea;

3-chloro-5-({[(3S)-1-{5-chloro-3H-imidazo[4,5-b]pyridin-2-yl}piperidin-3-yl]amino}methyl)benzonitrile;

or a pharmaceutically acceptable salt thereof.

2. A pharmaceutical composition comprising one or more of compounds according to claim 1 and pharmaceutically acceptable carrier, diluent, or excipient.

* * * * *